(12) United States Patent
Brauker et al.

(10) Patent No.: US 9,986,942 B2
(45) Date of Patent: Jun. 5, 2018

(54) ANALYTE SENSOR

(75) Inventors: James H. Brauker, San Diego, CA (US); Robert Boock, San Diego, CA (US); Monica Rixman, San Diego, CA (US); Peter C. Simpson, Encinitas, CA (US); Mark Brister, Encinitas, CA (US); Mark Shults, Madison, WI (US)

(73) Assignee: DexCom, Inc., San Diego, CA (US)

( * ) Notice: Subject to any disclaimer, the term of this patent is extended or adjusted under 35 U.S.C. 154(b) by 383 days.

(21) Appl. No.: 11/503,367

(22) Filed: Aug. 10, 2006

(65) Prior Publication Data

US 2007/0027370 A1 Feb. 1, 2007

Related U.S. Application Data

(63) Continuation-in-part of application No. 11/439,630, filed on May 23, 2006, which is a continuation-in-part
(Continued)

(51) Int. Cl.
| | |
|---|---|
| *A61B 5/1486* | (2006.01) |
| *A61B 5/1473* | (2006.01) |
| *G01N 33/66* | (2006.01) |
| *A61B 5/145* | (2006.01) |
| *A61B 5/00* | (2006.01) |
| *C12Q 1/00* | (2006.01) |
| *G01N 33/543* | (2006.01) |

(52) U.S. Cl.
CPC ...... *A61B 5/14865* (2013.01); *A61B 5/14532* (2013.01); *A61B 5/411* (2013.01); *A61B 5/6848* (2013.01); *C12Q 1/006* (2013.01); *G01N 33/54366* (2013.01); *G01N 33/66* (2013.01); *A61B 5/1473* (2013.01); *A61B 5/418* (2013.01); *A61B 2562/08* (2013.01)

(58) Field of Classification Search
CPC .......... A61B 2562/08; A61B 5/14532; A61B 5/14865; A61B 5/411; A61B 5/418; A61B 5/6848; A61B 5/1473; A61B 5/1468; C12Q 1/006; G01N 33/54366; G01N 33/66
USPC ......................................... 600/309, 345–366
See application file for complete search history.

(56) References Cited

U.S. PATENT DOCUMENTS

| | | | |
|---|---|---|---|
| 1,564,641 | A | 12/1925 | St. James |
| 2,057,029 | A | 10/1936 | Johnstone |

(Continued)

FOREIGN PATENT DOCUMENTS

| | | |
|---|---|---|
| DE | 4105222 A1 | 8/1992 |
| DE | 3933373 C2 | 9/1992 |

(Continued)

OTHER PUBLICATIONS

US 7,530,950, 05/2009, Brister et al. (withdrawn)
(Continued)

*Primary Examiner* — Navin Natnithithadha
(74) *Attorney, Agent, or Firm* — Knobbe Martens Olson & Bear, LLP

(57) ABSTRACT

Biointerface membranes are provided which can be utilized with implantable devices, such as devices for the detection of analyte concentrations in a biological sample. More particularly, methods for monitoring glucose levels in a biological fluid sample using an implantable analyte detection device incorporating such membranes are provided.

4 Claims, 19 Drawing Sheets

Related U.S. Application Data of application No. 11/077,715, filed on Mar. 10, 2005, now Pat. No. 7,497,827.

(60) Provisional application No. 60/587,787, filed on Jul. 13, 2004, provisional application No. 60/587,800, filed on Jul. 13, 2004, provisional application No. 60/614,683, filed on Sep. 30, 2004, provisional application No. 60/614,764, filed on Sep. 30, 2004, provisional application No. 60/683,923, filed on May 23, 2005.

(56) References Cited

U.S. PATENT DOCUMENTS

| | | |
|---|---|---|
| 2,402,306 A | 6/1946 | Turkel |
| 2,497,894 A | 2/1950 | Luke |
| 2,719,797 A | 10/1955 | Rosenblatt et al. |
| 3,210,578 A | 10/1965 | Sherer |
| 3,219,533 A | 11/1965 | Mullins |
| 3,381,371 A | 5/1968 | Russell |
| 3,556,950 A | 1/1971 | Dahms |
| 3,562,352 A | 2/1971 | Nyilas |
| 3,652,475 A | 3/1972 | Wada et al. |
| 3,728,678 A | 4/1973 | Tong |
| 3,780,727 A | 12/1973 | King |
| 3,791,871 A | 2/1974 | Rowley |
| 3,826,244 A | 7/1974 | Salcman et al. |
| 3,838,033 A | 9/1974 | Mindt et al. |
| 3,838,682 A | 10/1974 | Clark et al. |
| 3,874,850 A | 4/1975 | Sorensen et al. |
| 3,898,984 A | 8/1975 | Mandel et al. |
| 3,926,760 A | 12/1975 | Allen et al. |
| 3,930,462 A | 1/1976 | Day |
| 3,933,593 A | 1/1976 | Sternberg |
| 3,943,918 A | 3/1976 | Lewis |
| 3,957,613 A | 5/1976 | Macur |
| 3,957,651 A | 5/1976 | Kesting |
| 3,964,974 A | 6/1976 | Banauch et al. |
| 3,966,580 A | 6/1976 | Janata et al. |
| 3,979,274 A | 9/1976 | Newman |
| 3,982,530 A | 9/1976 | Storch |
| 4,003,621 A | 1/1977 | Lamp |
| 4,008,717 A | 2/1977 | Kowarski |
| 4,016,866 A | 4/1977 | Lawton |
| 4,024,312 A | 5/1977 | Korpman |
| 4,036,749 A | 7/1977 | Anderson |
| 4,037,563 A | 7/1977 | Pflueger et al. |
| 4,040,908 A | 8/1977 | Clark, Jr. |
| 4,052,754 A | 10/1977 | Homsy |
| 4,067,322 A | 1/1978 | Johnson |
| 4,068,660 A | 1/1978 | Beck |
| 4,073,713 A | 2/1978 | Newman |
| 4,076,656 A | 2/1978 | White et al. |
| 4,101,395 A | 7/1978 | Motani et al. |
| 4,116,920 A | 9/1978 | Honma et al. |
| 4,172,770 A | 10/1979 | Semersky et al. |
| 4,187,390 A | 2/1980 | Gore |
| 4,197,840 A | 4/1980 | Beck et al. |
| 4,215,703 A | 8/1980 | Willson |
| 4,240,889 A | 12/1980 | Yoda et al. |
| 4,253,469 A | 3/1981 | Aslan |
| 4,255,500 A | 3/1981 | Hooke |
| 4,259,540 A | 3/1981 | Sabia |
| 4,260,725 A | 4/1981 | Keogh et al. |
| 4,260,726 A | 4/1981 | Keogh et al. |
| 4,319,578 A | 3/1982 | Enger |
| 4,327,725 A | 5/1982 | Cortese et al. |
| 4,353,888 A | 10/1982 | Sefton |
| 4,366,040 A | 12/1982 | Marsoner et al. |
| 4,369,785 A | 1/1983 | Rehkopf et al. |
| 4,374,013 A | 2/1983 | Enfors |
| 4,378,016 A | 3/1983 | Loeb |
| 4,388,166 A | 6/1983 | Suzuki et al. |
| 4,402,694 A | 9/1983 | Ash et al. |
| 4,403,847 A | 9/1983 | Chrestensen |
| 4,403,984 A | 9/1983 | Ash et al. |
| 4,419,535 A | 12/1983 | O'hara |
| 4,431,004 A | 2/1984 | Bessman et al. |
| 4,431,507 A | 2/1984 | Nankai et al. |
| 4,432,366 A | 2/1984 | Margules |
| 4,442,841 A | 4/1984 | Uehara et al. |
| 4,453,537 A | 6/1984 | Spitzer |
| 4,457,339 A | 7/1984 | Juan et al. |
| 4,469,110 A | 9/1984 | Slama |
| 4,477,314 A | 10/1984 | Richter et al. |
| 4,478,222 A | 10/1984 | Koning et al. |
| 4,484,987 A | 11/1984 | Gough |
| 4,486,290 A | 12/1984 | Cahalan et al. |
| 4,492,575 A | 1/1985 | Mabille |
| 4,493,714 A | 1/1985 | Ueda et al. |
| 4,494,950 A | 1/1985 | Fischell |
| 4,506,680 A | 3/1985 | Stokes |
| 4,519,973 A | 5/1985 | Cahalan et al. |
| RE31,916 E | 6/1985 | Oswin et al. |
| 4,527,999 A | 7/1985 | Lee |
| 4,534,355 A | 8/1985 | Potter |
| 4,534,825 A | 8/1985 | Koning et al. |
| 4,538,616 A | 9/1985 | Rogoff |
| 4,545,382 A | 10/1985 | Higgins et al. |
| 4,554,927 A | 11/1985 | Fussell |
| 4,565,665 A | 1/1986 | Fogt |
| 4,565,666 A | 1/1986 | Cahalan et al. |
| 4,568,444 A | 2/1986 | Nakamura et al. |
| 4,577,642 A | 3/1986 | Stokes |
| 4,578,215 A | 3/1986 | Bradley |
| 4,579,120 A | 4/1986 | MacGregor |
| 4,583,976 A | 4/1986 | Ferguson |
| 4,592,824 A | 6/1986 | Smith et al. |
| 4,600,495 A | 7/1986 | Fogt |
| 4,602,922 A | 7/1986 | Cabasso et al. |
| 4,614,514 A | 9/1986 | Carr et al. |
| 4,619,793 A | 10/1986 | Lee |
| 4,625,730 A | 12/1986 | Fountain et al. |
| 4,626,104 A | 12/1986 | Pointon et al. |
| RE32,361 E | 2/1987 | Duggan |
| 4,647,643 A | 3/1987 | Zdrabala et al. |
| 4,650,547 A | 3/1987 | Gough |
| 4,655,880 A | 4/1987 | Liu |
| 4,663,824 A | 5/1987 | Kenmochi |
| 4,672,970 A | 6/1987 | Uchida et al. |
| 4,675,346 A | 6/1987 | Lin et al. |
| 4,680,268 A | 7/1987 | Clark, Jr. |
| 4,684,538 A | 8/1987 | Klemarczyk |
| 4,684,558 A | 8/1987 | Keush et al. |
| 4,685,463 A | 8/1987 | Williams |
| 4,686,137 A | 8/1987 | Ward, Jr. et al. |
| 4,689,149 A | 8/1987 | Kanno et al. |
| 4,694,861 A | 9/1987 | Goodale et al. |
| 4,703,756 A | 11/1987 | Gough et al. |
| 4,703,989 A | 11/1987 | Price et al. |
| 4,705,503 A | 11/1987 | Dorman et al. |
| 4,711,245 A | 12/1987 | Higgins |
| 4,711,251 A | 12/1987 | Stokes |
| 4,721,677 A | 1/1988 | Clark, Jr. |
| 4,726,381 A | 2/1988 | Jones |
| 4,731,726 A | 3/1988 | Allen |
| 4,734,092 A | 3/1988 | Millerd |
| 4,736,748 A | 4/1988 | Nakamura et al. |
| 4,750,496 A | 6/1988 | Reinhart et al. |
| 4,753,652 A | 6/1988 | Langer et al. |
| 4,757,022 A | 7/1988 | Shults et al. |
| 4,759,828 A | 7/1988 | Young et al. |
| 4,761,748 A | 8/1988 | Le Rat et al. |
| 4,763,648 A | 8/1988 | Wyatt |
| 4,763,658 A | 8/1988 | Jones |
| 4,776,343 A | 10/1988 | Hubbard et al. |
| 4,777,953 A | 10/1988 | Ash et al. |
| 4,781,680 A | 11/1988 | Redmond et al. |
| 4,784,157 A | 11/1988 | Halls et al. |
| 4,786,394 A | 11/1988 | Enzer et al. |
| 4,787,398 A | 11/1988 | Garcia et al. |
| 4,789,467 A | 12/1988 | Lindsay et al. |
| 4,793,555 A | 12/1988 | Lee et al. |

(56) References Cited

U.S. PATENT DOCUMENTS

| | | |
|---|---|---|
| 4,795,435 A | 1/1989 | Steer |
| 4,795,542 A | 1/1989 | Ross et al. |
| 4,803,243 A | 2/1989 | Fujimoto et al. |
| 4,805,624 A | 2/1989 | Yao et al. |
| 4,805,625 A | 2/1989 | Wyler |
| 4,808,089 A | 2/1989 | Buchholtz et al. |
| 4,809,704 A | 3/1989 | Sogawa et al. |
| 4,810,470 A | 3/1989 | Burkhardt et al. |
| 4,813,424 A | 3/1989 | Wilkins |
| 4,815,471 A | 3/1989 | Stobie |
| 4,820,281 A | 4/1989 | Lawler |
| 4,826,706 A | 5/1989 | Hilker et al. |
| 4,828,544 A | 5/1989 | Lane et al. |
| 4,830,013 A | 5/1989 | Maxwell |
| 4,831,070 A | 5/1989 | McInally et al. |
| 4,832,034 A | 5/1989 | Pizziconi |
| 4,838,281 A | 6/1989 | Rogers et al. |
| 4,849,458 A | 7/1989 | Reed et al. |
| 4,852,573 A | 8/1989 | Kennedy |
| 4,854,322 A | 8/1989 | Ash et al. |
| 4,858,615 A | 8/1989 | Meinema |
| 4,867,741 A | 9/1989 | Portnoy |
| 4,871,440 A | 10/1989 | Nagata et al. |
| 4,883,057 A | 11/1989 | Broderick |
| 4,883,467 A | 11/1989 | Franetzki et al. |
| 4,886,562 A | 12/1989 | Pinson |
| 4,889,744 A | 12/1989 | Quaid |
| 4,890,620 A | 1/1990 | Gough |
| 4,890,621 A | 1/1990 | Hakky |
| 4,894,339 A | 1/1990 | Hanazato et al. |
| 4,900,305 A | 2/1990 | Smith et al. |
| 4,902,294 A | 2/1990 | Gosserez |
| 4,907,857 A | 3/1990 | Giuliani et al. |
| 4,909,786 A | 3/1990 | Gijselhart et al. |
| 4,909,908 A | 3/1990 | Ross et al. |
| 4,919,141 A | 4/1990 | Zier et al. |
| 4,919,649 A | 4/1990 | Timothy et al. |
| 4,921,480 A | 5/1990 | Sealfon |
| 4,925,444 A | 5/1990 | Orkin et al. |
| 4,927,516 A | 5/1990 | Yamaguchi et al. |
| 4,928,694 A | 5/1990 | Maxwell |
| 4,934,369 A | 6/1990 | Maxwell |
| 4,934,375 A | 6/1990 | Cole et al. |
| 4,935,345 A | 6/1990 | Guilbeau et al. |
| 4,940,065 A | 7/1990 | Tanagho et al. |
| 4,944,299 A | 7/1990 | Silvian |
| 4,951,657 A | 8/1990 | Pfister et al. |
| 4,952,618 A | 8/1990 | Olsen |
| 4,953,552 A | 9/1990 | DeMarzo |
| 4,955,861 A | 9/1990 | Enegren et al. |
| 4,957,483 A | 9/1990 | Gonser et al. |
| 4,958,148 A | 9/1990 | Olson |
| 4,960,594 A | 10/1990 | Honeycutt |
| 4,961,434 A | 10/1990 | Stypulkowski |
| 4,963,595 A | 10/1990 | Ward et al. |
| 4,967,940 A | 11/1990 | Blette |
| 4,970,145 A | 11/1990 | Bennetto et al. |
| 4,974,592 A | 12/1990 | Branco |
| 4,975,175 A | 12/1990 | Karube et al. |
| 4,976,687 A | 12/1990 | Martin |
| 4,984,929 A | 1/1991 | Rock et al. |
| 4,986,271 A | 1/1991 | Wilkens et al. |
| 4,986,671 A | 1/1991 | Sun et al. |
| 4,988,341 A | 1/1991 | Columbus et al. |
| 4,988,758 A | 1/1991 | Fukuda et al. |
| 4,992,794 A | 1/1991 | Brouwers |
| 4,989,607 A | 2/1991 | Keush et al. |
| 4,990,231 A | 2/1991 | Stewart et al. |
| 4,994,026 A | 2/1991 | Fecondini |
| 4,994,167 A | 2/1991 | Shults et al. |
| 5,000,194 A | 3/1991 | van den Honert et al. |
| 5,002,590 A | 3/1991 | Friesen et al. |
| 5,006,050 A | 4/1991 | Cooke et al. |
| 5,007,929 A | 4/1991 | Quaid |
| 5,009,251 A | 4/1991 | Pike et al. |
| 5,030,199 A | 7/1991 | Barwick et al. |
| 5,030,310 A | 7/1991 | Wogoman |
| 5,030,333 A | 7/1991 | Clark, Jr. |
| 5,034,112 A | 7/1991 | Murase et al. |
| 5,037,497 A | 8/1991 | Stypulkowski |
| 5,041,092 A | 8/1991 | Barwick |
| 5,045,601 A | 9/1991 | Capelli et al. |
| 5,048,525 A | 9/1991 | Maxwell |
| 5,050,612 A | 9/1991 | Matsumura |
| 5,055,171 A | 10/1991 | Peck |
| 5,055,198 A | 10/1991 | Shettigar |
| 5,059,654 A | 10/1991 | Hou et al. |
| 5,063,081 A | 11/1991 | Cozzette et al. |
| 5,067,491 A | 11/1991 | Taylor, II et al. |
| 5,082,550 A | 1/1992 | Rishpon et al. |
| 5,089,112 A | 2/1992 | Skotheim et al. |
| 5,096,669 A | 3/1992 | Lauks et al. |
| 5,097,834 A | 3/1992 | Skrabal |
| 5,098,377 A | 3/1992 | Borsanyi et al. |
| 5,108,819 A | 4/1992 | Heller |
| 5,109,850 A | 5/1992 | Blanco et al. |
| 5,112,301 A | 5/1992 | Fenton et al. |
| 5,116,313 A | 5/1992 | Mcgregor |
| 5,120,813 A | 6/1992 | Ward, Jr. |
| 5,130,009 A | 7/1992 | Marsoner et al. |
| 5,135,297 A | 8/1992 | Valint et al. |
| 5,137,028 A | 8/1992 | Nishimura |
| 5,140,985 A | 8/1992 | Schroeder et al. |
| 5,145,565 A | 9/1992 | Kater et al. |
| 5,152,746 A | 10/1992 | Atkinson et al. |
| 5,160,418 A | 11/1992 | Mullen |
| 5,162,407 A | 11/1992 | Turner |
| 5,165,407 A * | 11/1992 | Wilson et al. ................. 600/345 |
| 5,174,291 A | 12/1992 | Schoonen et al. |
| 5,176,662 A | 1/1993 | Bartholomew et al. |
| 5,178,957 A | 1/1993 | Kolpe et al. |
| 5,182,004 A | 1/1993 | Kohno |
| 5,183,549 A | 2/1993 | Joseph et al. |
| 5,188,591 A | 2/1993 | Dorsey |
| 5,195,963 A | 3/1993 | Yafuso et al. |
| 5,200,051 A | 4/1993 | Cozzette et al. |
| 5,202,261 A | 4/1993 | Musho et al. |
| 5,207,218 A | 5/1993 | Carpenteir et al. |
| 5,208,147 A | 5/1993 | Kagenow et al. |
| 5,208,313 A | 5/1993 | Krishnan |
| 5,212,050 A | 5/1993 | Mier et al. |
| 5,220,917 A | 6/1993 | Cammilli et al. |
| 5,222,980 A | 6/1993 | Gealow |
| 5,224,929 A | 7/1993 | Remiszewski |
| 5,235,003 A | 8/1993 | Ward et al. |
| 5,243,696 A | 9/1993 | Carr et al. |
| 5,243,982 A | 9/1993 | Mostl et al. |
| 5,250,439 A | 10/1993 | Musho et al. |
| 5,261,892 A | 11/1993 | Bertaud et al. |
| 5,262,305 A | 11/1993 | Heller et al. |
| 5,264,104 A | 11/1993 | Gregg et al. |
| 5,265,999 A | 11/1993 | Wenschhof et al. |
| 5,266,179 A | 11/1993 | Nankai et al. |
| 5,269,891 A | 12/1993 | Colin |
| 5,271,736 A | 12/1993 | Picha |
| 5,279,294 A | 1/1994 | Anderson et al. |
| 5,281,319 A | 1/1994 | Kaneko et al. |
| 5,282,844 A | 2/1994 | Stokes et al. |
| 5,282,848 A | 2/1994 | Schmitt |
| 5,284,140 A | 2/1994 | Allen et al. |
| 5,284,570 A | 2/1994 | Savage et al. |
| 5,285,513 A | 2/1994 | Kaurman et al. |
| 5,286,364 A | 2/1994 | Yacynych et al. |
| 5,287,753 A | 2/1994 | Routh et al. |
| 5,296,144 A | 3/1994 | Sternina et al. |
| 5,298,144 A | 3/1994 | Spokane |
| 5,299,571 A | 4/1994 | Mastrototaro |
| 5,302,093 A | 4/1994 | Owens et al. |
| 5,302,440 A | 4/1994 | Davis |
| 5,307,263 A | 4/1994 | Brown |
| 5,310,469 A | 5/1994 | Cunningham et al. |
| 5,311,908 A | 5/1994 | Barone et al. |
| 5,312,361 A | 5/1994 | Zadini et al. |
| 5,314,471 A | 5/1994 | Brauker et al. |

(56) References Cited

U.S. PATENT DOCUMENTS

| | | |
|---|---|---|
| 5,316,008 A | 5/1994 | Suga et al. |
| 5,316,452 A | 5/1994 | Bogen et al. |
| 5,322,063 A | 6/1994 | Allen et al. |
| 5,324,322 A | 6/1994 | Grill et al. |
| 5,326,356 A | 7/1994 | Della Valle et al. |
| 5,326,449 A | 7/1994 | Cunningham |
| 5,330,521 A | 7/1994 | Cohen |
| 5,330,634 A | 7/1994 | Wong et al. |
| 5,331,555 A | 7/1994 | Hashimoto et al. |
| 5,335,658 A | 8/1994 | Bedingham |
| 5,336,102 A | 8/1994 | Cairns et al. |
| 5,337,747 A | 8/1994 | Neftel |
| 5,340,352 A | 8/1994 | Nakanishi et al. |
| 5,342,409 A | 8/1994 | Mullett |
| 5,342,789 A | 8/1994 | Chick et al. |
| 5,344,451 A | 9/1994 | Dayton |
| 5,344,454 A | 9/1994 | Clarke et al. |
| 5,345,932 A | 9/1994 | Yafuso et al. |
| 5,348,788 A | 9/1994 | White |
| 5,352,348 A | 10/1994 | Young et al. |
| 5,352,351 A | 10/1994 | White |
| 5,354,449 A | 10/1994 | Band et al. |
| 5,356,378 A | 10/1994 | Doan |
| 5,356,786 A | 10/1994 | Heller et al. |
| 5,358,409 A | 10/1994 | Obara |
| 5,362,761 A | 11/1994 | Uragami et al. |
| 5,368,224 A | 11/1994 | Richardson et al. |
| 5,372,133 A | 12/1994 | Hogen Esch |
| 5,372,709 A | 12/1994 | Hood |
| 5,372,719 A | 12/1994 | Afejan et al. |
| 5,376,070 A | 12/1994 | Purvis et al. |
| 5,378,229 A | 1/1995 | Layer et al. |
| 5,380,268 A | 1/1995 | Wheeler |
| 5,380,422 A | 1/1995 | Negishi et al. |
| 5,380,491 A | 1/1995 | Carver et al. |
| 5,380,536 A | 1/1995 | Hubbell et al. |
| 5,380,665 A | 1/1995 | Cusack et al. |
| 5,384,028 A | 1/1995 | Ito |
| 5,390,671 A | 2/1995 | Lord et al. |
| 5,391,250 A | 2/1995 | Cheney et al. |
| 5,393,401 A | 2/1995 | Knoll |
| 5,397,848 A | 3/1995 | Yang et al. |
| 5,404,877 A | 4/1995 | Nolan et al. |
| 5,411,052 A | 5/1995 | Murray |
| 5,411,647 A | 5/1995 | Johnson et al. |
| 5,411,866 A | 5/1995 | Luong |
| 5,417,115 A | 5/1995 | Burns |
| 5,421,328 A | 6/1995 | Bedingham |
| 5,421,923 A | 6/1995 | Clarke et al. |
| 5,423,738 A | 6/1995 | Robinson et al. |
| 5,425,717 A | 6/1995 | Mohiuddin |
| 5,426,032 A | 6/1995 | Phillips |
| 5,428,123 A | 6/1995 | Ward et al. |
| 5,429,485 A | 7/1995 | Dodge |
| 5,429,735 A | 7/1995 | Johnson et al. |
| 5,431,160 A | 7/1995 | Wilkins |
| 5,431,174 A | 7/1995 | Knute |
| 5,431,921 A | 7/1995 | Thombre |
| 5,437,635 A | 8/1995 | Fields et al. |
| 5,437,999 A | 8/1995 | Diebold et al. |
| 5,438,984 A | 8/1995 | Schoendorfer |
| 5,453,199 A | 9/1995 | Afejan et al. |
| 5,453,278 A | 9/1995 | Chan et al. |
| 5,462,051 A | 10/1995 | Oka et al. |
| 5,462,645 A | 10/1995 | Albery et al. |
| 5,466,356 A | 11/1995 | Schneider et al. |
| 5,466,575 A | 11/1995 | Cozzette et al. |
| 5,469,846 A | 11/1995 | Khan |
| 5,474,552 A | 12/1995 | Palti |
| 5,476,094 A | 12/1995 | Allen et al. |
| 5,476,776 A | 12/1995 | Wilkins |
| 5,480,711 A | 1/1996 | Ruefer |
| 5,482,008 A | 1/1996 | Stafford et al. |
| 5,482,446 A | 1/1996 | Williamson et al. |
| 5,482,473 A | 1/1996 | Lord et al. |
| 5,484,404 A | 1/1996 | Schulman et al. |
| 5,486,776 A | 1/1996 | Wilkins |
| 5,490,323 A | 2/1996 | Thacker et al. |
| 5,494,562 A | 2/1996 | Maley et al. |
| 5,496,453 A | 3/1996 | Uenoyama et al. |
| 5,497,772 A | 3/1996 | Schulman et al. |
| 5,502,396 A | 3/1996 | Desarzens et al. |
| 5,505,828 A | 4/1996 | Wong et al. |
| 5,507,288 A | 4/1996 | Bocker et al. |
| 5,509,888 A | 4/1996 | Miller |
| 5,512,248 A | 4/1996 | Van |
| 5,513,636 A | 5/1996 | Palti |
| 5,515,851 A | 5/1996 | Goldstein |
| 5,516,832 A | 5/1996 | Kennan et al. |
| 5,518,601 A | 5/1996 | Foos et al. |
| 5,531,679 A | 7/1996 | Schulman et al. |
| 5,531,878 A | 7/1996 | Vadgama et al. |
| 5,540,828 A | 7/1996 | Yacynych |
| 5,545,200 A | 8/1996 | West et al. |
| 5,545,220 A | 8/1996 | Andrews et al. |
| 5,545,223 A | 8/1996 | Neuenfeldt et al. |
| 5,549,547 A | 8/1996 | Cohen et al. |
| 5,549,548 A | 8/1996 | Larsson |
| 5,549,569 A | 8/1996 | Lynn et al. |
| 5,549,651 A | 8/1996 | Lynn |
| 5,549,675 A | 8/1996 | Neuenfeldt et al. |
| 5,551,850 A | 9/1996 | Williamson et al. |
| 5,552,112 A | 9/1996 | Schiffmann |
| 5,554,339 A | 9/1996 | Cozzette |
| 5,564,439 A | 10/1996 | Picha |
| 5,568,806 A | 10/1996 | Cheney et al. |
| 5,569,186 A | 10/1996 | Lord et al. |
| 5,569,462 A | 10/1996 | Martinson et al. |
| 5,575,293 A | 11/1996 | Miller et al. |
| 5,575,930 A | 11/1996 | Tietje-Girault et al. |
| 5,582,593 A | 12/1996 | Hultman |
| 5,582,697 A | 12/1996 | Noguchi |
| 5,584,813 A | 12/1996 | Livingston et al. |
| 5,584,876 A | 12/1996 | Bruchman et al. |
| 5,586,553 A | 12/1996 | Halili et al. |
| 5,587,273 A | 12/1996 | Yan et al. |
| 5,588,560 A | 12/1996 | Benedict et al. |
| 5,589,133 A | 12/1996 | Suzuki |
| 5,589,563 A | 12/1996 | Ward et al. |
| 5,590,651 A | 1/1997 | Shaffer et al. |
| 5,593,440 A | 1/1997 | Brauker et al. |
| 5,593,852 A | 1/1997 | Heller et al. |
| 5,607,565 A | 3/1997 | Azarnia et al. |
| 5,609,572 A | 3/1997 | Lang |
| 5,611,900 A | 3/1997 | Worden |
| 5,624,409 A | 4/1997 | Seale |
| 5,624,537 A | 4/1997 | Turner et al. |
| 5,626,561 A | 5/1997 | Butler et al. |
| 5,626,563 A | 5/1997 | Dodge et al. |
| 5,628,619 A | 5/1997 | Wilson |
| 5,630,978 A | 5/1997 | Domb |
| 5,637,083 A | 6/1997 | Bertrand et al. |
| 5,637,135 A | 6/1997 | Ottenstein et al. |
| 5,640,470 A | 6/1997 | Iyer et al. |
| 5,643,195 A | 7/1997 | Drevet et al. |
| 5,651,767 A | 7/1997 | Schulman et al. |
| 5,653,756 A | 8/1997 | Clarke et al. |
| 5,658,247 A | 8/1997 | Henley |
| 5,658,330 A | 8/1997 | Carlisle et al. |
| 5,658,802 A | 8/1997 | Hayes et al. |
| 5,660,163 A | 8/1997 | Schulman et al. |
| 5,662,616 A | 9/1997 | Bousquet |
| 5,665,065 A | 9/1997 | Colman et al. |
| 5,665,215 A | 9/1997 | Bussmann et al. |
| 5,673,694 A | 10/1997 | Rivers |
| 5,676,651 A | 10/1997 | Larson et al. |
| 5,676,820 A | 10/1997 | Wang et al. |
| 5,681,572 A | 10/1997 | Seare |
| 5,682,884 A | 11/1997 | Hill |
| 5,683,562 A | 11/1997 | Schaffer et al. |
| 5,686,829 A | 11/1997 | Girault |
| 5,688,239 A | 11/1997 | Walker |
| 5,695,623 A | 12/1997 | Michel et al. |
| 5,696,314 A | 12/1997 | McCaffrey et al. |

(56) References Cited

U.S. PATENT DOCUMENTS

| | | |
|---|---|---|
| 5,697,976 A | 12/1997 | Chesterfield et al. |
| 5,703,359 A | 12/1997 | Wampler, III |
| 5,706,807 A | 1/1998 | Picha |
| 5,707,502 A | 1/1998 | McCaffrey et al. |
| 5,711,302 A | 1/1998 | Lampropoulos et al. |
| 5,713,888 A | 2/1998 | Neuenfeldt et al. |
| 5,714,123 A | 2/1998 | Sohrab |
| 5,714,391 A | 2/1998 | Omura et al. |
| 5,733,336 A | 3/1998 | Neuenfeldt et al. |
| 5,735,273 A | 4/1998 | Kurnik et al. |
| 5,741,319 A | 4/1998 | Woloszko et al. |
| 5,741,330 A | 4/1998 | Brauker et al. |
| 5,741,634 A | 4/1998 | Nozoe et al. |
| 5,743,262 A | 4/1998 | Lepper, Jr. et al. |
| 5,787,900 A | 4/1998 | Brauker et al. |
| 5,749,832 A | 5/1998 | Vadgama et al. |
| 5,756,632 A | 5/1998 | Ward et al. |
| 5,763,787 A | 6/1998 | Gravel et al. |
| 5,766,151 A | 6/1998 | Valley et al. |
| 5,773,286 A | 6/1998 | Dionne et al. |
| 5,776,324 A | 7/1998 | Usala |
| 5,777,060 A | 7/1998 | Van Antwerp |
| 5,779,665 A | 7/1998 | Mastrototaro et al. |
| 5,781,455 A | 7/1998 | Hyodo et al. |
| 5,782,880 A | 7/1998 | Lahtinen et al. |
| 5,782,912 A | 7/1998 | Brauker et al. |
| 5,783,054 A | 7/1998 | Raguse et al. |
| 5,786,439 A | 7/1998 | Van Antwerp et al. |
| 5,791,880 A | 8/1998 | Wilson |
| 5,798,065 A | 8/1998 | Picha |
| 5,800,383 A | 9/1998 | Chandler et al. |
| 5,800,420 A | 9/1998 | Gross |
| 5,800,529 A | 9/1998 | Brauker et al. |
| 5,804,048 A | 9/1998 | Wong et al. |
| 5,807,312 A | 9/1998 | Dzwonkiewicz |
| 5,807,375 A | 9/1998 | Gross et al. |
| 5,807,406 A | 9/1998 | Brauker et al. |
| 5,810,770 A | 9/1998 | Chin et al. |
| 5,811,487 A | 9/1998 | Schulz, Jr. et al. |
| 5,814,599 A | 9/1998 | Mitragotri et al. |
| 5,820,622 A | 10/1998 | Gross et al. |
| 5,822,715 A | 10/1998 | Worthington et al. |
| 5,823,802 A | 10/1998 | Bartley |
| 5,824,651 A | 10/1998 | Nanci et al. |
| 5,827,183 A | 10/1998 | Kurnik et al. |
| 5,836,886 A | 11/1998 | Itoigawa et al. |
| 5,836,989 A | 11/1998 | Shelton |
| 5,837,454 A | 11/1998 | Cozzette et al. |
| 5,837,728 A | 11/1998 | Purcell |
| 5,840,148 A | 11/1998 | Campbell et al. |
| 5,840,240 A | 11/1998 | Stenoien et al. |
| 5,843,069 A | 12/1998 | Butler et al. |
| 5,851,197 A | 12/1998 | Marano et al. |
| 5,857,983 A | 1/1999 | Douglas et al. |
| 5,858,296 A | 1/1999 | Domb |
| 5,858,365 A | 1/1999 | Feller |
| 5,858,747 A | 1/1999 | Schinstine et al. |
| 5,861,019 A | 1/1999 | Sun et al. |
| 5,863,400 A | 1/1999 | Drummond et al. |
| 5,871,499 A | 2/1999 | Hahn et al. |
| 5,871,514 A | 2/1999 | Wiklund et al. |
| 5,872,198 A | 2/1999 | Mosbach et al. |
| 5,873,862 A | 2/1999 | Lopez |
| 5,874,500 A | 2/1999 | Rhee et al. |
| 5,879,373 A | 3/1999 | Roper et al. |
| 5,879,713 A | 3/1999 | Roth et al. |
| 5,879,828 A | 3/1999 | Debe et al. |
| 5,882,494 A | 3/1999 | Van Antwerp |
| 5,895,235 A | 4/1999 | Droz |
| 5,897,578 A | 4/1999 | Wiklund et al. |
| 5,897,955 A | 4/1999 | Drumheller |
| 5,904,666 A | 5/1999 | Dedecker et al. |
| 5,904,708 A | 5/1999 | Goedeke |
| 5,910,554 A | 6/1999 | Kempe et al. |
| 5,911,219 A | 6/1999 | Aylsworth et al. |
| 5,913,998 A | 6/1999 | Butler et al. |
| 5,914,026 A | 6/1999 | Blubaugh, Jr. et al. |
| 5,914,182 A | 6/1999 | Drumheller |
| 5,916,445 A | 6/1999 | Hjerten et al. |
| 5,917,346 A | 6/1999 | Gord |
| 5,919,215 A | 7/1999 | Wiklund et al. |
| 5,921,951 A | 7/1999 | Morris |
| 5,928,130 A | 7/1999 | Schmidt |
| 5,928,155 A | 7/1999 | Eggers et al. |
| 5,928,182 A | 7/1999 | Kraus et al. |
| 5,928,195 A | 7/1999 | Malamud et al. |
| 5,931,814 A | 8/1999 | Alex et al. |
| 5,932,175 A | 8/1999 | Knute et al. |
| 5,933,136 A | 8/1999 | Brown |
| 5,935,785 A | 8/1999 | Reber et al. |
| 5,938,636 A | 8/1999 | Kramer et al. |
| 5,944,661 A | 8/1999 | Swette et al. |
| 5,945,498 A | 8/1999 | Hopken et al. |
| 5,951,521 A | 9/1999 | Mastrototaro et al. |
| 5,954,643 A | 9/1999 | Van Antwerp et al. |
| 5,954,685 A | 9/1999 | Tierney |
| 5,954,954 A | 9/1999 | Houck et al. |
| 5,957,854 A | 9/1999 | Besson et al. |
| 5,959,050 A | 9/1999 | Mosbach et al. |
| 5,961,451 A | 10/1999 | Reber et al. |
| 5,963,132 A | 10/1999 | Yoakum |
| 5,964,261 A | 10/1999 | Neuenfeldt et al. |
| 5,964,745 A | 10/1999 | Lyles et al. |
| 5,964,804 A | 10/1999 | Brauker et al. |
| 5,965,125 A | 10/1999 | Mineau-Hanschke |
| 5,965,380 A | 10/1999 | Heller et al. |
| 5,967,986 A * | 10/1999 | Cimochowski et al. ..... 600/454 |
| 5,972,199 A | 10/1999 | Heller |
| 5,977,241 A | 11/1999 | Koloski et al. |
| 5,985,693 A | 11/1999 | Leedy |
| 5,987,352 A | 11/1999 | Klein et al. |
| 5,995,208 A | 11/1999 | Sarge et al. |
| 5,999,848 A | 12/1999 | Gord et al. |
| 5,999,849 A | 12/1999 | Gord et al. |
| 6,001,067 A * | 12/1999 | Shults et al. ................... 600/584 |
| 6,013,113 A | 1/2000 | Mika |
| 6,015,392 A | 1/2000 | Douglas et al. |
| 6,016,448 A | 1/2000 | Busacker et al. |
| 6,017,435 A | 1/2000 | Hassard et al. |
| 6,018,033 A | 1/2000 | Chen et al. |
| 6,024,720 A | 2/2000 | Chandler et al. |
| 6,027,479 A | 2/2000 | Alei et al. |
| 6,032,667 A | 3/2000 | Heinonen |
| 6,036,924 A | 3/2000 | Simons et al. |
| 6,045,671 A | 4/2000 | Wu et al. |
| 6,048,691 A | 4/2000 | Maracas |
| 6,051,372 A | 4/2000 | Bayerl et al. |
| 6,051,389 A | 4/2000 | Ahl et al. |
| 6,057,377 A | 5/2000 | Sasaki et al. |
| 6,059,946 A | 5/2000 | Yukawa et al. |
| 6,060,640 A | 5/2000 | Pauley et al. |
| 6,063,637 A | 5/2000 | Arnold et al. |
| 6,065,154 A | 5/2000 | Hulings et al. |
| 6,066,088 A | 5/2000 | Davis |
| 6,066,448 A | 5/2000 | Wohlstadter et al. |
| 6,068,668 A | 5/2000 | Mastroianni |
| 6,074,775 A | 6/2000 | Gartstein et al. |
| 6,077,299 A | 6/2000 | Adelberg et al. |
| 6,081,735 A | 6/2000 | Diab et al. |
| 6,081,736 A | 6/2000 | Colvin et al. |
| 6,083,523 A | 7/2000 | Dionne et al. |
| 6,083,710 A | 7/2000 | Heller et al. |
| 6,088,608 A | 7/2000 | Schulman et al. |
| 6,091,975 A | 7/2000 | Daddona et al. |
| 6,093,156 A | 7/2000 | Cunningham et al. |
| 6,093,172 A | 7/2000 | Funderburk et al. |
| 6,099,511 A | 8/2000 | Devos et al. |
| 6,101,404 A | 8/2000 | Yoon et al. |
| 6,103,033 A | 8/2000 | Say et al. |
| 6,103,533 A | 8/2000 | Hassard et al. |
| 6,106,486 A | 8/2000 | Tenerz et al. |
| 6,107,083 A | 8/2000 | Collins et al. |
| 6,115,622 A | 9/2000 | Minoz |
| 6,115,634 A | 9/2000 | Donders et al. |

(56) References Cited

U.S. PATENT DOCUMENTS

| | | |
|---|---|---|
| 6,117,290 A | 9/2000 | Say |
| 6,121,009 A | 9/2000 | Heller et al. |
| 6,122,536 A | 9/2000 | Sun et al. |
| 6,123,827 A | 9/2000 | Wong et al. |
| 6,134,461 A | 10/2000 | Say et al. |
| 6,135,978 A | 10/2000 | Houben et al. |
| 6,141,573 A | 10/2000 | Kurnik et al. |
| 6,144,869 A | 11/2000 | Berner et al. |
| 6,144,871 A | 11/2000 | Saito et al. |
| 6,156,051 A | 12/2000 | Schraga |
| 6,157,860 A | 12/2000 | Hauser et al. |
| 6,162,201 A | 12/2000 | Cohen et al. |
| 6,162,611 A | 12/2000 | Heller et al. |
| 6,165,154 A | 12/2000 | Gray et al. |
| 6,168,568 B1 | 1/2001 | Gavriely |
| 6,169,155 B1 | 1/2001 | Alvarez et al. |
| 6,171,276 B1 | 1/2001 | Lippe et al. |
| 6,175,752 B1 | 1/2001 | Say et al. |
| 6,175,767 B1 | 1/2001 | Doyle et al. |
| 6,183,437 B1 | 2/2001 | Walker |
| 6,187,062 B1 | 2/2001 | Oweis et al. |
| 6,189,536 B1 | 2/2001 | Martinez et al. |
| 6,198,969 B1 | 3/2001 | Kuzma |
| 6,200,772 B1 | 3/2001 | Vadgama et al. |
| 6,201,979 B1 | 3/2001 | Kurnik et al. |
| 6,201,980 B1 | 3/2001 | Darrow et al. |
| 6,201,993 B1 | 3/2001 | Kruse et al. |
| 6,206,856 B1 | 3/2001 | Mahurkar |
| 6,208,894 B1 | 3/2001 | Schulman et al. |
| 6,212,416 B1* | 4/2001 | Ward et al. .................. 600/345 |
| 6,213,739 B1 | 4/2001 | Phallen et al. |
| 6,214,901 B1 | 4/2001 | Chudzik et al. |
| 6,219,574 B1 | 4/2001 | Cormier et al. |
| 6,223,080 B1 | 4/2001 | Thompson |
| 6,223,083 B1 | 4/2001 | Rosar |
| 6,230,059 B1 | 5/2001 | Duffin |
| 6,231,879 B1 | 5/2001 | Li et al. |
| 6,232,783 B1 | 5/2001 | Merrill |
| 6,233,471 B1 | 5/2001 | Berner et al. |
| 6,248,067 B1 | 6/2001 | Causey, III et al. |
| 6,248,077 B1 | 6/2001 | Elson et al. |
| 6,248,093 B1 | 6/2001 | Moberg |
| 6,251,280 B1 | 6/2001 | Dai et al. |
| 6,254,586 B1 | 7/2001 | Mann et al. |
| 6,255,592 B1 | 7/2001 | Pennington et al. |
| 6,256,522 B1 | 7/2001 | Schultz |
| 6,259,937 B1 | 7/2001 | Schulman et al. |
| 6,263,222 B1 | 7/2001 | Diab et al. |
| 6,264,825 B1 | 7/2001 | Blackburn et al. |
| 6,266,551 B1 | 7/2001 | Osadchy et al. |
| 6,268,161 B1 | 7/2001 | Han et al. |
| 6,270,478 B1 | 8/2001 | Mern et al. |
| 6,272,382 B1 | 8/2001 | Faltys et al. |
| 6,274,285 B1 | 8/2001 | Gries et al. |
| 6,274,686 B1 | 8/2001 | Mosbach |
| 6,275,717 B1 | 8/2001 | Gross et al. |
| 6,280,408 B1 | 8/2001 | Sipin |
| 6,284,478 B1 | 9/2001 | Heller et al. |
| 6,285,897 B1* | 9/2001 | Kilcoyne et al. ............. 600/350 |
| 6,293,925 B1 | 9/2001 | Safabash et al. |
| 6,294,281 B1 | 9/2001 | Heller |
| 6,296,615 B1* | 10/2001 | Brockway et al. ........... 600/486 |
| 6,299,578 B1 | 10/2001 | Kurnik et al. |
| 6,300,002 B1 | 10/2001 | Webb et al. |
| 6,306,424 B1 | 10/2001 | Vyakarnam et al. |
| 6,309,351 B1 | 10/2001 | Kurnik et al. |
| 6,309,384 B1 | 10/2001 | Harrington et al. |
| 6,309,526 B1 | 10/2001 | Fujiwara et al. |
| 6,309,884 B1 | 10/2001 | Cooper et al. |
| 6,310,110 B1 | 10/2001 | Markowitz et al. |
| 6,315,738 B1 | 11/2001 | Nishikawa et al. |
| 6,319,566 B1 | 11/2001 | Polanyi et al. |
| 6,325,978 B1 | 12/2001 | Labuda et al. |
| 6,325,979 B1 | 12/2001 | Hahn et al. |
| 6,326,160 B1 | 12/2001 | Dunn et al. |
| 6,329,161 B1 | 12/2001 | Heller et al. |
| 6,329,488 B1 | 12/2001 | Terry et al. |
| 6,336,269 B1 | 1/2002 | Eldridge et al. |
| 6,341,232 B1 | 1/2002 | Conn et al. |
| 6,343,225 B1 | 1/2002 | Clark, Jr. |
| 6,346,114 B1 | 2/2002 | Schraga |
| 6,356,776 B1 | 3/2002 | Berner et al. |
| 6,358,225 B1 | 3/2002 | Butterfield |
| 6,360,888 B1 | 3/2002 | Melver et al. |
| 6,365,670 B1 | 4/2002 | Fry |
| 6,366,794 B1 | 4/2002 | Moussy et al. |
| 6,368,141 B1 | 4/2002 | VanAntwerp et al. |
| 6,368,658 B1 | 4/2002 | Schwarz et al. |
| 6,370,410 B2 | 4/2002 | Kurnik et al. |
| 6,371,963 B1 | 4/2002 | Nishtala et al. |
| 6,372,244 B1 | 4/2002 | Antanavich et al. |
| 6,379,317 B1 | 4/2002 | Kintzig et al. |
| 6,391,019 B1 | 5/2002 | Ito |
| 6,393,318 B1 | 5/2002 | Conn et al. |
| 6,398,562 B1 | 6/2002 | Butler et al. |
| 6,403,944 B1 | 6/2002 | Mackenzie et al. |
| 6,405,066 B1 | 6/2002 | Essenpreis et al. |
| 6,406,066 B1 | 6/2002 | Uegane |
| 6,407,195 B2 | 6/2002 | Sherman et al. |
| 6,413,393 B1 | 7/2002 | Van Antwerp et al. |
| 6,418,332 B1 | 7/2002 | Mastrototaro et al. |
| 6,424,847 B1 | 7/2002 | Mastrototaro et al. |
| 6,427,088 B1 | 7/2002 | Bowman et al. |
| 6,432,050 B1 | 8/2002 | Porat et al. |
| 6,438,414 B1 | 8/2002 | Conn et al. |
| 6,447,448 B1 | 9/2002 | Ishikawa et al. |
| 6,447,542 B1 | 9/2002 | Weadock |
| 6,459,917 B1 | 10/2002 | Gowda et al. |
| 6,461,496 B1 | 10/2002 | Feldman et al. |
| 6,464,849 B1 | 10/2002 | Say et al. |
| 6,465,066 B1 | 10/2002 | Rule et al. |
| 6,468,287 B1 | 10/2002 | Baugh |
| 6,471,689 B1 | 10/2002 | Joseph et al. |
| 6,471,993 B1 | 10/2002 | Shastri et al. |
| 6,474,360 B1 | 11/2002 | Ito |
| 6,475,750 B1 | 11/2002 | Han et al. |
| 6,477,395 B2 | 11/2002 | Schulman et al. |
| 6,481,440 B2 | 11/2002 | Gielen et al. |
| 6,484,045 B1 | 11/2002 | Holker et al. |
| 6,484,132 B1 | 11/2002 | Hively et al. |
| 6,485,449 B2 | 11/2002 | Ito |
| 6,487,429 B2 | 11/2002 | Hockersmith et al. |
| 6,488,652 B1 | 12/2002 | Weijand et al. |
| 6,494,830 B1 | 12/2002 | Wessel |
| 6,497,729 B1 | 12/2002 | Moussy et al. |
| 6,498,043 B1 | 12/2002 | Schulman et al. |
| 6,498,941 B1 | 12/2002 | Jackson |
| 6,510,329 B2 | 1/2003 | Heckel |
| 6,512,939 B1 | 1/2003 | Colvin et al. |
| 6,514,718 B2 | 2/2003 | Heller et al. |
| 6,520,326 B2 | 2/2003 | McIvor et al. |
| 6,520,477 B2 | 2/2003 | Trimmer |
| 6,520,997 B2 | 2/2003 | Pekkarinen et al. |
| 6,527,729 B1 | 3/2003 | Turcott |
| 6,528,584 B2 | 3/2003 | Kennedy et al. |
| 6,529,755 B2 | 3/2003 | Kurnik et al. |
| 6,534,711 B1 | 3/2003 | Pollack |
| 6,537,318 B1 | 3/2003 | Ita et al. |
| 6,541,107 B1 | 4/2003 | Zhong et al. |
| 6,542,765 B1 | 4/2003 | Guy et al. |
| 6,544,212 B2 | 4/2003 | Galley et al. |
| 6,545,085 B2 | 4/2003 | Kilgour et al. |
| 6,546,268 B1* | 4/2003 | Ishikawa et al. ............. 600/345 |
| 6,547,839 B2 | 4/2003 | Zhang et al. |
| 6,553,241 B2 | 4/2003 | Mannheimer et al. |
| 6,554,805 B2 | 4/2003 | Hiejima |
| 6,554,822 B1 | 4/2003 | Holschneider et al. |
| 6,558,320 B1 | 5/2003 | Causey et al. |
| 6,558,321 B1 | 5/2003 | Burd et al. |
| 6,558,351 B1 | 5/2003 | Steil et al. |
| 6,560,471 B1 | 5/2003 | Heller et al. |
| 6,561,978 B1 | 5/2003 | Conn et al. |
| 6,565,509 B1 | 5/2003 | Say et al. |
| 6,565,535 B2 | 5/2003 | Zaias et al. |

(56) References Cited

U.S. PATENT DOCUMENTS

| | | |
|---|---|---|
| 6,565,807 B1 | 5/2003 | Patterson et al. |
| 6,569,309 B2 | 5/2003 | Otsuka et al. |
| 6,572,579 B1 | 6/2003 | Raghavan et al. |
| 6,572,745 B2 | 6/2003 | Rappin et al. |
| 6,574,490 B2 | 6/2003 | Abbink et al. |
| 6,579,690 B1 | 6/2003 | Bonnecaze et al. |
| 6,584,335 B1 | 6/2003 | Haar et al. |
| 6,585,644 B2 | 7/2003 | Lebel et al. |
| 6,585,763 B1 | 7/2003 | Keilman et al. |
| 6,591,125 B1 | 7/2003 | Buse et al. |
| 6,592,745 B1 | 7/2003 | Feldman et al. |
| 6,595,756 B2 | 7/2003 | Gray et al. |
| 6,595,919 B2 | 7/2003 | Berner et al. |
| 6,602,221 B1 | 8/2003 | Saravia et al. |
| 6,605,072 B2 | 8/2003 | Struys et al. |
| 6,607,509 B2 | 8/2003 | Bobroff et al. |
| 6,612,984 B1 | 9/2003 | Kerr |
| 6,613,379 B2 | 9/2003 | Ward et al. |
| 6,618,603 B2 | 9/2003 | Varalli et al. |
| 6,618,934 B1 | 9/2003 | Feldman et al. |
| 6,633,772 B2 | 10/2003 | Ford et al. |
| 6,641,533 B2 | 11/2003 | Causey et al. |
| 6,645,181 B1 | 11/2003 | Lavi et al. |
| 6,645,219 B2 | 11/2003 | Roe |
| 6,648,821 B2 | 11/2003 | Lebel et al. |
| 6,654,625 B1 | 11/2003 | Say et al. |
| 6,656,157 B1 | 12/2003 | Duchon et al. |
| 6,663,615 B1 | 12/2003 | Madou et al. |
| 6,666,821 B2 | 12/2003 | Keimel |
| 6,673,022 B1 | 1/2004 | Bobo et al. |
| 6,673,596 B1 | 1/2004 | Sayler et al. |
| 6,683,535 B1 | 1/2004 | Utke |
| 6,689,265 B2 | 2/2004 | Heller et al. |
| 6,692,456 B1 | 2/2004 | Eppstein et al. |
| 6,694,191 B2 | 2/2004 | Starkweather et al. |
| 6,695,860 B1 | 2/2004 | Ward et al. |
| 1,670,285 A1 | 3/2004 | Brauker et al. |
| 6,699,218 B2 | 3/2004 | Flaherty et al. |
| 6,699,383 B2 | 3/2004 | Lemire et al. |
| 6,702,857 B2 | 3/2004 | Brauker et al. |
| 6,702,972 B1 | 3/2004 | Markle |
| 6,705,833 B2 | 3/2004 | Tam et al. |
| 6,721,587 B2 | 4/2004 | Gough |
| 6,730,200 B1 | 5/2004 | Stewart et al. |
| 6,733,655 B1 | 5/2004 | Davies et al. |
| 6,736,777 B2 | 5/2004 | Kim et al. |
| 6,737,158 B1 | 5/2004 | Thompson |
| 6,740,059 B2 | 5/2004 | Flaherty |
| 6,740,075 B2 | 5/2004 | Lebel et al. |
| 6,741,877 B1 | 5/2004 | Shults et al. |
| 6,742,635 B2 | 6/2004 | Neel et al. |
| 6,743,635 B2 | 6/2004 | Neel et al. |
| 6,749,587 B2 | 6/2004 | Flaherty |
| 6,770,030 B1 | 8/2004 | Schaupp et al. |
| 6,770,067 B2 | 8/2004 | Lorenzen et al. |
| 6,773,565 B2 | 8/2004 | Kunimoto et al. |
| 6,801,041 B2 | 10/2004 | Karinka et al. |
| 6,802,957 B2 | 10/2004 | Jung et al. |
| 6,805,693 B2 | 10/2004 | Gray et al. |
| 6,809,507 B2 | 10/2004 | Morgan et al. |
| 6,809,653 B1 | 10/2004 | Mann et al. |
| 6,810,290 B2 | 10/2004 | Lebel et al. |
| 6,811,548 B2 | 11/2004 | Jeffrey |
| 6,813,519 B2 | 11/2004 | Lebel et al. |
| 6,814,845 B2 | 11/2004 | Wilson et al. |
| 6,815,186 B2 | 11/2004 | Clark, Jr. |
| 6,830,551 B1 | 12/2004 | Uchigaki et al. |
| 6,849,052 B2 | 2/2005 | Uchigaki et al. |
| 6,850,790 B2 | 2/2005 | Berner et al. |
| 6,858,020 B2 | 2/2005 | Rusnak |
| 6,862,465 B2 | 3/2005 | Shults et al. |
| 6,863,800 B2* | 3/2005 | Karinka ............ G01N 27/3272 204/403.11 |
| 6,867,262 B1 | 3/2005 | Angel et al. |
| 6,875,386 B1 | 4/2005 | Ward et al. |
| 6,881,551 B2 | 4/2005 | Heller et al. |
| 6,885,883 B2 | 4/2005 | Parris et al. |
| 6,887,228 B2 | 5/2005 | Mckay |
| 6,891,317 B2 | 5/2005 | Pei et al. |
| 6,892,085 B2 | 5/2005 | McIvor et al. |
| 6,893,552 B1 | 5/2005 | Wang et al. |
| 6,895,263 B2 | 5/2005 | Shin et al. |
| 6,902,544 B2 | 6/2005 | Ludin et al. |
| 6,908,681 B2 | 6/2005 | Terry et al. |
| 6,926,691 B2 | 8/2005 | Miethke |
| 6,931,327 B2 | 8/2005 | Goode et al. |
| 6,932,584 B2 | 8/2005 | Gray et al. |
| 6,936,006 B2* | 8/2005 | Sabra ............................ 600/300 |
| 6,948,492 B2 | 9/2005 | Wermeling et al. |
| 6,952,604 B2 | 10/2005 | DeNuzzio et al. |
| 6,960,192 B1 | 11/2005 | Flaherty et al. |
| 6,965,791 B1 | 11/2005 | Hitchcock et al. |
| 6,966,325 B2 | 11/2005 | Erickson |
| 6,972,080 B1 | 12/2005 | Tomioka et al. |
| 6,975,893 B2 | 12/2005 | Say et al. |
| 6,990,366 B2 | 1/2006 | Say et al. |
| 6,997,921 B2 | 2/2006 | Gray et al. |
| 6,998,247 B2 | 2/2006 | Monfre et al. |
| 7,003,336 B2 | 2/2006 | Holker et al. |
| 7,003,341 B2 | 2/2006 | Say et al. |
| 7,008,979 B2 | 3/2006 | Schottman et al. |
| 7,022,219 B2 | 4/2006 | Mansouri et al. |
| 7,025,727 B2 | 4/2006 | Brockway et al. |
| 7,025,743 B2 | 4/2006 | Mann et al. |
| 7,033,322 B2 | 4/2006 | Sliver |
| 7,048,727 B1 | 5/2006 | Moss |
| 7,058,437 B2 | 6/2006 | Buse et al. |
| 7,060,059 B2 | 6/2006 | Keith et al. |
| 7,061,593 B2 | 6/2006 | Braig et al. |
| 7,063,086 B2 | 6/2006 | Shahbazpour et al. |
| 7,070,577 B1 | 7/2006 | Haller et al. |
| 7,070,580 B2 | 7/2006 | Nielsen |
| 7,074,307 B2 | 7/2006 | Simpson et al. |
| 7,078,582 B2 | 7/2006 | Stebbings et al. |
| 7,081,195 B2 | 7/2006 | Simpson et al. |
| 7,097,775 B2 | 8/2006 | Greenberg et al. |
| 7,098,803 B2 | 8/2006 | Mann et al. |
| 7,100,628 B1 | 9/2006 | Izenson et al. |
| 7,110,803 B2 | 9/2006 | Shults et al. |
| 7,114,502 B2 | 10/2006 | Schulman et al. |
| 7,115,884 B1 | 10/2006 | Walt et al. |
| 7,120,483 B2 | 10/2006 | Russell et al. |
| 7,131,967 B2 | 11/2006 | Gray et al. |
| 7,134,999 B2 | 11/2006 | Brauker et al. |
| 7,136,689 B2 | 11/2006 | Shults et al. |
| 7,141,034 B2 | 11/2006 | Eppstein et al. |
| 7,144,496 B2 | 12/2006 | Meserol et al. |
| 7,150,741 B2 | 12/2006 | Erickson et al. |
| 7,153,265 B2 | 12/2006 | Vachon |
| 7,163,511 B2 | 1/2007 | Conn et al. |
| 7,168,597 B1 | 1/2007 | Jones et al. |
| 7,169,289 B2 | 1/2007 | Schulein et al. |
| 7,172,075 B1 | 2/2007 | ji |
| 7,190,988 B2 | 3/2007 | Say et al. |
| 7,192,450 B2 | 3/2007 | Brauker et al. |
| 7,207,968 B1 | 4/2007 | Harcinske |
| 7,207,974 B2 | 4/2007 | Safabash et al. |
| 7,211,074 B2 | 5/2007 | Sansoucy |
| 7,221,970 B2 | 5/2007 | Parker |
| 7,225,535 B2 | 6/2007 | Feldman et al. |
| 7,228,162 B2 | 6/2007 | Ward et al. |
| 7,238,165 B2 | 7/2007 | Vincent et al. |
| 7,247,138 B2 | 7/2007 | Reghabi et al. |
| 7,248,906 B2 | 7/2007 | Dirac et al. |
| 7,254,450 B2 | 8/2007 | Christopherson et al. |
| 7,255,690 B2 | 8/2007 | Gray et al. |
| 7,267,665 B2 | 9/2007 | Steil et al. |
| 7,288,085 B2 | 10/2007 | Olsen |
| 7,295,867 B2 | 11/2007 | Berner et al. |
| 7,299,082 B2 | 11/2007 | Feldman et al. |
| 7,310,544 B2 | 12/2007 | Brister et al. |
| 7,311,690 B2 | 12/2007 | Burnett |
| 7,316,662 B2 | 1/2008 | Delnevo et al. |
| 7,318,814 B2 | 1/2008 | Levine et al. |

(56) References Cited

U.S. PATENT DOCUMENTS

| | | | |
|---|---|---|---|
| 7,324,012 B2 | 1/2008 | Mann et al. | |
| 7,329,234 B2 | 2/2008 | Sansoucy | |
| 7,335,286 B2 | 2/2008 | Abel et al. | |
| 7,344,499 B1 | 3/2008 | Prausnitz et al. | |
| 7,364,562 B2 | 4/2008 | Braig et al. | |
| 7,364,592 B2 | 4/2008 | Carr-Brendel et al. | |
| 7,366,556 B2 | 4/2008 | Brister et al. | |
| 7,366,566 B2 | 4/2008 | Brister et al. | |
| 7,381,184 B2 | 6/2008 | Funderburk et al. | |
| 7,392,080 B2 | 6/2008 | Eppstein et al. | |
| 7,396,353 B2 | 7/2008 | Lorenzen et al. | |
| 7,399,277 B2 | 7/2008 | Saidara et al. | |
| 7,402,153 B2 | 7/2008 | Steil et al. | |
| 7,404,819 B1 | 7/2008 | Darios et al. | |
| 7,417,164 B2 | 8/2008 | Suri | |
| 7,424,318 B2 | 9/2008 | Brister et al. | |
| 7,426,408 B2 | 9/2008 | DeNuzzio et al. | |
| 7,460,898 B2 | 12/2008 | Brister et al. | |
| 7,467,003 B2 | 12/2008 | Brister et al. | |
| 7,471,972 B2 | 12/2008 | Rhodes et al. | |
| 7,494,465 B2 | 2/2009 | Brister et al. | |
| 7,497,827 B2 | 3/2009 | Brister et al. | |
| 7,519,408 B2 | 4/2009 | Rasdal et al. | |
| 7,525,298 B2 | 4/2009 | Morgan et al. | |
| 7,582,059 B2 | 9/2009 | Funderburk et al. | |
| 7,591,801 B2 | 9/2009 | Brauker et al. | |
| 7,636,602 B2 | 12/2009 | Baru Fassio et al. | |
| 7,637,868 B2 | 12/2009 | Saint et al. | |
| 7,640,048 B2 | 12/2009 | Dobbles et al. | |
| 7,654,956 B2 | 2/2010 | Brister et al. | |
| 7,657,297 B2 | 2/2010 | Simpson et al. | |
| 7,687,586 B2* | 3/2010 | Ward | C08G 64/18 204/403.11 |
| 7,697,967 B2 | 4/2010 | Stafford | |
| 7,713,574 B2 | 5/2010 | Brister et al. | |
| 7,736,322 B2 | 6/2010 | Roe et al. | |
| 7,771,352 B2* | 8/2010 | Shults | A61B 5/0002 600/347 |
| 7,862,622 B2 | 1/2011 | Dunlap et al. | |
| 7,879,010 B2 | 2/2011 | Hunn et al. | |
| 7,885,697 B2 | 2/2011 | Brister et al. | |
| 7,899,511 B2* | 3/2011 | Shults | A61B 5/0002 600/345 |
| 7,901,354 B2* | 3/2011 | Shults | A61B 5/0002 600/345 |
| 7,920,906 B2 | 4/2011 | Goode, Jr. et al. | |
| 7,946,984 B2 | 5/2011 | Brister et al. | |
| 7,949,381 B2 | 5/2011 | Brister et al. | |
| 8,118,877 B2 | 2/2012 | Brauker et al. | |
| 8,229,534 B2 | 7/2012 | Brister et al. | |
| 8,277,713 B2 | 10/2012 | Petisce et al. | |
| 8,290,560 B2 | 10/2012 | Kamath et al. | |
| 8,364,229 B2* | 1/2013 | Simpson | A61B 5/14532 600/309 |
| 8,366,614 B2 | 2/2013 | Say et al. | |
| 8,457,708 B2 | 6/2013 | Brister et al. | |
| 8,463,350 B2 | 6/2013 | Kamath et al. | |
| 8,474,397 B2 | 7/2013 | Brister et al. | |
| 8,475,373 B2 | 7/2013 | Brister et al. | |
| 8,483,791 B2 | 7/2013 | Brister et al. | |
| 8,548,551 B2 | 10/2013 | Kamath et al. | |
| 8,792,953 B2* | 7/2014 | Brister | A61B 5/0002 600/345 |
| 8,989,833 B2* | 3/2015 | Brauker | A61B 5/0002 600/347 |
| 9,155,496 B2* | 10/2015 | Shults | A61B 5/0002 |
| 2001/0008187 A1 | 7/2001 | Hanssen et al. | |
| 2001/0016682 A1 | 8/2001 | Berner et al. | |
| 2001/0020546 A1 | 9/2001 | Eldridge | |
| 2001/0027327 A1 | 10/2001 | Schraga | |
| 2001/0039387 A1 | 11/2001 | Rutynowski et al. | |
| 2001/0041830 A1 | 11/2001 | Varalli et al. | |
| 2001/0044413 A1 | 11/2001 | Pierce et al. | |
| 2001/0051766 A1 | 12/2001 | Gazdzinski | |
| 2001/0051768 A1 | 12/2001 | Schulman et al. | |
| 2001/0053933 A1 | 12/2001 | Phaneuf et al. | |
| 2002/0016535 A1 | 2/2002 | Martin | |
| 2002/0019330 A1 | 2/2002 | Murray et al. | |
| 2002/0022883 A1 | 2/2002 | Burg | |
| 2002/0023852 A1 | 2/2002 | McIvor et al. | |
| 2002/0032531 A1 | 3/2002 | Mansky et al. | |
| 2002/0042090 A1 | 4/2002 | Heller et al. | |
| 2002/0042561 A1 | 4/2002 | Schulman et al. | |
| 2002/0043471 A1 | 4/2002 | Ikeda et al. | |
| 2002/0055673 A1* | 5/2002 | Van Antwerp et al. | 600/365 |
| 2002/0068860 A1 | 6/2002 | Clark, Jr. | |
| 2002/0077599 A1 | 6/2002 | Wojcik | |
| 2002/0084196 A1 | 7/2002 | Liamos et al. | |
| 2002/0099282 A1 | 7/2002 | Knobbe et al. | |
| 2002/0099997 A1 | 7/2002 | Piret | |
| 2002/0100474 A1 | 8/2002 | Kellner et al. | |
| 2002/0100725 A1 | 8/2002 | Lee et al. | |
| 2002/0119711 A1 | 8/2002 | Vanantwerp et al. | |
| 2002/0128419 A1 | 9/2002 | Terry et al. | |
| 2002/0128546 A1 | 9/2002 | Silver | |
| 2002/0132279 A1 | 9/2002 | Hockersmith | |
| 2002/0133063 A1 | 9/2002 | Hockersmith et al. | |
| 2002/0133224 A1 | 9/2002 | Shults et al. | |
| 2002/0137991 A1 | 9/2002 | Scarantino et al. | |
| 2002/0151796 A1 | 10/2002 | Koulik | |
| 2002/0151816 A1* | 10/2002 | Rich et al. | 600/547 |
| 2002/0161288 A1 | 10/2002 | Shin et al. | |
| 2002/0169369 A1 | 11/2002 | Ward et al. | |
| 2002/0177763 A1 | 11/2002 | Burns et al. | |
| 2002/0182241 A1 | 12/2002 | Boerenstein et al. | |
| 2002/0185384 A1 | 12/2002 | Leong et al. | |
| 2002/0188185 A1 | 12/2002 | Sohrab | |
| 2002/0188216 A1 | 12/2002 | Kayyali et al. | |
| 2002/0193885 A1 | 12/2002 | Legeay et al. | |
| 2002/0198513 A1 | 12/2002 | Lebel et al. | |
| 2003/0004457 A1 | 1/2003 | Andersson | |
| 2003/0006669 A1 | 1/2003 | Pei et al. | |
| 2003/0023317 A1 | 1/2003 | Brauker et al. | |
| 2003/0036773 A1 | 2/2003 | Whitehurst et al. | |
| 2003/0049166 A1 | 3/2003 | Pendo et al. | |
| 2003/0059631 A1 | 3/2003 | Al-Lamee | |
| 2003/0072741 A1 | 4/2003 | Berglund et al. | |
| 2003/0076082 A1 | 4/2003 | Morgan et al. | |
| 2003/0078481 A1 | 4/2003 | McIvor et al. | |
| 2003/0091433 A1 | 5/2003 | Tam et al. | |
| 2003/0096424 A1 | 5/2003 | Mao et al. | |
| 2003/0097082 A1 | 5/2003 | Purdy et al. | |
| 2003/0099682 A1 | 5/2003 | Moussy et al. | |
| 2003/0100040 A1 | 5/2003 | Bonnecaze et al. | |
| 2003/0100821 A1 | 5/2003 | Heller et al. | |
| 2003/0104119 A1 | 6/2003 | Wilson et al. | |
| 2003/0130616 A1 | 7/2003 | Steil et al. | |
| 2003/0132227 A1 | 7/2003 | Geisler | |
| 2003/0134100 A1 | 7/2003 | Mao et al. | |
| 2003/0134347 A1 | 7/2003 | Heller et al. | |
| 2003/0138674 A1 | 7/2003 | Zeikus et al. | |
| 2003/0146110 A1* | 8/2003 | Karinka | G01N 27/3272 205/777.5 |
| 2003/0157409 A1 | 8/2003 | Huang et al. | |
| 2003/0181794 A1 | 9/2003 | Rini et al. | |
| 2003/0186457 A1 | 10/2003 | Iwaki et al. | |
| 2003/0187338 A1 | 10/2003 | Say et al. | |
| 2003/0188427 A1 | 10/2003 | Say et al. | |
| 2003/0190383 A1 | 10/2003 | Kim | |
| 2003/0199744 A1 | 10/2003 | Buse et al. | |
| 2003/0199745 A1* | 10/2003 | Burson et al. | 600/347 |
| 2003/0199878 A1 | 10/2003 | Pohjonen | |
| 2003/0203498 A1 | 10/2003 | Neel et al. | |
| 2003/0203991 A1 | 10/2003 | Schottman et al. | |
| 2003/0212317 A1 | 11/2003 | Kovatchev et al. | |
| 2003/0212346 A1 | 11/2003 | Yuzhakov et al. | |
| 2003/0212347 A1 | 11/2003 | Sohrab | |
| 2003/0225324 A1 | 12/2003 | Anderson et al. | |
| 2003/0225360 A1 | 12/2003 | Eppstein et al. | |
| 2003/0225361 A1* | 12/2003 | Sabra | 604/19 |
| 2003/0225437 A1 | 12/2003 | Ferguson | |
| 2003/0228681 A1 | 12/2003 | Ritts et al. | |
| 2003/0235817 A1 | 12/2003 | Bartkowiak et al. | |

(56) References Cited

U.S. PATENT DOCUMENTS

| | | |
|---|---|---|
| 2004/0002682 A1 | 1/2004 | Kovelman et al. |
| 2004/0006263 A1 | 1/2004 | Anderson et al. |
| 2004/0010207 A1 | 1/2004 | Flaherty et al. |
| 2004/0011671 A1 | 1/2004 | Shults et al. |
| 2004/0015063 A1 | 1/2004 | DeNuzzio et al. |
| 2004/0015134 A1 | 1/2004 | Lavi et al. |
| 2004/0023253 A1 | 2/2004 | Kunwar et al. |
| 2004/0024327 A1 | 2/2004 | Brodnick |
| 2004/0030285 A1 | 2/2004 | Lavi et al. |
| 2004/0030294 A1 | 2/2004 | Mahurkar |
| 2004/0039342 A1 | 2/2004 | Eppstein et al. |
| 2004/0039343 A1 | 2/2004 | Eppstein et al. |
| 2004/0039406 A1 | 2/2004 | Jessen |
| 2004/0052689 A1 | 3/2004 | Yao |
| 2004/0054352 A1 | 3/2004 | Adames et al. |
| 2004/0064156 A1 | 4/2004 | Shah et al. |
| 2004/0068230 A1 | 4/2004 | Estes et al. |
| 2004/0074785 A1 | 4/2004 | Holker |
| 2004/0078219 A1 | 4/2004 | Kaylor |
| 2004/0088023 A1 | 5/2004 | Imran et al. |
| 2004/0106741 A1 | 6/2004 | Kriesel et al. |
| 2004/0106859 A1 | 6/2004 | Say et al. |
| 2004/0111017 A1 | 6/2004 | Say et al. |
| 2004/0120848 A1 | 6/2004 | Teodorczyk |
| 2004/0127818 A1 | 7/2004 | Roe et al. |
| 2004/0133131 A1 | 7/2004 | Kuhn et al. |
| 2004/0133164 A1 | 7/2004 | Funderburk et al. |
| 2004/0138543 A1 | 7/2004 | Russell et al. |
| 2004/0146909 A1 | 7/2004 | Duong et al. |
| 2004/0158207 A1 | 8/2004 | Hunn et al. |
| 2004/0167801 A1 | 8/2004 | Say et al. |
| 2004/0173472 A1 | 9/2004 | Jung et al. |
| 2004/0176672 A1 | 9/2004 | Silver et al. |
| 2004/0180391 A1 | 9/2004 | Gratzl et al. |
| 2004/0197846 A1 | 10/2004 | Hockersmith et al. |
| 2004/0199059 A1 | 10/2004 | Brauker et al. |
| 2004/0204687 A1 | 10/2004 | Morgensen |
| 2004/0219664 A1 | 11/2004 | Heller et al. |
| 2004/0228902 A1 | 11/2004 | Benz |
| 2004/0234575 A1 | 11/2004 | Horres et al. |
| 2004/0236200 A1 | 11/2004 | Say et al. |
| 2004/0236251 A1 | 11/2004 | Roe et al. |
| 2004/0242982 A1 | 12/2004 | Sakata et al. |
| 2004/0253365 A1 | 12/2004 | Warren et al. |
| 2004/0254433 A1 | 12/2004 | Bandis |
| 2004/0265940 A1 | 12/2004 | Slater et al. |
| 2005/0003399 A1 | 1/2005 | Blackburn et al. |
| 2005/0006122 A1 | 1/2005 | Burnette |
| 2005/0010265 A1 | 1/2005 | Baru Fassio et al. |
| 2005/0013842 A1 | 1/2005 | Qiu et al. |
| 2005/0027180 A1 | 2/2005 | Goode et al. |
| 2005/0027181 A1 | 2/2005 | Goode et al. |
| 2005/0027182 A1 | 2/2005 | Siddiqui et al. |
| 2005/0027462 A1 | 2/2005 | Goode et al. |
| 2005/0027463 A1 | 2/2005 | Goode et al. |
| 2005/0031689 A1 | 2/2005 | Shults et al. |
| 2005/0033132 A1 | 2/2005 | Shults et al. |
| 2005/0038332 A1 | 2/2005 | Saidara et al. |
| 2005/0043598 A1 | 2/2005 | Goode et al. |
| 2005/0026689 A1 | 3/2005 | Marks |
| 2005/0051427 A1 | 3/2005 | Brauker et al. |
| 2005/0051440 A1 | 3/2005 | Simpson et al. |
| 2005/0054909 A1 | 3/2005 | Petisce et al. |
| 2005/0056551 A1 | 3/2005 | White et al. |
| 2005/0056552 A1 | 3/2005 | Simpson et al. |
| 2005/0059871 A1* | 3/2005 | Gough et al. .................. 600/347 |
| 2005/0070770 A1 | 3/2005 | Dirac et al. |
| 2005/0077584 A1 | 4/2005 | Uhland et al. |
| 2005/0079200 A1 | 4/2005 | Rathenow et al. |
| 2005/0085839 A1 | 4/2005 | Allen et al. |
| 2005/0090607 A1 | 4/2005 | Tapsak et al. |
| 2005/0096519 A1 | 5/2005 | DeNuzzio et al. |
| 2005/0103625 A1 | 5/2005 | Rhodes et al. |
| 2005/0107677 A1 | 5/2005 | Ward et al. |
| 2005/0112169 A1 | 5/2005 | Brauker et al. |
| 2005/0115832 A1 | 6/2005 | Simpson et al. |
| 2005/0118344 A1 | 6/2005 | Pacetti |
| 2005/0119720 A1 | 6/2005 | Gale et al. |
| 2005/0121322 A1 | 6/2005 | Say |
| 2005/0124873 A1 | 6/2005 | Shults et al. |
| 2005/0131305 A1 | 6/2005 | Danielson et al. |
| 2005/0133368 A1 | 6/2005 | Davies et al. |
| 2005/0139489 A1 | 6/2005 | Oliver et al. |
| 2005/0143635 A1 | 6/2005 | Kamath et al. |
| 2005/0143636 A1 | 6/2005 | Zhang et al. |
| 2005/0143675 A1 | 6/2005 | Neel et al. |
| 2005/0154264 A1 | 7/2005 | Lecompte et al. |
| 2005/0154271 A1 | 7/2005 | Rasdal et al. |
| 2005/0154272 A1 | 7/2005 | Dirac et al. |
| 2005/0173245 A1 | 8/2005 | Feldman et al. |
| 2005/0176136 A1 | 8/2005 | Burd et al. |
| 2005/0176678 A1 | 8/2005 | Horres et al. |
| 2005/0177036 A1 | 8/2005 | Shults et al. |
| 2005/0181012 A1 | 8/2005 | Saint et al. |
| 2005/0182451 A1 | 8/2005 | Griffin et al. |
| 2005/0183954 A1 | 8/2005 | Hitchcock et al. |
| 2005/0187720 A1 | 8/2005 | Goode et al. |
| 2005/0192557 A1 | 9/2005 | Brauker et al. |
| 2005/0195930 A1 | 9/2005 | Spital et al. |
| 2005/0196747 A1 | 9/2005 | Stiene |
| 2005/0197554 A1 | 9/2005 | Polcha |
| 2005/0203360 A1 | 9/2005 | Brauker et al. |
| 2005/0203364 A1 | 9/2005 | Monfre et al. |
| 2005/0211571 A1 | 9/2005 | Schulein et al. |
| 2005/0215871 A1 | 9/2005 | Feldman et al. |
| 2005/0233407 A1 | 10/2005 | Pamidi et al. |
| 2005/0239154 A1 | 10/2005 | Feldman et al. |
| 2005/0251083 A1 | 11/2005 | Carr-Brendel et al. |
| 2005/0258037 A1 | 11/2005 | Hajizadeh et al. |
| 2005/0261563 A1 | 11/2005 | Zhou et al. |
| 2005/0272989 A1 | 12/2005 | Shah et al. |
| 2005/0288596 A1 | 12/2005 | Eigler et al. |
| 2006/0001550 A1 | 1/2006 | Mann et al. |
| 2006/0003398 A1 | 1/2006 | Heller et al. |
| 2006/0008370 A1 | 1/2006 | Massaro et al. |
| 2006/0015024 A1 | 1/2006 | Brister et al. |
| 2006/0020187 A1 | 1/2006 | Brister et al. |
| 2006/0047215 A1 | 3/2006 | Newman et al. |
| 2006/0065527 A1 | 3/2006 | Samproni |
| 2006/0079740 A1 | 4/2006 | Silver et al. |
| 2006/0079809 A1 | 4/2006 | Goldberger et al. |
| 2006/0094946 A1 | 5/2006 | Kellogg et al. |
| 2006/0118415 A1 | 6/2006 | Say et al. |
| 2006/0142651 A1 | 6/2006 | Brister et al. |
| 2006/0155180 A1 | 7/2006 | Brister et al. |
| 2006/0159718 A1 | 7/2006 | Rathenow et al. |
| 2006/0173444 A1 | 8/2006 | Choy et al. |
| 2006/0183871 A1* | 8/2006 | Ward .................... C08G 64/18 525/464 |
| 2006/0183984 A1 | 8/2006 | Dobbles et al. |
| 2006/0183985 A1 | 8/2006 | Brister et al. |
| 2006/0189856 A1 | 8/2006 | Petisce et al. |
| 2006/0189863 A1 | 8/2006 | Peyser et al. |
| 2006/0195029 A1 | 8/2006 | Shults et al. |
| 2006/0200020 A1 | 9/2006 | Brister et al. |
| 2006/0222566 A1 | 10/2006 | Brauker et al. |
| 2006/0224141 A1 | 10/2006 | Rush et al. |
| 2006/0229512 A1 | 10/2006 | Petisce et al. |
| 2006/0235285 A1 | 10/2006 | Brister et al. |
| 2006/0253085 A1 | 11/2006 | Geismar et al. |
| 2006/0257995 A1 | 11/2006 | Simpson et al. |
| 2006/0257996 A1 | 11/2006 | Simpson et al. |
| 2006/0258761 A1 | 11/2006 | Boock et al. |
| 2006/0258929 A1 | 11/2006 | Goode et al. |
| 2006/0263673 A1 | 11/2006 | Kim et al. |
| 2006/0263763 A1 | 11/2006 | Simpson et al. |
| 2006/0270922 A1 | 11/2006 | Brauker et al. |
| 2006/0270923 A1* | 11/2006 | Brauker ............. A61B 5/14532 600/345 |
| 2006/0275859 A1 | 12/2006 | Kjaer |
| 2006/0289307 A1 | 12/2006 | Yu et al. |
| 2006/0293576 A1 | 12/2006 | Van Antwerp et al. |
| 2007/0003588 A1 | 1/2007 | Chinn et al. |
| 2007/0007133 A1 | 1/2007 | Mang et al. |

(56) References Cited

U.S. PATENT DOCUMENTS

| | | |
|---|---|---|
| 2007/0017805 A1 | 1/2007 | Hodges et al. |
| 2007/0027370 A1* | 2/2007 | Brauker ............ A61B 5/14532 600/309 |
| 2007/0027384 A1 | 2/2007 | Brister et al. |
| 2007/0027385 A1 | 2/2007 | Brister et al. |
| 2007/0032717 A1 | 2/2007 | Brister et al. |
| 2007/0038044 A1 | 2/2007 | Dobbles et al. |
| 2007/0045902 A1 | 3/2007 | Brauker et al. |
| 2007/0073129 A1 | 3/2007 | Shah et al. |
| 2007/0093704 A1 | 4/2007 | Brister et al. |
| 2007/0116600 A1 | 5/2007 | Kocher et al. |
| 2007/0129524 A1 | 6/2007 | Sunkara |
| 2007/0135698 A1 | 6/2007 | Shah et al. |
| 2007/0142584 A1 | 6/2007 | Schorzman et al. |
| 2007/0151869 A1 | 7/2007 | Heller et al. |
| 2007/0163880 A1* | 7/2007 | Woo .................. A61B 5/0031 204/403.06 |
| 2007/0173706 A1 | 7/2007 | Neinast et al. |
| 2007/0173710 A1 | 7/2007 | Petisce et al. |
| 2007/0173711 A1 | 7/2007 | Shah et al. |
| 2007/0179436 A1 | 8/2007 | Braig et al. |
| 2007/0197889 A1 | 8/2007 | Brister et al. |
| 2007/0200254 A1 | 8/2007 | Curry |
| 2007/0200267 A1 | 8/2007 | Tsai |
| 2007/0202672 A1 | 8/2007 | Curry |
| 2007/0203407 A1 | 8/2007 | Hoss et al. |
| 2007/0203410 A1 | 8/2007 | Say et al. |
| 2007/0203966 A1 | 8/2007 | Brauker et al. |
| 2007/0208244 A1 | 9/2007 | Brauker et al. |
| 2007/0208246 A1 | 9/2007 | Brauker et al. |
| 2007/0213610 A1 | 9/2007 | Say et al. |
| 2007/0213611 A1 | 9/2007 | Simpson et al. |
| 2007/0215491 A1 | 9/2007 | Heller et al. |
| 2007/0218097 A1 | 9/2007 | Heller et al. |
| 2007/0227907 A1 | 10/2007 | Shah et al. |
| 2007/0232879 A1 | 10/2007 | Brister et al. |
| 2007/0233013 A1 | 10/2007 | Schoenberg |
| 2007/0235331 A1 | 10/2007 | Simpson et al. |
| 2007/0249916 A1 | 10/2007 | Pesach et al. |
| 2007/0259217 A1 | 11/2007 | Logan |
| 2007/0275193 A1 | 11/2007 | DeSimone et al. |
| 2007/0299385 A1 | 12/2007 | Santini et al. |
| 2007/0299409 A1 | 12/2007 | Whibourne et al. |
| 2008/0001318 A1 | 1/2008 | Schorzman et al. |
| 2008/0021666 A1 | 1/2008 | Goode et al. |
| 2008/0027245 A1 | 1/2008 | Suri |
| 2008/0033268 A1 | 2/2008 | Stafford |
| 2008/0034972 A1 | 2/2008 | Gough et al. |
| 2008/0045824 A1 | 2/2008 | Tapsak et al. |
| 2008/0064941 A1 | 3/2008 | Funderburk et al. |
| 2008/0064944 A1 | 3/2008 | Van Antwerp et al. |
| 2008/0072663 A1 | 3/2008 | Keenan et al. |
| 2008/0086040 A1 | 4/2008 | Heller et al. |
| 2008/0086041 A1 | 4/2008 | Heller et al. |
| 2008/0086043 A1 | 4/2008 | Heller et al. |
| 2008/0091094 A1 | 4/2008 | Heller et al. |
| 2008/0091095 A1 | 4/2008 | Heller et al. |
| 2008/0187655 A1 | 8/2008 | Markle et al. |
| 2008/0188722 A1 | 8/2008 | Markle et al. |
| 2008/0188725 A1 | 8/2008 | Markle et al. |
| 2008/0188731 A1 | 8/2008 | Brister et al. |
| 2008/0194935 A1 | 8/2008 | Brister et al. |
| 2008/0194938 A1 | 8/2008 | Brister et al. |
| 2008/0208025 A1 | 8/2008 | Shults et al. |
| 2008/0210557 A1 | 9/2008 | Heller et al. |
| 2008/0214915 A1 | 9/2008 | Brister et al. |
| 2008/0214918 A1 | 9/2008 | Brister et al. |
| 2008/0228051 A1 | 9/2008 | Shults et al. |
| 2008/0228054 A1 | 9/2008 | Shults et al. |
| 2008/0242961 A1 | 10/2008 | Brister et al. |
| 2008/0262469 A1 | 10/2008 | Brister et al. |
| 2008/0275313 A1 | 11/2008 | Brister et al. |
| 2008/0287764 A1 | 11/2008 | Rasdal et al. |
| 2008/0287765 A1 | 11/2008 | Rasdal et al. |
| 2008/0287766 A1 | 11/2008 | Rasdal et al. |
| 2008/0296155 A1 | 12/2008 | Shults et al. |
| 2008/0305009 A1 | 12/2008 | Gamsey et al. |
| 2008/0305506 A1 | 12/2008 | Suri |
| 2008/0306368 A1 | 12/2008 | Goode et al. |
| 2008/0306433 A1 | 12/2008 | Dobbles et al. |
| 2008/0306434 A1 | 12/2008 | Dobbles et al. |
| 2008/0306435 A1 | 12/2008 | Kamath et al. |
| 2008/0306444 A1 | 12/2008 | Brister et al. |
| 2008/0312397 A1 | 12/2008 | Lai et al. |
| 2009/0012379 A1 | 1/2009 | Goode et al. |
| 2009/0018418 A1 | 1/2009 | Markle et al. |
| 2009/0018426 A1 | 1/2009 | Markle et al. |
| 2009/0030294 A1 | 1/2009 | Petisce et al. |
| 2009/0036763 A1 | 2/2009 | Brauker et al. |
| 2009/0045055 A1 | 2/2009 | Rhodes et al. |
| 2009/0061528 A1 | 3/2009 | Suri |
| 2009/0062633 A1 | 3/2009 | Brauker et al. |
| 2009/0076356 A1 | 3/2009 | Simpson |
| 2009/0076360 A1 | 3/2009 | Brister et al. |
| 2009/0076361 A1 | 3/2009 | Kamath et al. |
| 2009/0081803 A1 | 3/2009 | Gamsey et al. |
| 2009/0099434 A1 | 4/2009 | Liu et al. |
| 2009/0099436 A1 | 4/2009 | Brister et al. |
| 2009/0124879 A1 | 5/2009 | Brister et al. |
| 2009/0143660 A1 | 6/2009 | Brister et al. |
| 2009/0156924 A1 | 6/2009 | Shariati et al. |
| 2009/0177143 A1 | 7/2009 | Markle et al. |
| 2009/0182217 A1 | 7/2009 | Li et al. |
| 2009/0187090 A1 | 7/2009 | Say et al. |
| 2009/0187091 A1 | 7/2009 | Say et al. |
| 2009/0192366 A1 | 7/2009 | Mensinger et al. |
| 2009/0192722 A1 | 7/2009 | Shariati et al. |
| 2009/0192751 A1 | 7/2009 | Kamath et al. |
| 2009/0216103 A1 | 8/2009 | Brister et al. |
| 2009/0240120 A1 | 9/2009 | Mensinger et al. |
| 2009/0240128 A1 | 9/2009 | Mensinger et al. |
| 2009/0240193 A1 | 9/2009 | Mensinger et al. |
| 2009/0242399 A1 | 10/2009 | Kamath et al. |
| 2009/0242425 A1 | 10/2009 | Kamath et al. |
| 2009/0264719 A1 | 10/2009 | Markle et al. |
| 2009/0299276 A1 | 12/2009 | Brauker et al. |
| 2010/0041971 A1 | 2/2010 | Goode, Jr. et al. |
| 2010/0049024 A1 | 2/2010 | Saint et al. |
| 2010/0069728 A1 | 3/2010 | Funderburk et al. |
| 2010/0076283 A1 | 3/2010 | Simpson et al. |
| 2010/0081908 A1 | 4/2010 | Dobbles et al. |
| 2010/0174157 A1 | 7/2010 | Brister et al. |
| 2010/0174158 A1 | 7/2010 | Kamath et al. |
| 2010/0174163 A1 | 7/2010 | Brister et al. |
| 2010/0174164 A1* | 7/2010 | Brister .................. A61B 5/0002 600/347 |
| 2010/0212583 A1 | 8/2010 | Brister et al. |
| 2010/0256779 A1* | 10/2010 | Brauker .................. A61L 31/10 623/23.76 |
| 2011/0087196 A1 | 4/2011 | Hunn et al. |
| 2011/0144465 A1* | 6/2011 | Shults .................. A61B 5/0002 600/347 |
| 2011/0178378 A1 | 7/2011 | Brister et al. |
| 2011/0190614 A1 | 8/2011 | Brister et al. |
| 2011/0290645 A1 | 12/2011 | Brister et al. |
| 2011/0313543 A1 | 12/2011 | Brauker et al. |
| 2012/0277562 A1 | 11/2012 | Brister et al. |
| 2013/0131478 A1* | 5/2013 | Simpson ............ A61B 5/14532 600/347 |
| 2013/0255570 A1 | 10/2013 | Brister et al. |
| 2013/0281931 A1 | 10/2013 | Hunn et al. |
| 2014/0128704 A1* | 5/2014 | Simpson ............... A61B 5/7203 600/347 |

FOREIGN PATENT DOCUMENTS

| | | |
|---|---|---|
| EP | 0098592 | 1/1984 |
| EP | 0 107 634 | 5/1984 |
| EP | 0 127 958 | 12/1984 |
| EP | 0 282 349 | 9/1988 |
| EP | 0 284 518 | 9/1988 |
| EP | 0 286 039 | 10/1988 |
| EP | 0143517 B1 | 4/1989 |

(56) References Cited

FOREIGN PATENT DOCUMENTS

| | | |
|---|---|---|
| EP | 0 320 109 | 6/1989 |
| EP | 0 351 892 | 1/1990 |
| EP | 0 352 138 | 1/1990 |
| EP | 0 352 610 | 1/1990 |
| EP | 0 352 631 | 1/1990 |
| EP | 0 352 708 | 1/1990 |
| EP | 0 353 328 | 2/1990 |
| EP | 0 390 390 | 10/1990 |
| EP | 0 396 788 | 11/1990 |
| EP | 0 441 394 | 8/1991 |
| EP | 0 457 292 | 11/1991 |
| EP | 0 471 391 | 2/1992 |
| EP | 0 473 065 | 3/1992 |
| EP | 0 476 980 | 3/1992 |
| EP | 0 275 139 B1 | 4/1992 |
| EP | 0 477 501 | 4/1992 |
| EP | 0 494 704 | 9/1992 |
| EP | 0 494 705 | 9/1992 |
| EP | 0 508 388 | 10/1992 |
| EP | 0520443 A2 | 12/1992 |
| EP | 0 262 328 B1 | 1/1993 |
| EP | 0319277 B1 | 3/1993 |
| EP | 0 264 036 B1 | 6/1993 |
| EP | 0 351 891 | 9/1993 |
| EP | 0 563 795 A1 | 10/1993 |
| EP | 0567725 A1 | 11/1993 |
| EP | 0 279 069 | 7/1994 |
| EP | 0 595 474 | 7/1994 |
| EP | 0 286 118 B1 | 1/1995 |
| EP | 0 647 849 | 4/1995 |
| EP | 0 424 634 | 6/1995 |
| EP | 0 677 743 | 10/1995 |
| EP | 0 191 640 B2 | 11/1995 |
| EP | 0 424 633 | 1/1996 |
| EP | 0 709 677 | 5/1996 |
| EP | 0 532 187 | 10/1996 |
| EP | 0 470 652 | 12/1996 |
| EP | 0 476 715 | 12/1996 |
| EP | 0 747 069 | 12/1996 |
| EP | 0 776 628 A2 | 6/1997 |
| EP | 0 387 696 | 8/1997 |
| EP | 0 593 096 | 12/1997 |
| EP | 0 838 230 A | 4/1998 |
| EP | 0 880 936 | 12/1998 |
| EP | 0 587 008 | 2/1999 |
| EP | 0 967 788 | 12/1999 |
| EP | 0 995 805 | 4/2000 |
| EP | 0 678 308 B1 | 5/2000 |
| EP | 1 028 320 A3 | 3/2001 |
| EP | 1 111 378 | 6/2001 |
| EP | 1 112 717 | 7/2001 |
| EP | 1 112 718 | 7/2001 |
| EP | 1 120 084 | 8/2001 |
| EP | 1 120 085 | 8/2001 |
| EP | 1 120 650 | 8/2001 |
| EP | 1 130 386 | 9/2001 |
| EP | 1 153 571 | 11/2001 |
| EP | 0777122 B1 | 4/2002 |
| EP | 1 251 137 | 10/2002 |
| EP | 1 258 728 | 11/2002 |
| EP | 0 824 900 B1 | 4/2003 |
| EP | 1 340 980 | 9/2003 |
| EP | 1 340 981 | 9/2003 |
| EP | 1 077 636 | 1/2004 |
| EP | 0 674 176 | 2/2004 |
| EP | 0 846 776 B1 | 3/2004 |
| EP | 1 413 245 | 4/2004 |
| EP | 1 498 428 | 1/2005 |
| EP | 1 614 464 | 1/2006 |
| EP | 0 922 959 B1 | 10/2006 |
| EP | 1 717 924 | 11/2006 |
| EP | 0 877 252 B1 | 1/2007 |
| EP | 1 234 053 B1 | 4/2007 |
| EP | 1 286 164 | 7/2007 |
| EP | 1 612 560 | 10/2007 |
| EP | 1 905 514 | 4/2008 |
| EP | 1 582 874 | 7/2008 |
| EP | 1 977 829 | 10/2008 |
| EP | 1 982 644 | 10/2008 |
| EP | 1 457 913 B1 | 12/2008 |
| EP | 2236077 A1 | 10/2010 |
| EP | 2327362 A1 | 6/2011 |
| EP | 2329770 B1 | 9/2014 |
| EP | 2335584 B1 | 6/2015 |
| GB | 2149918 | 6/1985 |
| JP | 57156004 | 9/1982 |
| JP | 62083649 | 4/1987 |
| JP | 02002913 | 1/1990 |
| JP | 3-293556 | 12/1991 |
| JP | 07-083871 | 3/1995 |
| JP | 2002-189015 | 7/2002 |
| JP | 2003-297163 A | 10/2003 |
| WO | WO 1981-003614 | 12/1981 |
| WO | WO 87/06706 | 11/1987 |
| WO | WO 88/08137 | 10/1988 |
| WO | WO 89/02720 | 4/1989 |
| WO | WO 89/04302 | 5/1989 |
| WO | WO 90/00738 | 1/1990 |
| WO | WO 90/02938 | 3/1990 |
| WO | WO 90/05296 | 5/1990 |
| WO | WO 90/05301 | 5/1990 |
| WO | WO 90/05302 | 5/1990 |
| WO | WO 90/05910 | 5/1990 |
| WO | WO 90/10716 | 9/1990 |
| WO | WO 90/10861 | 9/1990 |
| WO | WO 91/09302 | 6/1991 |
| WO | WO 91/17259 | 11/1991 |
| WO | WO 92/01315 | 1/1992 |
| WO | WO 92/01928 | 2/1992 |
| WO | WO 92/07525 | 5/1992 |
| WO | WO 92/08985 | 5/1992 |
| WO | WO 1992-007525 | 5/1992 |
| WO | WO 92/12255 | 7/1992 |
| WO | WO 92/14138 | 8/1992 |
| WO | WO 92/14139 | 8/1992 |
| WO | WO 92/18887 | 10/1992 |
| WO | WO 92/21772 | 12/1992 |
| WO | WO 93/01308 | 1/1993 |
| WO | WO 93/02703 | 2/1993 |
| WO | WO 93/03362 | 2/1993 |
| WO | WO 93/12256 | 6/1993 |
| WO | WO 93/13048 | 7/1993 |
| WO | WO 93/14693 | 8/1993 |
| WO | WO 93/19370 | 9/1993 |
| WO | WO 93/19701 | 10/1993 |
| WO | WO 93/20240 | 10/1993 |
| WO | WO 93/20440 | 10/1993 |
| WO | WO 93/20441 | 10/1993 |
| WO | WO 93/20443 | 10/1993 |
| WO | WO 93/20444 | 10/1993 |
| WO | WO 93/20450 | 10/1993 |
| WO | WO 93/23744 | 11/1993 |
| WO | WO 94/06011 | 3/1994 |
| WO | WO 94/06012 | 3/1994 |
| WO | WO 94/09506 | 4/1994 |
| WO | WO 94/09507 | 4/1994 |
| WO | WO 94/19695 | 9/1994 |
| WO | WO 94/21642 | 9/1994 |
| WO | WO 94/21643 | 9/1994 |
| WO | WO 94/21644 | 9/1994 |
| WO | WO 94/22367 | 10/1994 |
| WO | WO 94/26414 | 11/1994 |
| WO | WO 95/02357 | 1/1995 |
| WO | WO 96/25089 | 2/1995 |
| WO | WO 95/07109 | 3/1995 |
| WO | WO 95/08774 | 3/1995 |
| WO | WO 95/10044 | 4/1995 |
| WO | WO 95/11454 | 4/1995 |
| WO | WO 95/13838 | 5/1995 |
| WO | WO 95/17966 | 7/1995 |
| WO | WO 95/22597 | 8/1995 |
| WO | WO 95/28878 | 11/1995 |
| WO | WO 1997-019344 | 11/1995 |
| WO | WO 95/34814 | 12/1995 |

(56) References Cited

FOREIGN PATENT DOCUMENTS

| | | |
|---|---|---|
| WO | WO 96/01611 | 1/1996 |
| WO | WO 96/03117 | 2/1996 |
| WO | WO 96/05501 | 2/1996 |
| WO | WO 96/14026 | 5/1996 |
| WO | WO 96/22991 | 8/1996 |
| WO | WO 96/22992 | 8/1996 |
| WO | WO 96/24690 | 8/1996 |
| WO | WO 96/25088 | 8/1996 |
| WO | WO 96/25089 | 8/1996 |
| WO | WO 96/32076 | 10/1996 |
| WO | WO 96/36296 | 11/1996 |
| WO | WO 96/36870 | 11/1996 |
| WO | WO 96/41179 | 12/1996 |
| WO | WO 97/01986 | 1/1997 |
| WO | WO 97/06727 | 2/1997 |
| WO | WO 97/11080 | 3/1997 |
| WO | WO 97/13874 | 4/1997 |
| WO | WO 97/17884 | 5/1997 |
| WO | WO 97/28737 | 8/1997 |
| WO | WO 97/30628 | 8/1997 |
| WO | WO 97/33176 | 9/1997 |
| WO | WO 98/01071 | 1/1998 |
| WO | WO 98/06423 | 2/1998 |
| WO | WO 98/19159 | 5/1998 |
| WO | WO 98/24366 | 6/1998 |
| WO | WO 98/33549 | 8/1998 |
| WO | WO 98/34541 | 8/1998 |
| WO | WO 98/38904 | 9/1998 |
| WO | WO 98/38906 | 9/1998 |
| WO | WO 98/41854 | 9/1998 |
| WO | WO 1998-038906 | 9/1998 |
| WO | WO 98/42249 | 10/1998 |
| WO | WO 98/44347 | 10/1998 |
| WO | WO 98/44348 | 10/1998 |
| WO | WO 98/45331 | 10/1998 |
| WO | WO 98/45427 | 10/1998 |
| WO | WO 98/52043 | 11/1998 |
| WO | WO 98/56293 | 12/1998 |
| WO | WO 1998-058250 | 12/1998 |
| WO | WO 99/13101 | 3/1999 |
| WO | WO 99/13574 | 3/1999 |
| WO | WO 1999-012607 | 3/1999 |
| WO | WO 99/66613 | 4/1999 |
| WO | WO 99/27848 | 6/1999 |
| WO | WO 99/27852 | 6/1999 |
| WO | WO 99/29429 | 6/1999 |
| WO | WO 99/29892 | 6/1999 |
| WO | WO 1999-029230 | 6/1999 |
| WO | WO 99/33504 | 7/1999 |
| WO | WO 99/40848 | 8/1999 |
| WO | WO 99/49856 | 10/1999 |
| WO | WO 99/58051 | 11/1999 |
| WO | WO 99/64620 | 12/1999 |
| WO | WO 00/07013 | 2/2000 |
| WO | WO 00/13002 | 3/2000 |
| WO | WO 2000-013003 | 3/2000 |
| WO | WO 00/18449 | 4/2000 |
| WO | WO 00/20626 | 4/2000 |
| WO | WO 00/30530 | 6/2000 |
| WO | WO 00/35530 | 6/2000 |
| WO | WO 00/45696 | 8/2000 |
| WO | WO 00/49940 | 8/2000 |
| WO | WO 00/049941 | 8/2000 |
| WO | WO 00/049942 | 8/2000 |
| WO | WO 00/49942 | 8/2000 |
| WO | WO 00/59373 | 10/2000 |
| WO | WO 00/074753 | 12/2000 |
| WO | WO 00/78992 | 12/2000 |
| WO | WO 01/00865 | 1/2001 |
| WO | WO 01/12158 | 2/2001 |
| WO | WO 2001-012158 | 2/2001 |
| WO | WO 01/20019 A2 | 3/2001 |
| WO | WO 01/20334 A1 | 3/2001 |
| WO | WO 01/21827 | 3/2001 |
| WO | WO 01/36666 | 5/2001 |
| WO | WO 01/43660 | 6/2001 |
| WO | WO 01/052935 | 7/2001 |
| WO | WO 01/52935 | 7/2001 |
| WO | WO 01/54753 | 8/2001 |
| WO | WO 01/58348 | 8/2001 |
| WO | WO 01/064105 | 9/2001 |
| WO | WO 01/68901 | 9/2001 |
| WO | WO 01/69222 | 9/2001 |
| WO | WO 01/073109 | 10/2001 |
| WO | WO 01/88524 | 11/2001 |
| WO | WO 01/91634 | 12/2001 |
| WO | WO 02/07596 | 1/2002 |
| WO | WO 2002-007617 | 1/2002 |
| WO | WO 02/33407 | 4/2002 |
| WO | WO 2002-043585 | 6/2002 |
| WO | WO 02/056751 | 7/2002 |
| WO | WO 02/058537 | 8/2002 |
| WO | WO 02/062210 | 8/2002 |
| WO | WO 02/066509 | 8/2002 |
| WO | WO 02/066986 | 8/2002 |
| WO | WO 02/074161 | 9/2002 |
| WO | WO 02/087681 | 11/2002 |
| WO | WO 02/099097 | 12/2002 |
| WO | WO 02/099428 | 12/2002 |
| WO | WO 02/100474 | 12/2002 |
| WO | WO 2002-100457 | 12/2002 |
| WO | WO 03/008013 | 1/2003 |
| WO | WO 03/008014 | 1/2003 |
| WO | WO 03/009207 | 1/2003 |
| WO | WO 03/009208 | 1/2003 |
| WO | WO 03/033726 | 4/2003 |
| WO | WO 2003-028797 | 4/2003 |
| WO | WO 03/035117 | 5/2003 |
| WO | WO 03/036310 | 5/2003 |
| WO | WO 03/044511 | 5/2003 |
| WO | WO 03/057028 | 7/2003 |
| WO | WO 03/072269 | 9/2003 |
| WO | WO 03/082091 | 9/2003 |
| WO | WO 20013-072164 | 9/2003 |
| WO | WO 03/088832 | 10/2003 |
| WO | WO 03/094714 | 11/2003 |
| WO | WO 03/097866 | 11/2003 |
| WO | WO 03/101862 | 12/2003 |
| WO | WO 03/106031 | 12/2003 |
| WO | WO 03/106966 | 12/2003 |
| WO | WO 2005-065542 | 12/2003 |
| WO | WO 04/004905 | 1/2004 |
| WO | WO 2004-010844 | 2/2004 |
| WO | WO 03/076937 | 4/2004 |
| WO | WO 04/030726 | 4/2004 |
| WO | WO 04/036183 | 4/2004 |
| WO | WO 04/039265 | 5/2004 |
| WO | WO 04/052190 | 6/2004 |
| WO | WO 04/060455 | 7/2004 |
| WO | WO 04/063718 | 7/2004 |
| WO | WO 04/071291 | 8/2004 |
| WO | WO 04/073138 | 8/2004 |
| WO | WO 04/086970 | 10/2004 |
| WO | WO 04/098685 | 11/2004 |
| WO | WO 04/113901 | 12/2004 |
| WO | WO 2004105641 A2 * 12/2004 ............. A61L 31/10 |
| WO | WO 05/012873 | 2/2005 |
| WO | WO 05/013824 | 2/2005 |
| WO | WO 2005-011489 | 2/2005 |
| WO | WO 05/018443 | 3/2005 |
| WO | WO 05/026178 | 3/2005 |
| WO | WO 05/026689 | 3/2005 |
| WO | WO 05/026690 | 3/2005 |
| WO | WO 05/032362 | 4/2005 |
| WO | WO 05/048834 | 6/2005 |
| WO | WO 05/057175 | 6/2005 |
| WO | WO 05/067797 | 7/2005 |
| WO | WO 05/074811 | 8/2005 |
| WO | WO 05/078424 | 8/2005 |
| WO | WO 05/084530 | 9/2005 |
| WO | WO 05/084545 | 9/2005 |
| WO | WO 05/084546 | 9/2005 |
| WO | WO 05/026689 | 10/2005 |
| WO | WO 05/107594 | 11/2005 |

(56) References Cited

FOREIGN PATENT DOCUMENTS

| | | |
|---|---|---|
| WO | WO 05/114218 | 12/2005 |
| WO | WO 05/121355 | 12/2005 |
| WO | WO 06/001973 | 1/2006 |
| WO | WO 06/002960 | 1/2006 |
| WO | WO 06/005503 | 1/2006 |
| WO | WO 06/010533 | 2/2006 |
| WO | WO 06/017358 | 2/2006 |
| WO | WO 06/019665 | 2/2006 |
| WO | WO 06/024671 | 3/2006 |
| WO | WO 06/023241 | 5/2006 |
| WO | WO 06/050843 | 5/2006 |
| WO | WO 06/060806 | 6/2006 |
| WO | WO 06/071770 | 7/2006 |
| WO | WO 06/072089 | 7/2006 |
| WO | WO 06/076412 | 7/2006 |
| WO | WO 06/088576 | 8/2006 |
| WO | WO 06/102359 | 9/2006 |
| WO | WO 06/102412 | 9/2006 |
| WO | WO 06/104843 | 10/2006 |
| WO | WO 06/105146 | 10/2006 |
| WO | WO 06/108811 | 10/2006 |
| WO | WO 06/122048 | 11/2006 |
| WO | WO 06/122553 | 11/2006 |
| WO | WO 06/124759 | 11/2006 |
| WO | WO 06/130268 | 12/2006 |
| WO | WO 06/132884 | 12/2006 |
| WO | WO 06/133171 | 12/2006 |
| WO | WO 2008-088490 | 12/2006 |
| WO | WO 07/002579 | 1/2007 |
| WO | WO 07/006454 | 1/2007 |
| WO | WO 07/009911 | 1/2007 |
| WO | WO 07/011587 | 1/2007 |
| WO | WO 07/016399 | 2/2007 |
| WO | WO 07/021892 | 2/2007 |
| WO | WO 07/021894 | 2/2007 |
| WO | WO 07/025088 | 3/2007 |
| WO | WO 07/028138 | 3/2007 |
| WO | WO 07/033010 | 3/2007 |
| WO | WO 07/037970 | 4/2007 |
| WO | WO 07/037989 | 4/2007 |
| WO | WO 07/040559 | 4/2007 |
| WO | WO 07/041070 | 4/2007 |
| WO | WO 07/041072 | 4/2007 |
| WO | WO 07/041248 | 4/2007 |
| WO | WO 07/053832 | 5/2007 |
| WO | WO 07/058921 | 5/2007 |
| WO | WO 07/061992 | 5/2007 |
| WO | WO 07/070486 | 6/2007 |
| WO | WO 07/076303 | 7/2007 |
| WO | WO 07/079025 | 7/2007 |
| WO | WO 07/090037 | 8/2007 |
| WO | WO 07/097754 | 8/2007 |
| WO | WO 07/101223 | 9/2007 |
| WO | WO 07/109372 | 9/2007 |
| WO | WO 07/111885 | 10/2007 |
| WO | WO 07/112006 | 10/2007 |
| WO | WO 07/115094 | 10/2007 |
| WO | WO 07/120363 | 10/2007 |
| WO | WO 07/127606 | 11/2007 |
| WO | WO 07/127622 | 11/2007 |
| WO | WO 07/127879 | 11/2007 |
| WO | WO 07/127880 | 11/2007 |
| WO | WO 07/137286 | 11/2007 |
| WO | WO 08/001091 | 1/2008 |
| WO | WO 08/005780 | 1/2008 |
| WO | WO 08/013849 | 1/2008 |
| WO | WO 08/016486 | 2/2008 |
| WO | WO 08/022021 | 2/2008 |
| WO | WO 08/028644 | 3/2008 |
| WO | WO 08/031106 | 3/2008 |
| WO | WO 08/031110 | 3/2008 |
| WO | WO 08/037485 | 4/2008 |
| WO | WO 08/039944 | 4/2008 |
| WO | WO 08/039946 | 4/2008 |
| WO | WO 08/039949 | 4/2008 |
| WO | WO 08/048709 | 4/2008 |
| WO | WO 08/051407 | 5/2008 |
| WO | WO 08/051924 | 5/2008 |
| WO | WO 08/055128 | 5/2008 |
| WO | WO 08/055199 | 5/2008 |
| WO | WO 08/067314 | 6/2008 |
| WO | WO 08/069931 | 6/2008 |
| WO | WO 08/069932 | 6/2008 |
| WO | WO 08/073813 | 6/2008 |
| WO | WO 08/079616 | 7/2008 |
| WO | WO 08/080591 | 7/2008 |
| WO | WO 08/083379 | 7/2008 |
| WO | WO 08/101217 | 8/2008 |
| WO | WO 08/103620 | 8/2008 |
| WO | WO 07/079015 | 10/2008 |
| WO | WO 08/118257 | 10/2008 |
| WO | WO 08/119470 | 10/2008 |
| WO | WO 08/124597 | 10/2008 |
| WO | WO 08/134441 | 11/2008 |
| WO | WO 08/135453 | 11/2008 |
| WO | WO 08/137405 | 11/2008 |
| WO | WO 08/138006 | 11/2008 |
| WO | WO 08/150280 | 12/2008 |
| WO | WO 08/150917 | 12/2008 |
| WO | WO 08/150946 | 12/2008 |
| WO | WO 08/150949 | 12/2008 |
| WO | WO 2006-017358 | 2/2016 |

OTHER PUBLICATIONS

Armour et al., *Application of Chronic Intravascular Blood Glucose Sensor in Dogs*, , Diabetes, vol. 39, Dec. 1990 pp. 1519-1526.
Asberg et al., *Hydrogels of a Conducting Conjugated Polymer as 3-D Enzyme Electrode*, Biosensors Bioelectronics, pp. 199-207 (2003).
Atanasov et al. 1994. Biosensor for continuos glucose monitoring. *Biotechnology and Bioengineering*, 43:262-266.
Baker et al. 1993. Dynamic concentration challenges for biosensor characterization. *Biosensors & Bioelectronics*, 8:433-441.
Bland et al. 1990. A note on the e of the intraclass correlation coefficient in the evaluation of agreement between two methods of measurement. *Comput. Biol. Med.*, 20(5):337-340.
Bott, A. W. A Comparison of Cyclic Voltammetryand Cyclic Staircase Voltammetry. Current Separations 1997, 16:1, 23-26.
Brauker et al. Sustained expression of high levels of human factor IX from human cells implanted within an immunoisolation device into athymic rodents. Hum Gene Ther 1998, 9, 879-888.
Dai et al., *Hydrogel Membranes with Mesh Size Asymmetry Based on the Gradient Crosslink of Poly (vinyl alcohol)*, Journal of Membrane Science 156 (1999) 67-79.
D'Arrigo et al. Poro-Si based bioreactors for glucose monitoring and drugs production. Proc. of SPIE 2003, 4982, 178-184.
El-Sa'ad et al. Moisture Absorption by Epoxy Resins: the Reverse Thermal Effect. Journal of Materials Science 1990, 25, 3577-3582.
Fare et al. 1998. Functional characterization of a conducting polymer-based immunoassay system. *Biosensors & Bioelectronics*, 13(3-4):459-470.
Fraser et al. *Biosensors in the Body*, Continous in Vivo Monitoring, Wiley Series of Biomaterials Science and Engineering, 1997, Chapter 4, Principles of Long-term Fully Implantable Sensors with Emphasis on Radiotelemetric Monitoring of Blood Glucose from inside a Subcutaneous Foreign Body Capsule pp. 118-137.
Geller et al. Use of an immunoisolation device for cell transplantation and tumor immunotherapy. Ann NY Acad Sci 1997, 831, 438-451.
Gerritsen et al. Influence of inflammatory cells and serum on the performance of implantable glucose sensors. J Biomed Mater Res 2001, 54, 69-75.
Godsland et al., *Maximizing the Success Rate of Minimal Model Insulin Sensivity Mearsurement in Humans: The Importance of Basal Glucose Levels*, , The Biochemical Society and the Medical Research Society, (2001) 1-9.
Gregg et al. *Cross-Linked Redox Gels Containing Glucose Oxidase for Amperometric Biosensor Applications*, Anal. Chem. (1990) 62, 258-263.

(56) References Cited

OTHER PUBLICATIONS

Heller, A., *Electrical Connection of Enzyme Redox Centers to Electrodes*, J. Phys. Chem. 1992, 96, pp. 3579-3587.
Hitchman, M. L. 1978. "Measurement of Dissolved Oxygen." In Elving et al.(Eds.). Chemical Analysis, vol. 49, Chap. 3, pp. 34-49, 59-123. New York: John Wiley & Sons.
Jensen et al. 1997. Fast wave forms for pulsed electrochemical detection of glucose by incorporation of reductive desorption of oxidation products. *Analytical Chemistry*, 69(9):1776-1781.
Kargol et al. Studies on the structural properties of porous membranes: measurement of linear dimensions of solutes. Biophys Chem 2001, 91, 263-271.
Kurnik et al. 1999. Application of the mixtures of experts algorithm for signal processing in a noninvasive glucose monitoring system. *Sensors and Actuators*, B 60:19-26.
Lee et al. Effects of pore size, void volume, and pore connectivity on tissue responses. Society for Biomaterials 1999, 25$^{th}$ Annual Meeting, 171.
Luong et al., *Solubilization of Multiwall Carbon Nanotubes by 3-Aminopropyltriethoxysilane Towards the Fabrication of Electrochemical Biosensors with Promoted Elecron Transfer*, Electronanalysis 16 No. 1-2, pp. 132-139 (2004).
Makale et al. 2003. Tissue window chamber system for validation of implanted oxygen sensors. *Am. J. Physiol. Heart Circ. Physiol.*, 284:H2288-2294.
Mancy et al. 1962. A galvanic cell oxygen analyzer. *Journal of Electroanalytical Chemistry*, 4:65-92.
McKean, et al. *A Telemetry Instrumentation System for Chronically Implanted Glucose and Oxygen Sensors*, Transactions on Biomedical Engineering vol. 35, No. 7 Jul. 1988 pp. 526-532.
Miller, A. Human monocyte/macrophage activation and interleukin 1 generation by biomedical polymers. J Biomed Mater Res 1988, 23, 713-731.
Miller et al. Generation of IL-1 like activity in response to biomedical polymer implants: a comparison of in vitro and in vivo models. J Biomed Mater Res 1989, 23, 1007-1026.
Miller et al. In vitro stimulation of fibroblast activity by factors generated from human monocytes activated by biomedical polymers. Journal of J Biomed Mater Res 1989, 23, 911-930.
Mowery et al. Preparation and characterization of hydrophobic polymeric films that are thromboresistant via nitric oxide release. Biomaterials 2000, 21, 9-21.
Nam et al. A novel fabrication method of macroporous biodegradable polymer scaffolds using gas foaming salt as a porogen additive. J Biomed Mater Res 2000, 53, 1-7.
Okuda, J.; Miwa, I. Mutarotase effect on micro determinations of D-glucose and its anomers with—D-glucose oxidase. Anal Biochem 1971, 43, 312-315.
Pickup et al., *Responses and Calibration of Amperomehic Glucose Sensors Implanted in the Subcutaneous Tissue of Man*, ACTA Diabetol, pp. 143-148. (1993).
Ratner, B.D. Reducing capsular thickness and enhancing angiogenesis around implant drug release systems. J Control Release 2002, 78, 211-218.
Rhodes et al. 1994. Prediction of pocket-portable and implantable glucose enzyme electrode performance from combined species permeability and digital simulation analysis. *Analytical Chemistry*, 66(9):1520-1529.
Sakakida et al. *Development of Ferrocene-Mediated Needle-Type Glucose Sensor as a Measure of True Subcutaneous Tissue Glucose Concentrations*, Artif. Organs Today, vol. 2 No. 2, pp. 145-158 (1992).
Sakakida et al. *Ferrocene-Mediated Needle Type Glucose Sensor Covered with Newly Designed Biocompatible Membran*, Sensors and Actuators B, vol. 13-14, pp. 319-322 (1993).
Schmidt et al. 1993. Glucose concentration in subcutaneous extracellular space. *Diabetes Care*, 16(5):695-700.
Schmidtke, D. W.; Heller, A. Accuracy of the one-point in vivo calibration of "wired" glucose oxidase electrodes implanted in jugular veins of rats in periods of rapid rise and decline of the glucose concentration. Anal Chem 1998, 70, 2149-2155.
Shichiri et al. *Glycaemic Control in Pancreatectomized Dogs with a Wearable Artificial Endocrine Pancreas*, Diabetologia (1983) 24 pp. 179-184.
Shichiri et al., *Membrane Design for Extending the Long-Life of an Implantable Glucose Sensor*, Diab. Nutr. Metab., 2, pp. 309-313 (1989).
Shichiri et al., *Needle Type Glucose Sensor for Wearable Artificial Endocrine Pancreas*, Implantable Sensors for Closed-Loop Prosthetic Systems, Chapter 15, pp. 197-210.
Shichiri et al., *Telemetry Glucose Monitoring Device with Needle-Type Glucose Sensor: A Useful Tool for Blood Glucose Monitoring in Diabetic Individuals*, Diabetes Care, Inc. Vo. 9, No. 3, 1986 pp. 298-301.
Shults et al. *A Telemetry-Instrumentation System for Monitoring Multiple Subcutaneously Implanted Glucose Sensors*, Transactions on Biomedical Engineering vol. 41, No. 10 Oct. 1994. pp. 937-942.
Sieminski et al. Biomaterial-microvasculature interactions. Biomaterials 2000, 21, 2233-2241.
Sternberg et al. *Study and Development of Multilayer Needle-type Enzymebased Glucose Microsensors*, Biosensors vol. 4 pp. 27-40 (1988).
Tang et al. Fibrin(ogen) mediates acute inflammatory responses to biomaterials. J Exp Med 1993, 178, 2147-2156.
Tang et al. Inflammatory responses to biomaterials. Am J Clin Pathol 1995, 103, 466-471.
Tang et al. Mast cells mediate acute inflammatory responses to implanted biomaterials. Proc Nati Acad Sci U S A 1998, 95, 6841-8846.
Tang et al. Molecular determinants of acute inflammatory responses to biomaterials. J Clin Invest 1996, 97, 1329-1334.
Thompson et al., In Vivo *Probes: Problems and Perspectives*, Department of Chemistry, University of Toronto, Canada, pp. 255-261.
Tibell et al. Survival of macroencapsulated allogeneic parathyroid tissue one year after transplantation in nonimmunosuppressed humans. Cell Transplant 2001, 10, 591-9.
Trajanoski et al. 1998. Neural predictive controller for insulin delivery using the subcutaneous route. *IEEE Transactions on Biomedical Engineering*, 45(9):1122-1134.
Updike et al. 1982. Implanting the glucose enzyme electrode: Problems, progress, and alternative solutions. *Diabetes Care*, 5(3):207-212.
Velho et al., *Strategies for Calibrating a Subcutaneous Glucose Sensor*, Biomed. Biochim. 48, 11/12, 957-964.
Wade Jr., L.G. Organic Chemistry, Chapter 17, Reactions of Aromatic Compounds pp. 762-763.
Wilson et al., *Progress Toward the Development of an Implantable Sensor for Glucose*, Clinical Chemistry, vol. 38, No. 9, 1992 pp. 1613-1617.
Wood, W. et al., Hermetic Sealing with Epoxy. Mechanical Engineering Mar. 1990, 1-3.
Wu et al. 1999. In situ electrochemical oxygen generation with an immunoisolation device. *Ann. N. Y. Acad. Sci.*, 875:105-125.
Yang, et al., *A Comparison of Physical Properties and Fuel Cell Performance of Nafion and Zirconium Phosphate/Nafion Composite Membranes*, Journal of Membrane Science 237 (2004) 145-161.
Bellucci et al. Jan. 1986. Electrochemical behaviour of graphite-epoxy composite materials (GECM) in aqueous salt solutions, Journal of Applied Electrochemistry, 16(1):15-22.
Bindra et al. 1991. Design and In Vitro Studies of a Needle-Type Glucose Senso for Subcutaneous Monitoring. Anal. Chem 63:1692-96.
Bobbioni-Harsch et al. 1993. Lifespan of subcutaneous glucose sensors and their performances during dynamic glycaemia changes in rats, J. Biomed. Eng. 15:457-463.
Brooks et al. "Development of an on-line glucose sensor for fermentation monitoring," Biosensors, 3:45-56 (1987/88).
Cass et al. "Ferrocene-mediated enzyme electrodes for amperometric determination of glucose," Anal. Chem., 36:667-71 (1984).

(56) References Cited

OTHER PUBLICATIONS

Davies, et al. 1992. Polymer membranes in clinical sensor applications. I. An overview of membrane function, Biomaterials, 13(14):971-978.
Heller, "Electrical wiring of redox enzymes," Acc. Chem. Res., 23:128-134 (1990).
Hicks, 1985. In Situ Monitoring, Clinical Chemistry, 31(12):1931-1935.
Hu, et al. 1993. A needle-type enzyme-based lactate sensor for in vivo monitoring, Analytica Chimica Acta, 281:503-511.
Johnson et al. 1992. In vivo evaluation of an electroenzymatic glucose sensor implanted in subcutaneous tissue. Biosensors & Bioelectronics, 7:709-714.
Kawagoe et al. 1991. Enzyme-modified organic conducting salt microelectrode, Anal. Chem. 63:2961-2965.
Kerner et al. "The function of a hydrogen peroxide-detecting electroenzymatic glucose electrode is markedly impaired in human sub-cutaneous tissue and plasma," Biosensors & Bioelectronics, 8:473-482 (1993).
Ladd et al., Structure Determination by X-ray Crystallography, 3rd ed. Plenum, 1996, Ch. 1, pp. xxi-xxiv and -58.
Maidan et al. 1992. Elimination of Electrooxidizable Interferent-Produced Currents in Amperometric Biosensors, Analytical Chemistry, 64:2889-2896.
Mastrototaro et al. "An electroenzymatic glucose sensor fabricated on a flexible substrate," Sensors and Actuators B, 5:139-44 (1991).
Moatti-Sirat et al. 1992. Towards continuous glucose monitoring: in vivo evaluation of a miniaturized glucose sensor implanted for several days in rat subcutaneous tissue. Diabetologia 35:224-230.
Murphy, et al. 1992. Polymer membranes in clinical sensor applications. II. The design and fabrication of permselective hydrogels for electrochemical devices, Biomaterials, 13(14):979-990.
Ohara, et al. Dec. 1993. Glucose electrodes based on cross-linked bis(2,2'-bipyridine)chlorosmium(+/2+) complexed poly(1-vinylimidazole) films, Analytical Chemistry, 65:3512-3517.
Pickup et al. "Implantable glucose sensors: choosing the appropriate sensor strategy," Biosensors, 3:335-346 (1987/88).
Pickup et al. "In vivo molecular sensing in diabetes mellitus: an implantable glucose sensor with direct electron transfer," Diabetologia, 32:213-217 (1989).
Pishko et al. "Amperometric glucose microelectrodes prepared through immobilization of glucose oxidase in redox hydrogels," Anal. Chem., 63:2268-72 (1991).
Poitout, et al. 1991. In Vitro and In Vivo Evaluation in Dogs of a Miniaturized Glucose Sensor, ASAIO Transactions, 37:M298-M300.
Reach et al. 1992. Can continuous glucose monitoring be used for the treatment of diabetes? Analytical Chemistry 64(5):381-386.
Rebrin et al. "Automated feedback control of subcutaneous glucose concentration in diabetic dogs," Diabetologia, 32:573-76 (1989).
Sharkawy et al. 1996. Engineering the tissue which encapsulates subcutaneous implants. I. Diffusion properties, J Biomed Mater Res, 37:401-412.
Shaw et al. "In vitro testing of a simply constructed, highly stable glucose sensor suitable for implantation in diabetic patients," Biosensors & Bioelectronics, 6:401-406 (1991).
Turner and Pickup, "Diabetes mellitus: biosensors for research and management," *Biosensors*, 1:85-115 (1985).
Updike et al. 1997. Principles of long-term fully implanted sensors with emphasis on radiotelemetric monitoring of blood glucose form inside a subcutaneous foreign body capsule (FBC). In Fraser, ed., Biosensors in the Body. New York. John Wiley & Sons, pp. 117-137.
von Woedtke et al. 1989. In situ calibration of implanted electrochemical glucose sensors. Biomed Biochim. Acta 48(11/12):943-952.
ISR and WO for PCT/US06/31496, filed Aug. 10, 2006.
Office Action dated Mar. 24, 2008 in U.S. Appl. No. 10/838,912.
Office Action dated May 5, 2008 in U.S. Appl. No. 11/077,713.
Office Action dated Jun. 5, 2008 in U.S. Appl. No. 10/846,150.
Office Action dated Jun. 5, 2008 in U.S. Appl. No. 10/838,909.
Office Action dated Jun. 12, 2008 in U.S. Appl. No. 09/447,227.
Office Action dated Jul. 16, 2008 in U.S. Appl. No. 10/838,912.
Office Action dated Sep. 18, 2008 in U.S. Appl. No. 11/439,630.
Office Action dated Sep. 29, 2008 in U.S. Appl. No. 12/037,830.
Office Action dated Sep. 29, 2008 in U.S. Appl. No. 12/037,812.
Office Action dated Oct. 8, 2008 in U.S. Appl. No. 10/842,716.
Office Action dated Dec. 9, 2008 in U.S. Appl. No. 10/846,150.
Office Action dated Dec. 11, 2008 in U.S. Appl. No. 09/447,227.
Office Action dated Feb. 4, 2009 in U.S. Appl. No. 10/768,889.
Office Action dated Feb. 10, 2009 in U.S. Appl. No. 11/077,713.
Office Action dated Feb. 23, 2009 in U.S. Appl. No. 11/439,630.
Office Action dated Feb. 26, 2009 in U.S. Appl. No. 12/037,830.
Office Action dated Mar. 16, 2009 in U.S. Appl. No. 10/838,909.
Office Action dated Apr. 1, 2009 in U.S. Appl. No. 12/037,812.
Office Action dated May 26, 2009 in U.S. Appl. No. 09/447,227.
Office Action dated Jun. 9, 2009 in U.S. Appl. No. 10/846,150.
Office Action dated Jul. 10, 2009 in U.S. Appl. No. 10/842,716.
Office Action dated Jul. 24, 2009 in U.S. Appl. No. 12/037,812.
Alcock & Turner. 1994. Continuous Analyte Monitoring to Aid Clinical Practice. IEEE Engineering in Med. & Biol. Mag. 13:319-325.
American Heritage Dictionary, 4th Edition. 2000. Houghton Mifflin Company, p. 82.
Aussedat et al. 1997. A user-friendly method for calibrating a subcutaneous glucose sensor-based hypoglycaemic alarm. Biosensors & Bioelectronics 12(11):1061-1071.
Boedeker Plastics, Inc. 2009. Polyethylene Specifications Data Sheet, http://www.boedeker.com/polye_p.htm [Aug. 19, 2009 3:36:33 PM].
Freedman et al. 1991. Statistics, Second Edition, W.W. Norton & Company, p. 74.
Hamilton Syringe Selection Guide. 2006. Syringe Selection. www.hamiltoncompany.com.
Hoel, Paul G. 1976. Elementary Statistics, Fourth Edition. John Wiley & Sons, Inc.. pp. 113-114.
Ko, Wen H. 1985. Implantable Sensors for Closed-Loop Prosthetic Systems, Futura Pub. Co., Inc., Mt. Kisco, NY, Chapter 15:197-210.
Merriam-Webster Online Dictionary. Definition of "acceleration". http://www.merriam-webster.com/dictionary/Acceleration Jan. 11, 2010.
Merriam-Webster Online Dictionary. Definition of "system". http://www.merriam-webster.com/dictionary/System Jan. 11, 2010.
Oxford English Dictionary Online. Definition of "impending". http://www.askoxford.com/results/?view=dev dict&field-12668446 Impending&branch= Jan. 11, 2010.
Pickup et al. 1993. Developing glucose sensors for in vivo use. Elsevier Science Publishers Ltd (UK), TIBTECH vol. 11: 285-291.
Reusch. 2004. Chemical Reactivity. Organometallic Compounds. Virtual Textbook of Organic Chem. pp. 1-16, http://www.cem.msu.edu/~reusch/VirtualText/orgmetal.htm.
San Diego Plastics, Inc. 2009. Polyethylene Data Sheet, http://www.sdplastics.com/polyeth.html.
Vadgama. 1988. Diffusion limited enzyme electrodes. NATO ASI Series: Series C, Math and Phys. Sci. 226:359-377.
Wiley Electrical and Electronics Engineering Dictionary. 2004. John Wiley & Sons, Inc. pp. 141, 142, 548, 549.
Wilkins et al. 1995. Integrated implantable device for long-term glucose monitoring. Biosens. Bioelectron 10:485-494.
Ye et al. 1993. High Current Density 'Wired' Quinoprotein Glucose Dehydrogenase Electrode. Anal. Chem. 65:238-241.
Office Action dated Aug. 7, 2009 in U.S. Appl. No. 12/037,830.
Office Action dated Jun. 6, 2005 in U.S. Appl. No. 10/646,333.
Office Action dated Oct. 22, 2009 in U.S. Appl. No. 11/416,825.
Office Action dated Oct. 14, 2009 in U.S. Appl. No. 11/416,734.
Office Action dated Oct. 24, 2007 in U.S. Appl. No. 11/055,779.
Office Action dated Sep. 2, 2009 in U.S. Appl. No. 11/077,713.
Office Action dated Sep. 2, 2009 in U.S. Appl. No. 11/439,630.
Aalders et al. 1991. Development of a wearable glucose sensor; studies in healthy volunteers and in diabetic patients. The International Journal of Artificial Organs 14(2):102-108.
Abe et al. 1992. Characterization of glucose microsensors for intracellular measurements. Anal. Chem. 64(18):2160-2163.

(56) References Cited

OTHER PUBLICATIONS

Abel et al. 1984. Experience with an implantable glucose sensor as a prerequisite of an artificial beta cell, Biomed. Biochim. Acta 43(5):577-584.
Abel et al. 2002. Biosensors for in vivo glucose measurement: can we cross the experimental stage. Biosens Bioelectron 17:1059-1070.
Amin et al. 2003. Hypoglycemia prevalence in prepubertal children with type 1 diabetes on standard insulin regimen: Use of continuous glucose monitoring system. Diabetes Care 26(3):662-667.
Atanasov et al. 1997. Implantation of a refillable glucose monitoring-telemetry device. Biosens Bioelectron 12:669-680.
Bailey et al. 2007. Reduction in hemoglobin A1c with real-time continuous glucose monitoring: results from a 12-week observational study. Diabetes Technology & Therapeutics 9(3):203-210.
Bessman et al., Progress toward a glucose sensor for the artificial pancreas, Proceedings of a Workshop on Ion-Selective Microelectrodes, Jun. 4-5, 1973, Boston, MA, 189-197.
Biermann et al. 2008. How would patients behave if they were continually informed of their blood glucose levels? A simulation study using a "virtual" patient. Diab. Thechnol. & Therapeut., 10:178-187.
Bisenberger et al. 1995. A triple-step potential waveform at enzyme multisensors with thick-film gold electrodes for detection of glucose and sucrose. Sensors and Actuators, B 28:181-189.
Bode et al. 1999. Continuous glucose monitoring used to adjust diabetes therapy improves glycosylated hemoglobin: A pilot study. Diabetes Research and Clinical Practice 46:183-190.
Bode et al. 2000. Using the continuous glucose monitoring system to improve the management of type 1 diabetes. Diabetes Technology & Therapeutics, 2(Suppl 1):S43-48.
Bode, B. W. 2000. Clinical utility of the continuous glucose monitoring system. Diabetes Technol Ther, 2(Suppl 1):S35-41.
Boland et al. 2001. Limitations of conventional methods of self-monitoring of blood glucose. Diabetes Care 24(11):1858-1862.
Bowman, L.; Meindl, J. D. 1986. The packaging of implantable integrated sensors. IEEE Trans Biomed Eng BME33(2):248-255.
Brauker et al. 1996. Local Inflammatory Response Around Diffusion Chambers Containing Xenografts Transplantation 61(12):1671-1677.
Braunwald, 2008. Biomarkers in heart failure. N. Engl. J. Med., 358: 2148-2159.
Bremer et al. 2001. Benchmark data from the literature for evaluation of new glucose sensing technologies. Diabetes Technology & Therapeutics 3(3):409-418.
Bruckel et al. 1989. In vivo measurement of subcutaneous glucose concentrations with an enzymatic glucose sensor and a wick method. Klin Wochenschr 67:491-495.
Cai et al. 2004. A wireless, remote query glucose biosensor based on a pH-sensitive polymer. Anal Chem 76(4):4038-4043.
Campanella et al. 1993. Biosensor for direct determination of glucose and lactate in undiluted biological fluids. Biosensors & Bioelectronics 8:307-314.
Candas et al (1994). "An adaptive plasma glucose controller basedon a nonlinear insulin/glucose model." *IEEE Transactions on Biomedical Engineering*, 41(2): 116-124.
Cassidy et al., Apr. 1993. Novel electrochemical device for the detection of cholesterol or glucose, Analyst, 118:415-418.
Chase et al. 2001. Continuous subcutaneous glucose monitoring in children with type 1 diabetes. Pediatrics 107:222-226.
Chia et al. 2004. Glucose sensors: toward closed loop insulin delivery. Endocrinol Metab Clin North Am 33:175-95.
Ciba® Irgacure 2959 Photoinitiator Product Description, Ciba Specialty Chemicals Inc., Basel, Switzerland.
Claremont et al. 1986. Subcutaneous implantation of a ferrocene-mediated glucose sensor in pigs. Diabetologia 29:817-821.
Claremont et al. Jul. 1986. Potentially-implantable, ferrocene-mediated glucose sensor. J. Biomed. Eng. 8:272-274.
Clark et al. 1981. One-minute electrochemical enzymic assay for cholesterol in biological materials, Clin. Chem. 27(12):1978-1982.
Clark et al. 1987. Configurational cyclic voltammetry: increasing the specificity and reliablity of implanted electrodes, IEEE/Ninth Annual Conference of the Engineering in Medicine and Biology Society, pp. 0782-0783.
Clark et al. 1988. Long-term stability of electroenzymatic glucose sensors implanted in mice. Trans Am Soc Artif Intern Organs 34:259-265.
CLSI. Performance metrics for continuous interstitial glucose monitoring; approved guideline, CLSI document POCT05-A. Wayne, PA: Clinical and Laboratory Standards Institute: 2008 28(33), 72 pp.
Colangelo et al. 1967. Corrosion rate measurements in vivo, Journal of Biomedical Materials Research, 1:405-414.
Colowick et al. 1976. Methods in Enzymlology, vol. XLIV, Immobilized Enzymes. New York: Academic Press.
Cox et al. 1985. Accuracy of perceiving blood glucose in IDDM. Diabetes Care 8(6):529-536.
Csoregi et al., 1994. Design, characterization, and one-point in vivo calibration of a subcutaneously implanted glucose electrode. Anal Chem. 66(19):3131-3138.
Danielsson et al. 1988. Enzyme thermistors, Methods in Enzymology, 137:181-197.
Dassau et al., In silico evaluation platform for artifical pancreatic β-cell development—a dynamic simulator for closed loop control with hardware-in-the-loop, Diabetes Technology & Therapeutics, 11(3):1-8, 2009.
Davis et al. 1983. Bioelectrochemical fuel cell and sensor based on a quinoprotein, alcohol dehydrogenase. *Enzyme Microb. Technol.*, vol. 5, September, 383-388.
Direct 30/30® meter (Markwell Medical) (Catalog).
Dixon et al. 2002. Characterization in vitro and in vivo of the oxygen dependence of an enzyme/polymer biosensor for monitoring brain glucose. Journal of Neuroscience Methods 119:135-142.
DuPont Dimension AR® (Catalog), 1998.
Durliat et al. 1976. Spectrophotometric and electrochemical determinations of L(+)-lactate in blood by use of lactate dehydrogenase from yeast, Clin. Chem. 22(11):1802-1805.
Edwards Lifesciences. Accuracy for your and your patients. Marketing materials, 4 pp. 2002.
El Degheidy et al. 1986. Optimization of an implantable coated wire glucose sensor. J. Biomed Eng. 8: 121-129.
El-Khatib et al. 2007. Adaptive closed-loop control provides blood-glucose regulation using dual subcutaneous insulin and glucagon infusion in diabetic swine, Journal of Diabetes Science and Technology, 1(2):181-192.
Ernst et al. 2002. Reliable glucose monitoring through the use of microsystem technology. Anal. Bioanal. Chem. 373:758-761.
Fahy et al., An analysis: hyperglycemic intensive care patients need continuous glocuse monitoring—easier said than done, Journal of Diabetese Science and Technology, 2(2):201-204, Mar. 2008.
Feldman et al. 2003. A continuous glucose sensor based on wired enzyme technology—results from a 3-day trial in patients with type 1 diabetes. Diabetes Technol Ther 5(5):769-779.
Fischer et al. 1987. Assessment of subcutaneous glucose concentration: validation of the wick technique as a reference for implanted electrochemical sensors in normal and diabetic dogs, Diabetologia 30:940-945.
Fischer et al. 1989. Oxygen Tension at the Subcutaneous Implantation Site of Glucose Sensors. Biomed. Biochem 11/12:965-972.
Fischer et al. 1995. Hypoglycaemia-warning by means of subcutaneous electrochemical glucose sensors: an animal study, Horm. Metab. Rese. 27:53.
Frohnauer et al. 2001. Graphical human insulin time-activity profiles using standardized definitions. Diabetes Technology & Therapeutics 3(3):419-429.
Frost et al. 2002. Implantable chemical sensors for real-time clinical monitoring: Progress and challenges. Current Opinion in Chemical Biology 6:633-641.
Gabbay et al. 2008. Optical coherence tomography-based continuous noninvasive glucose monitoring in patients with diabetes. Diab. Thechnol. & Therapeut., 10:188-193.
Ganesan et al., Gold layer-based dual crosslinking procedure of glucose oxidase with ferrocene monocarboxylic acid provides a stable biosensor, Analytical Biochemistry 343:188-191, 2005.

(56) References Cited

OTHER PUBLICATIONS

Ganesh et al., Evaluation of the VIA® blood chemistry monitor for glucose in healthy and diabetic volunteers, Journal of Diabetese Science and Technology, 2(2):182-193, Mar. 2008.
Garg et al. 2004. Improved Glucose Excursions Using an Implantable Real-Time continuous Glucose Sensor in Adults with Type I Diabetes. Diabetes Care 27:734-738.
Gerritsen et al. 1999. Performance of subcutaneously implanted glucose sensors for continuous monitoring. The Netherlands Journal of Medicine 54:167-179.
Gerritsen, M. 2000. Problems associated with subcutaneously implanted glucose sensors. Diabetes Care 23(2):143-145.
Gilligan et al. 2004, Feasibility of continuous long-term glucose monitoring from a subcutaneous glucose sensor in humans. Diabetes Technol Ther 6:378-386.
Gouda et al., Jul. 4, 2003. Thermal inactiviation of glucose oxidase, The Journal of Biological Chemistry, 278(27):24324-24333.
Gough et al. 2000. Immobilized glucose oxidase in implantable glucose sensor technology. Diabetes Technology & Therapeutics 2(3):377-380.
Gough et al. 2003. Frequency characterization of blood glucose dynamics. Annals of Biomedical Engineering 31:91-97.
Gross et al. 2000. Efficacy and reliability of the continuous glucose monitoring system. Diabetes Technology & Therapeutics, 2(Suppl 1):S19-26.
Gross et al. 2000. Performance evaluation of the MiniMed® continuous glucose monitoring system during patient home use. Diabetes Technology & Therapeutics 2(1):49-56.
Guerci et al., Clinical performance of CGMS in type 1 diabetic patents treated by continuous subcutaneous insulin infusion using insulin analogs, Diabetes Care, 26:582-589, 2003.
Hall et al. 1998. Electrochemical oxidation of hydrogen peroxide at platinum electrodes. Part I: An adsorption-controlled mechanism. Electrochimica Acta, 43(5-6):579-588.
Hall et al. 1998. Electrochemical oxidation of hydrogen peroxide at platinum electrodes. Part II: Effect of potential. Electrochimica Acta 43(14-15):2015-2024.
Hall et al. 1999. Electrochemical oxidation of hydrogen peroxide at platinum electrodes. Part III: Effect of temperature. Electrochimica Acta, 44:2455-2462.
Hall et al. 1999. Electrochemical oxidation of hydrogen peroxide at platinum electrodes. Part IV: Phosphate buffer dependence. Electrochimica Acta, 44:4573-4582.
Hall et al. 2000. Electrochemical oxidation of hydrogen peroxide at platinum electrodes. Part V: Inhibition by chloride. Electrochimica Acta, 45:3573-3579.
Hashiguchi et al. (1994). "Development of a miniaturized glucose monitoring system by combining a needle-type glucose sensor with microdialysis sampling method: Long-term subcutaneous tissue glucose monitoring in ambulatory diabetic patients," *Diabetes C*.
Heller, A. 1999. Implanted electrochemical glucose sensors for the management of diabetes. Annu Rev Biomed Eng 1:153-175.
Heller, A. 2003. Plugging metal connectors into enzymes. Nat Biotechnol 21:631-2.
Hrapovic et al. 2003. Picoamperometric detection of glucose at ultrasmall platinum-based biosensors: preparation and characterization. Anal Chem 75:3308-3315.
http://www.merriam-webster.com/dictionary, definition for "aberrant," Aug. 19, 2008, p. 1.
Huang et al. A 0.5mV passive telemetry IC for biomedical applications. Swiss Federal Institute of Technology. 4 pp.
Huang et al. Aug. 1975. Electrochemical Generation of Oxygen. 1: The Effects of Anions and Cations on Hydrogen Chemisorption and Aniodic Oxide Film Formation on Platinum Electrode. 2: The Effects of Anions and Cations on Oxygen Generation on Platinum E.
Hunter et al. 2000. Minimally Invasive Glucose Sensor and Insulin Delivery System. MIT Home Automation and Healthcare Consortium. Progress Report No. 25.

Ishikawa et al. 1998. Initial evaluation of a 290-mm diameter subcutaneous glucose sensor: Glucose monitoring with a biocompatible, flexible-wire, enzyme-based amperometric microsensor in diabetic and nondiabetic humans. Journal of Diabetes and Its Compl.
Jeutter, D. C. 1982. A transcutaneous implanted battery recharging and biotelemeter power switching system. IEEE Trans Biomed Eng 29:314-321.
Johnson (1991). "Reproducible electrodeposition of biomolecules for the fabrication of miniature electroenzymatic biosensors," *Sensors and Actuators B*, 5:85-89.
Jovanovic, L. 2000. The role of continuous glucose monitoring in gestational diabetes mellitus. Diabetes Technology & Therapeutics, 2 Suppl 1, S67-71.
Kacaniklic May-Jun. 1994. Electroanalysis, 6(5-6):381-390.
Kamath et al. Calibration of a continuous glucose monitor: effect of glucose rate of change, Eighth Annual Diabetes Technology Meeting, Nov. 13-15, 2008, p. A88.
Kang et al. 2003. In vitro and short-term in vivo characteristics of a Kel-F thin film modified glucose sensor. Anal Sci 19:1481-1486.
Kaufman et al. 2001. A pilot study of the continuous glucose monitoring system. Diabetes Care 24(12):2030-2034.
Kaufman. 2000. Role of the continuous glucose monitoring system in pediatric patients. Diabetes Technology & Therapeutics 2(1):S-49-S-52.
Keedy et al. 1991. Determination of urate in undiluted whole blood by enzyme electrode. *Biosensors & Bioelectronics*, 6: 491-499.
Kerner et al. 1988. A potentially implantable enzyme electrode for amperometric measurement of glucose, Horm Metab Res Suppl. 20:8-13.
Klueh et al. 2003. Use of Vascular Endothelia Cell Growth Factor Gene Transfer to Enhance Implantable Sensor Function in Vivo, Biosensor Function and Vegf-Gene Transfer, pp. 1072-1086.
Kondo et al. 1982. A miniature glucose sensor, implantable in the blood stream. Diabetes Care. 5(3):218-221.
Koschinsky et al. 1988. New approach to technical and clinical evaluation of devices for self-monitoring of blood glucose. Diabetes Care 11(8): 619-619.
Koschinsky et al. 2001. Sensors for glucose monitoring: Technical and clinical aspects. Diabetes Metab. Res. Rev. 17:113-123.
Kost et al. 1985. Glucose-sensitive membranes containing glucose oxidase: activitiy, swelling, and permeability studies, Journal of Biomedical Materials Research 19:1117-1133.
Koudelka et al. 1989. In vivo response of microfabricated glucose sensors to glycemia changes in normal rats. Biomed Biochim Acta 48(11-12):953-956.
Koudelka et al. 1991. In-vivo behaviour of hypodermically implanted microfabricated glucose sensors. Biosensors & Bioelectronics 6:31-36.
Kraver et al. 2001. A mixed-signal sensor interface microinstrument. Sensors and Actuators A 91:266-277.
Kruger et al. 2000. Psychological motivation and patient education: A role for continuous glucose monitoring. Diabetes Technology & Therapeutics, 2(Suppl 1):S93-97.
Kulys et al., 1994. Carbon-paste biosensors array for long-term glucose measurement, Biosensors& Beioelectronics, 9:491-500.
Kunjan et al., Automated blood sampling and glocuse sensing in critical care settings, Journal of Diabetes Science and Technology 2(3):194-200, Mar. 2008.
Kurtz et al. 2005. Recommendations for blood pressure measurement in humans and experimental animals, Part 2: Blood pressure measurement in experimental animals, A statement for professionals from the subcommittee of professional and public education of.
Lehmann et al. May 1994. Retrospective valication of a physiological model of glucose-iunsulin interaaction in tyhpe 1 diabetes mellitus, Med. Eng. Phys. 16:193-202.
Lerner et al. 1984. An implantable electrochemical glucose sensor. Ann. N. Y. Acad. Sci. 428:263-278.
Lewandowski et al. 1988. Evaluation of a miniature blood glucose sensor. Trans Am Soc Artif Intern Organs 34:255-258.
Leypoldt et al. 1984. Model of a two-substrate enzyme electrode for glucose. Anal. Chem. 56:2896-2904.

(56) References Cited

OTHER PUBLICATIONS

Linke et al. 1994. Amperometric biosensor for in vivo glucose sensing based on glucose oxidase immobilized in a redox hydrogel. Biosensors & Bioelectronics 9:151-158.
Lowe, 1984. Biosensors, Trends in Biotechnology, 2(3):59-65.
Lyandres et al. (2008). Progress toward an in vivo surface-enhanced raman spectroscopy glucose sensor. *Diabetes Technology & Therapeutics*, 10(4): 257-265.
Malin et al. 1999. Noninvasive Prediction of Glucose by Near-Infrared Diffuse Reflectance Spectroscopy. Clinical Chemistry 45:9, 1651-1658.
Maran et al. 2002. Continuous subcutaneous glucose monitoring in diabetic patients: A multicenter analysis. Diabetes Care 25(2):347-352.
March, W. F. 2002. Dealing with the delay. Diabetes Technol Ther 4(1):49-50.
Marena et al. 1993. The artifical endocrine pancreas in clinical practice and research. Panminerva Medica 35(2):67-74.
Mascini et al. 1989. Glucose electrochemical probe with extended linearity for whole blood. *J Pharm Biomed Anal* 7(12): 1507-1512.
Mastrototaro et al. 2003. Reproducibility of the continuous glucose monitoring system matches previous reports and the intended use of the product. Diabetes Care 26:256; author reply p. 257.
Mastrototaro, J. J. 2000. The MiniMed continuous glucose monitoring system. Diabetes Technol Ther 2(Suppl 1):S13-8.
Matsumoto et al. 1998. A micro-planar amperometeric glucose sensor unsusceptible to interference species. Sensors and Actuators B 49:68-72.
Matthews et al. 1988. An amperometric needle-type glucose sensor testing in rats and man. Diabetic Medicine 5:248-252.
Mazze et al. 2008. Characterizing glucose exposure for individuals with normal glucose tolerance using continuous glucose monitoring and ambulatory glucose profile analysis. Diab. Thechnol. & Therapeut., 10:149-159.
McCartney et al. 2001. Near-infrared fluorescence lifetime assay for serum glucose based on allophycocyanin-labeled concanavalin A. Anal Biochem 292:216-221.
McGrath et al. 1995. The use of differential measurements with a glucose biosensor for interference compensation during glucose determinations by flow injection analysis. Biosens Bioelectron 10:937-943.
Memoli et al. 2002. A comparison between different immobilised glucoseoxidase-based electrodes. J Pharm Biomed Anal 29:1045-1052.
Merriam-Webster Online Dictionary. The term "nominal." http://www.m-w.com/dictionary/nominal.
Meyerhoff et al. 1992. On line continuous monitoring of subcutaneous tissue glucose in men by combining portable glucosensor with microdialysis. Diabetologia 35:1087-1092.
Moatti-Sirat et al. 1992. Evaluating in vitro and in vivo the interference of ascorbate and acetaminophen on glucose detection by a needle-type glucose sensor, Biosensors & Bioelectronics 7:345-352.
Moatti-Sirat et al., Reduction of acetaminophen interference in glucose sensors by a composite Nafion membrane: demonstration in rats and man, Diabetologia 37(6):610-616, Jun. 1994.
Morff et al. 1990. Microfabrication of reproducible, economical, electroenzymatic glucose sensors, Annual International Conference of the IEEE Engineering in Medicine and Biology Society, 12(2):0483-0484.
Mosbach et al. 1975. Determination of heat changes in the proximity of immobilized enzymes with an enzyme termistor and its use for the assay of metobolites, Biochim. Biophys. Acta. (Enzymology), 403:256-265.
Motonaka et al. 1993. Determination of cholesteral and cholesteral ester with novel enzyme microsensors, Anal. Chem. 65:3258-3261.
Muslu. 1991. Trickling filter performance. Apllied Biochemistry and Biotechnology 37:211-224.
Nafion® 117 Solution Product Description, Product No. 70160, Sigma-Aldrich Corp., St. Louis, MO.

Ohara et al. 1994. "Wired" enzyme electrodes for amperometric determination of glucose or lactate in the presence of interfering substances. Anal Chem 66:2451-2457.
Palmisano et al. 2000. Simultaneous monitoring of glucose and lactate by an interference and cross-talk free dual electrode amperometric biosensor based on electropolymerized thin films. Biosensors & Bioelectronics 15:531-539.
Patel et al. 2003. Amperometric glucose sensors based on ferrocene containing polymeric electron transfer systems—a preliminary report. Biosens Bioelectron 18:1073-6.
Peacock et al. 2008. Cardiac troponin and outcome in acute heart failure. N. Engl. J. Med., 358: 2117-2126.
Pfeiffer et al. 1992. On line continuous monitoring of subcutaneous tissue glucose is feasible by combining portable glucosensor with microdialysis. Horm. Metab. Res. 25:121-124.
Pfeiffer, E.F. 1990. The glucose sensor: the missing link in diabetes therapy, Horm Metab Res Suppl. 24:154-164.
Pichert et al. 2000. Issues for the coming age of continuous glucose monitoring Diabetes Educ 26(6):969-980.
Pickup et al. 1989. Potentially-implantable, amperometric glucose sensors with mediated electron transfer: improving the operating stability. Biosensors 4:109-119.
Pinner et al., Cross-linking of cellulose acetate by ionizing radiation, Nature, vol. 184, 1303-1304, Oct. 24, 1959.
Pitzer et al. 2001. Detection of hypoglycemia with the GlucoWatch biographer. Diabetes Care 24(5):881-885.
Poitout et al. 1993. A glucose monitoring system for on line estimation in man of blood glucose concentration using a miniaturized glucose sensor implanted in the subcutaneous tissue and a wearable control unit. Diabetologia 36:658-663.
Poitout et al. 1994. Development of a glucose sensor for glucose monitoring in man: the disposable implant concept. Clinical Materials 15:241-246.
Postlethwaite et al. 1996. Interdigitated array electrode as an alternative to the rotated ring-disk electrode for determination of the reaction products of dioxygen reduction. Analytical Chemistry 68:2951-2958.
Prabhu et al. 1981. Electrochemical studies of hydrogen peroxide at a platinum disc electrode, Electrochimica Acta 26(6):725-729.
Quinn et al. 1995. Kinetics of glucose delivery to subcutaneous tissue in rats measured with 0.3-mm amperometric microsensors. The American Physiological Society E155-E161.
Quinn et al. 1997. Biocompatible, glucose-permeable hydrogel for in situ coating of implantable biosensors. Biomaterials 18:1665-1670.
Rabah et al., 1991. Electrochemical wear of graphite anodes during electrolysis of brine, Carbon, 29(2):165-171.
Reach et al. 1986. A Method for Evaluating in vivo the Functional Characteristics of Glucose Sensors. Biosensors 2:211-220.
Reach, G. 2001. Which threshold to detect hypoglycemia? Value of receiver-operator curve analysis to find a compromise between sensitivity and specificity. Diabetes Care 24(5):803-804.
Reach, Gerard. 2001. Letters to the Editor Re: Diabetes Technology & Therapeutics, 2000;2:49-56. Diabetes Technology & Therapeutics 3(1):129-130.
Rebrin et al. 1992. Subcutaenous glucose monitoring by means of electrochemical sensors: fiction or reality? J. Biomed. Eng. 14:33-40.
Rigla et al. 2008. Real-time continuous glucose monitoring together with telemedical assitance improves glycemic control and glucose stability in pump-treated patients. Diab. Thechnol. & Therapeut., 10:194-199.
Rivers et al., Central venous oxygen saturation monitoring in the critically ill patient, Current Opinion in Critical Care, 7:204-211, 2001.
Salardi et al. 2002. The glucose area under the profiles obtained with continuous glucose monitoring system relationships with HbA1c in pediatric type 1 diabetic patients. Diabetes Care 25(10):1840-1844.
Sansen et al. 1985. "Glucose sensor with telemetry system." In Ko, W. H. (Ed.). Implantable Sensors for Closed Loop Prosthetic Systems. Chap. 12, pp. 167-175, Mount Kisco, NY: Futura Publishing Co.

(56) References Cited

OTHER PUBLICATIONS

Sansen et al. 1990. A smart sensor for the voltammetric measurement of oxygen or glucose concentrations. Sensors and Actuators B 1:298-302.
Schmidtke et al., Measurement and modeling of the transient difference between blood and subcutaneous glucose concentrations in the rat after injection of insulin. *Proc Natl Aced Sci U S A* 1998, 95, 294-299.
Schoemaker et al. 2003. The SCGM1 system: Subcutaneous continuous glucose monitoring based on microdialysis technique. Diabetes Technology & Therapeutics 5(4):599-608.
Schoonen et al. 1990 Development of a potentially wearable glucose sensor for patients with diabetes mellitus: design and in-vitro evaluation. Biosensors & Bioelectronics 5:37-46.
Service et al. 1970. Mean amplitude of glycemic excursions, a measure of diabetic instability. Diabetes, 19: 644-655.
Service et al. 1987. Measurements of glucose control. Diabetes Care, 10: 225-237.
Service, R. F. 2002. Can sensors make a home in the body? Science 297:962-3.
Shichiri et al. 1982. Wearable artificial endocrine pancrease with needle-type glucose sensor. Lancet 2:1129-1131.
Skyler, J. S. 2000. The economic burden of diabetes and the benefits of improved glycemic control: The potential role of a continuous glucose monitoring system. Diabetes Technology & Therapeutics 2 Suppl 1:S7-12.
Slater-Maclean et al. 2008. Accuracy of glycemic measurements in the critically ill. Diab. Thechnol. & Therapeut., 10:169-177.
Sokol et al. 1980, Immobilized-enzyme rate-determination method for glucose analysis, Clin. Chem. 26(1):89-92.
Sriyudthsak et al. 1996. Enzyme-epoxy membrane based glucose analyzing system and medical applications. Biosens Bioelectron 11:735-742.
Steil et al. 2003. Determination of plasma glucose during rapid glucose excursions with a subcutaneous glucose sensor. Diabetes Technology & Therapeutics 5(1):27-31.
Stern et al., 1957. Electrochemical polarization: 1. A theoretical analysis of the shape of polarization curves, Journal of the Electrochemical Society, 104(1):56-63.
Sumino T. et al. 1998. Preliminary study of continuous glucose monitoring with a microdialysis technique. Proceedings of the IEEE, 20(4):1775-1778.
Takegami et al. 1992. Pervaporation of ethanol water mixtures using novel hydrophobic membranes containing polydimethylsiloxane, Journal of Membrance Science, 75(93-105).
Tanenberg et al. 2000. Continuous glucose monitoring system: A new approach to the diagnosis of diabetic gastroparesis. Diabetes Technology & Therapeutics, 2 Suppl 1:S73-80.
Tatsuma et al. 1991. Oxidase/peroxidase bilayer-modified electrodes as sensors for lactate, pyruvate, cholesteral and uric acid, Analytica Chimica Acta, 242:85-89.
Thome et al. 1995. -Abstract—Can the decrease in subcutaneous glucose concentration precede the decrease in blood glucose level? Proposition for a push-pull kinetics hypothesis, Horm. Metab. Res. 27:53.
Thomé-Duret et al. 1996. Modification of the sensitivity of glucose sensor implanted into subcutaneous tissue. Diabetes Metabolism, 22:174-178.
Thome-Duret et al. 1996. Use of a subcutaneous glucose sensor to detect decreases in glucose concentration prior to observation in blood, Anal. Chem. 68:3822-3826.
Thomé-Duret et al. 1998. Continuous glucose monitoring in the free-moving rat. Metabolism, 47:799-803.
Tierney et al. 2000. Effect of acetaminophen on the accuracy of glucose measurements obtained with the GlucoWatch biographer. Diabetes Technol Ther 2:199-207.
Tierney et al. 2000. The GlucoWatch® biographer: A frequent, automatic and noninvasive glucose monitor. Ann. Med. 32:632-641.
Torjman et al., Glucose monitoring in acute care: technologies on the horizon, Journal of Deabetes Science and Technology, 2(2):178-181, Mar. 2008.
Trecroci, D. 2002. A Glimpse into the Future—Continuous Monitoring of Glucose with a Microfiber. Diabetes Interview 42-43.
Tse and Gough. 1987. Time-Dependent Inactivation of Immobilized Glucose Oxidase and Catalase. Biotechnol. Bioeng. 29:705-713.
Turner et al. 1984. Carbon Monoxide: Acceptor Oxidoreductase from Pseudomonas Thermocarboxydovorans Strain C2 and its use in a Carbon Monoxide Sensor. Analytica Chimica Acta, 163: 161-174.
Unger et al. 2004. Glucose control in the hospitalized patient. Emerg Med 36(9):12-18.
Updike et al. 1967. The enzyme electrode. Nature, 214:986-988.
Updike et al. 1979. Continuous glucose monitor based on an immobilized enzyme electrode detector. J Lab Clin Med, 93(4):518-527.
Updike et al. 1988. Laboratory Evaluation of New Reusable Blood Glucose Sensor. Diabetes Care, 11:801-807.
Updike et al. 1994. Enzymatic glucose sensor: Improved long-term performance in vitro and in vivo. ASAIO Journal, 40(2):157-163.
Updike et al. 2000. A subcutaneous glucose sensor with improved longevity, dynamic range, and stability of calibration. Diabetes Care 23(2):208-214.
Utah Medical Products Inc., Blood Pressure Tranducers product specifications. 6 pp. 2003-2006, 2003.
Vadgama, P. Nov. 1981. Enzyme electrodes as practical biosensors. Journal of Medical Engineering & Technology 5(6):293-298.
Van den Berghe 2004. Tight blood glucose control with insulin in "real-life" intensive care. Mayo Clin Proc 79(8):977-978.
Velho et al. 1989. In vitro and in vivo stability of electrode potentials in needle-type glucose sensors. Influence of needle material. Diabetes 38:164-171.
Wagner et al. 1998. Continuous amperometric monitoring of glucose in a brittle diabetic chimpanzee with a miniature subcutaneous electrode. Proc. Natl. Acad. Sci. A, 95:6379-6382.
Wang et al. 1994. Highly Selective Membrane-Free, Mediator-Free Glucose Biosensor. Anal. Chem. 66:3600-3603.
Wang et al. 1997. Improved ruggedness for membrane-based amperometric sensors using a pulsed amperometric method. Anal Chem 69:4482-4489.
Ward et al. 1999. Assessment of chronically implanted subcutaneous glucose sensors in dogs: The effect of surrounding fluid masses. ASAIO Journal, 45:555-561.
Ward et al. 2000. Understanding Spontaneous Output Fluctuations of an Amperometric Glucose Sensor: Effect of Inhalation Anesthesia and e of a Nonenzyme Containing Electrode. ASAIO Journal 540-546.
Ward et al. 2000. Rise in background current over time in a subcutaneous glucose sensor in the rabbit: Relevance to calibration and accuracy. Biosensors & Bioelectronics, 15:53-61.
Ward et al. 2002. A new amperometric glucose microsensor: in vitro and short-term in vivo evaluation. Biosensors & Bioelectronics, 17:181-189.
Wientjes, K. J. C. 2000. Development of a glucose sensor for diabetic patients (Ph.D. Thesis).
Wikipedia 2006. "Intravenous therapy," http://en.wikipedia.org/wiki/Intravenous_therapy, Aug. 15, 2006, 6 pp.
Wilkins et al. 1988. The coated wire electrode glucose sensor, Horm Metab Res Suppl., 20:50-55.
Wilkins et al. 1996. Glucose monitoring: state of the art and future possibilities. Med Eng Phys 18:273-288.
Wilson et al. 2000. Enzyme-based biosensors for in vivo measurements. Chem. Rev., 100:2693-2704.
Woodward. 1982. How Fibroblasts and Giant Cells Encapsulate Implants: Considerations in Design of Glucose Sensor. Diabetes Care 5:278-281.
Worsley et al., Measurement of glucose in blood with a phenylboronic acid optical sensor, Journal of Diabetes Science and Technology, 2(2):213-220, Mar. 2008.
Wright et al., Bioelectrochemical dehalogenations via direct electrochemistry of poly(ethylene oxide)-modified myoglobin, Electrochemistry Communications 1 (1999) 603-611.

(56) References Cited

OTHER PUBLICATIONS

Yamasaki et al. 1989. Direct measurement of whole blood glucose by a needle-type sensor. Clinica Chimica Acta. 93:93-98.
Yamasaki, Yoshimitsu. Sep. 1984. The development of a needle-type glucose sensor for wearable artificial endocrine pancreas. Medical Journal of Osaka University 35(1-2):25-34.
Yang et al (1996). "A glucose biosensor based on an oxygen electrode: In-vitro performances in a model buffer solution and in blood plasma," Biomedical Instrumentation & Technology, 30:55-61.
Yang et al. 1998. Development of needle-type glucose sensor with high selectivity. Science and Actuators B 46:249-256.
Zamzow et al. 1990. Development and evaluation of a wearable blood glucose monitor, ASAIO Transactions; 36(3): pp. M588-M591.
Zethelius et al. 2008. Use of multiple biomarkers to improve the prediction of death from cardiovascular causes. N. Engl. J. Med., 358: 2107-2116.
Zhang et al (1993). Electrochemical oxidation of $H_2O_2$ on Pt and Pt + Ir electrodes in physiological buffer and its applicability to $H_2O_2$-based biosensors. *J. Electroanal. Chem.*, 345:253-271.
Zhang et al. 1993. In vitro and in vivo evaluation of oxygen effects on a glucose oxidase based implantable glucose sensor. Analytica Chimica Acta, 281:513-520.
Zhu et al. (1994). "Fabrication and characterization of glucose sensors based on a microarray $H_2O_2$ electrode." *Biosensors & Bioelectronics*, 9: 295-300.
Zhu et al. 2002. Planar amperometric glucose sensor based on glucose oxidase immobilized by chitosan film on prussian blue layer. Sensors, 2:127-136.
IPRP for PCT/US05/024993 filed Jul. 13, 2005.
ISR and WO for PCT/US05/024993 filed Jul. 13, 2005.
Official Communication—EP Examination Report—in European App. No. 05771643.3, dated Aug. 19, 2009.
Office Action dated Jun. 19, 2008 in U.S. Appl. No. 11/021,162.
Office Action dated Dec. 26, 2007 in U.S. Appl. No. 11/021,046.
Office Action dated Jun. 23, 2008 in U.S. Appl. No. 11/021,046.
Office Action dated Feb. 4, 2009 in U.S. Appl. No. 11/021,046.
Office Action dated Aug. 19, 2009 in U.S. Appl. No. 11/021,046.
Office Action dated Oct. 8, 2008 in U.S. Appl. No. 10/896,637.
Office Action dated Mar. 5, 2009 in U.S. Appl. No. 10/896,637.
Office Action dated Jul. 20, 2009 in U.S. Appl. No. 10/896,637.
Office Action dated Jan. 13, 2010 in U.S. Appl. No. 12/139,305.
Office Action dated May 18, 2007 in U.S. Appl. No. 11/543,707.
Office Action dated Dec. 12, 2007 in U.S. Appl. No. 11/543,707.
Office Action dated Jan. 22, 2009 in U.S. Appl. No. 11/692,154.
Office Action dated Jul. 8, 2009 in U.S. Appl. No. 11/692,154.
Office Action dated May 23, 2007 in U.S. Appl. No. 11/543,539.
Office Action dated Dec. 12, 2007 in U.S. Appl. No. 11/543,539.
Office Action dated May 18, 2007 in U.S. Appl. No. 11/543,683.
Office Action dated Dec. 12, 2007 in U.S. Appl. No. 11/543,683.
Office Action dated Mar. 3, 2010 in U.S. Appl. No. 12/111,062.
Office Action dated Jun. 5, 2007 in U.S. Appl. No. 11/543,734.
Office Action dated Dec. 17, 2007 in U.S. Appl. No. 11/543,734.
Office Action dated Nov. 1, 2007 in U.S. Appl. No. 11/034,343.
Office Action dated Jul. 10, 2008 in U.S. Appl. No. 11/034,343.
Office Action dated Dec. 30, 2008 in U.S. Appl. No. 11/034,343.
Office Action dated May 17, 2007 in U.S. Appl. No. 11/077,759.
Office Action dated Mar. 31, 2008 in U.S. Appl. No. 11/077,759.
Office Action dated Jul. 10, 2008 in U.S. Appl. No. 11/077,759.
Office Action dated May 26, 2009 in U.S. Appl. No. 11/077,759.
Office Action dated Oct. 31, 2006 in U.S. Appl. No. 11/077,715.
Office Action dated Apr. 10, 2007 in U.S. Appl. No. 11/077,715.
Office Action dated Jul. 26, 2007 in U.S. Appl. No. 11/077,715.
Office Action dated Jan. 28, 2008 in U.S. Appl. No. 11/077,715.
Office Action dated May 12, 2008 in U.S. Appl. No. 11/077,715.
Office Action dated Nov. 12, 2008, 2008 in U.S. Appl. No. 11/077,715.
Office Action dated Oct. 9, 2007 in U.S. Appl. No. 11/077,883.
Office Action dated Jun. 24, 2008 in U.S. Appl. No. 11/077,883.
Office Action dated Sep. 18, 2008 in U.S. Appl. No. 11/077,883.
Office Action dated Apr. 6, 2009 in U.S. Appl. No. 11/077,883.
Office Action dated Nov. 12, 2009 in U.S. Appl. No. 11/077,883.
Office Action dated May 12, 2010 in U.S. Appl. No. 11/077,883.
Office Action dated Sep. 18, 2007 in U.S. Appl. No. 11/078,230.
Office Action dated Jun. 30, 2008 in U.S. Appl. No. 11/078,230.
Office Action dated Sep. 5, 2008 in U.S. Appl. No. 11/078,230.
Office Action dated Jan. 26, 2009 in U.S. Appl. No. 11/078,230.
Office Action dated May 5, 2008 in U.S. Appl. No. 11/078,232.
Office Action dated Nov. 12, 2008 in U.S. Appl. No. 11/078,232.
Office Action dated Mar. 5, 2009 in U.S. Appl. No. 11/078,232.
Office Action dated Jul. 21, 2009 in U.S. Appl. No. 11/078,232.
Office Action dated Jan. 5, 2010 in U.S. Appl. No. 11/078,232.
Office Action dated Apr. 27, 2010 in U.S. Appl. No. 11/078,232.
Office Action dated Oct. 11, 2006 in U.S. Appl. No. 11/077,714.
Office Action dated Apr. 10, 2007 in U.S. Appl. No. 11/077,714.
Office Action dated Jul. 27, 2007 in U.S. Appl. No. 11/077,714.
Office Action dated Jan. 10, 2008 in U.S. Appl. No. 11/077,714.
Office Action dated Sep. 16, 2008 in U.S. Appl. No. 11/077,714.
Office Action dated Apr. 16, 2009 in U.S. Appl. No. 11/077,714.
Office Action dated Dec. 31, 2009 in U.S. Appl. No. 11/077,714.
Office Action dated Jan. 27, 2010 in U.S. Appl. No. 11/077,714.
Office Action dated Jan. 30, 2007 in U.S. Appl. No. 11/077,763.
Office Action dated Apr. 21, 2008 in U.S. Appl. No. 11/077,643.
Office Action dated Oct. 1, 2008 in U.S. Appl. No. 11/077,643.
Office Action dated Mar. 11, 2009 in U.S. Appl. No. 11/077,643.
Office Action dated Sep. 2, 2009 in U.S. Appl. No. 11/078,072.
Office Action dated Feb. 18, 2010 in U.S. Appl. No. 11/078,072.
Office Action dated Aug. 21, 2009 in U.S. Appl. No. 11/360,299.
Office Action dated May 12, 2010 in U.S. Appl. No. 11/360,299.
Office Action dated Jan. 3, 2008 in U.S. Appl. No. 11/157,746.
Office Action dated May 1, 2008 in U.S. Appl. No. 11/157,746.
Office Action dated Jun. 26, 2008 in U.S. Appl. No. 11/157,365.
Office Action dated Jan. 7, 2009 in U.S. Appl. No. 11/157,365.
Office Action dated Jul. 21, 2009 in U.S. Appl. No. 11/157,365.
Office Action dated Jan. 21, 2010 in U.S. Appl. No. 11/157,365.
Office Action dated Oct. 4, 2006 in U.S. Appl. No. 11/334,876.
Office Action dated Sep. 25, 2007 in U.S. Appl. No. 11/334,876.
Office Action dated Jun. 30, 2008 in U.S. Appl. No. 11/360,252.
Office Action dated Jan. 29, 2009, in U.S. Appl. No. 11/360,252.
Office Action dated Jul. 23, 2009, in U.S. Appl. No. 11/360,252.
Office Action dated Aug. 11, 2008 in U.S. Appl. No. 11/360,819.
Office Action dated Dec. 26, 2008 in U.S. Appl. No. 11/360,819.
Office Action dated Oct. 29, 2009 in U.S. Appl. No. 11/360,819.
Office Action dated Apr. 7, 2010 in U.S. Appl. No. 11/360,819.
Office Action dated Nov. 28, 2008 in U.S. Appl. No. 11/333,837.
Office Action dated Jun. 29, 2009 in U.S. Appl. No. 11/333,837.
Office Action dated Apr. 12, 2010 in U.S. Appl. No. 11/333,837.
Office Action dated Feb. 23, 2010 in U.S. Appl. No. 12/113,508.
Office Action dated Nov. 28, 2008 in U.S. Appl. No. 11/360,250.
Office Action dated Jun. 15, 2009 in U.S. Appl. No. 11/360,250.
Office Action dated Nov. 20, 2009 in U.S. Appl. No. 11/360,250.
Office Action dated Mar. 5, 2010 in U.S. Appl. No. 11/360,250.
Bard et al. 1980. Electrochemical Methods. John Wiley & Sons, pp. 173-175.
Beach et al. 1999. Subminiature implantable potentiostat and modified commercial telemetry device for remote glucose monitoring. IEEE Transactions on Instrumentation and Measurement 48(6):1239-1245.
Official Communication in European App. No. 05771646.6, dated Jun. 2, 2010.
Office Action dated Sep. 30, 2002 in U.S. Appl. No. 09/636,369.
Office Action dated Jan. 11, 2005 in U.S. Appl. No. 10/896,772.
Office Action dated Jul. 19, 2005 in U.S. Appl. No. 10/896,772.
Office Action dated Dec. 14, 2005 in U.S. Appl. No. 10/896,772.
Office Action dated May 22, 2006 in U.S. Appl. No. 10/896,772.
Office Action dated Jan. 27, 2006 in U.S. Appl. No. 11/007,635.
Office Action dated Nov. 28, 2007 in U.S. Appl. No. 10/991,966.
Office Action dated Jul. 22, 2008 in U.S. Appl. No. 10/991,966.
Office Action dated Nov. 27, 2006 in U.S. Appl. No. 10/789,359.
Office Action dated Mar. 20, 2008 in U.S. Appl. No. 10/789,359.
Office Action dated Oct. 3, 2008 in U.S. Appl. No. 10/789,359.
Office Action dated Jun. 3, 2010 in U.S. Appl. No. 12/264,160.

(56) References Cited

OTHER PUBLICATIONS

Office Action dated Jan. 15, 2008 in U.S. Appl. No. 11/034,344.
Office Action dated Jan. 22, 2010 in U.S. Appl. No. 11/439,630.
Office Action dated May 2, 2008 in U.S. Appl. No. 11/334,876.
Office Action dated Aug. 26, 2008 in U.S. Appl. No. 11/334,876.
Office Action dated Aug. 25, 2009 in U.S. Appl. No. 11/334,876.
Ciba® Irgacure® 2959 Photoinitiator, Product Description. Apr. 2, 1998. Ciba Specialty Chemicals Inc., Basel, Switzerland. 3 pages.
Direct 30/30® Blood Glucose Sensor, (Markwell Medical) Catalog, © 1990, ELCO Diagnostics Company. 1 page. [corrected cite].
Huang et al., Sep. 1997, A 0.5mW Passive Telemetry IC for Biomedical Applications, Proceedings of the 23rd European Solid-State Circuits Conference (ESSCIRC '97), pp. 172-175, Southampton, UK. [corrected cite].
Huang et al. Aug. 1975. Electrochemical Generation of Oxygen. 1: The Effects of Anions and Cations on Hydrogen Chemisorption and Anodic Oxide Film Formation on Platinum Electrode. 2: The Effects of Anions and Cations on Oxygen Generation on Platinum Electrode. U.S. Department of Commerce/NTIS, pp. 1-116. [corrected cite].
Hunter et al. Mar. 31, 2000. Minimally Invasive Glucose Sensor and Insulin Delivery System. MIT Home Automation and Healthcare Consortium. Progress Report No. 2-5. 17 pages. . [corrected cite].
Ishikawa et al. 1998. Initial evaluation of a 290-mm diameter subcutaneous glucose sensor: Glucose monitoring with a biocompatible, flexible-wire, enzyme-based amperometric microsensor in diabetic and nondiabetic humans. Journal of Diabetes and Its Complications, 12:295-301. [corrected cite].
Kurtz et al. 2005. Recommendations for blood pressure measurement in humans and experimental animals, Part 2: Blood pressure measurement in experimental animals, A statement for professionals from the subcommittee of professional and public education of the American Heart Association Council on High Blood Pressure Research. Hypertension 45:299-310. [corrected cite].
Merriam-Webster Online Dictionary. Apr. 23, 2007. Definition of "nominal". http://www.merriam-webster.com/dictionary/nominal [corrected cited].
Nafion® 117 Solution Product Description, Product No. 70160, Sigma-Aldrich Corp., St. Louis, MO. Downloaded from https://www.signaaldrich.com/cgi-bin/hsrun/Suite7/Suite/HAHTpage/Suite.HsExternal Prod . . . on Apr. 7, 2005. [corrected cite].
Bergveld et al., "Fabrication and Mass Production," Advances in Biosensors, Supplement 1 (1993) Chapter 6; 165-186.
Jablecki et al. 2000. Simulations of the frequency response of implantable glucose sensors. Analytical Chemistry 72:1853-1859.
Kovatchev et al. Aug. 2004. Evaluating the accuracy of continuous glucose-monitoring sensors: continuous glucose-error grid analysis illustrated by TheraSense Freestyle Navigator data. Diabetes Care 27(8):1922-1928.
Kusano, H. Glucose enzyme electrode with percutaneous interface which operates independently of dissolved oxygen. Clin Phys Physiol Meas. 1989. 10(1): 1-9.
Reach et al., "Clinical Needs for In Vivo Monitoring," Advances in Biosensors, Supplement 1 (1993) Chapter 1; 7-28.
Shichiri et al., "In Vivo Characteristics of Needle-Type Glucose Sensor—Measurements of Subcutaneous Glucose Concentrations in Human Volunteers," Implantable Glucose Sensors—The State of the Art, Hormone and Metabolic Research Supplement Series vol. No. 20 (1988) 17-20.
Office Action dated Jan. 20, 2012 for U.S. Appl. No. 12/359,207, filed Jan. 23, 2009.
European Office Action dated Dec. 15, 2011 in EP 10195496.4, filed Jul. 13, 2005.
European Response filed Jun. 22, 2012 in EP 10195496.4, filed Jul. 13, 2005.
European Extended Search Report dated Aug. 3, 2011 for Application No. EP 10195520.1, filed Jul. 13, 2005; 6 pages.
European Office Action dated Jul. 19, 2012 for Application No. EP 10195520.1, filed Jul. 13, 2005; 4 pages.
European Response/Claims to Office Action filed Jan. 16, 2013 for Application No. EP 10195520.1, filed Jul. 13, 2005; 7 pages.
Notice of Opposition dated Jul. 25, 2012 in European Patent No. 1986543, granted Dec. 14, 2011.
European Office Action dated Sep. 18, 2013 and Applicant Response filed Mar. 22, 2013 for Application No. EP 11182622.8, filed Feb. 22, 2006; 9 pages.
Japanese Office Action dated May 22, 2012 for Application No. 2011-121598, filed Jul. 13, 2005.
Request for Ex Parte Reexamination dated Apr. 29, 2011 for U.S. Appl. No. 11/077,693, filed Mar. 10, 2005 (U.S. Pat. No. 7,713,574), 4 pgs.
Request for Ex Parte Reexamination dated Sep. 13, 2012 for U.S. Appl. No. 11/077,763, filed Mar. 10, 2005 (U.S. Pat. No. 7,310,544), 3 pgs.
Request for Inter Partes Reexamination dated Sep. 14, 2012 for U.S. Pat. No. 7,713,574, issued Jun. 5, 2012; TOC. pp. 3.
European Office Action dated Feb. 17, 2012 in EP 06748336.2, filed Mar. 10, 2006.
Alberts et al. 1994. Molecular Biology of the Cell, $3^{rd}$ Ed., p. G19.
Amato et al. 1989. J. Thorac Cardiovasc Surg 97(6):929-934. Experience with the Polytetrafluoroethylene surgical membrane for pericardial closure in operations for congenital cardiac defects.
Answers.com, "xenogenic." The American Heritage Stedman's Medical Dictionary. Houghton Mifflin Company, 2002. Answers. com Nov. 7, 2006 http:--www.answers.com-topic-xenogenic.
Brauker et al. 1995. J. Biomed Mater Res 29:1517-1524. Neovascularization of synthetic membranes directed by membrane microarchitecture.
Copeland et al. 2001. J. Heart and Lung Tranpl 20(6):654-656. Synthetic Membrane Neo-Pericardium Facilitates Total Artificial Heart Explanation.
Dobson et al. 1990. Cell 61(2):223-230. 1-Butyrul-glycerol: A novel angiogenesis factor secreted by differentiating adipocytes.
English et al. 2001. Cardiovasc Res 49(3):588-599. Platelet-released phospholipids link haemostasis and angiogenesis.
Gore Preclude ® Pericardial Membrane Brochure, Jun. 2009. W.L. Gore & Associates, Inc., Flagstaff, AZ 86004.
Gore Preclude® Pericardial Membrane Brochure Nov. 2001, W.L. Gore & Associates, Inc., Flagstaff, AZ 86004.
Halvorsen et al. 1993. J. Clin Invest 92(6):2872-2876. Vasodilation of rat retinal microvessels induced by monobutyrin.
Harada et al. 1988. J. Thorac Cardiovasc Surg 96(5):811-815. Long-term Results fo the Clinical use of an Expanded Polytetrafluoroethylene Surgical Membrane as a Pericardial Substitute.
Heydorn et al. 1987. J. Thorac Cardiovasc Surg 94(2):291-296, A New Look at Pericardial Substitutes.
Kidd et al. 2001. J Biomed Mater Research 59(2):366-377. Angiogenesis and neovascularization associated with extra cellular matrix-modified porous implants.
Kugler et al. 1990. PACE 13:976-981. A new steroid-eluting epicardial lead: experience with atrial and ventricular implantation in the immature swine.
Ladd et al. 1996, Structure Determination by X-Ray Chrystallography, $3^{rd}$ Ed. Plenum, Chapter 1, pp. xx1-xxiv and 1-58.
LePrince et al. 2001. Eur. J. Cardiothoracic Surg 19:302-306. Expanded Polytetrafluoroethylene Membranes to Wrap Surfaces of Circulatory Support Devices in Patients Undergoing Bridge to Heart Transplantation.
Loebe et al. 1993. Texas Heart Institute Journal 20(3):213-217. Use of Polytetrafluoroethylene Surgical Membranes as a Pericardial Substitute, PTFE Membrane in Correction of Congenital Heart Defects.
Mathivanar et al. 1990. PACE 13()11):1883-1886. In vivo elution rate of drug eluting ceramic leads with a reduced dose of dexamethasone sodium phosphate.
Minale et al. 1988. J. Card Surg 3(3):193-201. Clinical Experience with Expanded Polytetrafluoroethylene Gore-Tex® Surgical Membrane for Pericardial Closer: A Study of 110 Cases.
Mond et al. 1992. PACE 15:95-107, The electrode-tissue interface: The revolutionary role of steroid elution.

(56) References Cited

OTHER PUBLICATIONS

Panetti 2002. Biochimca et Biophysica Acta 1582: 190-196. Differential effects of sphingosine 1-phosphate and lysophosphatidic acid on endothelial cells.
Radovsky et al. 1989. Am Heart JH. 117:1288-1297. Effects of dexamethasone elution on tissue reaction around stimulating electrodes of endocardial pacing leads in dogs.
Revuelta et al. 1985. J. Thorac Cardiovasc Surg 89(3):451-455. Expanded Polytetrafluoroethylene Surgical membrane for Pericardial Closure.
Sharkawy et al. 1997. J Biomed Mater Res 37:401-412. Engineering the tissue which encapsulates subcutaneous implants. I. Diffusion Properties.
Ward et al. 1999. ASAIO Journal 45:555-561. Assessment of chronically implanted subcutaneous glucose sensors in dogs: The effect of surrounding fluid masses.
Zhang et al. 1994. Analytical Chemistry 66(7):1183-1188, Elimination of the acetaminophen interference in an implantable glucose sensor.

* cited by examiner

ANALYTE SENSOR

RELATED APPLICATIONS

This application is a continuation-in-part of U.S. application Ser. No. 11/439,630, filed May 23, 2006, which is a continuation-in-part of U.S. application Ser. No. 11/077,715, filed Mar. 10, 2005 now U.S. Pat. No. 7,497,827, which claims the benefit of U.S. Provisional Application No. 60/587,787 filed Jul. 13, 2004; U.S. Provisional Application No. 60/587,800 filed Jul. 13, 2004; U.S. Provisional Application No. 60/614,683 filed Sep. 30, 2004; and U.S. Provisional Application No. 60/614,764 filed Sep. 30, 2004. U.S. application Ser. No. 11/439,630 claims the benefit of U.S. Provisional Application No. 60/683,923 filed May 23, 2005. Each of the aforementioned applications is incorporated by reference herein in its entirety, and each is hereby expressly made a part of this specification.

FIELD OF THE INVENTION

Biointerface membranes are provided which can be utilized with implantable devices, such as devices for the detection of analyte concentrations in a biological sample. More particularly, methods for monitoring glucose levels in a biological fluid sample using an implantable analyte detection device incorporating such membranes are provided.

BACKGROUND OF THE INVENTION

One of the most heavily investigated analyte sensing devices is the implantable glucose device for detecting glucose levels in hosts with diabetes. Despite the increasing number of individuals diagnosed with diabetes and recent advances in the field of implantable glucose monitoring devices, currently used devices are unable to provide data safely and reliably for certain periods of time. There are two commonly used types of subcutaneously implantable glucose sensing devices. These types include those that are implanted transcutaneously and those that are wholly implanted.

SUMMARY OF THE INVENTION

Accordingly, in a first aspect, an analyte sensing device adapted for implantation into a host's tissue is provided, comprising a sensor configured to measure an analyte in a host, wherein the sensor comprises a biointerface configured to promote at least one function selected from the group consisting of increasing fluid bulk surrounding at least a portion of the sensor in vivo, increasing bulk fluid flow surrounding at least a portion of the sensor in vivo, and increasing diffusion rates surrounding at least a portion of the sensor in vivo.

In an embodiment of the first aspect, the biointerface comprises a spacer.

In an embodiment of the first aspect, the spacer comprises a mesh.

In an embodiment of the first aspect, the spacer comprises a hydrogel.

In an embodiment of the first aspect, the hydrogel comprises from about 20 wt. % to about 99 wt. % water.

In an embodiment of the first aspect, the hydrogel comprises from about 80 wt. % to about 99 wt. % water.

In an embodiment of the first aspect, the spacer comprises a shedding layer.

In an embodiment of the first aspect, the spacer is a fibrous structure.

In an embodiment of the first aspect, the spacer is a porous polymer membrane.

In an embodiment of the first aspect, the spacer comprises a material selected from the group consisting of polysulfone, polytetrafluoroethylene, polyvinylidene difluoride, polyacrylonitrile, silicone, polytetrafluoroethylene, expanded polytetrafluoroethylene, polyethylene-co-tetrafluoroethylene, polyolefin, polyester, polycarbonate, biostable polytetrafluoroethylene, polyurethane, polypropylene, polyvinylchloride, polyvinylidene fluoride, polyvinyl alcohol, polybutylene terephthalate, polymethylmethacrylate, polyether ether ketone, polyamides, cellulosic polymer, poly(ethylene oxide), poly(propylene oxide), hydrogel polymer, poly(2-hydroxyethyl methacrylate), hydroxyethyl methacrylate, high density polyethylene, acrylic copolymer, nylon, polyvinyl difluoride, polyanhydride, poly(l-lysine), poly (L-lactic acid), hydroxyethylmethacrylate, homopolymers thereof, copolymers thereof, di-block copolymers thereof, tri-block copolymers thereof, alternating copolymers thereof, random copolymers thereof, graft copolymers thereof, terpolymers thereof, and blends thereof.

In an embodiment of the first aspect, the spacer comprises a material selected from the group consisting of metal, ceramic, hydroxyapeptite, alumina, zirconia, carbon fiber, aluminum, calcium phosphate, titanium, titanium alloy, nintinol, stainless steel, CoCr alloy, and combinations thereof.

In an embodiment of the first aspect, the spacer has an average nominal pore size of from about 0.6 µm to about 20 µm.

In an embodiment of the first aspect, at least 50% of the pores of the spacer have an average size of from about 0.6 µm to about 20 µm.

In an embodiment of the first aspect, the biointerface is configured to provide a fluid pocket.

In an embodiment of the first aspect, the biointerface comprises a roughened surface.

In an embodiment of the first aspect, the roughened surface is a vasodilating surface.

In an embodiment of the first aspect, the biointerface comprises an irregular surface.

In an embodiment of the first aspect, the biointerface comprises a nanoporous material, a swellable material, or a collapsible material.

In an embodiment of the first aspect, the biointerface comprises an irritating superstructure.

In an embodiment of the first aspect, the irritating superstructure comprises a coiled silver wire.

In an embodiment of the first aspect, the biointerface comprises a biodegradable material.

In an embodiment of the first aspect, the biodegradable material is a biodegradable polymer.

In an embodiment of the first aspect, the biodegradable polymer comprises an irritating polymer.

In an embodiment of the first aspect, the spacer comprises a self-assembling material.

In an embodiment of the first aspect, the self-assembling material comprises a self-assembling peptide.

In an embodiment of the first aspect, the biointerface comprises a bioactive agent.

In an embodiment of the first aspect, the bioactive agent is selected from the group consisting of anti-barrier cell agent, an anti-infective agent, a necrosing agent, an inflammatory agent, a growth factor, an angiogenic factor, an adjuvant, an antiplatelet agent, an anticoagulant, an ACE inhibitor, a cytotoxic agent, a vascularization compound, an anti-sense molecule, an enzyme, a metal, a hydrophilic biodegradable polymer, a glycolic acid-based polymer, a lactic acid-based polymer, polyethylene oxide, silver, and combinations thereof.

In an embodiment of the first aspect, the sensor is configured to measure a signal that is indicative of a quantity of the analyte within a fluid surrounding at least a portion of the sensor.

In an embodiment of the first aspect, the fluid surrounding at least a portion of the sensor comprises wound fluid.

In an embodiment of the first aspect, the device further comprises electronics operably connected to the sensor and adapted for detecting a signal from the sensor, wherein the signal is indicative of a quantity of analyte within the host.

In an embodiment of the first aspect, the device further comprises a housing adapted for placement adjacent to the host's skin, wherein at least a portion of the electronics are disposed in the housing.

In an embodiment of the first aspect, the sensor is adapted for short-term implantation.

In an embodiment of the first aspect, the sensor is a transcutaneous sensor.

In a second aspect, an analyte sensing device adapted for implantation into a host's tissue is provided, comprising a sensor for measuring an analyte in the host, wherein the sensor comprises a biointerface configured to irritate a surrounding in vivo environment.

In an embodiment of the second aspect, the biointerface comprises a shedding layer.

In an embodiment of the second aspect, the biointerface comprises a roughened surface.

In an embodiment of the second aspect, the biointerface comprises an irritating superstructure.

In an embodiment of the second aspect, the irritating superstructure comprises a coiled silver wire.

In an embodiment of the second aspect, the biointerface comprises an irregular surface.

In an embodiment of the second aspect, the biointerface comprises a biodegradable material.

In an embodiment of the second aspect, the biodegradable material is a biodegradable polymer.

In an embodiment of the second aspect, the biodegradable polymer comprises an irritating polymer.

In an embodiment of the second aspect, the biointerface comprises a bioactive agent.

In an embodiment of the second aspect, the bioactive agent is selected from the group consisting of an anti-barrier cell agent, an anti-infective agent, a necrosing agent, an inflammatory agent, a growth factor, an angiogenic factor, an adjuvant, an antiplatelet agent, an anticoagulant, an ACE inhibitor, a cytotoxic agent, a vascularization compound, an anti-sense molecule, an enzyme, a metal, a hydrophilic biodegradable polymer, a glycolic acid-based polymer, a lactic acid-based polymer, polyethylene oxide, silver, and combinations thereof.

In an embodiment of the second aspect, the sensor is configured to measure a signal that is indicative of a quantity of the analyte within a fluid surrounding at least a portion of the sensor.

In an embodiment of the second aspect, the fluid surrounding at least a portion of the sensor comprises wound fluid.

In an embodiment of the second aspect, the device further comprises electronics operably connected to the sensor and adapted for detecting a signal from the sensor, wherein the signal is indicative of a quantity of the analyte within the host.

In an embodiment of the second aspect, the device further comprises a housing adapted for placement adjacent to the host's skin, wherein at least a portion of the electronics are disposed in the housing.

In an embodiment of the second aspect, the sensor is adapted for short-term implantation.

In an embodiment of the second aspect, the sensor is a transcutaneous sensor.

In a third aspect, an analyte sensing device adapted for implantation into a host's tissue is provided, comprising a sensor for measuring an analyte in a host, wherein the sensor comprises a biointerface configured to suppress wound healing around at least a portion of the sensor in vivo.

In an embodiment of the third aspect, the biointerface comprises a scavenging agent.

In an embodiment of the third aspect, the biointerface comprises a bioactive agent.

In an embodiment of the third aspect, the bioactive agent is selected from the group consisting of an anti-inflammatory agent, an anti-infective agent, an anesthetic, a growth factor, an angiogenic factor, an immunosuppressive agent, an antiplatelet agent, an anticoagulant, a scavenging agent, an anti-histamine, and combinations thereof.

In an embodiment of the third aspect, the bioactive agent comprises an anti-histamine.

In an embodiment of the third aspect, the biointerface comprises an architecture configured to suppress wounding.

In an embodiment of the third aspect, the biointerface comprises an anti-inflammatory architecture.

In an embodiment of the third aspect, the biointerface comprises a pro-inflammatory architecture.

In an embodiment of the third aspect, the biointerface comprises an artificial protective coating.

In an embodiment of the third aspect, the artificial protective coating comprises a substance selected from the group consisting of albumin, fibrin, collagen, endothelial cells, would closure chemicals, blood products, platelet-rich plasma, growth factors, and combinations thereof.

In an embodiment of the third aspect, the sensor is configured to measure a signal that is indicative of a quantity of the analyte within a fluid surrounding at least a portion of the sensor.

In an embodiment of the third aspect, the fluid surrounding at least a portion of the sensor comprises wound fluid.

In an embodiment of the third aspect, the device further comprises electronics operably connected to the sensor and adapted for detecting a signal from the sensor, wherein the signal is indicative of a quantity of the analyte within the host.

In an embodiment of the third aspect, the device further comprises a housing adapted for placement adjacent to the host's skin, wherein at least a portion of the electronics are disposed in the housing.

In an embodiment of the third aspect, the sensor is adapted for short-term implantation.

In an embodiment of the third aspect, the sensor is a transcutaneous sensor.

In a fourth aspect, a method for detecting an analyte in a host is provided, comprising providing an analyte sensing device adapted for transcutaneous insertion into the host, the device comprising a sensor for measuring the analyte in the host, wherein the sensor is configures to reduce noise in vivo; inserting the sensor through the host's skin and into the host; waiting a first period of time, during which first period of time the sensor remains in the host, wherein the first period of time is sufficient for at least partial wound healing to occur; initiating a sensor function; and detecting a signal from the sensor, wherein the signal is indicative of a concentration of an analyte in the host.

In an embodiment of the fourth aspect, the first time period is at least about 1 hour.

In an embodiment of the fourth aspect, the first time period is at least about 24 hours.

In an embodiment of the fourth aspect, the first period of time is from about 1 hour to about 48 hours.

In an embodiment of the fourth aspect, the method further comprises a step of waiting a second period of time during which the sensor remains in the host, wherein the step of waiting a second period of time is conducted after the step of initiating a sensor function and before the step of detecting a signal from the sensor.

In an embodiment of the fourth aspect, the second period of time is at least about 1 hour.

In an embodiment of the fourth aspect, the second period of time is at least about 24 hours.

In an embodiment of the fourth aspect, the second period of time is from about 1 hour to about 48 hours.

DETAILED DESCRIPTION OF THE PREFERRED EMBODIMENT

Figure 1A:
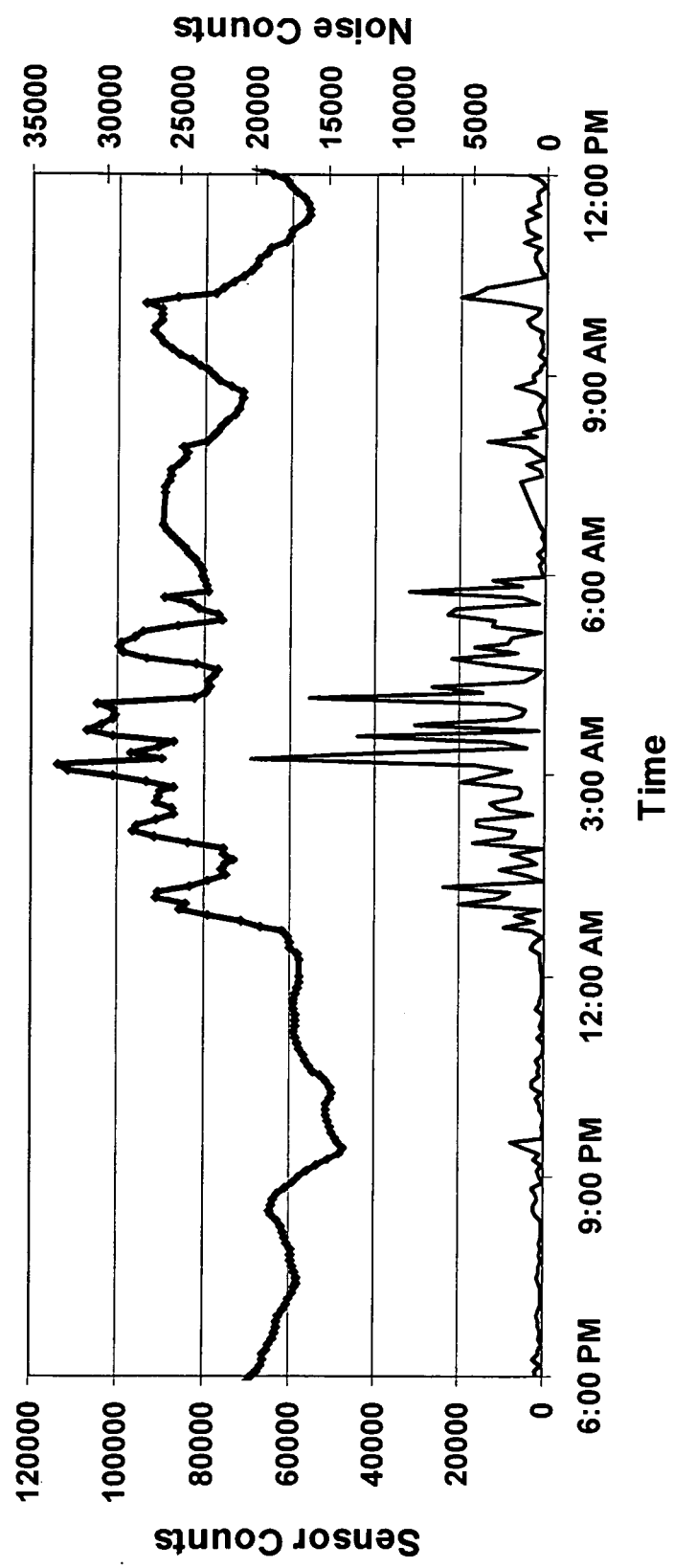
FIG. 1A is a graph of intermittent, sedentary noise in a non-diabetic host wearing a STS glucose sensor. The upper line shows the sensor signal. The lower line shows the noise within the sensor signal.

The following description and examples illustrate a preferred embodiment of the present invention in detail. Those of skill in the art will recognize that there are numerous variations and modifications of this invention that are encompassed by its scope. Accordingly, the description of a preferred embodiment should not be deemed to limit the scope of the present invention.

Definitions

In order to facilitate an understanding of the preferred embodiment, a number of terms are defined below.

The term "biointerface" as used herein is a broad term, and is to be given its ordinary and customary meaning to a person of ordinary skill in the art (and is not to be limited to a special or customized meaning), and refers without limitation to any structure or substance that interfaces between host (tissue or body fluid) and an implantable device.

The term "biointerface membrane" as used herein is a broad term, and is to be given its ordinary and customary meaning to a person of ordinary skill in the art (and is not to be limited to a special or customized meaning), and refers without limitation to a membrane that functions as an interface between host (tissue or body fluid) and an implantable device.

The term "interface" as used herein is a broad term, and is to be given its ordinary and customary meaning to a person of ordinary skill in the art (and is not to be limited to a special or customized meaning), and refers without limitation to 1) a common boundary, such as the surface, place, or point where two things touch each other or meet, or 2) a point of interaction, including the place, situation, or way in which two things act together or affect each other, or the point of connection between things.

The term "barrier cell layer" as used herein is a broad term, and is to be given its ordinary and customary meaning to a person of ordinary skill in the art (and is not to be limited to a special or customized meaning), and refers without limitation to a part of a foreign body response that forms a cohesive monolayer of cells (for example, macrophages and foreign body giant cells) that substantially block the transport of molecules and other substances to the implantable device.

The term "cell processes" as used herein is a broad term, and is to be given its ordinary and customary meaning to a person of ordinary skill in the art (and is not to be limited to a special or customized meaning), and refers without limitation to pseudopodia of a cell.

The term "cellular attachment" as used herein is a broad term, and is to be given its ordinary and customary meaning to a person of ordinary skill in the art (and is not to be limited to a special or customized meaning), and refers without limitation to adhesion of cells and/or cell processes to a material at the molecular level, and/or attachment of cells and/or cell processes to microporous material surfaces or macroporous material surfaces. One example of a material used in the prior art that encourages cellular attachment to its porous surfaces is the BIOPORE™ cell culture support marketed by Millipore (Bedford, Mass.), and as described in Brauker et al., U.S. Pat. No. 5,741,330.

The term "solid portions" as used herein is a broad term, and is to be given its ordinary and customary meaning to a person of ordinary skill in the art (and is not to be limited to a special or customized meaning), and refers without limitation to portions of a membrane's material having a mechanical structure that demarcates cavities, voids, pores, or other non-solid portions.

The term "co-continuous" as used herein is a broad term, and is to be given its ordinary and customary meaning to a person of ordinary skill in the art (and is not to be limited to a special or customized meaning), and refers without limitation to a solid portion or cavity or pore wherein an unbroken curved line in three dimensions can be drawn between two sides of a membrane.

The term "biostable" as used herein is a broad term, and is to be given its ordinary and customary meaning to a person of ordinary skill in the art (and is not to be limited to a special or customized meaning), and refers without limitation to materials that are relatively resistant to degradation by processes that are encountered in vivo.

The terms "bioresorbable" or "bioabsorbable" as used herein are broad terms, and are to be given their ordinary and customary meaning to a person of ordinary skill in the art (and are not to be limited to a special or customized meaning), and refer without limitation to materials that can be absorbed, or lose substance, in a biological system.

The terms "nonbioresorbable" or "nonbioabsorbable" as used herein are broad terms, and are to be given their ordinary and customary meaning to a person of ordinary skill in the art (and are not to be limited to a special or customized meaning), and refer without limitation to materials that are not substantially absorbed, or do not substantially lose substance, in a biological system.

The term "analyte" as used herein is a broad term, and is to be given its ordinary and customary meaning to a person of ordinary skill in the art (and is not to be limited to a special or customized meaning), and refers without limitation to a substance or chemical constituent in a biological fluid (for example, blood, interstitial fluid, cerebral spinal fluid, lymph fluid or urine) that can be analyzed. Analytes can include naturally occurring substances, artificial substances, metabolites, and/or reaction products. In some embodiments, the analyte for measurement by the sensing regions, devices, and methods is glucose. However, other analytes are contemplated as well, including but not limited to acarboxyprothrombin; acylcarnitine; adenine phosphoribosyl transferase; adenosine deaminase; albumin; alpha-fetoprotein; amino acid profiles (arginine (Krebs cycle), histidine/urocanic acid, homocysteine, phenylalanine/tyrosine, tryptophan); andrenostenedione; antipyrine; arabinitol enantiomers; arginase; benzoylecgonine (cocaine); biotinidase; biopterin; c-reactive protein; carnitine; carnosinase; CD4; ceruloplasmin; chenodeoxycholic acid; chloroquine; cholesterol; cholinesterase; conjugated 1-$\beta$ hydroxy-cholic acid; cortisol; creatine kinase; creatine kinase MM isoenzyme; cyclosporin A; d-penicillamine; de-ethylchloroquine; dehydroepiandrosterone sulfate; DNA (acetylator polymorphism, alcohol dehydrogenase, alpha 1-antitrypsin, cystic fibrosis, Duchenne/Becker muscular dystrophy, glucose-6-phosphate dehydrogenase, hemoglobin A, hemoglobin S, hemoglobin C, hemoglobin D, hemoglobin E, hemoglobin F, D-Punjab, beta-thalassemia, hepatitis B virus, HCMV, HIV-1, HTLV-1, Leber hereditary optic neuropathy, MCAD, RNA, PKU, Plasmodium vivax, sexual differentiation, 21-deoxycortisol); desbutylhalofantrine; dihydropteridine reductase; diptheria/tetanus antitoxin; erythrocyte arginase; erythrocyte protoporphyrin; esterase D; fatty acids/acylglycines; free $\beta$-human chorionic gonadotropin; free erythrocyte porphyrin; free thyroxine (FT4); free tri-iodothyronine (FT3); fumarylacetoacetase; galactose/gal-1-phosphate; galactose-1-phosphate uridyltransferase; gentamicin; glucose-6-phosphate dehydrogenase; glutathione; glutathione peroxidase; glycocholic acid; glycosylated hemoglobin; halofantrine; hemoglobin variants; hexosaminidase A; human erythrocyte carbonic anhydrase I; 17-alpha-hydroxy-progesterone; hypoxanthine phosphoribosyl transferase; immunoreactive trypsin; lactate; lead; lipoproteins ((a), B/A-1, $\beta$); lysozyme; mefloquine; netilmicin; phenobarbitone; phenytoin; phytanic/pristanic acid; progesterone; prolactin; prolidase; purine nucleoside phosphorylase; quinine; reverse tri-iodothyronine (rT3); selenium; serum pancreatic lipase; sissomicin; somatomedin C; specific antibodies (adenovirus, anti-nuclear antibody, anti-zeta antibody, arbovirus, Aujeszky's disease virus, dengue virus, Dracunculus medinensis, Echinococcus granulosus, Entamoeba histolytica, enterovirus, Giardia duodenalisa, Helicobacter pylori, hepatitis B virus, herpes virus, HIV-1, IgE (atopic disease), influenza virus, Leishmania donovani, leptospira, measles/mumps/rubella, Mycobacterium leprae, Mycoplasma pneumoniae, Myoglobin, Onchocerca volvulus, parainfluenza virus, Plasmodium falciparum, poliovirus, Pseudomonas aeruginosa, respiratory syncytial virus, rickettsia (scrub typhus), Schistosoma mansoni, Toxoplasma gondii, Trepenoma pallidium, Trypanosoma cruzi/rangeli, vesicular stomatis virus, Wuchereria bancrofti, yellow fever virus); specific antigens (hepatitis B virus, HIV-1); succinylacetone; sulfadoxine; theophylline; thyrotropin (TSH); thyroxine (T4); thyroxine-binding globulin; trace elements; transferrin; UDP-galactose-4-epimerase; urea; uroporphyrinogen I synthase; vitamin A; white blood cells; and zinc protoporphyrin. Salts, sugar, protein, fat, vitamins, and hormones naturally occurring in blood or interstitial fluids can also constitute analytes in certain embodiments. The analyte can be naturally present in the biological fluid, for example, a metabolic product, a hormone, an antigen, an antibody, and the like. Alternatively, the analyte can be introduced into the body, for example, a contrast agent for imaging, a radioisotope, a chemical agent, a fluorocarbon-based synthetic blood, or a drug or pharmaceutical composition, including but not limited to insulin; ethanol; cannabis (marijuana, tetrahydrocannabinol, hashish); inhalants (nitrous oxide, amyl nitrite, butyl nitrite, chlorohydrocarbons, hydrocarbons); cocaine (crack cocaine); stimulants (amphetamines, methamphetamines, Ritalin, Cylert, Preludin, Didrex, PreState, Voranil, Sandrex, Plegine); depressants (barbiturates, methaqualone, tranquilizers such as Valium, Librium, Miltown, Serax, Equanil, Tranxene); hallucinogens (phencyclidine, lysergic acid, mescaline, peyote, psilocybin); narcotics (heroin, codeine, morphine, opium, meperidine, Percocet, Percodan, Tussionex, Fentanyl, Darvon, Talwin, Lomotil); designer drugs (analogs of fentanyl, meperidine, amphetamines, methamphetamines, and phencyclidine, for example, Ecstasy); anabolic steroids; and nicotine. The metabolic products of drugs and pharmaceutical compositions are also contemplated analytes. Analytes such as neurochemicals and other chemicals generated within the body can also be analyzed, such as, for example, ascorbic acid, uric acid, dopamine, noradrenaline, 3-methoxytyramine (3MT), 3,4-dihydroxyphenylacetic acid (DOPAC), homovanillic acid (HVA), 5-hydroxytryptamine (5HT), 5-hydroxyindoleacetic acid (FHIAA), and histamine.

The term "host" as used herein is a broad term, and is to be given its ordinary and customary meaning to a person of ordinary skill in the art (and is not to be limited to a special or customized meaning), and refers without limitation to mammals, preferably humans.

The phrase "continuous analyte sensing" as used herein is a broad term, and is to be given its ordinary and customary meaning to a person of ordinary skill in the art (and is not to be limited to a special or customized meaning), and refers without limitation to the period in which monitoring of analyte concentration is continuously, continually, and/or intermittently (but regularly) performed, for example, from about every 5 seconds or less to about 10 minutes or more, preferably from about 10, 15, 20, 25, 30, 35, 40, 45, 50, 55, or 60 second to about 1.25, 1.50, 1.75, 2.00, 2.25, 2.50, 2.75, 3.00, 3.25, 3.50, 3.75, 4.00, 4.25, 4.50, 4.75, 5.00, 5.25, 5.50, 5.75, 6.00, 6.25, 6.50, 6.75, 7.00, 7.25, 7.50, 7.75, 8.00, 8.25, 8.50, 8.75, 9.00, 9.25, 9.50 or 9.75 minutes.

The terms "analyte measuring device," "sensor," "sensing region," and "sensing mechanism" as used herein are broad terms, and are to be given their ordinary and customary meaning to a person of ordinary skill in the art (and are not to be limited to a special or customized meaning), and refer without limitation to an area of an analyte-monitoring device that enables the detection of a particular analyte. For example, the sensing region can comprise a non-conductive body, a working electrode, a reference electrode, and a counter electrode (optional), forming an electrochemically reactive surface at one location on the body and an electronic connection at another location on the body, and a sensing membrane affixed to the body and covering the electrochemically reactive surface. During general operation of the device, a biological sample, for example, blood or interstitial fluid, or a component thereof contacts, either directly or after passage through one or more membranes, an enzyme, for example, glucose oxidase. The reaction of the biological sample or component thereof results in the formation of reaction products that permit a determination of the analyte level, for example, glucose, in the biological sample. In some embodiments, the sensing membrane further comprises an enzyme domain, for example, an enzyme layer, and an electrolyte phase, for example, a free-flowing liquid phase comprising an electrolyte-containing fluid described further below. The terms are broad enough to include the entire device, or only the sensing portion thereof (or something in between).

The term "electrochemically reactive surface" as used herein is a broad term, and is to be given its ordinary and customary meaning to a person of ordinary skill in the art (and is not to be limited to a special or customized meaning), and refers without limitation to the surface of an electrode where an electrochemical reaction takes place. In a working electrode, hydrogen peroxide produced by an enzyme-catalyzed reaction of an analyte being detected reacts can create a measurable electronic current. For example, in the detection of glucose, glucose oxidase produces $H_2O_2$ peroxide as a byproduct. The $H_2O_2$ reacts with the surface of the working electrode to produce two protons ($2H^+$), two electrons ($2e^-$) and one molecule of oxygen ($O_2$), which produces the electronic current being detected. In a counter electrode, a reducible species, for example, $O_2$ is reduced at the electrode surface so as to balance the current generated by the working electrode.

The term "sensing membrane" as used herein is a broad term, and is to be given its ordinary and customary meaning to a person of ordinary skill in the art (and is not to be limited to a special or customized meaning), and refers without limitation to a permeable or semi-permeable membrane that can comprise one or more domains and that is constructed of material having a thickness of a few microns or more, and that are permeable to reactants and/or co-reactants employed in determining the analyte of interest. As an example, a sensing membrane can comprise an immobilized glucose oxidase enzyme, which catalyzes an electrochemical reaction with glucose and oxygen to permit measurement of a concentration of glucose.

The term "proximal as used herein is a broad term, and is to be given its ordinary and customary meaning to a person of ordinary skill in the art (and is not to be limited to a special or customized meaning), and refers without limitation to a region near to a point of reference, such as an origin or a point of attachment.

The term "distal" as used herein is a broad term, and is to be given its ordinary and customary meaning to a person of ordinary skill in the art (and is not to be limited to a special or customized meaning), and refers without limitation to a region spaced relatively far from a point of reference, such as an origin or a point of attachment.

The terms "operably connected," "operably linked" and "operatively coupled" as used herein are broad terms, and are to be given their ordinary and customary meaning to a person of ordinary skill in the art (and are not to be limited to a special or customized meaning), and refer without limitation to one or more components linked to another component(s) in a manner that facilitates transmission of signals between the components. For example, one or more electrodes can be used to detect an analyte in a sample and convert that information into a signal; the signal can then be transmitted to an electronic circuit. In this example, the electrode is "operably linked" to the electronic circuit.

The term "adhere" and "attach" as used herein are broad terms, and are to be given their ordinary and customary meaning to a person of ordinary skill in the art (and are not to be limited to a special or customized meaning), and refer without limitation to hold, bind, or stick, for example, by gluing, bonding, grasping, interpenetrating, or fusing.

The term "bioactive agent" as used herein is a broad term, and is to be given its ordinary and customary meaning to a person of ordinary skill in the art (and is not to be limited to a special or customized meaning), and refers without limitation to any substance that has an effect on or elicits a response from living tissue.

The term "bioerodible" or "biodegradable" as used herein are a broad terms, and are to be given their ordinary and customary meaning to a person of ordinary skill in the art (and are not to be limited to a special or customized meaning), and refer without limitation to materials that are enzymatically degraded or chemically degraded in vivo into simpler components. One example of a biodegradable material includes a biodegradable polymer that is broken down into simpler components by the body.

The terms "small diameter sensor," "small structured sensor," and "micro-sensor," as used herein are broad terms, and are to be given their ordinary and customary meaning to a person of ordinary skill in the art (and are not to be limited to a special or customized meaning), and refer without limitation to sensing mechanisms that are less than about 2 mm in at least one dimension, and more preferably less than about 1 mm in at least one dimension. In some embodiments, the sensing mechanism (sensor) is less than about 0.95, 0.9, 0.85, 0.8, 0.75, 0.7, 0.65, 0.6, 0.5, 0.4, 0.3, 0.2, or 0.1 mm. In some embodiments, the sensing mechanism is a needle-type sensor, wherein the diameter is less than about 1 mm, see, for example, U.S. Pat. No. 6,613,379 to Ward et al. and co-pending U.S. patent application Ser. No. 11/077,715, filed on Mar. 10, 2005 and entitled, "TRANSCUTANEOUS ANALYTE SENSOR," both of which are incorporated herein by reference in their entirety. In some alternative embodiments, the sensing mechanism includes electrodes deposited on a planar substrate, wherein the thickness of the implantable portion is less than about 1 mm, see, for example U.S. Pat. No. 6,175,752 to Say et al. and U.S. Pat. No. 5,779,665 to Mastrototaro et al., both of which are incorporated herein by reference in their entirety.

The term "electrospinning" as used herein is a broad term, and is to be given its ordinary and customary meaning to a person of ordinary skill in the art (and is not to be limited to a special or customized meaning), and refers without limitation to a process by which fibers are drawn out from a viscous polymer solution or melt by applying an electric field to a droplet of the solution (most often at a metallic needle tip). The electric field draws this droplet into a structure called a Taylor cone. If the viscosity and surface tension of the solution are appropriately tuned, varicose breakup (electrospray) is avoided and a stable jet is formed. A bending instability results in a whipping process which stretches and elongates this fiber until it has a diameter of micrometers (or nanometers).

The terms "interferants," "interferents" and "interfering species," as used herein are broad terms, and are to be given their ordinary and customary meaning to a person of ordinary skill in the art (and are not to be limited to a special or customized meaning), and refer without limitation to effects and/or species that interfere with the measurement of an analyte of interest in a sensor to produce a signal that does not accurately represent the analyte measurement. In one example of an electrochemical sensor, interfering species are compounds with oxidation potentials that overlap with the oxidation potential of the analyte to be measured.

The term "drift," as used herein is a broad term, and is to be given its ordinary and customary meaning to a person of ordinary skill in the art (and is not to be limited to a special or customized meaning), and refers without limitation to a progressive increase or decrease in signal over time that is unrelated to changes in host systemic analyte concentrations, such as host postprandial glucose concentrations, for example. While not wishing to be bound by theory, it is believed that drift can be the result of a local decrease in glucose transport to the sensor, due to cellular invasion, which surrounds the sensor and forms a FBC, for example. It is also believed that an insufficient amount of interstitial fluid is surrounding the sensor, which results in reduced oxygen and/or glucose transport to the sensor, for example. An increase in local interstitial fluid can slow or reduce drift and thus improve sensor performance.

The term "sensing region" as used herein is a broad term, and is to be given its ordinary and customary meaning to a person of ordinary skill in the art (and is not to be limited to a special or customized meaning), and refers without limitation to the region of a monitoring device responsible for the detection of a particular analyte. The sensing region generally comprises a non-conductive body, a working electrode (anode), a reference electrode (optional), and/or a counter electrode (cathode) passing through and secured within the body forming electrochemically reactive surfaces on the body and an electronic connective means at another location on the body, and a multi-domain membrane affixed to the body and covering the electrochemically reactive surface.

The term "domain" as used herein is a broad term, and is to be given its ordinary and customary meaning to a person of ordinary skill in the art (and is not to be limited to a special or customized meaning), and refers without limitation to a region of the membrane system that can be a layer, a uniform or non-uniform gradient (for example, an anisotropic region of a membrane), or a portion of a membrane.

The term "membrane system," as used herein is a broad term, and is to be given its ordinary and customary meaning to a person of ordinary skill in the art (and is not to be limited to a special or customized meaning), and refers without limitation to a permeable or semi-permeable membrane that can be comprised of two or more domains and is typically constructed of materials of a few microns thickness or more, which is permeable to oxygen and is optionally permeable to, e.g., glucose or another analyte. In one example, the membrane system comprises an immobilized glucose oxidase enzyme, which enables a reaction to occur between glucose and oxygen whereby a concentration of glucose can be measured.

The terms "processor module" and "microprocessor," as used herein are broad terms, and are to be given their ordinary and customary meaning to a person of ordinary skill in the art (and are not to be limited to a special or customized meaning), and refer without limitation to a computer system, state machine, processor, or the like designed to perform arithmetic or logic operations using logic circuitry that responds to and processes the basic instructions that drive a computer.

The term "STS" or short-term sensor as used herein is a broad term, and is to be given its ordinary and customary meaning to a person of ordinary skill in the art (and is not to be limited to a special or customized meaning), and refers without limitation to sensors used during a short period of time (e.g., short-term), such as 1-3 days, 1-7 days, or longer. In some embodiments, the sensor is used during a short period of time, such as, for 1 day or less, 2, 3, 4, 5, 6, 7, 8, 9, 10, 11, 12, 13, 24, or 15 days. In some embodiments, the sensor is used for a short period of time, such as prior to tissue ingrowth or FBC formation. In some embodiments, a STS is transcutaneous.

The term "bulk fluid flow," as used herein is a broad term, and is to be given its ordinary and customary meaning to a person of ordinary skill in the art (and is not to be limited to a special or customized meaning), and refers without limitation to the movement of fluid(s) within an area or space, or in or out of the area or space. In one embodiment, the fluid moves in and/or out of a fluid pocket surrounding the sensor. In another embodiment, the fluid moves within the fluid pocket. In yet another embodiment, the fluid moves by convection (e.g., the circulatory motion that occurs in a fluid at a non-uniform temperature owing to the variation of its density and the action of gravity).

The term "fluid influx," as used herein is a broad term, and is to be given its ordinary and customary meaning to a person of ordinary skill in the art (and is not to be limited to a special or customized meaning), and refers without limitation to the movement of fluid(s) into the locality of an implanted sensor.

The term "fluid efflux," as used herein is a broad term, and is to be given its ordinary and customary meaning to a person of ordinary skill in the art (and is not to be limited to a special or customized meaning), and refers without limitation to the movement of fluid(s) out of the locality of an implanted sensor.

The term "adipose" as used herein is a broad term, and is to be given its ordinary and customary meaning to a person of ordinary skill in the art (and is not to be limited to a special or customized meaning), and refers without limitation to fat under the skin and surrounding major organs. For example, "adipose tissue" is fat tissue. In another example, an "adipocyte" is a fat cell.

The term "edema" as used herein is a broad term, and is to be given its ordinary and customary meaning to a person of ordinary skill in the art (and is not to be limited to a special or customized meaning), and refers without limitation to an abnormal infiltration and excess accumulation of serous fluid in connective tissue or in a serous cavity. In one example, edematous fluid is the fluid an edema.

The term "comprising" as used herein is a broad term, and is to be given its ordinary and customary meaning to a person of ordinary skill in the art (and is not to be limited to a special or customized meaning), and without limitation to is synonymous with "including," "containing," or "characterized by," and is inclusive or open-ended and does not exclude additional, unrecited elements or method steps.

The term "shedding layer" as used herein is a broad term, and is to be given its ordinary and customary meaning to a person of ordinary skill in the art (and is not to be limited to a special or customized meaning), and refers without limitation to a layer of material (e.g., incorporated into a biointerface) that leaches or releases molecules or components into the surrounding area. One example of a shedding layer includes, a coating of a biodegradable material (e.g., polyvinylalcohol or polyethylene oxide) that is eroded by tissue surrounding the sensor. In another example, the shedding layer includes a polymer hydrogel that degrades and is engulfed by circulating macrophages, which can be stimulated to release inflammatory factors.

The term "noise," as used herein is a broad term, and is to be given its ordinary and customary meaning to a person of ordinary skill in the art (and is not to be limited to a special or customized meaning), and refers without limitation to a signal detected by the sensor that is substantially non-analyte related (e.g., non-glucose related) and can result in less accurate sensor performance. One type of noise has been observed during the few hours (e.g., about 2 to about 36 hours) after sensor insertion. After the first 24-36 hours, the noise often disappears, but in some hosts, the noise can last for about three to four days.

The term "nanoporous," as used herein is a broad term, and is to be given its ordinary and customary meaning to a person of ordinary skill in the art (and is not to be limited to a special or customized meaning), and refers without limitation to materials consist of a regular organic or inorganic framework supporting a regular, porous structure having pores roughly in the nanometer range (e.g., between $1 \times 10^{-7}$ and $0.2 \times 10^{-9}$ m).

All references cited herein, including but not limited to published and unpublished applications, patents, and literature references, are incorporated herein by reference in their entirety and are hereby made a part of this specification. To the extent publications and patents or patent applications incorporated by reference contradict the disclosure contained in the specification, the specification is intended to supersede and/or take precedence over any such contradictory material.

All numbers expressing quantities of ingredients, reaction conditions, and so forth used in the specification are to be understood as being modified in all instances by the term "about." Accordingly, unless indicated to the contrary, the numerical parameters set forth herein are approximations that can vary depending upon the desired properties sought to be obtained. At the very least, and not as an attempt to limit the application of the doctrine of equivalents to the scope of any claims in any application claiming priority to the present application, each numerical parameter should be construed in light of the number of significant digits and ordinary rounding approaches.

Overview

Noise

Generally, implantable sensors measure a signal (e.g., counts) related to an analyte of interest in a host. For example, an electrochemical sensor can measure glucose, creatinine, or urea in a host, such as an animal, especially a human. Generally, the signal is converted mathematically to a numeric value indicative of analyte status, such as analyte concentration. It is not unusual for a sensor to experience a certain level of noise. "Noise," as used herein, is a broad term and is used in its ordinary sense, including, without limitation, a signal detected by the sensor that is substantially non-analyte related (e.g., non-glucose related) and can result in reduced sensor performance. Noise can be caused by a variety of factors, such as interfering species, macro- or micro-motion, ischemia, pH changes, temperature changes, pressure, stress, or even unknown sources of mechanical, electrical and/or biochemical noise for example. Since noise can obscure analyte data, reduction of noise is desirable.

There are a variety of ways noise can be recognized and/or analyzed. In preferred embodiments, the sensor data stream is monitored, signal artifacts are detected and data processing is based at least in part on whether or not a signal artifact has been detected, such as described in U.S. Publication No. US-2005-0043598-A1.

It was observed that some inserted sensors functioned more poorly during the first few hours or days after insertion than they did later. This was exemplified by noise and/or a suppression of the signal during the first about 2-36 hours or more after insertion. These anomalies often resolved spontaneously, after which the sensors became less noisy, had improved sensitivity, and were more accurate than during the early period. Moreover, the noise predominated when hosts were sleeping or sedentary for a period of time.

FIG. 1A illustrates this phenomenon of noise associated with the above-described intermittent sedentary activity during the first few days of insertion of a STS glucose sensor containing active enzyme (in a non-diabetic host). The X-axis represents time; the left Y-axis represents sensor signal in counts (e.g., signal to be converted into glucose level in mg/dL) and the right Y-axis represents noise within the sensor signal in counts (determined algorithmically according to copending U.S. patent application Ser. No. 11/498,410, filed Aug. 2, 2006 and entitled "SYSTEMS AND METHODS FOR REPLACING SIGNAL ARTIFACTS IN A GLUCOSE SENSOR DATA STREAM" herein incorporated by reference in its entirety). An enzymatic glucose sensor was built, including enzyme, as described in U.S. Publication No. US-2005-0020187-A1. During the day, the sensor signal (upper line) varied and substantially correlated with glucose concentration. But, when the host went to sleep at about midnight, noise (lower line) began to occur. Between midnight and 6 AM, when the host was asleep, there was a lot of noise, as evidenced by the large number of high peaks in the noise plot (lower line). When the host awoke and began moving around, at about 6 AM, the noise dissipated and signal substantially represented glucose concentration again.

Figure 1B:
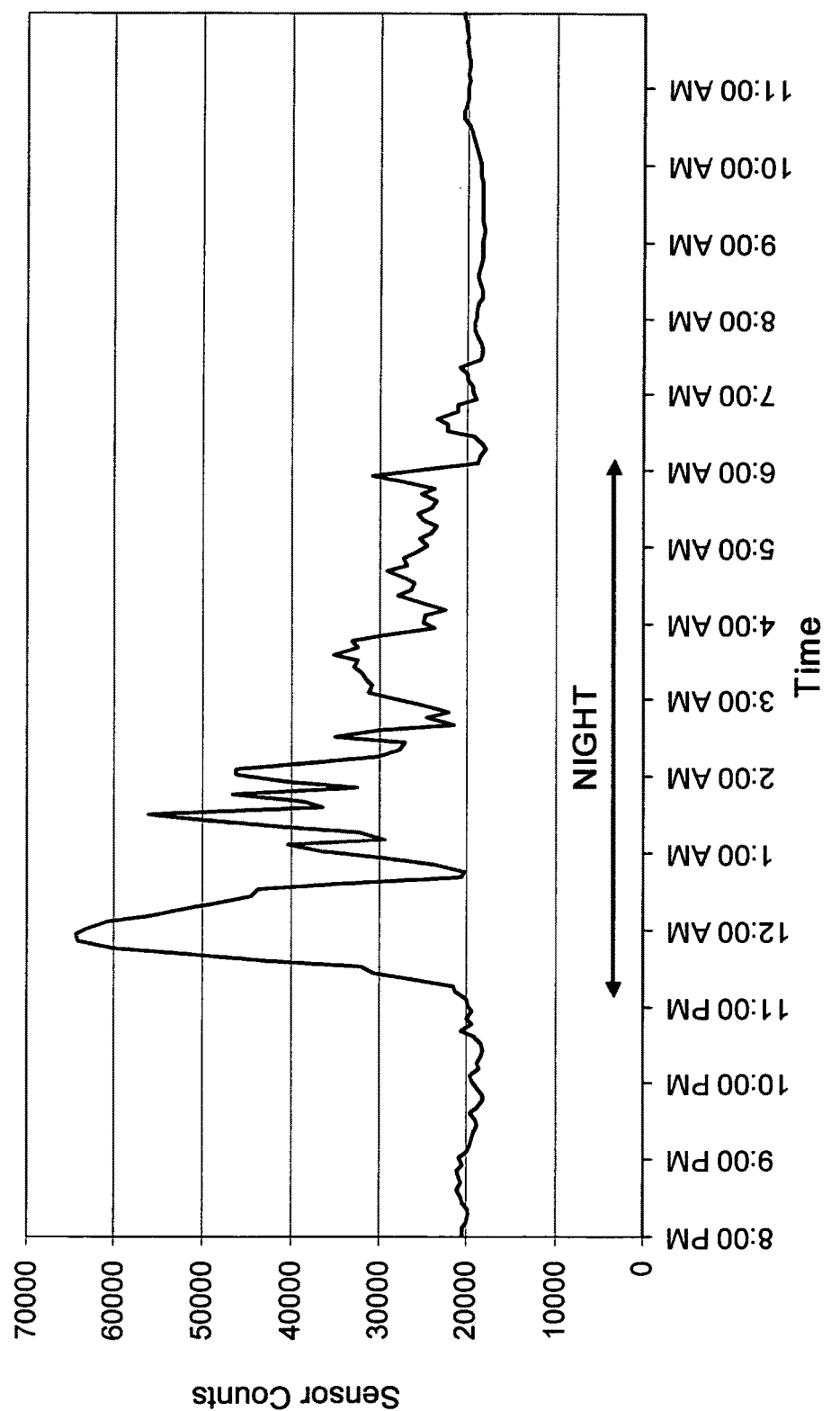
FIG. 1B is a graph illustrating nighttime noise in a non-diabetic host wearing a STS glucose sensor built without enzyme. The black line shows the sensor signal from the sensor without enzyme.

Studies using enzymatic-type glucose sensors built without enzyme were tested in non-diabetic individuals. These sensors (without enzyme) do not react with or measure glucose and therefore provide a signal due to non-glucose effects (e.g., baseline, interferants, and noise). These studies demonstrated that the noise observed during sedentary periods was caused by something other than glucose concentration. FIG. 1B shows one example of the experimental results, in a non-diabetic host wearing a STS glucose sensor built without enzyme. When the host was asleep, the no-enzyme sensor showed large, sustained positive signals that resembled glucose peaks, but could not represent actual glucose concentration because the sensor lacked enzyme. In the morning, when the host awoke and moved around, the no-enzyme signal rapidly corrected, becoming measurably reduced and smoother. From these results, the inventors believe that a reactant was diffusing to the electrodes and producing the unexpected positive signal.

Additional, in vitro experiments were conducted to determine if a sensor (e.g., electrode) component might have leached into the area surrounding the sensor. These in vitro experiments provided evidence that the non-glucose signals (observed during host sedentary periods) were not produced by contaminants of the sensor itself, or products of the chemical reaction at the electrodes, because the noise and non-glucose peaks did not occur in vitro.

While not wishing to be bound by theory, it is believed that intermittent, sedentary noise is caused by an interferant that is likely produced by local cellular activity (e.g., associated with wound healing) at the site of sensor insertion. Physiologic activity at a wound site is complex and involves the interaction of a variety of body processes. In order to fully understand the cause of intermittent, sedentary noise (as well as solutions), we must understand wound healing, fluid transport within the body (e.g., lymph transport) and tissue response to implanted materials (e.g., foreign body response). Each of these processes is discussed in greater detail below.

Wound Healing

When a foreign body is inserted into a host, it creates a wound, by breaking the skin and some of the underlying tissue, thereby initiating the wound-healing cascade of events. A wound is also produced, when a sensor, such as an implantable glucose sensor, is implanted into the subcutaneous tissue. For short-term use sensors, as described elsewhere herein, wounding occurs at least from the penetration of the sharp needle or device, which can be used to deliver the sensor. The wound can be relatively extensive, including bruising and/or bleeding, or it can be relatively benign, with little tissue damage and little or virtually no bleeding. Wound healing is initiated immediately upon wounding and is directed by a series of signaling cascades. Wound healing has four main phases: 1) hemostasis, 2) inflammation, 3) granulation, and 4) remodeling, which are discussed in more detail below.

The "hemostasis" phase begins during the first few seconds and minutes after wounding and entails a cascade of molecular events that lead to cessation of bleeding, and the formation of a fibrin scaffold that will be used as a support for cellular responses that follow. During hemostasis, blood platelets are activated by exposure to extravascular collagen and release soluble mediators (growth factors and cAMP) and adhesive glycoproteins that cause the platelets to aggregate and form a fibrin clot. Neutrophils and monocytes are attracted to the wound by platelet-derived growth factor (PDGR) and transforming growth factor beta (TGF-$\beta$), to clean the wound of infectious material, foreign matter and devitalized tissue. Vascular endothelial growth factor (VEGF or VPF), transforming growth factor alpha (TGF-$\alpha$) and basic fibroblast growth factor (bFGF), which are also secreted by activated platelets, activate endothelial cells that begin angiogenesis. "Angiogenesis" is a physiological process involving the growth of new blood vessels from pre-existing vessels. Platelet secreted PDGF also activates and recruits fibroblasts to produce extracellular matrix components.

The "inflammation" stage begins within the first 24 hours after injury and can last for several weeks in normal wounds and significantly longer in chronic nonhealing wounds. This occurs within several hours after implantation, and is the stage that most closely correlates with the anomalous behavior of the short-term sensor (STS). Inflammation involves the influx of polymorphonuclear cells and the formation of an edematous fluid pocket surrounding the implant. The vascular epithelium becomes highly permeable to cells and fluid so that invading cells (neutrophils, monocytes, and macrophages) can get to the wound site. Mast cells in the wound site release enzymes, histamine, and active amines can cause swelling, redness, heat, and pain depending on the severity of the wound. In most needle track wounds, the extent of the reaction is not sufficient to cause noticeable welling, redness, heat, or pain. Neutrophils, monocytes and macrophages release proinflammatory cytokines (IL-1, IL-6, IL-8 and TNF-$\alpha$) and cleanse the wound by engulfing bacteria, debris and devitalized tissue. These cells are highly active phagocytic cells with high metabolic requirements, and in an early wound they are proliferating exponentially, creating a need for oxygen, glucose and other molecules. Fibroblasts and epithelial cells are recruited and activated by PDGF, TGF-$\beta$, TGF-$\alpha$, insulin-like growth factor 1 (IGF-1) and FGF, in preparation for the next phase of wound healing.

The "granulation" phase occurs after several days, involving the full participation of a large number of macrophages, and the initiation of fibrosis and vascularization. During the proliferative phase of wound healing, fibroblasts proliferate and deposit granulation tissue components (various types of collagen, elastin, and proteoglycans). Angiogenesis also takes place at this time. Angiogenesis is stimulated by local low oxygen tension. Oxygen promotes angiogenesis by binding hypoxia-inducible factor (HIF) within capillary endothelial cells. When oxygen is low around capillary endothelial cells, HIF levels inside the cells increase and stimulate the production of VEGF, which stimulates angiogenesis. Low pH, high lactate levels, bFGF, and TGF-β also stimulate angiogenesis. Epithelial cells also proliferate and form a new epidermis over the wound.

The "remodeling" phase occurs after several weeks and is not relevant to sensors used for short periods of time, such as about 1 to 3 days, or up to about 7 days or more, or up to about 2 weeks. In the case of long-term wholly implantable sensors, this process is involved in remodeling tissue around the wholly implantable sensor.

The rate of these responses can vary dramatically in a host population, especially among diabetics, who are known to suffer from vascular and wound-healing disorders. Moreover, there is wide variability in the amount, texture, morphology, color, and vascularity of subcutaneous tissue. Therefore it is to be expected that the rate of progress of the wound-healing response, and the quality of the response can vary dramatically among hosts.

Dramatic differences in wounding and noise exist among individuals. Some people sound easily (e.g., bruise more easily or have more bleeding) while others do not. Some people exhibit more noise (e.g., are noisier) in their sensor signal than others. In one example, a glucose tracking study was performed with two non-diabetic volunteer hosts. Samples were collected from the fingertip and the lower abdomen, (e.g., where some short-term sensors are usually implanted). Concurrent blood samples were collected from both the fingertip and abdomen, using a lancet device. The collected blood samples were measured with a hand-held glucose meter.

Figure 1C:
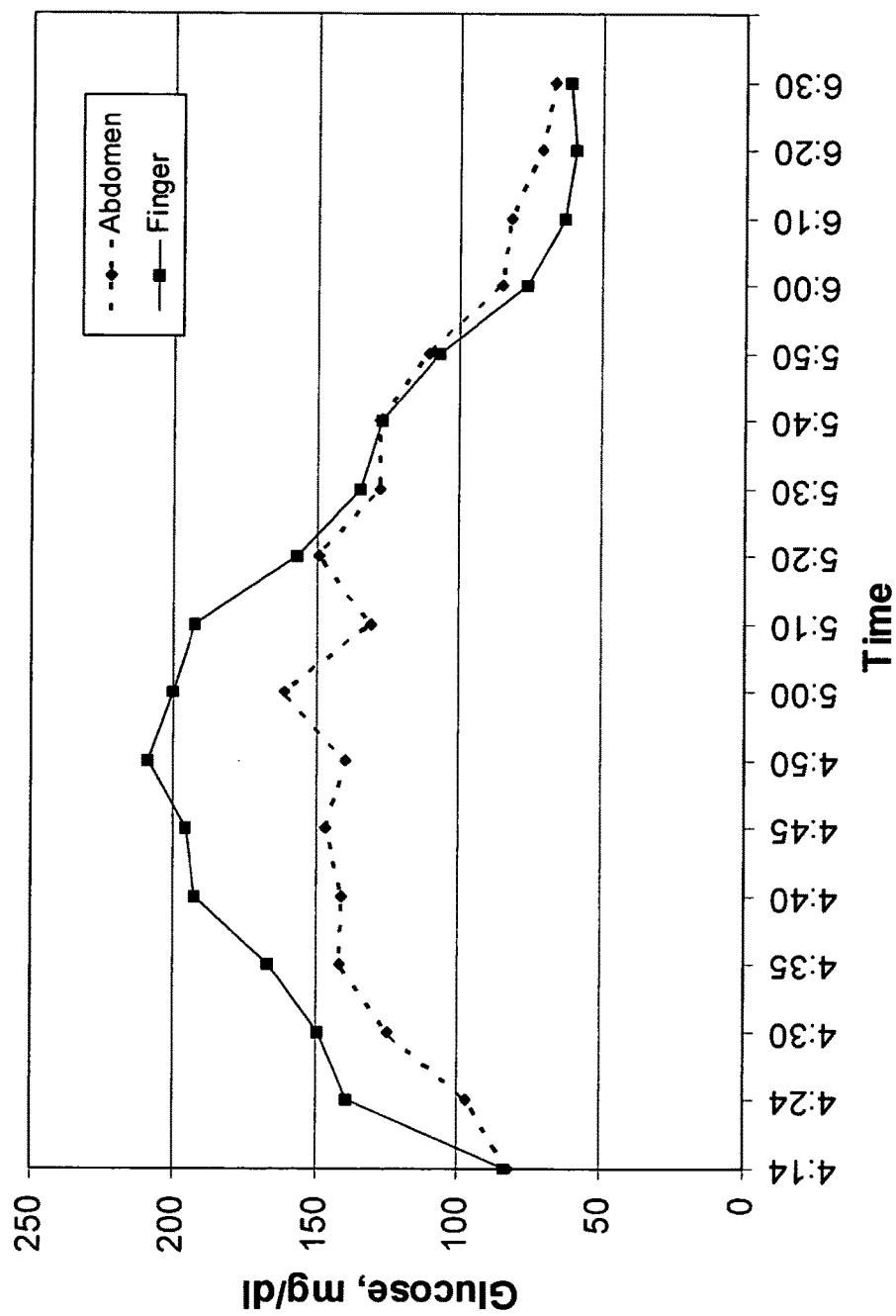
FIG. 1C is a graph comparing glucose measurements from blood samples collected from the lower abdomen (diamonds, dashed line) and the fingertip (squares, solid line) using a lancet, in a normal host that has high levels of nighttime noise. Measurements were made with a hand-held glucose monitor.

FIG. 1C illustrates the difference in responses of finger and abdominal tissue to oral sugar consumption, in a first non-diabetic volunteer host (Host 1). The solid line (with squares) shows glucose concentration at the fingertip. The dashed line (with diamonds) shows glucose concentration at the lower abdomen. When Host 1 ingested about 100 μm of oral sucrose, there was a dramatic and rapid increase in glucose signal from the fingertip samples. Host 1's abdominal signal exhibited a slower and reduced rise, when compared with the fingertip samples.

Figure 1D:
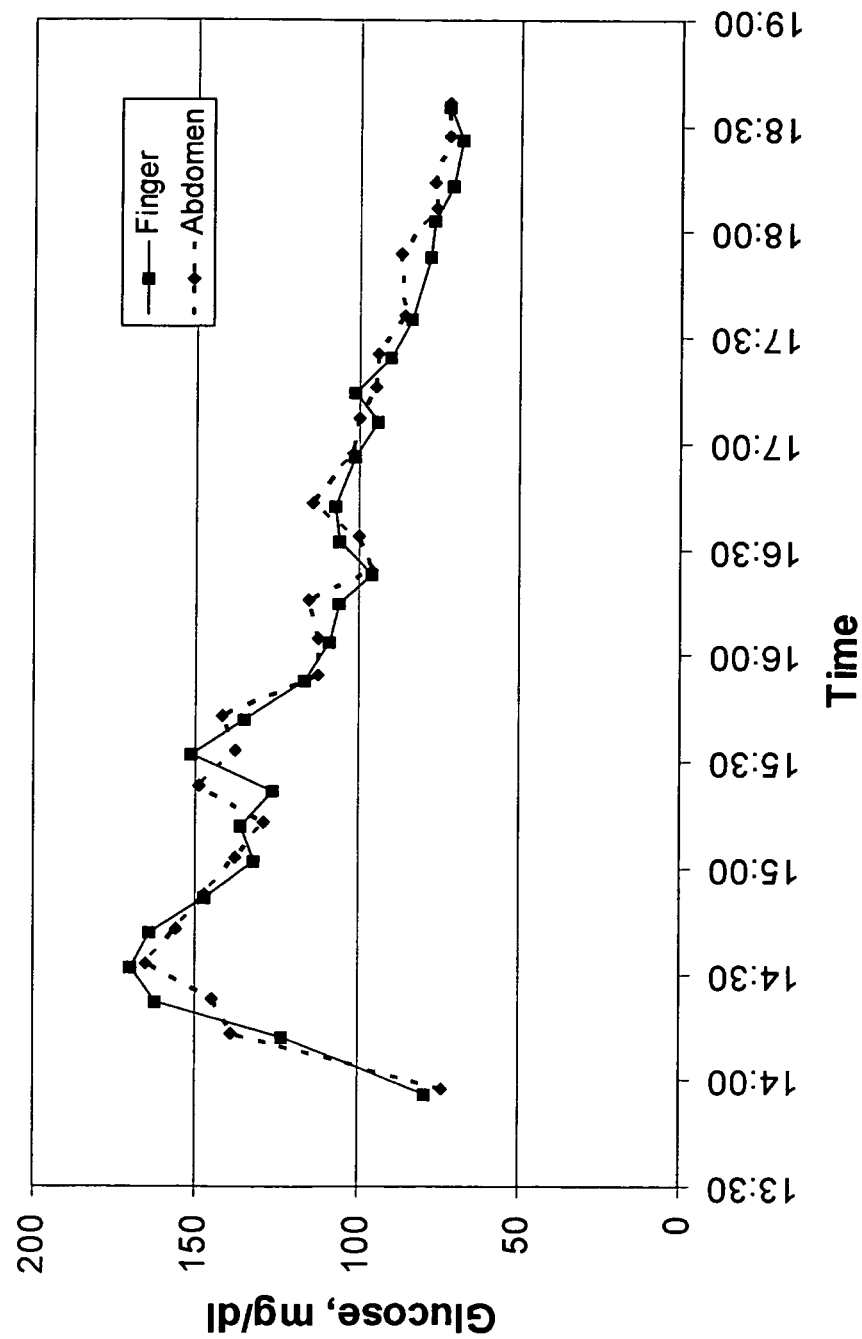
FIG. 1D is a graph comparing signals from samples collected from the lower abdomen (diamonds, dashed line) and the fingertip (squares, solid line) using a lancet, in a normal host that has low levels of nighttime noise. Measurements were made with a hand-held glucose monitor.

FIG. 1D illustrates the difference in responses of finger and abdominal tissue to oral sugar consumption, in a second volunteer non-diabetic host (Host 2). The solid line (with squares) shows glucose concentration at the fingertip. The dashed line (with diamonds) shows glucose concentration at the lower abdomen. When Host 2 was challenged with sucrose consumption, he exhibited little difference between his fingertip and abdominal samples. These data suggest that sensors implanted in different individuals can behave differently.

Different individuals experience relatively different amounts of intermittent, sedentary noise. For example, Host 1, when wearing a short-term sensor, typically was known to experience high levels of nighttime noise, whereas Host 2 experienced very little noise at any time while wearing an exemplary STS.

Figure 1F:
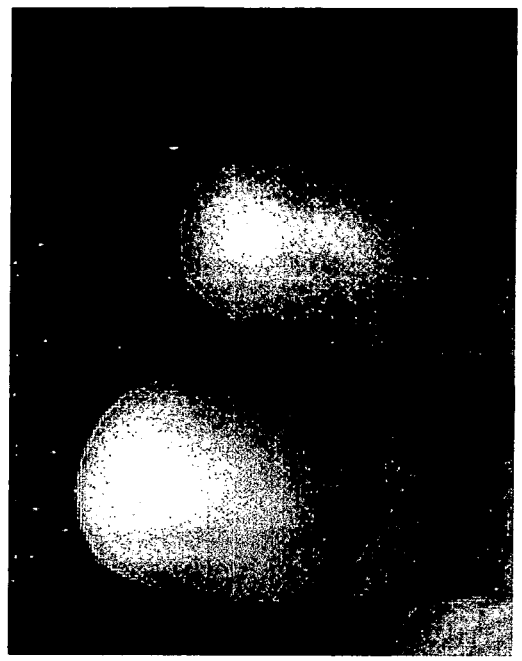
FIG. 1F is a photo of the index and middle fingers (where samples were collected) of the host of FIG. 1C.
Figure 1E:
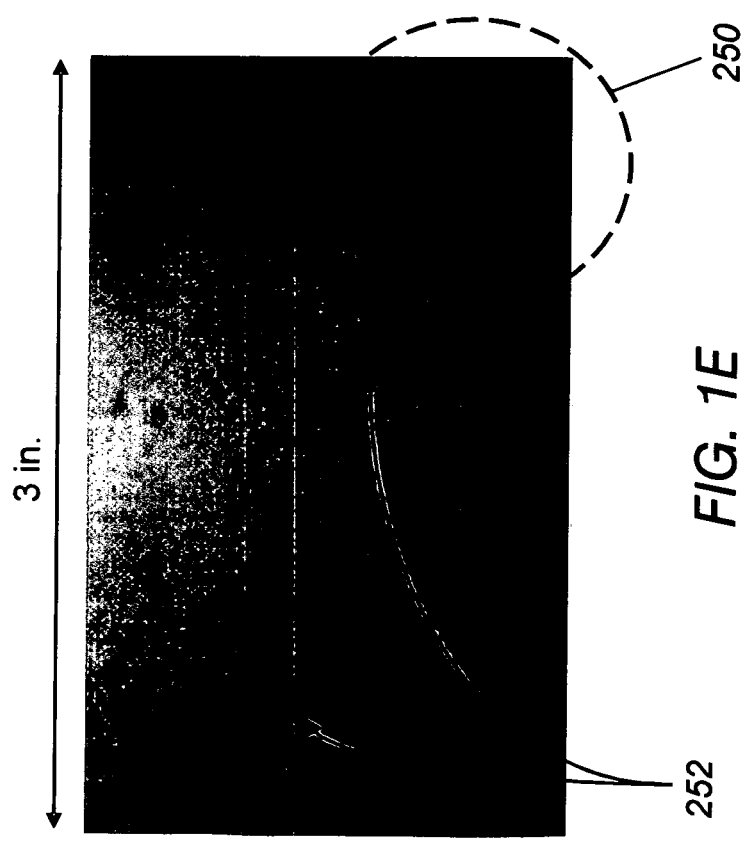
FIG. 1E is a photograph of an approximately 3-inch portion of the abdomen (where samples were collected) of the host of FIG. 1C.

In addition, the amount of wounding varies between individuals as well as between body sites of a single individual. For example, the next day, Host 1's lower abdomen exhibited extensive bruising (e.g., approximately 20 hours after completing the study). Note the many bruises 250, 252 in FIG. 1E. However, Host 1's fingertips had very little observable wounding the next day (FIG. 1F). In contrast, Host 2 (not shown) sustained little visible wounding the next day (from the lancet), at either the lower abdomen or fingertips.

When a sensor is first inserted into the subcutaneous tissue, it comes into contact with a wide variety of possible tissue conformations. Subcutaneous tissue in different hosts can be relatively fat free in cases of very athletic people, or can be mostly composed of fat as in the majority of people. The fat comes in a wide array of textures from very white, puffy fat to very dense, fibrous fat. Some fat is very yellow and dense in appearance; some is very clear, puffy, and white in appearance, while in other cases it is more red or brown in appearance. The fat can be several inches thick or only 1 cm thick. It can be very vascular or relatively nonvascular. Many diabetes hosts have some subcutaneous scar tissue due to years of insulin pump use or insulin injection. At times, sensors can come to rest in such a scarred area. The subcutaneous tissue can even vary greatly from one location to another in the abdomen of a given host. Moreover, by chance, the sensor can come to rest near a more densely vascularized area of a given host or in a less vascularized area.

Figure 2A:
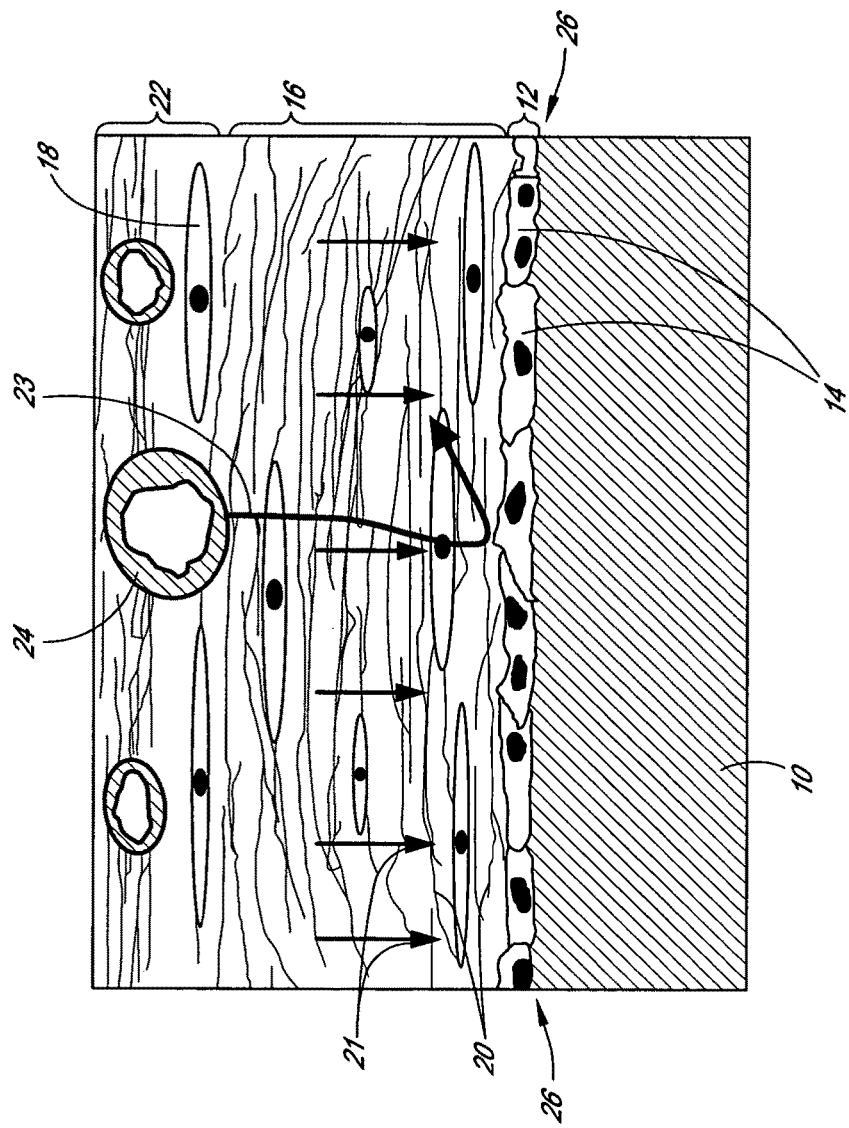
FIG. 2A is an illustration of classical three-layered foreign body response to a conventional synthetic membrane implanted under the skin.
Figure 2B:
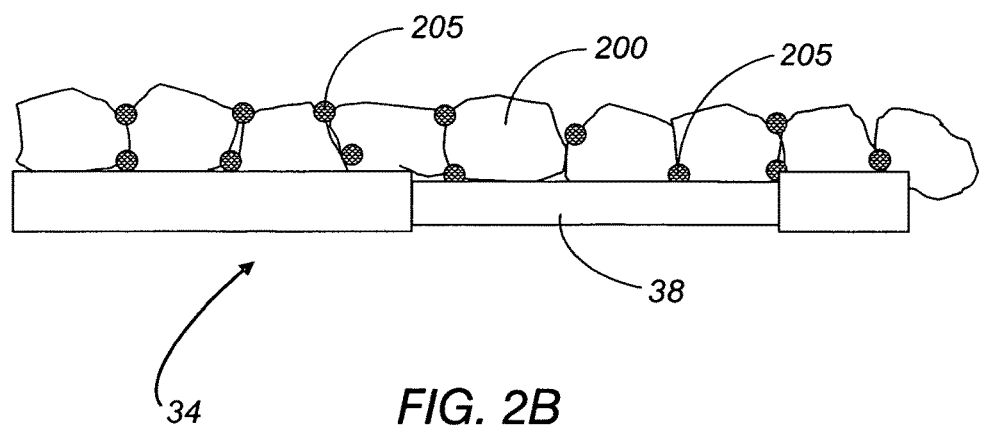
FIG. 2B is a side schematic view of adipose cell contact with an inserted transcutaneous sensor or an implanted sensor.

FIG. 2B is a side schematic view of adipose cell contact with an inserted transcutaneous sensor or an implanted sensor 34. In this case, the sensor is firmly inserted into a small space with adipose cells pressing up against the surface. Close association of the adipose cells with the sensor can also occur, for example wherein the surface of the sensor is hydrophobic. For example, the adipose cells 200 can physically block the surface of the sensor.

Typically adipose cells are about 120 microns in diameter and are typically fed by tiny capillaries 205. When the sensor is pressed against the fat tissue, as shown in FIG. 2B, very few capillaries can actually come near the surface of the sensor. This can be analogous to covering the surface of the sensor with an impermeable material such as plastic wrap, for example. Even if there were a few small holes in the plastic wrap, the sensor's function would likely be compromised. Additionally, the surrounding tissue has a low metabolic rate and therefore does not require high amounts of glucose and oxygen. While not wishing to be bound by theory, it is believed that, during this early period, the sensor's signal can be noisy and the signal can be suppressed due to close association of the sensor surface with the adipose cells and decreased availability of oxygen and glucose both for physical-mechanical reasons and physiological reasons.

Because of the host-to-host variability, the location variability in a given host, and the random possibility of hitting a favorable or unfavorable spot in a host, every time an implantable device (e.g., a sensor) is inserted into a host it has the chance of responding differently than it did in another host or at another time or place in the same host. For example, another host can insert a needle or device on day 1 and have no bleeding or bruising, but when she inserts another needle or device on day 3 she can have bleeding with an associated bruise. The wound healing response in a bloody wound will be expected to be considerably different than in a less traumatized wound. As another example, another host can have produced considerable trauma on insertion of a needle/device, without visible bleeding or bruising.

In the case of a less traumatic wound, we believe the inflammatory phase of the wound response would be delayed for some length of time. In the case of a more traumatized wound, we believe it would be accelerated. For example, a fluid pocket can take hours to form in the less traumatic wound whereas it could take much less time in the case of the more traumatic wound.

In the case of a less traumatic wound, when an implantable device, such as a glucose sensor, is initially inserted, relatively little tissue damage occurs. The device finds itself firmly inserted into a small space with adipose tissue pressing up against the surface. Because the surface of the sensor (e.g., a STS sensor as described herein) is mainly very hydrophobic, it can associate very closely with the adipose tissue. Because no edema (e.g., wound fluid) is forming or is forming slowly, there will be very little fluid around the sensor for glucose transport. Accordingly, adipose cells can physically block the surface of the sensor. When the sensor is pressed against the adipose tissue, it is believed that very few capillaries come near the surface of the sensor. Additionally, the surrounding tissue has a low metabolic rate and therefore does not require high amounts of glucose and oxygen. While not wishing to be bound by hypothesis, it is believed that during this period (prior to the formation of an edematous pocket and the influx of cells and glucose) the sensor signal can be noisy and suppressed due to close association of the sensor surface with the adipose cells and lack of availability of oxygen and glucose both for physical-mechanical reasons and physiological reasons. While not wishing to be bound by theory, it is believed that the short-term sensor measures wound fluid surrounding the sensor. Thus, if the rate of edema collection (e.g., collection of wound fluid into a fluid pocket) can be increased then early noise can be alleviated or reduced.

Lymph System and Fluid Transport

The circulatory and lymph systems are the body's means of moving fluids, cells, protein, lipids, and the like throughout the body in an organized fashion. The two systems parallel each other, throughout the body. The circulatory system is a closed system that relies on a pump (the heart) for control of bulk flow. In contrast, the lymph system is an open system with no central pump. The lymph system relies upon pressure differentials, local muscle contraction, among other things, for fluid movement. Gravity and inactivity can have dramatic effects on lymph movement throughout the body, and consequently on noise and sensor function.

Lymph forms when dissolved proteins and solutes filter out of the circulatory system into the surrounding tissues, because of local differences in luminal hydrostatic and osmotic pressure. The fluid within the extracellular spaces is called interstitial fluid. A portion of the interstitial fluid flows back into the circulatory system, while the remaining fluid is collected into the lymph capillaries through valve-like openings between the endothelial cells of the lymph capillaries.

Lymph is generally a clear and transparent semifluid medium. It is known in the art that normal cellular metabolism produces waste species that are removed from the local environment by the lymphatics. Lymph contains a "lymphatic load" of protein, water, lymphocytes, cellular components, metabolic waste and particles, and fat. The lymphatics return the lymph to the circulatory system at the thoracic duct. It is known that lymph has almost the same composition as the original interstitial fluid.

In contrast to the circulatory system, the lymph system is an open system with no central pump. Lymph capillaries take in fluid through "open junctions," until they are filled to capacity. When the pressure inside the capillary is greater than that of the surrounding interstitial tissue, the open junctions close. The lymph moves freely toward larger, downstream portions of the lymph system, where pressure is lower. As the lymph moves forward, it is picked up by "lymph collectors," which have valves that prevent fluid back-flow. Larger portions of the lymph system segmentally contract, to push the lymph forward, from one segment to the next. Breathing movements and skeletal muscle contractions also push the lymph forward. Eventually, the lymph is returned to the circulatory system via the thoracic duct.

Lymph capillaries are delicate and easily flattened. When lymph capillaries are flattened, fluid cannot enter them. Consequently, lymph flow is impeded by a local collapse of the lymph capillaries. Gravity and local pinching of lymph capillaries affect the movement of lymph. For example, it is well known in the medical community that a tourniquet placed on the upper arm can impede lymph flow out of the arm. It is also known that during sleep lymph pools on the side of the body on which a person is lying. In another example, sitting can pinch some of the lower lymphatics, causing lymph to pool in the legs over an extended period of time.

As discussed with reference to FIG. 1B, above, the inventors have found that, soon after insertion of a sensor, noise (e.g., signal) not associated with glucose concentration can occur intermittently during sedentary activities, such as sleeping, watching television or reading a book. The inventors have demonstrated experimentally that early intermittent, sedentary noise is, at least in part, the result of unknown interferants that affect the sensor during periods of sustained inactivity.

While not wishing to be bound by theory, it is believed that a local build up of electroactive interferants, such as electroactive metabolites from cellular metabolism and wound healing, interfere with sensor function and cause early intermittent, sedentary noise. Local lymph pooling, when parts of the body are compressed or when the body is inactive can cause, in part, this local build up of interferants (e.g., electroactive metabolites). Interferants can include but are not limited to compounds with electroactive acidic, amine or sulfhydryl groups, urea, lactic acid, phosphates, citrates, peroxides, amino acids (e.g., L-arginine), amino acid precursors or break-down products, nitric oxide (NO), NO-donors, NO-precursors or other electroactive species or metabolites produced during cell metabolism and/or wound healing, for example.

Foreign Body Response

Devices and probes that are transcutaneously inserted or implanted into subcutaneous tissue conventionally elicit a foreign body response (FBR), which includes invasion of flammatory cells that ultimately forms a foreign body capsule (FBC), as part of the body's response to the introduction of a foreign material. Specifically, insertion or implantation of a device, for example, a glucose sensing device, can result in an acute inflammatory reaction resolving to chronic inflammation with concurrent building of fibrotic tissue, such as is described in detail above. Eventually, over a period of two to three weeks, a mature FBC, including primarily contractile fibrous tissue forms around the device. See Shanker and Greisler, Inflammation and Biomaterials in Greco RS, ed., "Implantation Biology: The Host Response and Biomedical Devices" pp 68-80, CRC Press (1994). The FBC surrounding conventional implanted devices has been shown to hinder or block the transport of analytes across the device-tissue interface. Thus, continuous extended life analyte transport (e.g., beyond the first few days) in vivo has been conventionally believed to be unreliable or impossible.

FIG. 2A is a schematic drawing that illustrates a classical FBR to a conventional cell-impermeable synthetic membrane 10 implanted under the skin. There are three main layers of a FBR. The innermost FBR layer 12, adjacent to the device, is composed generally of macrophages and foreign body giant cells 14 (herein referred to as the "barrier cell layer"). These cells form a monolayer of closely opposed cells over the entire surface of a microscopically smooth membrane, a macroscopically smooth (but microscopically rough) membrane, or a microporous (i.e., average pore size of less than about 1 μm) membrane. A membrane can be adhesive or non-adhesive to cells; however, its relatively smooth surface causes the downward tissue contracture 21 (discussed below) to translate directly to the cells at the device-tissue interface 26. The intermediate FBR layer 16 (herein referred to as the "fibrous zone"), lying distal to the first layer with respect to the device, is a wide zone (about 30 to 100 μm) composed primarily of fibroblasts 18, fibrous matrixes, and contractile fibrous tissue 20. The organization of the fibrous zone, and particularly the contractile fibrous tissue 20, contributes to the formation of the monolayer of closely opposed cells due to the contractile forces 21 around the surface of the foreign body (for example, membrane 10). The outermost FBR layer 22 is loose connective granular tissue containing new blood vessels 24 (herein referred to as the "vascular zone"). Over time, this FBR tissue becomes muscular in nature and contracts around the foreign body so that the foreign body remains tightly encapsulated. Accordingly, the downward forces 21 press against the tissue-device interface 26, and without any counteracting forces, aid in the formation of a barrier cell layer 14 that blocks and/or refracts the transport of analytes 23 (for example, glucose) across the tissue-device interface 26.

A consistent feature, of the innermost layers 12, 16, is that they are devoid of blood vessels. This has led to widely supported speculation that poor transport of molecules across the device-tissue interface 26 is due to a lack of vascularization near the interface. See Scharp et al., World J. Surg., 8:221-229 (1984); and Colton et al., J. Biomech. Eng., 113:152-170 (1991). Previous efforts to overcome this problem have been aimed at increasing local vascularization at the device-tissue interface, but have achieved only limited success.

Although local vascularization can aid in sustenance of local tissue over time, the presence of a barrier cell layer 14 prevents the passage of molecules that cannot diffuse through the layer. For example, when applied to an implantable glucose-measuring device, it is unlikely that glucose would enter the cell via glucose transporters on one side of the cell and exit on the other side. Instead, it is likely that any glucose that enters the cell is phosphorylated and remains within the cell. The only cells known to facilitate transport of glucose from one side of the cell to another are endothelial cells. Consequently, little glucose reaches the implant's membrane through the barrier cell layer. The known art purports to increase the local vascularization in order to increase solute availability. See Brauker et al., U.S. Pat. No. 5,741,330. However, it has been observed by the inventors that once the monolayer of cells (barrier cell layer) is established adjacent to a membrane, increasing angiogenesis is not sufficient to increase transport of molecules such as glucose and oxygen across the device-tissue interface 26. In fact, the barrier cell layer blocks and/or reflects the analytes 23 from transport across the device-tissue interface 26.

Referring now to short-term sensors, or the short-term function of long-term sensors, it is believed that certain aspects of the FBR in the first few days can play a role in noise. It has been observed that some sensors function more poorly during the first few hours after insertion than they do later. This is exemplified by noise and/or a suppression of the signal during the first few hours (e.g., about 2 to about 36 hours) after insertion. These anomalies often resolve spontaneously after which the sensors become less noisy, have improved sensitivity, and are more accurate than during the early period. It has been observed that some transcutaneous sensors and wholly implantable sensors are subject to noise for a period of time after application to the host (i.e., inserted transcutaneously or wholly implanted below the skin). "Noise," as used herein, is a broad term and is used in its ordinary sense, including, without limitation, a signal detected by the sensor that is unrelated to analyte concentration and can result in less accurate sensor performance. One type of noise has been observed during the few hours (e.g., about 2 to about 36 hours) after sensor insertion. After the first few hours to 36 hours, the noise often disappears, but in some hosts, the noise can last longer.

Referring now to long-term function of a sensor, after a few days to two or more weeks of implantation, many prior art devices typically lose their function. In some applications, cellular attack or migration of cells to the sensor can cause reduced sensitivity and/or function of the device, particularly after the first day of implantation. See also, for example, U.S. Pat. No. 5,791,344 and Gross et al. and "Performance Evaluation of the MiniMed Continuous Monitoring System During Host home Use," Diabetes Technology and Therapeutics, (2000) 2(1):49-56, which have reported a glucose oxidase-based device, approved for use in humans by the Food and Drug Administration, that functions well for several days following implantation but loses function quickly after the several days (e.g., a few days up to about 14 days).

It is believed that this lack of device function is most likely due to cells, such as polymorphonuclear cells and monocytes, which migrate to the sensor site during the first few days after implantation. These cells consume local glucose and oxygen. If there is an overabundance of such cells, they can deplete glucose and/or oxygen before it is able to reach the device enzyme layer, thereby reducing the sensitivity of the device or rendering it non-functional. Further inhibition of device function can be due to inflammatory cells, for example, macrophages, that associate with the implantable device (for example, align at an interface) and physically block the transport of glucose into the device (for example, by formation of a barrier cell layer). Additionally, these inflammatory cells can biodegrade many artificial biomaterials (some of which were, until recently, considered non-biodegradable). When activated by a foreign body, tissue macrophages degranulate, releasing hypochlorite (bleach) and other oxidative species. Hypochlorite and other oxidative species are known to break down a variety of polymers.

In some circumstances, for example in long-term sensors, it is believed that the foreign body response is the dominant event surrounding extended implantation of an implanted device, and can be managed or manipulated to support rather than hinder or block analyte transport. In another aspect, in order to extend the lifetime of the sensor, preferred embodiments employ materials that promote vascularized tissue ingrowth, for example within a porous biointerface membrane. For example tissue in-growth into a porous biointerface material surrounding a long-term sensor can promote sensor function over extended periods of time (e.g., weeks, months, or years). It has been observed that in-growth and formation of a tissue bed can take up to about 3 weeks or more. Tissue ingrowth and tissue bed formation is believed to be part of the foreign body response. As will be discussed herein, the foreign body response can be manipulated by the use of porous biointerface materials that surround the sensor and promote ingrowth of tissue and microvasculature over time. Long-term use sensors (LTS), for use over a period of weeks, months or even years, have also been produced. LTS can be wholly implantable, and placed within the host's soft tissue below the skin, for example.

Accordingly, a long-term sensor including a biointerface, including but not limited to, for example, porous biointerface materials including a solid portion and interconnected cavities, all of which are described in more detail elsewhere herein, can be employed to improve sensor function in the long-term (e.g., after tissue ingrowth).

Reduction of Intermittent Sedentary Noise

As discussed above, noise can occur during the first few hours or days after sensor implantation, during periods of inactivity. While not wishing to be bound by theory, the inventors believe noise that occurs during these early intermittent sedentary time periods can be caused by a local increase in interferants (e.g., electroactive metabolites) that disrupt sensor function, resulting in apparent glucose signals that are generally unrelated to the host's glucose concentration. Accordingly, the noise intensity and/or number of intermittent, sedentary noise occurrences can be reduced or eliminated by reducing the local concentration of interferants produced during normal cellular metabolism and/or wound healing.

In some circumstances, the inventors believe that intermittent, sedentary noise can be addressed either by affecting wounding and/or the wound healing process. For example, in some circumstances a wounding response initiated when the sensor (e.g., a glucose sensor) is implanted can lead to in insubstantial transport of interferents away from the sensor during sedentary periods, which can result in increased intermittent, sedentary noise. Thus, it interferent concentration is reduced, such as by increasing fluid bulk, bulk fluid flow, or diffusion rates (e.g., with vasodilation agents or inflammatory agents), prolonging wounding (e.g., with irritating structures or agents) or promoting wound healing's inflammation stage, then noise can be reduced.

The present invention provides, among other things, devices, and methods for reducing or eliminating noise caused by intermittent interferant build-up in the area surrounding an inserted sensor during the first few hours or days post-implantation. As will be discussed in greater detail below, these devices and methods contemplate, among other things, increasing bulk fluid flow in and/or out of the sensor locality, increased fluid bulk, production of increased or continued wounding of the insertion site, suppression, and/or prevention of wounding during and after sensor insertion, and combinations thereof. Those knowledgeable in the art will recognize that the various structures and bioactive agents disclosed herein can be employed in a plurality of combinations, depending upon the desired effect and the noise reduction strategy selected.

Increasing Fluid Bulk or Bulk Fluid Flow

Analyte sensors for in vivo use over various lengths of time have been developed. For example, sensors to be used for a short period of time, such as about 1 to about 14 days, have been produced. Herein, this sensor will be referred to as a short-term sensor (STS). A STS can be a transcutaneous device, in that a portion of the device can be inserted through the host's skin and into the underlying soft tissue while a portion of the device remains on the surface of the host's skin. In one aspect, in order to overcome the problems associated with noise, such as intermittent, sedentary noise, or other sensor function in the short-term (e.g., short-term sensors or short-term function of long-term sensors), preferred embodiments employ materials that promote formation of a fluid pocket around the sensor, for example architectures such as porous biointerface membrane, matrices or other membrane/mechanical structures that create a space between the sensor and the surrounding tissue.

The concentration of interferants (e.g., electroactive metabolites) surrounding the sensor can be reduced by, among other things, increasing fluid bulk (e.g., a fluid pocket), an increased bulk fluid flow and/or an increased diffusion rate around at least a portion of the sensor, such as the sensing portion of the sensor. One embodiment of the present invention provides a device with reduced intermittent sedentary noise having an architecture that allows and/or promotes increased fluid bulk and/or increased bulk fluid flow in the area surrounding at least a portion of an implanted sensor in vivo.

A variety of structures can be incorporated into the sensor to allow and/or promote increased (e.g., to stimulate or to promote) fluid bulk, bulk fluid flow, and/or diffusion rate. These structures can include but are not limited to spacers, meshes, shedding layers, roughened surfaces, machineable materials, nanoporous materials, shape-memory materials, porous memory materials, self-assembly materials, collapsible materials, biodegradable materials, combinations thereof, and the like. Structures that promote increased fluid bulk and/or increased bulk fluid flow can also include but are not limited to structures that promote fluid influx or efflux (e.g., fluid influx-promoting architecture, fluid efflux-promoting architecture), that promote vasodilation (e.g., vasodilating architecture), that promote inflammation (e.g., inflammatory architecture), that promote wound healing or perpetuate wounding (e.g., wound-healing architecture and wounding architecture, respectively), that promote angiogenesis (e.g., angiogenic architecture), that suppress inflammation (e.g., an anti-inflammatory architecture) or combinations thereof.

In one embodiment, a porous material that results in increased fluid bulk, bulk fluid flow and/or diffusion rate, as well as formation of close vascular structures, is a porous polymer membrane, such as but not limited to polytetrafluoroethylene (PTFE), polysulfone, polyvinylidene difluoride, polyacrylonitrile, silicone, polytetrafluoroethylene, expanded polytetrafluoroethylene, polyethylene-co-tetrafluoroethylene, polyolefin, polyester, polycarbonate, biostable polytetrafluoroethylene, homopolymers, copolymers, terpolymers of polyurethanes, polypropylene (PP), polyvinylchloride (PVC), polyvinylidene fluoride (PVDF), polyvinyl alcohol (PVA), polybutylene terephthalate (PBT), polymethylmethacrylate (PMMA), polyether ether ketone (PEEK), polyamides, polyurethanes, cellulosic polymers, poly(ethylene oxide), poly(propylene oxide) and copolymers and blends thereof, polysulfones and block copolymers thereof including, for example, di-block, tri-block, alternating, random and graft copolymers, as well as metals, ceramics, cellulose, hydrogel polymers, poly (2-hydroxyethyl methacrylate, pHEMA), hydroxyethyl methacrylate, (HEMA), polyacrylonitrile-polyvinyl chloride (PAN-PVC), high density polyethylene, acrylic copolymers, nylon, polyvinyl difluoride, polyanhydrides, poly(1-lysine), poly (L-lactic acid), and hydroxyethylmethacrylate, having an average nominal pore size of at least about 0.6 to 20 µm, using conventional methods for determination of pore size in the trade. In one embodiment, at least approximately 50% of the pores of the membrane have an average size of approximately 0.6 to about 20 µm, such as described in U.S. Pat. No.

5,882,354. In this exemplary embodiment, the structural elements, which provide the three-dimensional conformation, can include fibers, strands, globules, cones or rods of amorphous or uniform geometry that is smooth or rough. These elements, hereafter referred to as "strands," have in general one dimension larger than the other two and the smaller dimensions do not exceed five microns.

In another further embodiment, the porous polymer membrane material, as described above, consists of strands that define "apertures" formed by a frame of the interconnected strands. The apertures have an average size of no more than about 20 µm in any but the longest dimension. The apertures of the material form a framework of interconnected apertures, defining "cavities" that are no greater than an average of about 20 µm in any but the longest dimension. In another embodiment the porous polymer membrane material has at least some apertures having a sufficient size to allow at least some vascular structures to be created within the cavities. At least some of these apertures, while allowing vascular structures to form within the cavities, prevent connective tissue from forming therein because of size restrictions.

In a further embodiment, the porous membrane has frames of elongated strands of material that are less than 5 microns in all but the longest dimension and the frames define apertures which interconnect to form three-dimensional cavities which permit substantially all inflammatory cells migrating into the cavities to maintain a rounded morphology. Additionally, the porous material promotes vascularization adjacent but not substantially into the porous material upon implantation into a host. Exemplary materials include but are not limited to polyethylene, polypropylene, polytetrafluoroethylene (PTFE), cellulose acetate, cellulose nitrate, polycarbonate, polyester, nylon, polysulfone, mixed esters of cellulose, polyvinylidene difluoride, silicone, polyacrylonitrile, and the like.

In some embodiments, a short-term sensor is provided with a spacer adapted to provide a fluid pocket between the sensor and the host's tissue. It is believed that this spacer, for example a biointerface material, matrix, mesh, hydrogel and like structures and the resultant fluid pocket provide for oxygen and/or glucose transport to the sensor.

Figure 2C:
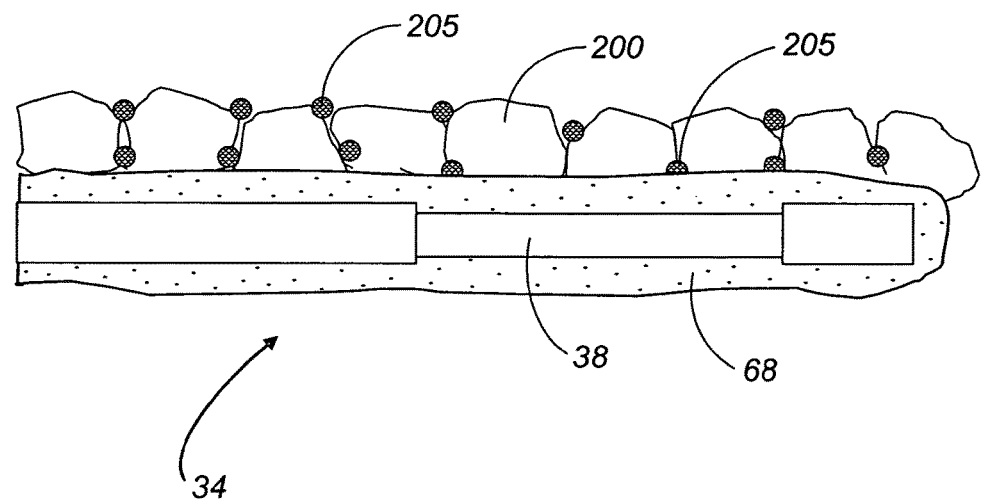
FIG. 2C is a side schematic view of a biointerface membrane preventing adipose cell contact with an inserted transcutaneous sensor or an implanted sensor.

FIG. 2C is a side schematic view of a biointerface membrane as the spacer preventing adipose cell contact with an inserted transcutaneous sensor or an implanted sensor in one exemplary embodiment. In this illustration, a porous biointerface membrane 68 surrounds the sensor 34, covering the sensing mechanism (e.g., at least a working electrode 38) and is configured to fill with fluid in vivo, thereby creating a fluid pocket surrounding the sensor. Accordingly, the adipose cells surrounding the sensor are held a distance away (such as the thickness of the porous biointerface membrane, for example) from the sensor surface. Accordingly, as the porous biointerface membrane fills with fluid (e.g., creates a fluid pocket), oxygen and glucose are transported to the sensing mechanism in quantities sufficient to maintain accurate sensor function. Additionally, as discussed elsewhere herein, interferants are diluted, suppressing or reducing interference with sensor function.

Accordingly, a short-term sensor (or short-term function of a long-term sensor) including a biointerface, including but not limited to, for example, porous biointerface materials, mesh cages, and the like, all of which are described in more detail elsewhere herein, can be employed to improve sensor function in the short-term (e.g., first few hours to days). Porous biointerface membranes need not necessarily include interconnected cavities for creating a fluid pocket in the short-term.

In certain embodiments, the device includes a physical spacer between the sensor and the surrounding tissue. A spacer allows for a liquid sheath to form around at least a portion of the sensor, such as the area surrounding the electrodes, for example. A fluid sheath can provide a fluid bulk that dilutes or buffers interferants while promoting glucose and oxygen transport to the sensor.

In some embodiments, the spacer is a mesh or optionally a fibrous structure. Suitable mesh materials are known in the art and include open-weave meshes fabricated of biocompatible materials such as but not limited to PLA, PGA, PP, nylon and the like. Mesh spacers can be applied directly to the sensing mechanism or over a biointerface membrane, such as a porous biointerface membrane disclosed elsewhere herein. Mesh spacers can act as a fluid influx- or efflux-promoting structure and provides the advantage of relatively more rapid fluid movement, mixing and/or diffusion within the mesh to reduce local interferant concentrations and increasing glucose and oxygen concentrations. The increased fluid volume within the mesh can also promote increased fluid movement in and out of the area, which brings in glucose and oxygen while removing or diluting interferants.

Furthermore, a physical spacer can reduce the effect of lymph pooling due to local compression (during sedentary activity) by mechanically maintaining the fluid pocket. When the host is sedentary (e.g., lies down to sleep) the area surrounding the sensor can be compressed. For example, if the sensor is on the right side of the host's abdomen and he lies down on that side for a few hours, the lymphatics on the abdominal right side will be pinched off. When the tissue is compressed/pinched, fluid will not be able to move into the pinched lymphatic capillaries and interferants (from local tissue metabolism) can build up and cause noise. When the host gets up, the compression/pinching is relieved and the interferants can be removed via the lymphatics. Since a spacer can maintain the fluid bulk around the sensor during local compression, the effect of interferant concentration increases can be suppressed or reduced, thereby reducing noise and promoting optimal sensor function.

In one exemplary embodiment, the sensor is wrapped with a single layer of open weave polypropylene (PP) biocompatible mesh. When the sensor is inserted, the mesh holds the surrounding tissue away from the sensor surface and allows an influx of extracellular fluid to enter the spaces within the mesh, thereby creating a fluid pocket around the sensor. Within the fluid pocket, fluid can mix substantially rapidly as extracellular fluid enters and leaves the fluid pocket or due to host movement. Interferants are carried by the fluid and therefore can be mixed and/or diluted. Since the host can wear the sensor for a plurality of days, sedentary periods will inevitably occur. During these periods interferants can accumulate. However, the increased fluid volume provided by the mesh can substantially buffer accumulated interferants until the sedentary period ends. When the sedentary period is over, any accumulated interferants can be diluted or carried away by an influx or efflux of fluid.

In an alternative embodiment, a mesh can be applied to a sensor either symmetrically or asymmetrically. For example, the mesh can be tightly wrapped around the sensor. In another example, a strip of mesh can be applied to only one side of the sensor. In yet another example, the mesh can form a flat envelope about a few millimeters to about a centimeter wide, with the sensor sandwiched within the envelope. In some embodiments, the mesh can cover only a portion of the sensor, such as the portion containing the electrochemically reactive surface(s). In other embodiments, the mesh can cover the entire sensor.

In another alternative embodiment, noise can be reduced by inclusion of a hydrogel on the surface of at least a portion of the sensor, such as the sensing region. A hydrogel is a network of super absorbent (they can contain 20%-99% or weight % water, preferably 80% to over 99% weight % water) natural or synthetic polymer chains. Hydrogels are sometimes found as a colloidal gel in which water is the dispersion medium. Since hydrogels are nonporous, fluid and interferants within the hydrogel move by diffusion. Accordingly, the movement of molecules within hydrogels is relatively slower than that possible within mesh-based fluid pockets as described above. Optionally, the hydrogel can be biodegradable. A biodegradable hydrogel can provide a fluid pocket that gradually diminishes and is eventually eliminated by the surrounding tissue.

In a further embodiment, a hydrogel includes a flexible, water-swellable, film (as disclosed elsewhere herein) having a "dry film" thickness of from about 0.05 micron or less to about 20 microns or more, more preferably from about 0.05, 0.1, 0.15, 0.2, 0.25, 0.3, 0.35, 0.4, 0.45, 0.5, 1, 1.5, 2, 2.5, 3, or 3.5 to about 4, 5, 6, 7, 8, 9, 10, 11, 12, 13, 14, 15, 16, 17, 18, 19, or 19.5 microns, and more preferably from about 2, 2.5 or 3 microns to about 3.5, 4, 4.5, or 5 microns. "Dry film" thickness refers to the thickness of a cured film cast from a coating formulation by standard coating techniques. The hydrogel material can be applied to the entire sensor or a portion of it, using any method known in the art, such as but not limited to dipping, painting, spraying, wrapping, and the like.

In certain embodiments, scavenging agents (e.g., bioactive agents that can scavenge, bind-up or substantially inactivate interferants) can be incorporated into the hydrogel or other aspect of the device (e.g., membrane system). Scavenging agents can suppress prolonged wounding and inflammation by removing irritating substances from the locality of the sensor.

One exemplary scavenging agent embodiment incorporates an $H_2O_2$-degrading enzyme, such as but not limited to glutathione peroxidase (GSH peroxidase), heme-containing peroxidases, eosinophil peroxidase, thyroid peroxidase or horseradish peroxidase (HRP) into the hydrogel to degrade the available $H_2O_2$ and produce oxygen. The scavenging agent can act within the hydrogel or can be released into the local environment to act outside the hydrogel.

In a further embodiment, a mesh and a hydrogel can be used in combination to provide greater mechanical support (to hold the surrounding tissue away from the sensor) while slowing down the diffusion rate within the mesh-hydrogel layer. For example, a PP mesh can be applied to the sensor followed by spraying a dry hydrogel material onto the PP-wrapped sensor. Alternatively, the hydrogel can be dried within the mesh before application to the sensor. Upon sensor implantation, the hydrogel can absorb fluid from the surrounding tissue, expand and fill the mesh pores. In a further example, the hydrogel can be biodegradable. In this example, the hydrogel can initially slow fluid movement. But as the hydrogel is biodegraded, the pores of the mesh are opened up and fluid movement can speed up or increase.

A variety of alterative materials can be used to create architectures that create a fluid pocket. For example, shape-memory materials can be used as an alternative to a mesh, to form a fluid pocket around the sensor. Shape-memory materials are metals or polymers that "remember" their geometries. Shape-memory metals (e.g., memory metals or smart wire) include copper-zinc-aluminum, copper-aluminum-nickel, and nickel-titanium (NiTi) alloys. Shape-memory polymers include materials such as polynorbornene, segmented poly(epsilon-caprolactone) polyurethanes, poly(ethylene glycol)-poly(epsilon-caprolactone) diblock copolymers, and the like, for example. A shape-memory material can be deformed from its "original" conformation and regains its original geometry by itself in response to a force, such as temperature or pressure.

In one embodiment, a porous memory material that has been collapsed into a flat, nonporous sheet can be applied to the exterior of the sensor as a flat film. After insertion into the body, increased temperature or moisture exposure can stimulate the memory material to transform to a 3-dimensional, porous architecture that promotes fluid pocket formation, for example.

In an alternative embodiment, nanoporous materials, which act as molecular sieves, can be used to exclude interferants surrounding the sensor. In another alternative embodiment, a swellable material (e.g., a material having an initial volume that absorbs fluid, such as water, when it contacts the fluid to become a second volume that is greater than the initial volume) or collapsible material (e.g., a material having an initial volume that collapse to a second volume that is smaller than the initial volume) can produce or maintain a fluid pocket.

In yet another embodiment, materials with differing characteristics can be applied in combination, such as alternating bands or layers, to suppress uniform capsule formation. For example, alternating bands of collapsible and non-collapsible swellable material can be applied around a portion of the sensor. Upon implantation, both materials swell with fluid from the surrounding tissue. However, only the segments of collapsible material can deform. Since the material surrounding the sensor will be irregular, it can disrupt formation of a continuous cell layer, thereby reducing noise and extending sensor life.

Wound Irritation

Another aspect of the present invention employs wound irritation either by physical structure or chemical irritants, to stimulate and/or prolong the wound healing process. Preferably, an irritating architecture stimulates adjacent cells to release soluble mediators of wound healing and/or inflammation. The released soluble mediators are believed to increase the rates of hemostasis and inflammation (e.g., promoting fluid bulk increase or an increase in bulk fluid flow) and resulting in dilution/removal of irritants and noise reduction.

Accordingly, one embodiment of an irritating biointerface includes a structure having a roughened surface, which can rub or poke adjacent cells in vivo. The sensor surface can be roughened by coating the sensor with a machineable material that is or can be etched to form ridges, bristles, spikes, grids, grooves, circles, spirals, dots, bumps, pits or the like, for example. The material can be any convenient, biocompatible material, such as machined porous structures that are overlaid on the sensor, such as but not limited to machineable metal matrix composites, bone substrates such as hydroxyapatite, coral hydroxyapatite and β-tricalcium phosphate (TCP), porous titanium (Ti) mixtures made by sintering of elemental powders, bioglasses (calcium and silicon-based porous glass), ceramics and the like. The material can be "machined" by any convenient means, such as but not limited to scraping, etching, lathing or lasering, for example.

Micro-motion of the sensor can increase the irritating effect of a roughened surface. Micro-motion is an inherent property of any implanted device, such as an implanted glucose sensor. Micro-motion of the device (e.g., minute movements of the device within the host) is caused by host movements, ranging from breathing and small local muscle movements to gross motor movements, such as walking, running or even getting up and sitting down. External forces, such as external pressure application, can also cause micro-motion. Micro-motion includes movement of the sensor back and forth, rotation, twisting and/or turning. Accordingly, as the sensor is moved by micro-motion, the sensor's rough surface can rub more vigorously against the surrounding tissue, causing increased or extended wounding, resulting in additional stimulation of the wound healing process and increases in fluid bulk, bulk fluid flow and/or fluid pocket formation, with a concomitant reduction in noise.

In another embodiment, an irritating architecture is formed from self-assembly materials. Self-assembly biomaterials comprise specific polypeptides that are designed a priori to self-assemble into targeted nano- and microscopic structures. Intramolecular self-assembling molecules are often complex polymers with the ability to assemble from the random coil conformation into a well-defined stable structure (secondary and tertiary structure). A variety of self-assembly materials known in the art can find use in the present embodiment. For example, PuraMatrix™ (3DM Inc., Cambridge, Mass., USA) can be used to create synthetic self-assembling peptide nanofiber scaffolds and defined 3-D microenvironments.

In an exemplary embodiment of an irritating biointerface, an irritating superstructure is applied to the working electrode or the completed sensor. A "superstructure," as used herein is a broad term and used in its ordinary sense, including, without limitation, to refer to any structure built on something else, such as but not limited to the overlying portion of a structure. An irritating superstructure can include any substantial structure that prevents cell attachment and is irritating to the surrounding tissue in vivo. In one example, an irritating superstructure can include large spaces, such as at least about 50 μm wide and at least about 50 μm deep. Cells surrounding the sensor can be prevented from attachment in the spaces within the superstructure, allowing fluid to fill these spaces. In some exemplary embodiments, an irritating superstructure takes advantage of sensor micromotion, to prevent cell attachment and stimulate fluid pocket formation.

In one exemplary embodiment, an irritating superstructure is comprised of ridges at least about 0.25 to 0.50 μm in diameter and about 50 μm high, and separated by at least about 0.25 to 0.50 μm. In another exemplary embodiment, an exposed silver wire, at least about 0.25 to 0.50 μm in diameter, is applied to the sensor exterior to form grooves about 50 μm wide and about 50 μm deep. Since silver is pro-inflammatory and stimulates fluid influx from the surrounding tissues, the combination of an irritating superstructure and a chemical irritant could promote an increased rate of fluid influx or prolong irritation and fluid influx. In yet another exemplary embodiment, with reference to the embodiment shown in FIG. 3A, the configuration (e.g., diameter) of the reference electrode 30 can be changed (e.g., increased in size and/or coil spacing) such that the reference electrode, itself, becomes an irritating superstructure, with or without a coating 32 as disclosed elsewhere herein.

Inflammation and fluid pocket formation can also be induced by inclusion of irritating chemicals or agents that promote fluid influx or efflux, vasodilating agents, inflammatory agents, wounding agents, some wound-healing agents and the like. In some embodiments, irritation and fluid pocket forming agents can include but are not limited to enzymes, cytotoxic or necrosing agents (e.g., pactataxyl, actinomycin, doxorubicin, daunorubicin, epirubicin, bleomycin, plicamycin, mitomycin), cyclophosphamide, chlorambucil, uramustine, melphalan, bryostatins, inflammatory bacterial cell wall components, histamines, pro-inflammatory factors and the like. Chemical systems/methods of irritation include any materials that do not adversely affect the performance or safety of the device such as pro-inflammatory agents. Generally, pro-inflammatory agents are irritants or other substances that induce chronic inflammation and chronic granular response at the wound-site.

Chemical systems/methods of irritation can be applied to the exterior of the sensor by any useful means known in the art, such as by dipping, spraying or painting, for example. In one exemplary embodiment, the completed sensor is dipped into a dilute solution of histamine for about five seconds and dried at room temperature. Upon insertion into a host, the histamine can be solublized and stimulate an accelerated wound healing response, causing an influx of fluid and inflammatory cell migration to the sensor within the first few hours of sensor implantation, such as about 2 to 5 hours, or longer.

In another exemplary embodiment, only the operative sensing portion of the sensor is painted with a dilute necrosing agent (e.g., compounds that stimulate tissue devitalization), such as bleomycin) and dried. When the dried sensor is inserted into the host, the necrosing agent can leach off the sensor and devitalize a small amount of tissue around the sensing portion of the sensor. Generally, wound healing rapidly ensues, resulting in vasodilatation, fluid influx and an influx of macrophages and polymorphonuclear leukocytes, which remove the devitalized tissue. The space created by the removal of the devitalized tissue is filled with fluid and acts as a substantial fluid pocket.

Chemical systems/methods of irritation can also be incorporated into an exterior sensor structure, such as the biointerface membrane (described below) or a shedding layer that releases the irritating agent into the local environment. For example, in some embodiments, a "shedding layer" releases (e.g., sheds or leaches) molecules into the local vicinity of the sensor and can speed up osmotic fluid shifts. In some embodiments, a shedding layer can provide a mild irritation and encourage a mild inflammatory/foreign body response, thereby preventing cells from stabilizing and building up an ordered, fibrous capsule and promoting fluid pocket formation.

A shedding layer can be constructed of any convenient, biocompatible material, include but not limited to hydrophilic, degradable materials such as polyvinylalcohol (PVA), PGC, Polyethylene oxide (PEO), polyethylene glycol-polyvinylpyrrolidone (PEG-PVP) blends, PEG-sucrose blends, hydrogels such as polyhydroxyethyl methacrylate (pHEMA), polymethyl methacrylate (PMMA) or other polymers with quickly degrading ester linkages. In certain embodiment, absorbable suture materials, which degrade to compounds with acid residues, can be used. The acid residues are chemical irritants that stimulate inflammation and wound healing. In certain embodiments, these compounds include glycolic acid and lactic acid based polymers, polyglactin, polydioxone, polydyconate, poly(dioxanone), poly (trimethylene carbonate) copolymers, and poly (-caprolactone) homopolymers and copolymers, and the like.

In other exemplary embodiments, the shedding layer can be a layer of materials listed elsewhere herein for the first domain, including copolymers or blends with hydrophilic polymers such as polyvinylpyrrolidone (PVP), polyhydroxyethyl methacrylate, polyvinylalcohol, polyacrylic acid, polyethers, such as polyethylene glycol, and block copolymers thereof including, for example, di-block, tri-block, alternating, random and graft copolymers (block copolymers are discussed in U.S. Pat. Nos. 4,803,243 and 4,686,044, hereby incorporated by reference). In one preferred embodiment, the shedding layer is comprised of polyurethane and a hydrophilic polymer. For example, the hydrophilic polymer can be polyvinylpyrrolidone. In one embodiment of this aspect of the invention, the shedding layer is polyurethane comprising not less than 5 weight percent polyvinylpyrrolidone and not more than 45 weight percent polyvinylpyrrolidone. Preferably, the shedding layer comprises not less than 20 weight percent polyvinylpyrrolidone and not more than 35 weight percent polyvinylpyrrolidone and, most preferably, polyurethane comprising about 27 weight percent polyvinylpyrrolidone.

In other exemplary embodiments, the shedding layer can include a silicone elastomer, such as a silicone elastomer and a poly(ethylene oxide) and poly(propylene oxide) co-polymer blend, as disclosed in copending U.S. patent application Ser. No. 11/404,417, filed Apr. 14, 2006 and entitled "SILICONE BASED MEMBRANES FOR USE IN IMPLANTABLE GLUCOSE SENSORS." In one embodiment, the silicone elastomer is a dimethyl- and methylhydrogen-siloxane copolymer. In one embodiment, the silicone elastomer comprises vinyl substituents. In one embodiment, the silicone elastomer is an elastomer produced by curing a MED-4840 mixture. In one embodiment, the copolymer comprises hydroxy substituents. In one embodiment, the co-polymer is a triblock poly(ethylene oxide)-poly(propylene oxide)-poly(ethylene oxide) polymer. In one embodiment, the co-polymer is a triblock poly(propylene oxide)-poly(ethylene oxide)-poly(propylene oxide) polymer. In one embodiment, the co-polymer is a PLURONIC® polymer. In one embodiment, the co-polymer is PLURONIC® F-127. In one embodiment, at least a portion of the co-polymer is cross-linked. In one embodiment, from about 5% w/w to about 30% w/w of the membrane is the co-polymer.

A shedding layer can take any shape or geometry, symmetrical or asymmetrical, to promote fluid influx in a desired location of the sensor, such as the sensor head or the electrochemically reactive surfaces, for example. Shedding layers can be located on one side of sensor or both sides. In another example, the shedding layer can be applied to only a small portion of the sensor or the entire sensor.

In one exemplary embodiment, a shedding layer comprising polyethylene oxide (PEO) is applied to the exterior of the sensor, where the tissue surrounding the sensor can directly access the shedding layer. PEO leaches out of the shedding layer and is ingested by local cells that release pro-inflammatory factors. The pro-inflammatory factors diffuse through the surrounding tissue and stimulate an inflammation response that includes an influx of fluid. Accordingly, early noise can be reduced or eliminated and sensor function can be improved.

In another exemplary embodiment, the shedding layer is applied to the sensor in combination with an outer porous layer, such as a mesh or a porous biointerface as disclosed elsewhere herein. In one embodiment, local cells access the shedding layer through the through pores of a porous silicone biointerface. In one example, the shedding layer material is applied to the sensor prior to application of the porous silicone. In another example, the shedding layer material can be absorbed into the lower portion of the porous silicone (e.g., the portion of the porous silicone that will be proximal to the sensor after the porous silicone has been applied to the sensor) prior to application of the porous silicone to the sensor.

Vasodilatation

As discussed elsewhere herein, increased fluid bulk, bulk fluid flow and/or diffusion rates can reduce local interferant concentrations (e.g., electroactive species produced via cellular metabolism in the local area) and promote glucose and oxygen influx or transport, thereby reducing noise frequency or amplitude and improving early sensor performance. In addition to the structural and chemical systems/methods discussed above, increased fluid bulk, fluid bulk flow and/or diffusion rates can be promoted by vasodilation. Vasodilation occurs when the tight junctions of the endothelial layer of the microvasculature open. This allows serum and certain inflammatory cells to leave the circulatory system and enter the extracellular matrix (ECM). A portion of the fluid in the ECM can move back into the vasculature. Another portion of the ECM fluid can leave the area via the lymphatics. Vasodilation promotes "bulk fluid transport" (e.g., bulk fluid flow) in and out of the local region and/or increase in fluid bulk around at least a portion of the sensor. Increased fluid bulk and/or bulk fluid transport ensures homeostasis with the local environment and the blood system. Furthermore, rapid diffusion of solutes may be facilitated by permeabilization of the blood vessels and increased local temperature due to inflammation. Fluids leaving the local extracellular spaces remove metabolites, such as the interferants discussed herein. Preferably, as interferants are carried with the moving fluid, noise is reduced and sensor function improved.

In some exemplary embodiments of the present invention, bioactive agents that promote vasodilation are included in sensor construction. In one example, the bioactive agents promote an influx of fluid, causing an increase in fluid bulk. Noise is reduced as the larger fluid volume reduces the interferant concentration. In another example, the bioactive agents promote an efflux of fluid out of the local area. Noise is reduced as the leaving fluid carries interferants away with it.

A variety of bioactive agents can be found useful in preferred embodiments. Exemplary bioactive agents include but are not limited to blood-brain barrier disruptive agents and vasodilating agents, such as mannitol, sodium thiosulfate, VEGF/VPF, NO, NO-donors, leptin, bradykinin, histamines, blood components, platelet rich plasma (PRP) and the like.

Bioactive agents can be added during manufacture of the sensor by incorporating the desired bioactive agent in the manufacturing material for one or more sensor layers or into an exterior biomaterial, such as a porous silicone membrane. For example, bioactive agents can be mixed with a solution during membrane formation, which is subsequently applied onto the sensor during manufacture. Alternatively, the completed sensor can be dipped into or sprayed with absolution of a bioactive agent, for example. The amount of bioactive agent can be controlled by varying its concentration, varying the indwell time during dipping, applying multiple layers until a desired thickness is reached, and the like, as disclosed elsewhere herein.

VEGF is a bioactive agent that is known to be a vasodilator and can promote fluid influx from the microvasculature. In one embodiment, VEGF is sprayed onto the exterior of the completed sensor. After insertion, VEGF is directly released into the local environment when the VEGF-coated sensor is implanted into a host. The released VEGF stimulates vasodilation around the implanted sensor. In another embodiment, VEGF is mixed into the biointerface material prior to sensor construction. After the sensor is inserted, VEGF leaches form the biointerface, causing vasodilation around the sensor. In an alternative embodiment, upstream or downstream components of the VEGF signaling cascade can be incorporated into the sensor, to affect vasodilatation around the implanted sensor.

In one embodiment, biodegradable or bioerodible material can be employed to release bioactive agents in a controlled manner. In one exemplary embodiment, VEGF is incorporated into a biodegradable material (e.g., shedding layer or hydrogel) that is applied to the sensor exterior. Upon implantation, the surrounding tissue begins to degrade the biodegradable material. As the material degrades, VEGF is released into the local environment in a desired rate-limiting manner. The rate of bioactive agent release (e.g., VEGF) can be manipulated by the selection of the biodegradable material and the thickness of the biodegradable material layer. Thus, constant bioactive agent release can be achieved for a predetermined extended period of time and possibly promote vasodilatation and fluid influx during that period of time.

In an alternative embodiment, the bioactive agent is microencapsulated before application to the sensor. For example, microencapsulated VEGF can be sprayed onto a completed sensor or incorporated into a structure, such as an outer mesh layer or a shedding layer. Microencapsulation can offer increased flexibility in controlling bioactive agent release rate, time of release occurrence and/or release duration.

In still another embodiment, vasodilation is achieved by matrix metalloproteinases (MMP) incorporation into the sensor. MMPs can degrade the proteins that keep blood vessel walls solid. This proteolysis allows endothelial cells to escape into the interstitial matrix and concomitantly fluid to enter and leave the vasculature. Accordingly, MMPs can promote interferant concentration reduction and intermittent, sedentary noise reduction or elimination.

In another embodiment, angiogenic and/or preangiogenic compounds or factors are included in the sensor to promote vasodilation. Angiogenesis is the physiological process involving the growth of new blood vessels from pre-existing vessels. Formation of new vessels can reduce the frequency or magnitude of intermittent, sedentary noise by increasing fluid flow, for example. Angiogenic agents include, but are not limited to, Basic Fibroblast Growth Factor (bFGF), (also known as Heparin Binding Growth Factor-II and Fibroblast Growth Factor II), Acidic Fibroblast Growth Factor (aFGF), (also known as Heparin Binding Growth Factor-I and Fibroblast Growth Factor-I), Vascular Endothelial Growth Factor (VEGF), Platelet Derived Endothelial Cell Growth Factor BB (PDEGF-BB), Angiopoietin-1, Transforming Growth Factor Beta (TGF-Beta), Transforming Growth Factor Alpha (TGF-Alpha), Hepatocyte Growth Factor, Tumor Necrosis Factor-Alpha (TNF-Alpha), Placental Growth Factor (PLGF), Angiogenin, Interleukin-8 (IL-8), Hypoxia Inducible Factor-I (HIF-1), Angiotensin-Converting Enzyme (ACE) Inhibitor Quinaprilat, Angiotropin, Thrombospondin, Peptide KGHK, Low Oxygen Tension, Lactic Acid, Insulin, Leptin, Copper Sulphate, Estradiol, prostaglandins, cox inhibitors, endothelial cell binding agents (for example, decorin or vimentin), glenipin, hydrogen peroxide, nicotine, and Growth Hormone.

Wound Suppression

Wound suppression to reduce noise is an alternative aspect of the preferred embodiment. Wound suppression includes any systems or methods by which an amount of wounding that occurs upon sensor insertion is reduced and/or eliminated. While not wishing to be bound by theory, it is believed that if wounding is suppressed or at least significantly reduced, the sensor will be surrounded by substantially normal tissue (e.g., tissue that is substantially similar to the tissue prior to sensor insertion). Substantially normal tissue is believed to have a lower metabolism than wounded tissue, producing fewer interferants and reducing early noise.

Wounds can be suppressed or minimized by adaptation of the sensor's architecture to one that either suppresses wounding or promotes rapid healing, such as an architecture that does not cause substantial wounding (e.g., an architecture configured to prevent wounding), an architecture that promotes wound healing, an anti-inflammatory architecture, and the like. In one exemplary embodiment, the sensor is configured to have a low profile, a zero-footprint or a smooth surface. For example, the sensor can be formed of substantially thin wires, such as wires about 50-150 μm in diameter, for example. Preferably, the sensor is small enough to fit within a very small gauge needle, such as a 30, 31, 32, 33, 34, or 35-gauge needle (or smaller) on the Stubs scale, for example. In general, a smaller needle, the more reduces the amount of wounding during insertion. For example, a very small needle can reduce the amount of tissue disruption and thereby reduce the subsequent wound healing response. In an alterative embodiment, the sensor's surface is smoothed with a lubricious coating, to reduce wounding upon sensor insertion.

Wounding can also be reduced by inclusion of wound-suppressive agents that either reduce the amount of initial wounding or suppress the wound healing process. While not wishing to be bound by theory, it is believed that application of a wound-suppressing agent, such as an anti-inflammatory, an immunosuppressive agent, an anti-infective agent, or a scavenging agent, to the sensor can create a locally quiescent environment and suppress wound healing. In a quiescent environment, bodily processes, such as the increased cellular metabolism associated with wound healing, can minimally affect the sensor. If the tissue surrounding the sensor is undisturbed, it can continue its normal metabolism and promote sensor function.

It has been observed that anti-histamines can suppress or eliminate early sedentary noise. Namely, it has been shown that oral anti-histamines taken at nighttime can result in substantially diminished early sedentary noise. While not wishing to be bound by theory, it is believed that histamines, which are chemicals released during wounding, produce electrochemical interference in the sensor signal. Namely, histamine release is believed to promote release of electrochemical interferants, which in certain circumstances produce "noise" on the sensor signal.

Further, the inventors believe that during sedentary periods (e.g., sleeping or long periods of sitting) host immobility can cause local pooling of the interstitial and/or lymph fluids, which results in a back up of lymph surrounding the sensor with a corresponding build-up of electroactive species as a result of normal cellular metabolism. Pooling of the wound fluid around the sensor can suppress the usual movement of the wound fluids that would enable accurate analyte measurement. The lack of fluid movement results in modified sample fluid, including but not limited to a local increase in electroactive species (e.g., histamines or other resulting products) during these periods of intermittent sedentary noise. When the host moves or shifts body position, the fluid is released and fluid flow is restored, allowing an influx of oxygen and glucose and removal of electroactive metabolic species (e.g., interfering species).

Accordingly, one embodiment of the present invention provides for a sensor including an anti-histamine. Anti-histamines are any drugs that serve to reduce or eliminate the effects mediated by histamine. Some examples of conventional anti-histamines suitable for incorporation into or onto the present invention include, but are not limited to first-generation $H_1$-receptor antagonists: ethylenediamines (e.g., mepyramine (pyrilamine), antazoline), ethanolamines (e.g., diphenhydramine, carbinoxamine, doxylamine, clemastine, and dimenhydrinate), alkylamines (pheniramine, chlorphenamine (chlorpheniramine), dexchlorphenamine, brompheniramine, and triprolidine), piperazines (cyclizine, hydroxyzine, and meclizine), and tricyclics (promethazine, alimemazine (trimeprazine), cyproheptadine, and azatadine).

Additionally, Second-generation $H_1$-receptor antagonists are newer antihistamine drugs that are much more selective for peripheral $H_1$ receptors in preference to the central nervous system histaminergic and cholinergic receptors. This selectivity significantly reduces the occurrence of adverse drug reactions compared with first-generation agents, while still providing effective relief of allergic conditions. Both systemic (acrivastine, astemizole, cetirizine, loratadine, mizolastine) and topical (azelastine, levocabastine, and olopatadine) could be used.

In some alternative embodiments, other inhibitors of histamine release, which appear to stabilize the mast cells to suppress degranulation and mediator release, can be used (e.g., cromoglicate (cromolyn) and nedocromil).

Anti-histamine can be incorporated into the sensor by any convenient system or technique known to those skilled in the art. In one exemplary embodiment, anti-histamine is incorporated into a biodegradable shedding layer. As the shedding layer is degraded, the anti-histamine is released into the surrounding area, to suppress histamine release and downstream inflammation processes, thereby suppressing interferant build up and improving sensor function. In another exemplary embodiment, anti-histamine is sprayed on the surface of the completed sensor and dried. Upon insertion, the anti-histamine is solublized, suppresses histamine production and downstream inflammation mediators, thereby reducing noise.

Other agents that suppress the body's response to wounding can also be incorporated into the sensor or the present invention. In one embodiment, wounding can be suppressed by the inclusion of anti-inflammatory agents. Generally, anti-inflammatory agents reduce acute and/or chronic inflammation adjacent to the implant, in order to decrease the formation of a FBC capsule to reduce or prevent barrier cell layer formation. Suitable anti-inflammatory agents include but are not limited to, for example, nonsteroidal anti-inflammatory drugs (NSAIDs) such as acetometaphen, aminosalicylic acid, aspirin, celecoxib, choline magnesium trisalicylate, diclofenac potassium, diclofenac sodium, diflunisal, etodolac, fenoprofen, flurbiprofen, ibuprofen, indomethacin, interleukin (IL)-10, IL-6 mutein, anti-IL-6 iNOS inhibitors (for example, L-NAME or L-NMDA), Interferon, ketoprofen, ketorolac, leflunomide, melenamic acid, mycophenolic acid, mizoribine, nabumetone, naproxen, naproxen sodium, oxaprozin, piroxicam, rofecoxib, salsalate, sulindac, and tolmetin; and corticosteroids such as cortisone, hydrocortisone, methylprednisolone, prednisone, prednisolone, betamethesone, beclomethasone dipropionate, budesonide, dexamethasone sodium phosphate, flunisolide, fluticasone propionate, paclitaxel, tacrolimus, tranilast, triamcinolone acetonide, betamethasone, fluocinolone, fluocinonide, betamethasone dipropionate, betamethasone valerate, desonide, desoximetasone, fluocinolone, triamcinolone, triamcinolone acetonide, clobetasol propionate, and dexamethasone.

In one example, glucocorticoids stimulate the movement of lipocortin-1 into the extracellular space, where it binds to leukocyte membrane receptors and inhibits various inflammatory events: such as epithelial adhesion, emigration, chemotaxis, phagocytosis, respiratory burst and the release of various inflammatory mediators (lysosomal enzymes, cytokines, tissue plasminogen activator, chemokines etc.) from neutrophils, macrophages and mastocytes.

In one exemplary embodiment, the sensor is coated with dexamethasone or dexamethasone is incorporated into a protective layer or film, such as a hydrophilic silicone protective film. In vivo, the dexamethasone is released from the surface of the sensor and interacts with the surrounding tissue, thereby reducing or eliminating local inflammation and early noise.

In another embodiment, an immunosuppressive and/or immunomodulatory agent is included in the sensor to suppress wound healing and/or fluid pocket formation, thereby reducing noise. Generally, immunosuppressive and/or immunomodulatory agents interfere directly with several key mechanisms necessary for involvement of different cellular elements in the inflammatory response. Suitable immunosuppressive and/or immunomodulatory agents include anti-proliferative, cell-cycle inhibitors, (for example, paclitaxel, cytochalasin D, infiximab), taxol, actinomycin, mitomycin, thospromote VEGF, estradiols, NO donors, QP-2, tacrolimus, tranilast, actinomycin, everolimus, methothrexate, mycophenolic acid, angiopeptin, vincristing, mitomycine, statins, C MYC antisense, sirolimus (and analogs), RestenASE, 2-chloro-deoxyadenosine, PCNA Ribozyme, batimstat, prolyl hydroxylase inhibitors, PPARγ ligands (for example troglitazone, rosiglitazone, pioglitazone), halofuginone, C-proteinase inhibitors, probucol, BCP671, EPC antibodies, catchins, glycating agents, endothelin inhibitors (for example, Ambrisentan, Tesosentan, Bosentan), Statins (for example, Cerivasttin), *E. coli* heat-labile enterotoxin, and advanced coatings. While not wishing to be bound by theory, it is believed that inflammation suppression will promote a quiescent sensor environment and a substantially normal local metabolism.

In another embodiment, the biointerface comprises a pro-inflammatory architecture configured to promote substantially rapid fluid influx (e.g., due to inflammation and the like) after sensor insertion followed by an extended quiescent period (e.g., during which wound healing is suppressed). While not wishing to be bound by theory, it is believed that, within a wound healing time line, a brief period of inflammation, followed by wound healing suppression can promote initial fluid pocket formation with subsequent suppression of interferent concentration increase. Initial fluid pocket formation can facilitate analyte (e.g., glucose) and oxygen transport from the surrounding tissues to the working electrode. The subsequent suppression of interferent build-up can reduce noise.

In yet another embodiment, an anti-infective agent is incorporated into the sensor, to prevent a local infection that would stimulate inflammation around the sensor. Accordingly, the inflammation signal cascade and concomitant metabolic changes will be suppressed, resulting in noise suppression. Generally, anti-infective agents are substances capable of acting against infection by inhibiting the spread of an infectious agent or by killing the infectious agent outright, which can serve to reduce immuno-response without inflammatory response at the implant site. Anti-infective agents include, but are not limited to, anthelmintics (mebendazole), antibiotics including aminoclycosides (gentamicin, neomycin, tobramycin), antifungal antibiotics (amphotericin b, fluconazole, griseofulvin, itraconazole, ketoconazole, nystatin, micatin, tolnaftate), cephalosporins (cefaclor, cefazolin, cefotaxime, ceftazidime, ceftriaxone, cefuroxime, cephalexin), beta-lactam antibiotics (cefotetan, meropenem), chloramphenicol, macrolides (azithromycin, clarithromycin, erythromycin), penicillins (penicillin G sodium salt, amoxicillin, ampicillin, dicloxacillin, nafcillin, piperacillin, ticarcillin), tetracyclines (doxycycline, minocycline, tetracycline), bacitracin; clindamycin; colistimethate sodium; polymyxin b sulfate; vancomycin; antivirals including acyclovir, amantadine, didanosine, efavirenz, foscarnet, ganciclovir, indinavir, lamivudine, nelfinavir, ritonavir, saquinavir, silver, stavudine, valacyclovir, valganciclovir, zidovudine; quinolones (ciprofloxacin, levofloxacin); sulfonamides (sulfadiazine, sulfisoxazole); sulfones (dapsone); furazolidone; metronidazole; pentamidine; sulfanilamidum crystallinum; gatifloxacin; and sulfamethoxazole/trimethoprim. While not wishing to be bound by theory, it is believed that infection suppression will promote a quiescent sensor environment and a substantially normal local metabolism.

In another embodiment, interferant scavengers can be applied to the sensor, to remove electroactive interferants. While not wishing to be bound by theory, it is believed that removal of electroactive interferants around the sensor can reduce early noise and promote increased sensor sensitivity during the first few hours or days of sensor use. Interferant scavengers can include enzymes, such as superoxide dismutase (SOD), thioredoxin, glutathione peroxidase and catalase, anti-oxidants, such as uric acid and vitamin C, iron compounds, Heme compounds, and some heavy metals. In one exemplary embodiment, a hydrogel containing SOD and horseradish peroxidase (HRP) is coated on the surface of the sensor. After sensor implantation, the SOD decomposes superoxide radicals from the surrounding cells into $O_2$ and $H_2O_2$. The $H_2O_2$ is subsequently broken down into water by HRP. Thus, electroactive interferants, such as superoxide and hydrogen peroxide, can be removed and oxygen provided for the glucose oxidase component of the sensor.

In another embodiment, at least a portion of the sensor is coated with an artificial protective coating to reduce wounding. The term "protective coating" as used herein is a broad term and is used in its ordinary sense, including, without limitation, a coating of proteins and other molecules, such as those found in serous fluid. While not wishing to be bound by theory, it is believed that after the first about 2 to about 36 hours of sensor insertion, the host's biological processes provide a protective coating surrounding the sensor that protects the sensor from these endogenous interferants or other in vivo effects. In one exemplary embodiment, at least a portion of the sensor is coated with an artificial protective coating. The artificial protective coating components can include but are not limited to albumin, fibrin, collagen, endothelial cells, wound closure chemicals, blood products, platelet-rich plasma, growth factors and the like. A protective coating can be applied to the sensor in any convenient way, such as but not limited to dipping the sensor into a mixture of protective coating components, spraying or incorporating the protective coating components into a biointerface membrane. Advantageously, a protective film can prevent sensor degradation associated with the local environment and promote integration of the biointerface into the surrounding tissue.

In a further embodiment, a silicone coating or hydrophilic shedding layer can be applied to the sensor. While not wishing to be bound by theory, it is believed that a silicone bioprotective coating or shedding layer can promote formation and maintenance of a fluid pocket around the sensor, to enhance glucose and fluid transport as well as clearance of interferants. A silicone bioprotective coating can create a local environment with enhanced vascular permeability and/or vascularization. Such a coating is believed to speed up the inflammatory response to achieve a substantially consistent wound environment more quickly than without the coating. Furthermore, a silicone bioprotective coating is believed to be able to subdue the inflammatory response to reduce production of cellular byproducts that are believed to be electrochemical interferants.

In one embodiment, a silicone bioprotective coating can consist of one or more layer(s) formed from a composition that, in addition to providing high oxygen solubility, allows for the transport of glucose or other such water-soluble molecules (for example, drugs). In one embodiment, these layers comprise a blend of a silicone polymer with a hydrophilic polymer. By "hydrophilic polymer," it is meant that the polymer has a substantially hydrophilic domain in which aqueous substances can easily dissolve. In one embodiment, the hydrophilic polymer has a molecular weight of at least about 1000 g/mol, 5,000 g/mol, 8,000 g/mol, 10,000 g/mol, or 15,000 g/mol. In one embodiment, the hydrophilic polymer comprises both a hydrophilic domain and a partially hydrophobic domain (e.g., a copolymer). The hydrophobic domain(s) facilitate the blending of the hydrophilic polymer with the hydrophobic silicone polymer. In one embodiment, the hydrophobic domain is itself a polymer (i.e., a polymeric hydrophobic domain). For example, in one embodiment, the hydrophobic domain is not a simple molecular head group but is rather polymeric. In various embodiments, the molecular weight of any covalently continuous hydrophobic domain within the hydrophilic polymer is at least about 500 g/mol, 700 g/mol, 1000 g/mol, 2000 g/mol, 5000 g/mol, or 8,000 g/mol. In various embodiments, the molecular weight of any covalently continuous hydrophilic domain within the hydrophilic polymer is at least about 500 g/mol, 700 g/mol, 1000 g/mol, 2000 g/mol, 5000 g/mol, or 8,000 g/mol. In various embodiments, the layers comprise a blend of a silicone polymer with a hydrophilic polymer as disclosed in copending U.S. patent application Ser. No. 11/404,417, filed Apr. 14, 2006 and entitled "SILICONE BASED MEMBRANES FOR USE IN IMPLANTABLE GLUCOSE SENSORS."

Many of the above disclosed methods and structures for forming a fluid pocket, diluting interferants, reducing noise and the like can be used in combination to facilitate a desired effect or outcome. For example, in one embodiment, a shedding layer composed of a hydrophilic silicone film and a necrosing agent can be applied in combination to at least a portion of the sensor. The silicone film can suppress protein adherence to the sensor surface while the necrosing agent can devitalize a small portion of tissue adjacent to the sensor, stimulating formation of a fluid pocket around the hydrophilic silicone film. Preferably, the increased volume of fluid surrounding the sensor dilutes interferants while the shedding layer provides a physical separation between the sensor and the surrounding tissue.

In another exemplary embodiment, a mesh sprayed with dexamethasone is wrapped around the exterior of the sensor. The mesh can provide a physical spacer for a fluid pocket while the dexamethasone inhibits inflammation. Preferably, fluid can fill the mesh and the dexamethasone can promote normal tissue metabolism around the sensor by inhibiting an influx of inflammatory cells. Consequently, glucose and oxygen can travel freely between the tissue and the sensor through the fluid filled mesh without a buildup of interferants, even during periods of tissue compression, thereby promoting sensor sensitivity and thereby reducing noise.

Sensing Mechanism

Figure 3A:
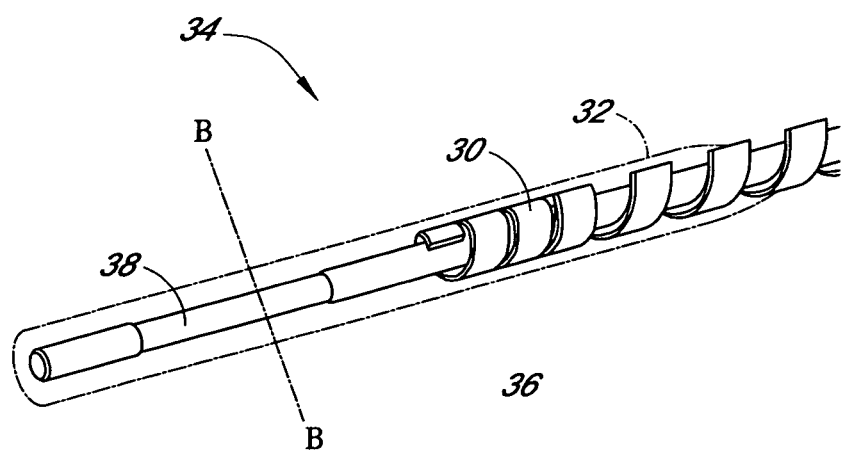
FIG. 3A is an expanded view of an exemplary embodiment of a continuous analyte sensor.

In general, the analyte sensors 34 of the preferred embodiments include a sensing mechanism 36 with a small structure (e.g., small structured-, micro- or small diameter sensor, see FIG. 3A), for example, a needle-type sensor, in at least a portion thereof. As used herein a "small structure" preferably refers to an architecture with at least one dimension less than about 1 mm. The small structured sensing mechanism can be wire-based, substrate based, or any other architecture. In some alternative embodiments, the term "small structure" can also refer to slightly larger structures, such as those having their smallest dimension being greater than about 1 mm, however, the architecture (e.g., mass or size) is designed to minimize the foreign body response due to size and/or mass. In the preferred embodiments, a biointerface membrane is formed onto the sensing mechanism 36 as described in more detail below.

FIG. 3A is an expanded view of an exemplary embodiment of a continuous analyte sensor 34, also referred to as a transcutaneous analyte sensor, or needle-type sensor, particularly illustrating the sensing mechanism 36. Preferably, the sensing mechanism comprises a small structure as defined herein and is adapted for insertion under the host's skin, and the remaining body of the sensor (e.g., electronics, etc) can reside ex vivo. In the illustrated embodiment, the analyte sensor 34, includes two electrodes, i.e., a working electrode 38 and at least one additional electrode 30, which can function as a counter and/or reference electrode, hereinafter referred to as the reference electrode 30.

In some exemplary embodiments, each electrode is formed from a fine wire with a diameter of from about 0.001 or less to about 0.010 inches or more, for example, and is formed from, e.g., a plated insulator, a plated wire, or bulk electrically conductive material. Although the illustrated electrode configuration and associated text describe one preferred method of forming a transcutaneous sensor, a variety of known transcutaneous sensor configurations can be employed with the transcutaneous analyte sensor system of the preferred embodiments, such as described in U.S. Pat. No. 6,695,860 to Ward et al., U.S. Pat. No. 6,565,509 to Say et al., U.S. Pat. No. 6,248,067 to Causey III, et al., and U.S. Pat. No. 6,514,718 to Heller et al.

In preferred embodiments, the working electrode comprises a wire formed from a conductive material, such as platinum, platinum-iridium, palladium, graphite, gold, carbon, conductive polymer, alloys, or the like. Although the electrodes can by formed by a variety of manufacturing techniques (bulk metal processing, deposition of metal onto a substrate, or the like), it can be advantageous to form the electrodes from plated wire (e.g., platinum on steel wire) or bulk metal (e.g., platinum wire). It is believed that electrodes formed from bulk metal wire provide superior performance (e.g., in contrast to deposited electrodes), including increased stability of assay, simplified manufacturability, resistance to contamination (e.g., which can be introduced in deposition processes), and improved surface reaction (e.g., due to purity of material) without peeling or delamination.

The working electrode 38 is configured to measure the concentration of an analyte. In an enzymatic electrochemical sensor for detecting glucose, for example, the working electrode measures the hydrogen peroxide produced by an enzyme catalyzed reaction of the analyte being detected and creates a measurable electronic current. For example, in the detection of glucose wherein glucose oxidase produces hydrogen peroxide as a byproduct, hydrogen peroxide reacts with the surface of the working electrode producing two protons ($2H^+$), two electrons ($2e^-$) and one molecule of oxygen ($O_2$), which produces the electronic current being detected.

The working electrode 38 is covered with an insulating material, for example, a non-conductive polymer. Dip-coating, spray-coating, vapor-deposition, or other coating or deposition techniques can be used to deposit the insulating material on the working electrode. In one embodiment, the insulating material comprises parylene, which can be an advantageous polymer coating for its strength, lubricity, and electrical insulation properties. Generally, parylene is produced by vapor deposition and polymerization of paraxylylene (or its substituted derivatives). However, any suitable insulating material can be used, for example, fluorinated polymers, polyethyleneterephthalate, polyurethane, polyimide, other nonconducting polymers, or the like. Glass or ceramic materials can also be employed. Other materials suitable for use include surface energy modified coating systems such as are marketed under the trade names AMC18, AMC148, AMC141, and AMC321 by Advanced Materials Components Express of Bellafonte, Pa. In some alternative embodiments, however, the working electrode cannot require a coating of insulator.

Preferably, the reference electrode 30, which can function as a reference electrode alone, or as a dual reference and counter electrode, is formed from silver, silver/silver chloride, or the like. Preferably, the electrodes are juxtapositioned and/or twisted with or around each other; however other configurations are also possible. In one example, the reference electrode 30 is helically wound around the working electrode 38 as illustrated in FIG. 3A. The assembly of wires can then be optionally coated together with an insulating material, similar to that described above, in order to provide an insulating attachment (e.g., securing together of the working and reference electrodes).

In embodiments wherein an outer insulator is disposed, a portion of the coated assembly structure can be stripped or otherwise removed, for example, by hand, excimer lasing, chemical etching, laser ablation, grit-blasting (e.g., with sodium bicarbonate or other suitable grit), or the like, to expose the electroactive surfaces. Alternatively, a portion of the electrode can be masked prior to depositing the insulator in order to maintain an exposed electroactive surface area. In one exemplary embodiment, grit blasting is implemented to expose the electroactive surfaces, preferably utilizing a grit material that is sufficiently hard to ablate the polymer material, while being sufficiently soft so as to minimize or avoid damage to the underlying metal electrode (e.g., a platinum electrode). Although a variety of "grit" materials can be used (e.g., sand, talc, walnut shell, ground plastic, sea salt, and the like), in some preferred embodiments, sodium bicarbonate is an advantageous grit-material because it is sufficiently hard to ablate, e.g., a parylene coating without damaging, e.g., an underlying platinum conductor. One additional advantage of sodium bicarbonate blasting includes its polishing action on the metal as it strips the polymer layer, thereby eliminating a cleaning step that might otherwise be necessary.

In some embodiments, a radial window is formed through the insulating material to expose a circumferential electroactive surface of the working electrode. Additionally, sections of electroactive surface of the reference electrode are exposed. For example, the sections of electroactive surface can be masked during deposition of an outer insulating layer or etched after deposition of an outer insulating layer. In some applications, cellular attack or migration of cells to the sensor can cause reduced sensitivity and/or function of the device, particularly after the first day of implantation. However, when the exposed electroactive surface is distributed circumferentially about the sensor (e.g., as in a radial window), the available surface area for reaction can be sufficiently distributed so as to minimize the effect of local cellular invasion of the sensor on the sensor signal. Alternatively, a tangential exposed electroactive window can be formed, for example, by stripping only one side of the coated assembly structure. In other alternative embodiments, the window can be provided at the tip of the coated assembly structure such that the electroactive surfaces are exposed at the tip of the sensor. Other methods and configurations for exposing electroactive surfaces can also be employed.

Preferably, the above-exemplified sensor has an overall diameter of not more than about 0.020 inches (about 0.51 mm), more preferably not more than about 0.018 inches (about 0.46 mm), and most preferably not more than about 0.016 inches (0.41 mm). In some embodiments, the working electrode has a diameter of from about 0.001 inches or less to about 0.010 inches or more, preferably from about 0.002 inches to about 0.008 inches, and more preferably from about 0.004 inches to about 0.005 inches. The length of the window can be from about 0.1 mm (about 0.004 inches) or less to about 2 mm (about 0.078 inches) or more, and preferably from about 0.5 mm (about 0.02 inches) to about 0.75 mm (0.03 inches). In such embodiments, the exposed surface area of the working electrode is preferably from about 0.000013 in$^2$ (0.0000839 cm$^2$) or less to about 0.0025 in$^2$ (0.016129 cm$^2$) or more (assuming a diameter of from about 0.001 inches to about 0.010 inches and a length of from about 0.004 inches to about 0.078 inches). The preferred exposed surface area of the working electrode is selected to produce an analyte signal with a current in the picoAmp range, such as is described in more detail elsewhere herein. However, a current in the picoAmp range can be dependent upon a variety of factors, for example the electronic circuitry design (e.g., sample rate, current draw, A/D converter bit resolution, etc.), the membrane system (e.g., permeability of the analyte through the membrane system), and the exposed surface area of the working electrode. Accordingly, the exposed electroactive working electrode surface area can be selected to have a value greater than or less than the above-described ranges taking into consideration alterations in the membrane system and/or electronic circuitry. In preferred embodiments of a glucose sensor, it can be advantageous to minimize the surface area of the working electrode while maximizing the diffusivity of glucose in order to optimize the signal-to-noise ratio while maintaining sensor performance in both high and low glucose concentration ranges.

In some alternative embodiments, the exposed surface area of the working (and/or other) electrode can be increased by altering the cross-section of the electrode itself. For example, in some embodiments the cross-section of the working electrode can be defined by a cross, star, cloverleaf, ribbed, dimpled, ridged, irregular, or other non-circular configuration; thus, for any predetermined length of electrode, a specific increased surface area can be achieved (as compared to the area achieved by a circular cross-section). Increasing the surface area of the working electrode can be advantageous in providing an increased signal responsive to the analyte concentration, which in turn can be helpful in improving the signal-to-noise ratio, for example.

In some alternative embodiments, additional electrodes can be included within the assembly, for example, a three-electrode system (working, reference, and counter electrodes) and/or an additional working electrode (e.g., an electrode which can be used to generate oxygen, which is configured as a baseline subtracting electrode, or which is configured for measuring additional analytes). U.S. Pat. No. 7,081,195 and U.S. Publication No. US-2005-0143635-A1 describe some systems and methods for implementing and using additional working, counter, and/or reference electrodes. In one implementation wherein the sensor comprises two working electrodes, the two working electrodes are juxtapositioned (e.g., extend parallel to each other), around which the reference electrode is disposed (e.g., helically wound). In some embodiments wherein two or more working electrodes are provided, the working electrodes can be formed in a double-, triple-, quad-, etc. helix configuration along the length of the sensor (for example, surrounding a reference electrode, insulated rod, or other support structure.) The resulting electrode system can be configured with an appropriate membrane system, wherein the first working electrode is configured to measure a first signal comprising glucose and baseline and the additional working electrode is configured to measure a baseline signal consisting of baseline only (e.g., configured to be substantially similar to the first working electrode without an enzyme disposed thereon.) In this way, the baseline signal can be subtracted from the first signal to produce a glucose-only signal that is substantially not host to fluctuations in the baseline and/or interfering species on the signal. Accordingly, the above-described dimensions can be altered as desired. Although the preferred embodiments illustrate one electrode configuration including one bulk metal wire helically wound around another bulk metal wire, other electrode configurations are also contemplated. In an alternative embodiment, the working electrode comprises a tube with a reference electrode disposed or coiled inside, including an insulator there between. Alternatively, the reference electrode comprises a tube with a working electrode disposed or coiled inside, including an insulator there between. In another alternative embodiment, a polymer (e.g., insulating) rod is provided, wherein the electrodes are deposited (e.g., electro-plated) thereon. In yet another alternative embodiment, a metallic (e.g., steel) rod is provided, coated with an insulating material, onto which the working and reference electrodes are deposited. In yet another alternative embodiment, one or more working electrodes are helically wound around a reference electrode.

While the methods of preferred embodiments are especially well suited for use with small structured-, micro- or small diameter sensors, the methods can also be suitable for use with larger diameter sensors, e.g., sensors of 1 mm to about 2 mm or more in diameter.

In some alternative embodiments, the sensing mechanism includes electrodes deposited on a planar substrate, wherein the thickness of the implantable portion is less than about 1 mm, see, for example U.S. Pat. No. 6,175,752 to Say et al. and U.S. Pat. No. 5,779,665 to Mastrototaro et al., both of which are incorporated herein by reference in their entirety.

Sensing Membrane

Figure 3B:
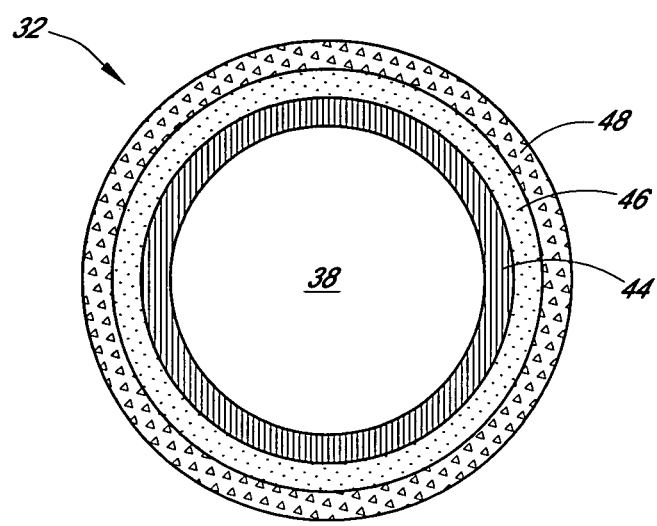
FIG. 3B is a cross-sectional view through the sensor of FIG. 3A on line B-B.

Preferably, a sensing membrane 32 is disposed over the electroactive surfaces of the sensor 34 and includes one or more domains or layers (FIG. 3B, for example). In general, the sensing membrane functions to control the flux of a biological fluid there through and/or to protect sensitive regions of the sensor from contamination by the biological fluid, for example. Some conventional electrochemical enzyme-based analyte sensors generally include a sensing membrane that controls the flux of the analyte being measured, protects the electrodes from contamination of the biological fluid, and/or provides an enzyme that catalyzes the reaction of the analyte with a co-factor, for example. See, e.g., U.S. Publication No. 2005-0245799-A1 and U.S. Publication No. US-2006-0020187-A1.

The sensing membranes of the preferred embodiments can include any membrane configuration suitable for use with any analyte sensor (such as described in more detail above). In general, the sensing membranes of the preferred embodiments include one or more domains, all or some of which can be adhered to or deposited on the analyte sensor as is appreciated by one skilled in the art. In one embodiment, the sensing membrane generally provides one or more of the following functions: 1) protection of the exposed electrode surface from the biological environment, 2) diffusion resistance (limitation) of the analyte, 3) a catalyst for enabling an enzymatic reaction, 4) limitation or blocking of interfering species, and 5) hydrophilicity at the electrochemically reactive surfaces of the sensor interface, such as described in the above-referenced co-pending U.S. Patent Applications.

Electrode Domain

In some embodiments, the membrane system comprises an optional electrode domain. The electrode domain is provided to ensure that an electrochemical reaction occurs between the electroactive surfaces of the working electrode and the reference electrode, and thus the electrode domain is preferably situated more proximal to the electroactive surfaces than the enzyme domain. Preferably, the electrode domain includes a semipermeable coating that maintains a layer of water at the electrochemically reactive surfaces of the sensor, for example, a humectant in a binder material can be employed as an electrode domain; this allows for the full transport of ions in the aqueous environment. The electrode domain can also assist in stabilizing the operation of the sensor by overcoming electrode start-up and drifting problems caused by inadequate electrolyte. The material that forms the electrode domain can also protect against pH-mediated damage that can result from the formation of a large pH gradient due to the electrochemical activity of the electrodes.

In one embodiment, the electrode domain includes a flexible, water-swellable, hydrogel film having a "dry film" thickness of from about 0.05 micron or less to about 20 microns or more, more preferably from about 0.05, 0.1, 0.15, 0.2, 0.25, 0.3, 0.35, 0.4, 0.45, 0.5, 1, 1.5, 2, 2.5, 3, or 3.5 to about 4, 5, 6, 7, 8, 9, 10, 11, 12, 13, 14, 15, 16, 17, 18, 19, or 19.5 microns, and more preferably from about 2, 2.5 or 3 microns to about 3.5, 4, 4.5, or 5 microns. "Dry film" thickness refers to the thickness of a cured film cast from a coating formulation by standard coating techniques.

In certain embodiments, the electrode domain is formed of a curable mixture of a urethane polymer and a hydrophilic polymer. Particularly preferred coatings are formed of a polyurethane polymer having carboxylate functional groups and non-ionic hydrophilic polyether segments, wherein the polyurethane polymer is crosslinked with a water soluble carbodiimide (e.g., 1-ethyl-3-(3-dimethylaminopropyl)carbodiimide (EDC))) in the presence of polyvinylpyrrolidone and cured at a moderate temperature of about 50° C.

Preferably, the electrode domain is deposited by spray or dip-coating the electroactive surfaces of the sensor. More preferably, the electrode domain is formed by dip-coating the electroactive surfaces in an electrode solution and curing the domain for a time of from about 15 to about 30 minutes at a temperature of from about 40 to about 55° C. (and can be accomplished under vacuum (e.g., 20 to 30 mmHg)). In embodiments wherein dip-coating is used to deposit the electrode domain, a preferred insertion rate of from about 1 to about 3 inches per minute, with a preferred dwell time of from about 0.5 to about 2 minutes, and a preferred withdrawal rate of from about 0.25 to about 2 inches per minute provide a functional coating. However, values outside of those set forth above can be acceptable or even desirable in certain embodiments, for example, dependent upon viscosity and surface tension as is appreciated by one skilled in the art. In one embodiment, the electroactive surfaces of the electrode system are dip-coated one time (one layer) and cured at 50° C. under vacuum for 20 minutes.

Although an independent electrode domain is described herein, in some embodiments, sufficient hydrophilicity can be provided in the interference domain and/or emzyme domain (the domain adjacent to the electroactive surfaces) so as to provide for the full transport of icons in the aqueous environment (e.g. without a distinct electrode domain).

Interference Domain

In some embodiments, an optional interference domain is provided, which generally includes a polymer domain that restricts the flow of one or more interferants. In some embodiments, the interference domain functions as a molecular sieve that allows analytes and other substances that are to be measured by the electrodes to pass through, while preventing passage of other substances, including interferants such as ascorbate and urea (see U.S. Pat. No. 6,002,067 to Shults). Some known interferants for a glucose-oxidase based electrochemical sensor include acetaminophen, ascorbic acid, bilirubin, cholesterol, creatinine, dopamine, ephedrine, ibuprofen, L-dopa, methyldopa, salicylate, tetracycline, tolazamide, tolbutamide, triglycerides, and uric acid.

Several polymer types that can be utilized as a base material for the interference domain include polyurethanes, polymers having pendant ionic groups, and polymers having controlled pore size, for example. In one embodiment, the interference domain includes a thin, hydrophobic membrane that is non-swellable and restricts diffusion of low molecular weight species. The interference domain is permeable to relatively low molecular weight substances, such as hydrogen peroxide, but restricts the passage of higher molecular weight substances, including glucose and ascorbic acid. Other systems and methods for reducing or eliminating interference species that can be applied to the membrane system of the preferred embodiments are described in U.S. Pat. No. 7,074,307, U.S. Publication No. US-2005-0176136-A1, U.S. Pat. No. 7,081,195 and U.S. Publication No. US-2005-0143635-A1. In some alternative embodiments, a distinct interference domain is not included.

In preferred embodiments, the interference domain is deposited onto the electrode domain (or directly onto the electroactive surfaces when a distinct electrode domain is not included) for a domain thickness of from about 0.05 micron or less to about 20 microns or more, more preferably from about 0.05, 0.1, 0.15, 0.2, 0.25, 0.3, 0.35, 0.4, 0.45, 0.5, 1, 1.5, 2, 2.5, 3, or 3.5 to about 4, 5, 6, 7, 8, 9, 10, 11, 12, 13, 14, 15, 16, 17, 18, 19, or 19.5 microns, and more preferably from about 2, 2.5 or 3 microns to about 3.5, 4, 4.5, or 5 microns. Thicker membranes can also be useful, but thinner membranes are generally preferred because they have a lower impact on the rate of diffusion of hydrogen peroxide from the enzyme membrane to the electrodes. Unfortunately, the thin thickness of the interference domains conventionally used can introduce variability in the membrane system processing. For example, if too much or too little interference domain is incorporated within a membrane system, the performance of the membrane can be adversely affected.

Enzyme Domain

In preferred embodiments, the membrane system further includes an enzyme domain (e.g., FIG. 3B, 46) disposed more distally from the electroactive surfaces than the interference domain (or electrode domain when a distinct interference is not included). In some embodiments, the enzyme domain is directly deposited onto the electroactive surfaces (when neither an electrode or interference domain is included; e.g., FIG. 3B, 44). In the preferred embodiments, the enzyme domain provides an enzyme to catalyze the reaction of the analyte and its co-reactant, as described in more detail below. Preferably, the enzyme domain includes glucose oxidase, however other oxidases, for example, galactose oxidase or uricase oxidase, can also be used.

For an enzyme-based electrochemical glucose sensor to perform well, the sensor's response is preferably limited by neither enzyme activity nor co-reactant concentration. Because enzymes, including glucose oxidase, are subject to deactivation as a function of time even in ambient conditions, this behavior is compensated for in forming the enzyme domain. Preferably, the enzyme domain is constructed of aqueous dispersions of colloidal polyurethane polymers including the enzyme. However, in alternative embodiments the enzyme domain is constructed from an oxygen enhancing material, for example, silicone or fluorocarbon, in order to provide a supply of excess oxygen during transient ischemia. Preferably, the enzyme is immobilized within the domain. See U.S. Publication No. US-2005-0054909-A1.

In preferred embodiments, the enzyme domain is deposited onto the interference domain for a domain thickness of from about 0.05 micron or less to about 20 microns or more, more preferably from about 0.05, 0.1, 0.15, 0.2, 0.25, 0.3, 0.35, 0.4, 0.45, 0.5, 1, 1.5, 2, 2.5, 3, or 3.5 to about 4, 5, 6, 7, 8, 9, 10, 11, 12, 13, 14, 15, 16, 17, 18, 19, or 19.5 microns, and more preferably from about 2, 2.5 or 3 microns to about 3.5, 4, 4.5, or 5 microns. However in some embodiments, the enzyme domain is deposited onto the electrode domain or directly onto the electroactive surfaces. Preferably, the enzyme domain 46 is deposited by spray or dip coating. More preferably, the enzyme domain is formed by dip-coating the electrode domain into an enzyme domain solution and curing the domain for from about 15 to about 30 minutes at a temperature of from about 40 to about 55° C. (and can be accomplished under vacuum (e.g., 20 to 30 mmHg)). In embodiments wherein dip-coating is used to deposit the enzyme domain at room temperature, a preferred insertion rate of from about 1 inch per minute to about 3 inches per minute, with a preferred dwell time of from about 0.5 minutes to about 2 minutes, and a preferred withdrawal rate of from about 0.25 inch per minute to about 2 inches per minute provide a functional coating. However, values outside of those set forth above can be acceptable or even desirable in certain embodiments, for example, dependent upon viscosity and surface tension as is appreciated by one skilled in the art. In one embodiment, the enzyme domain is formed by dip coating two times (namely, forming two layers) in a coating solution and curing at 50° C. under vacuum for 20 minutes. However, in some embodiments, the enzyme domain can be formed by dip-coating and/or spray-coating one or more layers at a predetermined concentration of the coating solution, insertion rate, dwell time, withdrawal rate, and/or desired thickness.

Resistance Domain

In preferred embodiments, the membrane system includes a resistance domain disposed more distal from the electroactive surfaces than the enzyme domain (e.g., FIG. 3B, 48). Although the following description is directed to a resistance domain for a glucose sensor, the resistance domain can be modified for other analytes and co-reactants as well.

There exists a molar excess of glucose relative to the amount of oxygen in blood; that is, for every free oxygen molecule in extracellular fluid, there are typically more than 100 glucose molecules present (see Updike et al., Diabetes Care 5:207-21(1982)). However, an immobilized enzyme-based glucose sensor employing oxygen as co-reactant is preferably supplied with oxygen in non-rate-limiting excess in order for the sensor to respond linearly to changes in glucose concentration, while not responding to changes in oxygen concentration. Specifically, when a glucose-monitoring reaction is oxygen limited, linearity is not achieved above minimal concentrations of glucose. Without a semi-permeable membrane situated over the enzyme domain to control the flux of glucose and oxygen, a linear response to glucose levels can be obtained only for glucose concentrations of up to about 40 mg/dL. However, in a clinical setting, a linear response to glucose levels is desirable up to at least about 400 mg/dL.

The resistance domain includes a semi permeable membrane that controls the flux of oxygen and glucose to the underlying enzyme domain, preferably rendering oxygen in a non-rate-limiting excess. As a result, the upper limit of linearity of glucose measurement is extended to a much higher value than that which is achieved without the resistance domain. In one embodiment, the resistance domain exhibits an oxygen to glucose permeability ratio of from about 50:1 or less to about 400:1 or more, preferably about 200:1. As a result, one-dimensional reactant diffusion is adequate to provide excess oxygen at all reasonable glucose and oxygen concentrations found in the subcutaneous matrix (See Rhodes et al., Anal. Chem., 66:1520-1529 (1994)).

In alternative embodiments, a lower ratio of oxygen-to-glucose can be sufficient to provide excess oxygen by using a high oxygen solubility domain (for example, a silicone or fluorocarbon-based material or domain) to enhance the supply/transport of oxygen to the enzyme domain. If more oxygen is supplied to the enzyme, then more glucose can also be supplied to the enzyme without creating an oxygen rate-limiting excess. In alternative embodiments, the resistance domain is formed from a silicone composition, such as is described in U.S. Publication No. US-2005-0090607-A1.

In a preferred embodiment, the resistance domain includes a polyurethane membrane with both hydrophilic and hydrophobic regions to control the diffusion of glucose and oxygen to an analyte sensor, the membrane being fabricated easily and reproducibly from commercially available materials. A suitable hydrophobic polymer component is a polyurethane, or polyetherurethaneurea. Polyurethane is a polymer produced by the condensation reaction of a diisocyanate and a difunctional hydroxyl-containing material. A polyurethaneurea is a polymer produced by the condensation reaction of a diisocyanate and a difunctional amine-containing material. Preferred diisocyanates include aliphatic diisocyanates containing from about 4 to about 8 methylene units. Diisocyanates containing cycloaliphatic moieties can also be useful in the preparation of the polymer and copolymer components of the membranes of preferred embodiments. The material that forms the basis of the hydrophobic matrix of the resistance domain can be any of those known in the art as appropriate for use as membranes in sensor devices and as having sufficient permeability to allow relevant compounds to pass through it, for example, to allow an oxygen molecule to pass through the membrane from the sample under examination in order to reach the active enzyme or electrochemical electrodes. Examples of materials which can be used to make non-polyurethane type membranes include vinyl polymers, polyethers, polyesters, polyamides, inorganic polymers such as polysiloxanes and polycarbosiloxanes, natural polymers such as cellulosic and protein based materials, and mixtures or combinations thereof.

In a preferred embodiment, the hydrophilic polymer component is polyethylene oxide as disclosed in copending U.S. patent application Ser. No. 11/404,417, filed Apr. 14, 2006 and entitled "SILICONE BASED MEMBRANES FOR USE IN IMPLANTABLE GLUCOSE SENSORS." For example, one useful hydrophobic-hydrophilic copolymer component is a polyurethane polymer that includes about 20% hydrophilic polyethylene oxide. The polyethylene oxide portions of the copolymer are thermodynamically driven to separate from the hydrophobic portions of the copolymer and the hydrophobic polymer component. The 20% polyethylene oxide-based soft segment portion of the copolymer used to form the final blend affects the water pick-up and subsequent glucose permeability of the membrane.

In preferred embodiments, the resistance domain is deposited onto the enzyme domain to yield a domain thickness of from about 0.05 micron or less to about 20 microns or more, more preferably from about 0.05, 0.1, 0.15, 0.2, 0.25, 0.3, 0.35, 0.4, 0.45, 0.5, 1, 1.5, 2, 2.5, 3, or 3.5 to about 4, 5, 6, 7, 8, 9, 10, 11, 12, 13, 14, 15, 16, 17, 18, 19, or 19.5 microns, and more preferably from about 2, 2.5 or 3 microns to about 3.5, 4, 4.5, or 5 microns. Preferably, the resistance domain is deposited onto the enzyme domain by spray coating or dip coating. In certain embodiments, spray coating is the preferred deposition technique. The spraying process atomizes and mists the solution, and therefore most or all of the solvent is evaporated prior to the coating material settling on the underlying domain, thereby minimizing contact of the solvent with the enzyme. One additional advantage of spray-coating the resistance domain as described in the preferred embodiments includes formation of a membrane system that substantially blocks or resists ascorbate (a known electrochemical interferant in hydrogen peroxide-measuring glucose sensors). While not wishing to be bound by theory, it is believed that during the process of depositing the resistance domain as described in the preferred embodiments, a structural morphology is formed, characterized in that ascorbate does not substantially permeate there through.

In preferred embodiments, the resistance domain is deposited on the enzyme domain by spray-coating a solution of from about 1 wt. % to about 5 wt. % polymer and from about 95 wt. % to about 99 wt. % solvent. In spraying a solution of resistance domain material, including a solvent, onto the enzyme domain, it is desirable to mitigate or substantially reduce any contact with enzyme of any solvent in the spray solution that can deactivate the underlying enzyme of the enzyme domain. Tetrahydrofuran (THF) is one solvent that minimally or negligibly affects the enzyme of the enzyme domain upon spraying. Other solvents can also be suitable for use, as is appreciated by one skilled in the art.

Although a variety of spraying or deposition techniques can be used, spraying the resistance domain material and rotating the sensor at least one time by 180° can provide adequate coverage by the resistance domain. Spraying the resistance domain material and rotating the sensor at least two times by 120 degrees provides even greater coverage (one layer of 360° coverage), thereby ensuring resistivity to glucose, such as is described in more detail above.

In preferred embodiments, the resistance domain is spray-coated and subsequently cured for a time of from about 15 to about 90 minutes at a temperature of from about 40 to about 60° C. (and can be accomplished under vacuum (e.g., 20 to 30 mmHg)). A cure time of up to about 90 minutes or more can be advantageous to ensure complete drying of the resistance domain. While not wishing to be bound by theory, it is believed that complete drying of the resistance domain aids in stabilizing the sensitivity of the glucose sensor signal. It reduces drifting of the signal sensitivity over time, and complete drying is believed to stabilize performance of the glucose sensor signal in lower oxygen environments.

In one embodiment, the resistance domain is formed by spray-coating at least six layers (namely, rotating the sensor seventeen times by 120° for at least six layers of 360° coverage) and curing at 50° C. under vacuum for 60 minutes. However, the resistance domain can be formed by dip-coating or spray-coating any layer or plurality of layers, depending upon the concentration of the solution, insertion rate, dwell time, withdrawal rate, and/or the desired thickness of the resulting film.

Advantageously, sensors with the membrane system of the preferred embodiments, including an electrode domain and/or interference domain, an enzyme domain, and a resistance domain, provide stable signal response to increasing glucose levels of from about 40 to about 400 mg/dL, and sustained function (at least 90% signal strength) even at low oxygen levels (for example, at about 0.6 mg/L $O_2$). While not wishing to be bound by theory, it is believed that the resistance domain provides sufficient resistivity, or the enzyme domain provides sufficient enzyme, such that oxygen limitations are seen at a much lower concentration of oxygen as compared to prior art sensors.

In preferred embodiments, a sensor signal with a current in the picoAmp range is preferred, which is described in more detail elsewhere herein. However, the ability to produce a signal with a current in the picoAmp range can be dependent upon a combination of factors, including the electronic circuitry design (e.g., A/D converter, bit resolution, and the like), the membrane system (e.g., permeability of the analyte through the resistance domain, enzyme concentration, and/or electrolyte availability to the electrochemical reaction at the electrodes), and the exposed surface area of the working electrode. For example, the resistance domain can be designed to be more or less restrictive to the analyte depending upon to the design of the electronic circuitry, membrane system, and/or exposed electroactive surface area of the working electrode.

Accordingly, in preferred embodiments, the membrane system is designed with a sensitivity of from about 1 pA/mg/dL to about 100 pA/mg/dL, preferably from about 5 pA/mg/dL to 25 pA/mg/dL, and more preferably from about 4 to about 7 pA/mg/dL. While not wishing to be bound by any particular theory, it is believed that membrane systems designed with a sensitivity in the preferred ranges permit measurement of the analyte signal in low analyte and/or low oxygen situations. Namely, conventional analyte sensors have shown reduced measurement accuracy in low analyte ranges due to lower availability of the analyte to the sensor and/or have shown increased signal noise in high analyte ranges due to insufficient oxygen necessary to react with the amount of analyte being measured. While not wishing to be bound by theory, it is believed that the membrane systems of the preferred embodiments, in combination with the electronic circuitry design and exposed electrochemical reactive surface area design, support measurement of the analyte in the picoAmp range, which enables an improved level of resolution and accuracy in both low and high analyte ranges not seen in the prior art.

Although sensors of some embodiments described herein include an optional interference domain in order to block or reduce one or more interferants, sensors with the membrane system of the preferred embodiments, including an electrode domain, an enzyme domain, and a resistance domain, have been shown to inhibit ascorbate without an additional interference domain. Namely, the membrane system of the preferred embodiments, including an electrode domain, an enzyme domain, and a resistance domain, has been shown to be substantially non-responsive to ascorbate in physiologically acceptable ranges. While not wishing to be bound by theory, it is believed that the process of depositing the resistance domain by spray coating, as described herein, results in a structural morphology that is substantially resistance resistant to ascorbate.

Interference-Free Membrane Systems

In general, it is believed that appropriate solvents and/or deposition methods can be chosen for one or more of the domains of the membrane system that form one or more transitional domains such that interferants do not substantially permeate there through. Thus, sensors can be built without distinct or deposited interference domains, which are non-responsive to interferants. While not wishing to be bound by theory, it is believed that a simplified multilayer membrane system, more robust multilayer manufacturing process, and reduced variability caused by the thickness and associated oxygen and glucose sensitivity of the deposited micron-thin interference domain can be provided. Additionally, the optional polymer-based interference domain, which usually inhibits hydrogen peroxide diffusion, is eliminated, thereby enhancing the amount of hydrogen peroxide that passes through the membrane system.

Oxygen Conduit

As described above, certain sensors depend upon an enzyme within the membrane system through which the host's bodily fluid passes and in which the analyte (for example, glucose) within the bodily fluid reacts in the presence of a co-reactant (for example, oxygen) to generate a product. The product is then measured using electrochemical methods, and thus the output of an electrode system functions as a measure of the analyte. For example, when the sensor is a glucose oxidase based glucose sensor, the species measured at the working electrode is $H_2O_2$. An enzyme, glucose oxidase, catalyzes the conversion of oxygen and glucose to hydrogen peroxide and gluconate according to the following reaction:

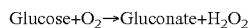

Glucose+$O_2$→Gluconate+$H_2O_2$

Because for each glucose molecule reacted there is a proportional change in the product, $H_2O_2$, one can monitor the change in $H_2O_2$ to determine glucose concentration. Oxidation of $H_2O_2$ by the working electrode is balanced by reduction of ambient oxygen, enzyme generated $H_2O_2$ and other reducible species at a counter electrode, for example.

See Fraser, D. M., "An Introduction to In Vivo Biosensing: Progress and Problems." In "Biosensors and the Body," D. M. Fraser, ed., 1997, pp. 1-56 John Wiley and Sons, New York))

In vivo, glucose concentration is generally about one hundred times or more that of the oxygen concentration. Consequently, oxygen is a limiting reactant in the electrochemical reaction, and when insufficient oxygen is provided to the sensor, the sensor is unable to accurately measure glucose concentration. Thus, depressed sensor function or inaccuracy is believed to be a result of problems in availability of oxygen to the enzyme and/or electroactive surface(s).

Accordingly, in an alternative embodiment, an oxygen conduit (for example, a high oxygen solubility domain formed from silicone or fluorochemicals) is provided that extends from the ex vivo portion of the sensor to the in vivo portion of the sensor to increase oxygen availability to the enzyme. The oxygen conduit can be formed as a part of the coating (insulating) material or can be a separate conduit associated with the assembly of wires that forms the sensor.

FIG. 3B is a cross-sectional view through the sensor of FIG. 3A on line B-B, showing an exposed electroactive surface of at least a working electrode 38 surrounded by a sensing membrane. In general, the sensing membranes of the preferred embodiments include a plurality of domains or layers, for example, an interference domain 44, an enzyme domain 46, and a resistance domain 48, and can include additional domains, such as an electrode domain, a cell impermeable domain, and/or an oxygen domain (not shown), such as described in more detail in the above-cited co-pending U.S. Patent Applications. However, it is understood that a sensing membrane modified for other sensors, for example, by including fewer or additional domains is within the scope of the preferred embodiments. In some embodiments, one or more domains of the sensing membranes are formed from materials such as silicone, polytetrafluoroethylene, polyethylene-co-tetrafluoroethylene, polyolefin, polyester, polycarbonate, biostable polytetrafluoroethylene, homopolymers, copolymers, terpolymers of polyurethanes, polypropylene (PP), polyvinylchloride (PVC), polyvinylidene fluoride (PVDF), polybutylene terephthalate (PBT), polymethylmethacrylate (PMMA), polyether ether ketone (PEEK), polyurethanes, cellulosic polymers, poly(ethylene oxide), poly(propylene oxide) and copolymers and blends thereof, polysulfones and block copolymers thereof including, for example, di-block, tri-block, alternating, random and graft copolymers. Co-pending U.S. patent application Ser. No. 10/838,912, which is incorporated herein by reference in its entirety, describes biointerface and sensing membrane configurations and materials that can be applied to the preferred embodiments.

The sensing membrane can be deposited on the electroactive surfaces of the electrode material using known thin or thick film techniques (for example, spraying, electro-depositing, dipping, or the like). The sensing membrane that surrounds the working electrode does not have to be the same structure as the sensing membrane that surrounds a reference electrode, etc. For example, the enzyme domain deposited over the working electrode does not necessarily need to be deposited over the reference and/or counter electrodes.

In the illustrated embodiment, the sensor is an enzyme-based electrochemical sensor, wherein the working electrode 38 measures the hydrogen peroxide produced by the enzyme catalyzed reaction of glucose being detected and creates a measurable electronic current (for example, detection of glucose utilizing glucose oxidase produces hydrogen peroxide as a by-product, $H_2O_2$ reacts with the surface of the working electrode producing two protons ($2H^+$), two electrons ($2e^-$) and one molecule of oxygen ($O_2$) which produces the electronic current being detected), such as described in more detail above and as is appreciated by one skilled in the art. Preferably, one or more potentiostat is employed to monitor the electrochemical reaction at the electroactive surface of the working electrode(s). The potentiostat applies a constant potential to the working electrode and its associated reference electrode to determine the current produced at the working electrode. The current that is produced at the working electrode (and flows through the circuitry to the counter electrode) is substantially proportional to the amount of $H_2O_2$ that diffuses to the working electrode. The output signal is typically a raw data stream that is used to provide a useful value of the measured analyte concentration in a host to the host or doctor, for example.

Some alternative analyte sensors that can benefit from the systems and methods of the preferred embodiments include U.S. Pat. No. 5,711,861 to Ward et al., U.S. Pat. No. 6,642,015 to Vachon et al., U.S. Pat. No. 6,654,625 to Say et al., U.S. Pat. No. 6,565,509 to Say et al., U.S. Pat. No. 6,514,718 to Heller, U.S. Pat. No. 6,465,066 to Essenpreis et al., U.S. Pat. No. 6,214,185 to Offenbacher et al., U.S. Pat. No. 5,310,469 to Cunningham et al., and U.S. Pat. No. 5,683,562 to Shaffer et al., U.S. Pat. No. 6,579,690 to Bonnecaze et al., U.S. Pat. No. 6,484,046 to Say et al., U.S. Pat. No. 6,512,939 to Colvin et al., U.S. Pat. No. 6,424,847 to Mastrototaro et al., U.S. Pat. No. 6,424,847 to Mastrototaro et al, for example. All of the above patents are not inclusive of all applicable analyte sensors; in general, it should be understood that the disclosed embodiments are applicable to a variety of analyte sensor configurations.

Exemplary Sensor Configurations

Figure 4A:
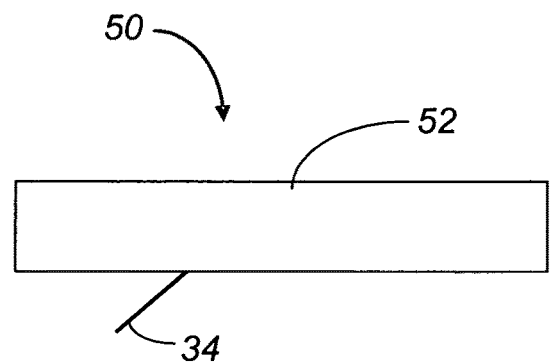
FIG. 4A is a side schematic view of a transcutaneous analyte sensor in one embodiment.

FIG. 4A is a side schematic view of a transcutaneous analyte sensor 50 in one embodiment. The sensor 50 includes a mounting unit 52 adapted for mounting on the skin of a host, a small diameter sensor 34 (as defined herein) adapted for transdermal insertion through the skin of a host, and an electrical connection configured to provide secure electrical contact between the sensor and the electronics preferably housed within the mounting unit 52. In general, the mounting unit 52 is designed to maintain the integrity of the sensor in the host so as to reduce or eliminate translation of motion between the mounting unit, the host, and/or the sensor. See U.S. Publication No. US-2006-0020187-A1. Preferably, a biointerface membrane is formed onto the sensing mechanism 34 as described in more detail below.

Figure 4B:
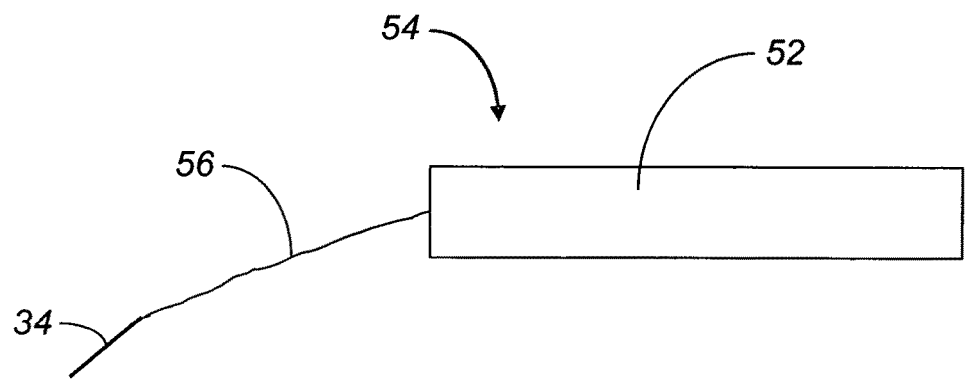
FIG. 4B is a side schematic view of a transcutaneous analyte sensor in an alternative embodiment.

FIG. 4B is a side schematic view of a transcutaneous analyte sensor 54 in an alternative embodiment. The sensor 54 includes a mounting unit 52 wherein the sensing mechanism 34 comprises a small structure as defined herein and is tethered to the mounting unit 52 via a cable 56 (alternatively, a wireless connection can be utilized). The mounting unit is adapted for mounting on the skin of a host and is operably connected via a tether, or the like, to a small structured sensor 34 adapted for transdermal insertion through the skin of a host and measurement of the analyte therein; see, for example, U.S. Pat. No. 6,558,330 to Causey III, et al., which is incorporated herein by reference in its entirety. In the preferred embodiments, a biointerface membrane is formed onto the sensing mechanism 34 as described in more detail below.

The short-term sensor of the preferred embodiments can be inserted into a variety of locations on the host's body, such as the abdomen, the thigh, the upper arm, and the neck or behind the ear. Although the preferred embodiments illustrate insertion through the abdominal region, the systems and methods described herein are limited neither to the abdominal nor to the subcutaneous insertions. One skilled in the art appreciates that these systems and methods can be implemented and/or modified for other insertion sites and can be dependent upon the type, configuration, and dimensions of the analyte sensor.

In one embodiment, an analyte-sensing device adapted for transcutaneous short-term insertion into the host is provided. For example, the device includes a sensor, for measuring the analyte in the host, a porous, biocompatible matrix covering at least a portion of the sensor, and an applicator, for inserting the sensor through the host's skin. In some embodiments, the sensor has architecture with at least one dimension less than about 1 mm. Examples of such a structure are shown in FIGS. 4A and 4B, as described elsewhere herein. However, one skilled in the art will recognize that alternative configurations are possible and can be desirable, depending upon factors such as intended location of insertion, for example. The sensor is inserted through the host's skin and into the underlying tissue, such as soft tissue or fatty tissue.

After insertion, fluid moves into the spacer, e.g., a biocompatible matrix or membrane, creating a fluid-filled pocket therein. This process can occur immediately or can take place over a period of time, such as several minutes or hours post insertion. A signal from the sensor is then detected, such as by the sensor electronics unit located in the mounting unit on the surface of the host's skin. In general, the sensor can be used continuously for a short period of days, such as 1 to 14 days. After use, the sensor is simply removed from the host's skin. In preferred embodiments, the host can repeat the insertion and detection steps as many times as desired. In some implementations, the sensor can be removed after about 3 days, and then another sensor inserted, and so on. Similarly in other implementations, the sensor is removed after about 3, 5, 7, 10 or 14 days, followed by insertion of a new sensor, and so on.

Some examples of transcutaneous analyte sensors are described in co-pending U.S. patent application Ser. No. 11/360,250, filed Feb. 22, 2006 and entitled "ANALYTE SENSOR." In general, transcutaneous analyte sensors comprise the sensor and a mounting unit with electronics associated therewith.

In general, the mounting unit includes a base adapted for mounting on the skin of a host, a sensor adapted for transdermal insertion through the skin of a host, and one or more contacts configured to provide secure electrical contact between the sensor and the sensor electronics. The mounting unit is designed to maintain the integrity of the sensor in the host so as to reduce or eliminate translation of motion between the mounting unit, the host, and/or the sensor.

The base can be formed from a variety of hard or soft materials, and preferably comprises a low profile for minimizing protrusion of the device from the host during use. In some embodiments, the base is formed at least partially from a flexible material, which is believed to provide numerous advantages over conventional transcutaneous sensors, which, unfortunately, can suffer from motion-related artifacts associated with the host's movement when the host is using the device. For example, when a transcutaneous analyte sensor is inserted into the host, various movements of the sensor (for example, relative movement between the in vivo portion and the ex vivo portion, movement of the skin, and/or movement within the host (dermis or subcutaneous)) create stresses on the device and can produce noise in the sensor signal. It is believed that even small movements of the skin can translate to discomfort and/or motion-related artifact, which can be reduced or obviated by a flexible or articulated base. Thus, by providing flexibility and/or articulation of the device against the host's skin, better conformity of the sensor system to the regular use and movements of the host can be achieved. Flexibility or articulation is believed to increase adhesion (with the use of an adhesive pad) of the mounting unit onto the skin, thereby decreasing motion-related artifact that can otherwise translate from the host's movements and reduced sensor performance.

In certain embodiments, the mounting unit is provided with an adhesive pad, preferably disposed on the mounting unit's back surface and preferably including a releasable backing layer. Thus, removing the backing layer and pressing the base portion of the mounting unit onto the host's skin adheres the mounting unit to the host's skin. Additionally or alternatively, an adhesive pad can be placed over some or all of the sensor system after sensor insertion is complete to ensure adhesion, and optionally to ensure an airtight seal or watertight seal around the wound exit-site (or sensor insertion site). Appropriate adhesive pads can be chosen and designed to stretch, elongate, conform to, and/or aerate the region (e.g., host's skin).

In preferred embodiments, the adhesive pad is formed from spun-laced, open- or closed-cell foam, and/or non-woven fibers, and includes an adhesive disposed thereon, however a variety of adhesive pads appropriate for adhesion to the host's skin can be used, as is appreciated by one skilled in the art of medical adhesive pads. In some embodiments, a double-sided adhesive pad is used to adhere the mounting unit to the host's skin. In other embodiments, the adhesive pad includes a foam layer, for example, a layer wherein the foam is disposed between the adhesive pad's side edges and acts as a shock absorber.

In some embodiments, the surface area of the adhesive pad is greater than the surface area of the mounting unit's back surface. Alternatively, the adhesive pad can be sized with substantially the same surface area as the back surface of the base portion. Preferably, the adhesive pad has a surface area on the side to be mounted on the host's skin that is greater than about 1, 1.25, 1.5, 1.75, 2, 2.25, or 2.5, times the surface area of the back surface of the mounting unit base. Such a greater surface area can increase adhesion between the mounting unit and the host's skin, minimize movement between the mounting unit and the host's skin, and/or protect the wound exit-site (sensor insertion site) from environmental and/or biological contamination. In some alternative embodiments, however, the adhesive pad can be smaller in surface area than the back surface assuming a sufficient adhesion can be accomplished.

In some embodiments, the adhesive pad is substantially the same shape as the back surface of the base, although other shapes can also be advantageously employed, for example, butterfly-shaped, round, square, or rectangular. The adhesive pad backing can be designed for two-step release, for example, a primary release wherein only a portion of the adhesive pad is initially exposed to allow adjustable positioning of the device, and a secondary release wherein the remaining adhesive pad is later exposed to firmly and securely adhere the device to the host's skin once appropriately positioned. The adhesive pad is preferably waterproof. Preferably, a stretch-release adhesive pad is provided on the back surface of the base portion to enable easy release from the host's skin at the end of the useable life of the sensor.

In some circumstances, it has been found that a conventional bond between the adhesive pad and the mounting unit can not be sufficient, for example, due to humidity that can cause release of the adhesive pad from the mounting unit. Accordingly, in some embodiments, the adhesive pad can be bonded using a bonding agent activated by or accelerated by an ultraviolet, acoustic, radio frequency, or humidity cure. In some embodiments, a eutectic bond of first and second composite materials can form a strong adhesion. In some embodiments, the surface of the mounting unit can be pretreated utilizing ozone, plasma, chemicals, or the like, in order to enhance the bondability of the surface.

A bioactive agent is preferably applied locally at the insertion site prior to or during sensor insertion. Suitable bioactive agents include those which are known to discourage or prevent bacterial growth and infection, for example, anti-inflammatory agents, antimicrobials, antibiotics, or the like. It is believed that the diffusion or presence of a bioactive agent can aid in prevention or elimination of bacteria adjacent to the exit-site. Additionally or alternatively, the bioactive agent can be integral with or coated on the adhesive pad, or no bioactive agent at all is employed.

In some embodiments, an applicator is provided for inserting the sensor through the host's skin at the appropriate insertion angle with the aid of a needle, and for subsequent removal of the needle using a continuous push-pull action. Preferably, the applicator comprises an applicator body that guides the applicator and includes an applicator body base configured to mate with the mounting unit during insertion of the sensor into the host. The mate between the applicator body base and the mounting unit can use any known mating configuration, for example, a snap-fit, a press-fit, an interference-fit, or the like, to discourage separation during use. One or more release latches enable release of the applicator body base, for example, when the applicator body base is snap fit into the mounting unit.

The sensor electronics includes hardware, firmware, and/or software that enable measurement of levels of the analyte via the sensor. For example, the sensor electronics can comprise a potentiostat, a power source for providing power to the sensor, other components useful for signal processing, and preferably an RF module for transmitting data from the sensor electronics to a receiver. Electronics can be affixed to a printed circuit board (PCB), or the like, and can take a variety of forms. For example, the electronics can take the form of an integrated circuit (IC), such as an Application-Specific Integrated Circuit (ASIC), a microcontroller, or a processor. Preferably, sensor electronics comprise systems and methods for processing sensor analyte data. Examples of systems and methods for processing sensor analyte data are described in more detail below and in U.S. Publication No. US-2005-0027463-A1.

In this embodiment, after insertion of the sensor using the applicator, and subsequent release of the applicator from the mounting unit, the sensor electronics are configured to releasably mate with the mounting unit. In one embodiment, the electronics are configured with programming, for example initialization, calibration reset, failure testing, or the like, each time it is initially inserted into the mounting unit and/or each time it initially communicates with the sensor.

Sensor Electronics

The following description of electronics associated with the sensor is applicable to a variety of continuous analyte sensors, such as non-invasive, minimally invasive, and/or invasive (e.g., transcutaneous and wholly implantable) sensors. For example, the sensor electronics and data processing as well as the receiver electronics and data processing described below can be incorporated into the wholly implantable glucose sensor disclosed in U.S. Publication No. US-2005-0245799-A1 and U.S. Publication No. US-2006-0015020-A1.

In one embodiment, a potentiostat, which is operably connected to an electrode system (such as described above) provides a voltage to the electrodes, which biases the sensor to enable measurement of a current signal indicative of the analyte concentration in the host (also referred to as the analog portion). In some embodiments, the potentiostat includes a resistor that translates the current into voltage. In some alternative embodiments, a current to frequency converter is provided that is configured to continuously integrate the measured current, for example, using a charge counting device. An A/D converter digitizes the analog signal into a digital signal, also referred to as "counts" for processing. Accordingly, the resulting raw data stream in counts, also referred to as raw sensor data, is directly related to the current measured by the potentiostat.

A processor module includes the central control unit that controls the processing of the sensor electronics. In some embodiments, the processor module includes a microprocessor, however a computer system other than a microprocessor can be used to process data as described herein, for example an ASIC can be used for some or all of the sensor's central processing. The processor typically provides semi-permanent storage of data, for example, storing data such as sensor identifier (ID) and programming to process data streams (for example, programming for data smoothing and/or replacement of signal artifacts such as is described in U.S. Publication No. US-2005-0043598-A1. The processor additionally can be used for the system's cache memory, for example for temporarily storing recent sensor data. In some embodiments, the processor module comprises memory storage components such as ROM, RAM, dynamic-RAM, static-RAM, non-static RAM, EEPROM, rewritable ROMs, flash memory, or the like.

In some embodiments, the processor module comprises a digital filter, for example, an IIR or FIR filter, configured to smooth the raw data stream from the A/D converter. Generally, digital filters are programmed to filter data sampled at a predetermined time interval (also referred to as a sample rate.) In some embodiments, wherein the potentiostat is configured to measure the analyte at discrete time intervals, these time intervals determine the sample rate of the digital filter. In some alternative embodiments, wherein the potentiostat is configured to continuously measure the analyte, for example, using a current-to-frequency converter as described above, the processor module can be programmed to request a digital value from the A/D converter at a predetermined time interval, also referred to as the acquisition time. In these alternative embodiments, the values obtained by the processor are advantageously averaged over the acquisition time due the continuity of the current measurement. Accordingly, the acquisition time determines the sample rate of the digital filter. In preferred embodiments, the processor module is configured with a programmable acquisition time, namely, the predetermined time interval for requesting the digital value from the A/D converter is programmable by a user within the digital circuitry of the processor module. An acquisition time of from about 2 seconds to about 512 seconds is preferred; however any acquisition time can be programmed into the processor module. A programmable acquisition time is advantageous in optimizing noise filtration, time lag, and processing/battery power.

Preferably, the processor module is configured to build the data packet for transmission to an outside source, for example, an RF transmission to a receiver as described in more detail below. Generally, the data packet comprises a plurality of bits that can include a sensor ID code, raw data, filtered data, and/or error detection or correction. The processor module can be configured to transmit any combination of raw and/or filtered data.

In some embodiments, the processor module further comprises a transmitter portion that determines the transmission interval of the sensor data to a receiver, or the like. In some embodiments, the transmitter portion, which determines the interval of transmission, is configured to be programmable. In one such embodiment, a coefficient can be chosen (e.g., a number of from about 1 to about 100, or more), wherein the coefficient is multiplied by the acquisition time (or sampling rate), such as described above, to define the transmission interval of the data packet. Thus, in some embodiments, the transmission interval is programmable between about 2 seconds and about 850 minutes, more preferably between about 30 second and 5 minutes; however, any transmission interval can be programmable or programmed into the processor module. However, a variety of alternative systems and methods for providing a programmable transmission interval can also be employed. By providing a programmable transmission interval, data transmission can be customized to meet a variety of design criteria (e.g., reduced battery consumption, timeliness of reporting sensor values, etc.)

Conventional glucose sensors measure current in the nanoAmp range. In contrast to conventional glucose sensors, the preferred embodiments are configured to measure the current flow in the picoAmp range, and in some embodiments, femtoAmps. Namely, for every unit (mg/dL) of glucose measured, at least one picoAmp of current is measured. Preferably, the analog portion of the A/D converter is configured to continuously measure the current flowing at the working electrode and to convert the current measurement to digital values representative of the current. In one embodiment, the current flow is measured by a charge counting device (e.g., a capacitor). Thus, a signal is provided, whereby a high sensitivity maximizes the signal received by a minimal amount of measured hydrogen peroxide (e.g., minimal glucose requirements without sacrificing accuracy even in low glucose ranges), reducing the sensitivity to oxygen limitations in vivo (e.g., in oxygen-dependent glucose sensors).

A battery is operably connected to the sensor electronics and provides the power for the sensor. In one embodiment, the battery is a lithium manganese dioxide battery; however, any appropriately sized and powered battery can be used (for example, AAA, nickel-cadmium, zinc-carbon, alkaline, lithium, nickel-metal hydride, lithium-ion, zinc-air, zinc-mercury oxide, silver-zinc, and/or hermetically-sealed). In some embodiments, the battery is rechargeable, and/or a plurality of batteries can be used to power the system. The sensor can be transcutaneously powered via an inductive coupling, for example. In some embodiments, a quartz crystal is operably connected to the processor and maintains system time for the computer system as a whole, for example for the programmable acquisition time within the processor module.

Optional temperature probe can be provided, wherein the temperature probe is located on the electronics assembly or the glucose sensor itself. The temperature probe can be used to measure ambient temperature in the vicinity of the glucose sensor. This temperature measurement can be used to add temperature compensation to the calculated glucose value.

An RF module is operably connected to the processor and transmits the sensor data from the sensor to a receiver within a wireless transmission via antenna. In some embodiments, a second quartz crystal provides the time base for the RF carrier frequency used for data transmissions from the RF transceiver. In some alternative embodiments, however, other mechanisms, such as optical, infrared radiation (IR), ultrasonic, or the like, can be used to transmit and/or receive data.

In the RF telemetry module of the preferred embodiments, the hardware and software are designed for low power requirements to increase the longevity of the device (for example, to enable a life of from about 3 to about 24 months, or more) with maximum RF transmittance from the in vivo environment to the ex vivo environment for wholly implantable sensors (for example, a distance of from about one to ten meters or more). Preferably, a high frequency carrier signal of from about 402 MHz to about 433 MHz is employed in order to maintain lower power requirements. Additionally, in wholly implantable devices, the carrier frequency is adapted for physiological attenuation levels, which is accomplished by tuning the RF module in a simulated in vivo environment to ensure RF functionality after implantation; accordingly, the preferred glucose sensor can sustain sensor function for 3 months, 6 months, 12 months, or 24 months or more.

In some embodiments, output signal (from the sensor electronics) is sent to a receiver (e.g., a computer or other communication station). The output signal is typically a raw data stream that is used to provide a useful value of the measured analyte concentration to a patient or a doctor, for example. In some embodiments, the raw data stream can be continuously or periodically algorithmically smoothed or otherwise modified to diminish outlying points that do not accurately represent the analyte concentration, for example due to signal noise or other signal artifacts, such as described in U.S. Pat. No. 6,931,327.

When a sensor is first implanted into host tissue, the sensor and receiver are initialized. This can be referred to as start-up mode, and involves optionally resetting the sensor data and calibrating the sensor 32. In selected embodiments, mating the electronics unit 16 to the mounting unit triggers a start-up mode. In other embodiments, the start-up mode is triggered by the receiver.

Receiver

In some embodiments, the sensor electronics are wirelessly connected to a receiver via one- or two-way RF transmissions or the like. However, a wired connection is also contemplated. The receiver provides much of the processing and display of the sensor data, and can be selectively worn and/or removed at the host's convenience. Thus, the sensor system can be discreetly worn, and the receiver, which provides much of the processing and display of the sensor data, can be selectively worn and/or removed at the host's convenience. Particularly, the receiver includes programming for retrospectively and/or prospectively initiating a calibration, converting sensor data, updating the calibration, evaluating received reference and sensor data, and evaluating the calibration for the analyte sensor, such as described in more detail with reference to co-pending U.S. Publication No. US-2005-0027463-A1.

Figure 4C:
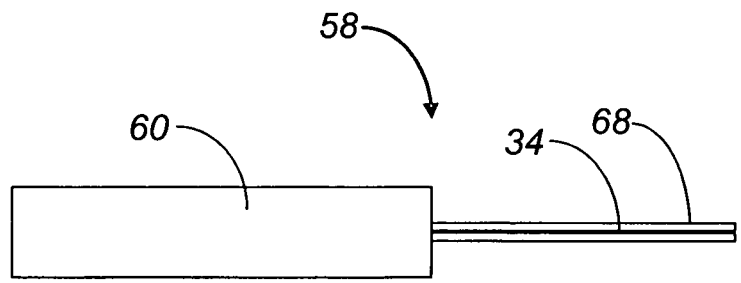
FIG. 4C is a side schematic view of a wholly implantable analyte sensor in one embodiment.

FIG. 4C is a side schematic view of a wholly implantable analyte sensor 58 in one embodiment. The sensor includes a sensor body 60 suitable for subcutaneous implantation and includes a small structured sensor 34 as defined herein. Published U.S. Patent Application No. 2004/0199059 to Brauker et al. describe systems and methods suitable for the sensor body 60, and is incorporated herein by reference in its entirety. In the preferred embodiments, a biointerface membrane 68 is formed onto the sensing mechanism 34 as described in more detail elsewhere herein. The sensor body 60 includes sensor electronics and preferably communicates with a receiver as described in more detail, above.

Figure 4D:
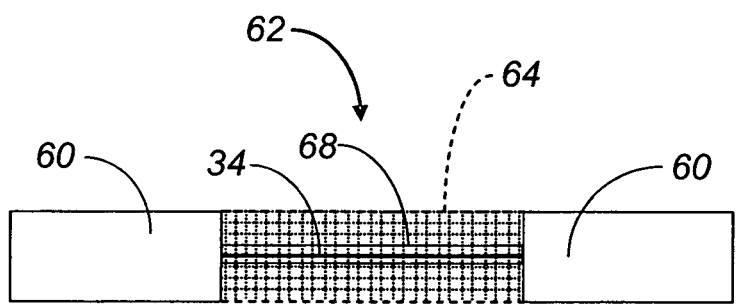
FIG. 4D is a side schematic view of a wholly implantable analyte sensor in an alternative embodiment.

FIG. 4D is a side schematic view of a wholly implantable analyte sensor 62 in an alternative embodiment. The sensor 62 includes a sensor body 60 and a small structured sensor 34 as defined herein. The sensor body 60 includes sensor electronics and preferably communicates with a receiver as described in more detail, above.

In preferred embodiments, a biointerface membrane 68 is formed onto the sensing mechanism 34 as described in more detail elsewhere herein. Preferably, a matrix or framework 64 surrounds the sensing mechanism 34 for protecting the sensor from some foreign body processes, for example, by causing tissue to compress against or around the framework 64 rather than the sensing mechanism 34.

In general, the optional protective framework 64 is formed from a two-dimensional or three-dimensional flexible, semi-rigid, or rigid matrix (e.g., mesh), and which includes spaces or pores through which the analyte can pass. In some embodiments, the framework is incorporated as a part of the biointerface membrane, however a separate framework can be provided. While not wishing to be bound by theory, it is believed that the framework 64 protects the small structured sensing mechanism from mechanical forces created in vivo.

Figure 4E:
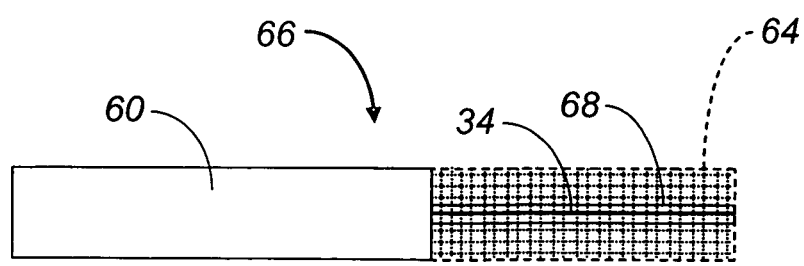
FIG. 4E is a side schematic view of a wholly implantable analyte sensor in another alternative embodiment.

FIG. 4E is a side schematic view of a wholly implantable analyte sensor 66 in another alternative embodiment. The sensor 66 includes a sensor body 60 and a small structured sensor 34, as defined herein, with a biointerface membrane 68 such as described in more detail elsewhere herein. Preferably, a framework 64 protects the sensing mechanism 34 such as described in more detail above. The sensor body 60 includes sensor electronics and preferably communicates with a receiver as described in more detail, above.

In certain embodiments, the sensing device, which is adapted to be wholly implanted into the host, such as in the soft tissue beneath the skin, is implanted subcutaneously, such as in the abdomen of the host, for example. One skilled in the art appreciates a variety of suitable implantation sites available due to the sensor's small size. In some embodiments, the sensor architecture is less than about 0.5 mm in at least one dimension, for example a wire-based sensor with a diameter of less than about 0.5 mm. In another exemplary embodiment, for example, the sensor can be 0.5 mm thick, 3 mm in length and 2 cm in width, such as possibly a narrow substrate, needle, wire, rod, sheet or pocket. In another exemplary embodiment, a plurality of about 1 mm wide wires about 5 mm in length could be connected at their first ends, producing a forked sensor structure. In still another embodiment, a 1 mm wide sensor could be coiled, to produce a planar, spiraled sensor structure. Although a few examples are cited above, numerous other useful embodiments are contemplated by the present invention, as is appreciated by one skilled in the art.

Post implantation, a period of time is allowed for tissue ingrowth within the biointerface. The length of time required for tissue ingrowth varies from host to host, such as about a week to about 3 weeks, although other time periods are also possible. Once a mature bed of vascularized tissue has grown into the biointerface, a signal can be detected from the sensor, as described elsewhere herein and in U.S. Publication No. 2005-0245799-A1. Long-term sensors can remain implanted and produce glucose signal information from months to years, as described in the above-cited patent application.

In certain embodiments, the device is configured such that the sensing unit is separated from the electronics unit by a tether or cable, or a similar structure, similar to that illustrated in FIG. 4B. One skilled in the art will recognize that a variety of known and useful means can be used to tether the sensor to the electronics. While not wishing to be bound by theory, it is believed that the FBR to the electronics unit alone can be greater than the FBR to the sensing unit alone, due to the electronics unit's greater mass, for example. Accordingly, separation of the sensing and electronics units effectively reduces the FBR to the sensing unit and results in improved device function. As described elsewhere herein, the architecture and/or composition of the sensing unit (e.g., inclusion of a biointerface with certain bioactive agents) can be implemented to further reduce the foreign body response to the tethered sensing unit.

In another embodiment, an analyte sensor is designed with separate electronics and sensing units, wherein the sensing unit is inductively coupled to the electronics unit. In this embodiment, the electronics unit provides power to the sensing unit and/or enables communication of data therebetween. FIGS. 3F and 3G illustrate exemplary systems that employ inductive coupling between an electronics unit 52 and a sensing unit 58.

Figure 4F:
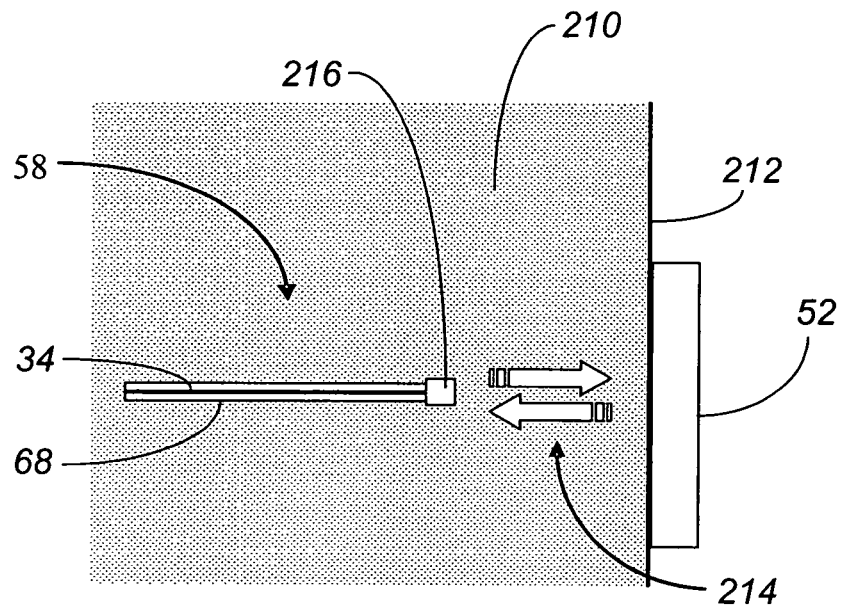
FIG. 4F is a side view of one embodiment of an implanted sensor inductively coupled to an electronics unit within a functionally useful distance on the host's skin.

FIG. 4F is a side view of one embodiment of an implanted sensor inductively coupled to an electronics unit within a functionally useful distance on the host's skin. FIG. 4F illustrates a sensing unit 58, including a sensing mechanism 34, biointerface 68 and small electronics chip 216 implanted below the host's skin 212, within the host's tissue 210. In this example, the majority of the electronics associated with the sensor are housed in an electronics unit 52 (also referred to as a mounting unit) located within suitably close proximity on the host's skin. The electronics unit 52 is inductively coupled to the small electronics chip 216 on the sensing unit 58 and thereby transmits power to the sensor and/or collects data, for example. The small electronics chip 216 coupled to the sensing unit 58 provides the necessary electronics to provide a bias potential to the sensor, measure the signal output, and/or other necessary requirements to allow the sensing mechanism 58 to function (e.g., chip 216 can include an ASIC (application specific integrated circuit), antenna, and other necessary components appreciated by one skilled in the art).

In yet another embodiment, the implanted sensor additionally includes a capacitor to provide necessary power for device function. A portable scanner (e.g., wand-like device) is used to collect data stored on the circuit and/or to recharge the device.

In general, inductive coupling, as described herein, enables power to be transmitted to the sensor for continuous power, recharging, and the like. Additionally, inductive coupling utilizes appropriately spaced and oriented antennas (e.g., coils) on the sensing unit and the electronics unit so as to efficiently transmit/receive power (e.g., current) and/or data communication therebetween. One or more coils in each of the sensing and electronics unit can provide the necessary power induction and/or data transmission.

In this embodiment, the sensing mechanism can be, for example, a wire-based sensor as described in more detail with reference to FIGS. 4A and 4B and as described in published U.S. Patent Application US2006-0020187, or a planar substrate-based sensor such as described in U.S. Pat. No. 6,175,752 to Say et al. and U.S. Pat. No. 5,779,665 to Mastrototaro et al., all of which are incorporated herein by reference in their entirety. The biointerface 68 can be any suitable biointerface as described in more detail elsewhere herein, for example, a layer of porous biointerface membrane material, a mesh cage and the like. In one exemplary embodiment, the biointerface 68 is a single- or multi-layer sheet (e.g., pocket) of porous membrane material, such as ePTFE, in which the sensing mechanism 34 is incorporated.

Figure 4G:
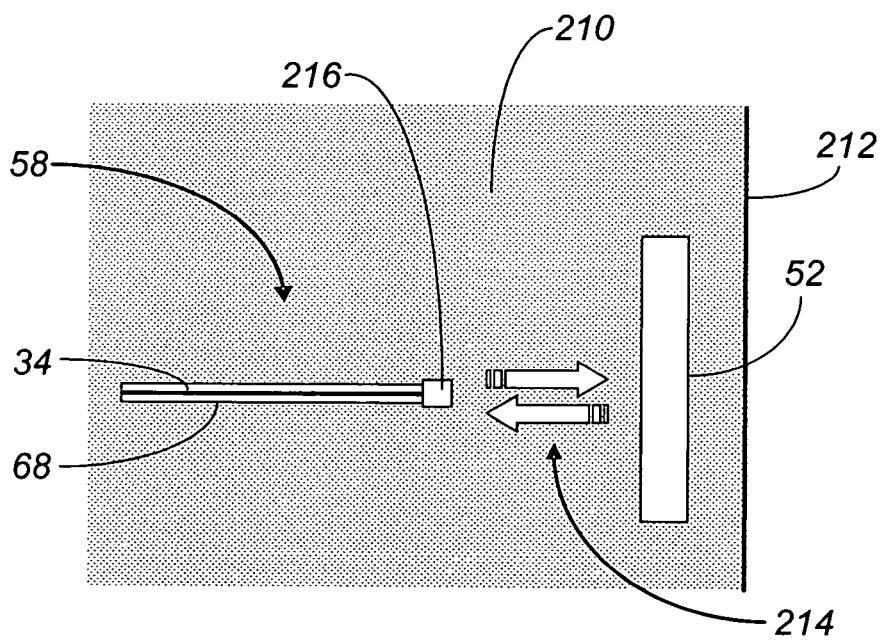
FIG. 4G is a side view of one embodiment of an implanted sensor inductively coupled to an electronics unit implanted in the host's tissue at a functionally useful distance.

FIG. 4G is a side view of on embodiment of an implanted sensor inductively coupled to an electronics unit implanted in the host's tissue at a functionally useful distance. FIG. 4G illustrates a sensor unit 58 and an electronics unit 52 similar to that described with reference to FIG. 4F, above, however both are implanted beneath the host's skin in a suitably close proximity.

In general, it is believed that when the electronics unit 52, which carries the majority of the mass of the implantable device, is separate from the sensing unit 58, a lesser foreign body response will occur surrounding the sensing unit (e.g., as compared to a device of greater mass, for example, a device including certain electronics and/or power supply). Thus, the configuration of the sensing unit, including a biointerface, can be optimized to minimize and/or modify the host's tissue response, for example with minimal mass as described in more detail elsewhere.

Biointerface

In some embodiments, the sensor includes a porous material disposed over some portion thereof, which modifies the host's tissue response to the sensor. In some embodiments, the porous material surrounding the sensor advantageously enhances and extends sensor performance and lifetime in the short-term by slowing or reducing cellular migration to the sensor and associated degradation that would otherwise be caused by cellular invasion if the sensor were directly exposed to the in vivo environment. Alternatively, the porous material can provide stabilization of the sensor via tissue ingrowth into the porous material in the long-term. Suitable porous materials include silicone, polytetrafluoroethylene, expanded polytetrafluoroethylene, polyethylene-co-tetrafluoroethylene, polyolefin, polyester, polycarbonate, biostable polytetrafluoroethylene, homopolymers, copolymers, terpolymers of polyurethanes, polypropylene (PP), polyvinylchloride (PVC), polyvinylidene fluoride (PVDF), polyvinyl alcohol (PVA), polybutylene terephthalate (PBT), polymethylmethacrylate (PMMA), polyether ether ketone (PEEK), polyamides, polyurethanes, cellulosic polymers, poly(ethylene oxide), poly (propylene oxide) and copolymers and blends thereof, polysulfones and block copolymers thereof including, for example, di-block, tri-block, alternating, random and graft copolymers, as well as metals, ceramics, cellulose, hydrogel polymers, poly (2-hydroxyethyl methacrylate, pHEMA), hydroxyethyl methacrylate, (HEMA), polyacrylonitrile-polyvinyl chloride (PAN-PVC), high density polyethylene, acrylic copolymers, nylon, polyvinyl difluoride, polyanhydrides, poly(1-lysine), poly (L-lactic acid), hydroxyethylmethacrylate, hydroxyapeptite, alumina, zirconia, carbon fiber, aluminum, calcium phosphate, titanium, titanium alloy, nintinol, stainless steel, and CoCr alloy, or the like, such as are described in U.S. Publication No. US-2005-0031689-A1 and U.S. Publication No. US-2005-0112169-A1.

In some embodiments, the porous material surrounding the sensor provides unique advantages in the short-term (e.g., one to 14 days) that can be used to enhance and extend sensor performance and lifetime. However, such materials can also provide advantages in the long-term too (e.g., greater than 14 days). Particularly, the in vivo portion of the sensor (the portion of the sensor that is implanted into the host's tissue) is encased (partially or fully) in a porous material. The porous material can be wrapped around the sensor (for example, by wrapping the porous material around the sensor or by inserting the sensor into a section of porous material sized to receive the sensor). Alternately, the porous material can be deposited on the sensor (for example, by electrospinning of a polymer directly thereon). In yet other alternative embodiments, the sensor is inserted into a selected section of porous biomaterial. Other methods for surrounding the in vivo portion of the sensor with a porous material can also be used as is appreciated by one skilled in the art.

The porous material surrounding the sensor advantageously slows or reduces cellular migration to the sensor and associated degradation that would otherwise be caused by cellular invasion if the sensor were directly exposed to the in vivo environment. Namely, the porous material provides a barrier that makes the migration of cells towards the sensor more tortuous and therefore slower (providing short-term advantages). It is believed that this reduces or slows the sensitivity loss normally observed in a short-term sensor over time.

In an embodiment wherein the porous material is a high oxygen solubility material, such as porous silicone, the high oxygen solubility porous material surrounds some of or the entire in vivo portion of the sensor. In some embodiments, a lower ratio of oxygen-to-glucose can be sufficient to provide excess oxygen by using a high oxygen soluble domain (for example, a silicone- or fluorocarbon-based material) to enhance the supply/transport of oxygen to the enzyme membrane and/or electroactive surfaces. It is believed that some signal noise normally seen by a conventional sensor can be attributed to an oxygen deficit. Silicone has high oxygen permeability, thus promoting oxygen transport to the enzyme layer. By enhancing the oxygen supply through the use of a silicone composition, for example, glucose concentration can be less of a limiting factor. In other words, if more oxygen is supplied to the enzyme and/or electroactive surfaces, then more glucose can also be supplied to the enzyme without creating an oxygen rate-limiting excess. While not being bound by any particular theory, it is believed that silicone materials provide enhanced bio-stability when compared to other polymeric materials such as polyurethane.

In certain aspects, modifying a small structured sensor with a biointerface structure, material, matrix, and/or membrane that creates a space appropriate for filling with fluid in vivo can enhance sensor performance. In some embodiments, the small structured sensor includes a porous biointerface material, which allows fluid from the surrounding tissues to form a fluid-filled pocket around at least a portion of the sensor. It is believed that the fluid-filled pocket provides a sufficient source of analyte-containing fluid for accurate sensor measurement in the short-term. Additionally or alternatively, inclusion of bioactive agents can modify the host's tissue response, for example to reduce or eliminate tissue ingrowth or other cellular responses into the biointerface.

In some aspects, modifying a small structured sensor with a structure, material, and/or membrane/matrix that allows tissue ingrowth without barrier cell formation can enhance sensor performance. For example, a vascularized bed of tissue for long-term analyte sensor measurement. In some embodiments, a porous biointerface membrane, including a plurality of interconnected cavities and a solid portion, covering at least the sensing portion of a small structured sensor allows vascularized tissue ingrowth therein. Vascularized tissue ingrowth provides a sufficient source of analyte-containing tissue in the long-term. Additionally or alternatively, inclusion of bioactive agents can modify the host's tissue response, for example to reduce or eliminate barrier cell layer formation within the membrane.

When used herein, the terms "membrane" and "matrix" are meant to be interchangeable. In these embodiments first domain is provided that includes an architecture, including cavity size, configuration, and/or overall thickness, that modifies the host's tissue response, for example, by creating a fluid pocket, encouraging vascularized tissue ingrowth, disrupting downward tissue contracture, resisting fibrous tissue growth adjacent to the device, and/or discouraging barrier cell formation. The biointerface preferably covers at least the sensing mechanism of the sensor and can be of any shape or size, including uniform, asymmetrically, or axi-symmetrically covering or surrounding a sensing mechanism or sensor.

A second domain is optionally provided that is impermeable to cells and/or cell processes. A bioactive agent is optionally provided that is incorporated into the at least one of the domain, the second domain, the sensing membrane, or other part of the implantable device, wherein the bioactive agent is configured to modify a host tissue response.

Figure 5A:
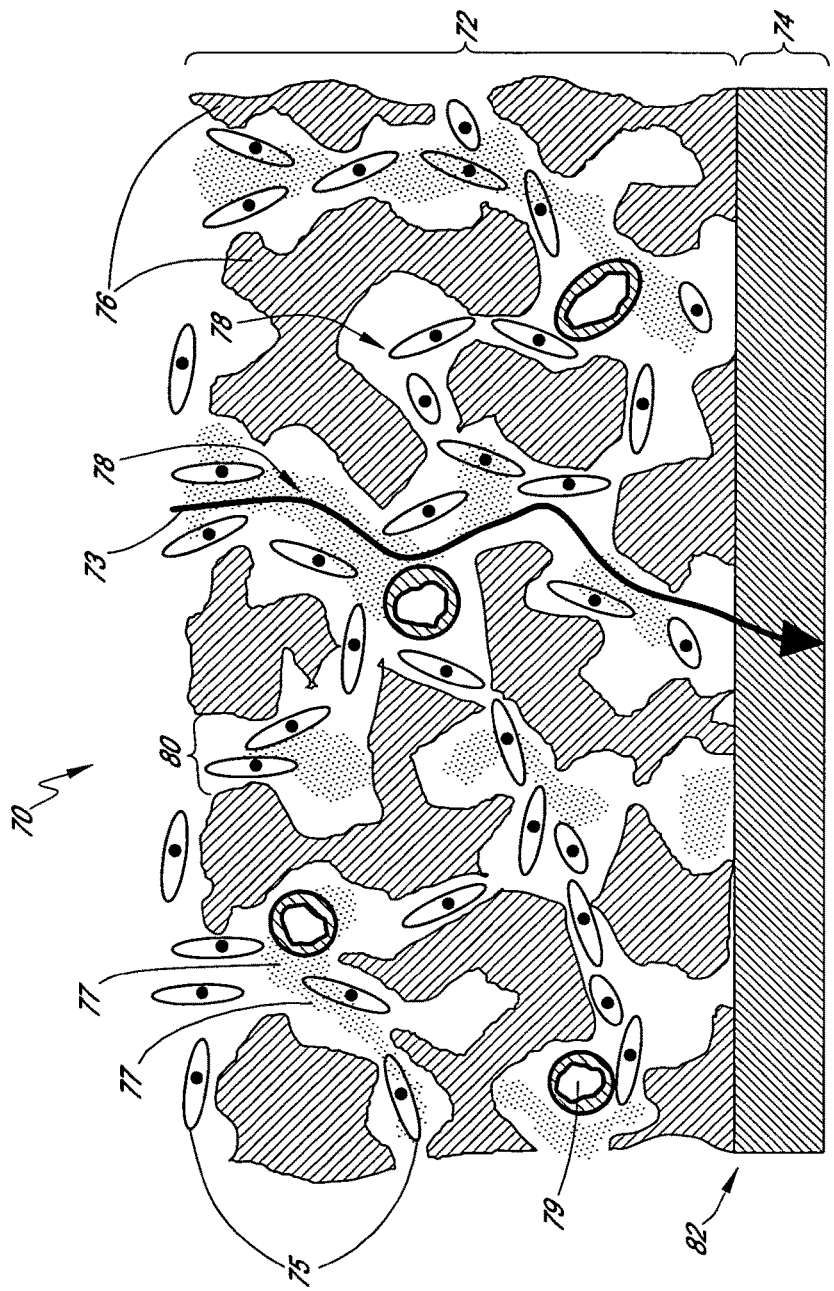
FIG. 5A is a cross-sectional schematic view of a membrane of a preferred embodiment that facilitates vascularization of the first domain without barrier cell layer formation.

FIG. 5A is a cross-sectional schematic view of a biointerface membrane 70 in vivo in one exemplary embodiment, wherein the membrane comprises a first domain 72 and an optional second domain 74. In the short-term, the architecture of the biointerface membrane provides a space between the sensor and the host's tissue that allows a fluid filled pocket to form for transport of fluid therein. In the long-term, the architecture of the membrane provides a robust, implantable membrane that facilitates the transport of analytes through vascularized tissue growth without the formation of a barrier cell layer.

The first domain 72 comprises a solid portion 76 and a plurality of interconnected three-dimensional cavities 78 formed therein. In this embodiment, the cavities 78 have sufficient size and structure to allow invasive cells, such as fibroblasts 75, a fibrous matrix 77, and blood vessels 79 to enter into the apertures 80 that define the entryway into each cavity 78, and to pass through the interconnected cavities toward the interface 82 between the first and second domains. The cavities comprise an architecture that encourages the ingrowth of vascular tissue in vivo, as indicated by the blood vessels 79 formed throughout the cavities. Because of the vascularization within the cavities, solutes 73 (for example, oxygen, glucose and other analytes) pass through the first domain with relative ease, and/or the diffusion distance (namely, distance that the glucose diffuses) is reduced.

Architecture of the First Domain

In some embodiments, the first domain of the biointerface membrane includes an architecture that supports tissue ingrowth, disrupts contractile forces typically found in a foreign body response, encourages vascularity within the membrane, and disrupts the formation of a barrier cell layer. In some alternative embodiments, the first domain of the biointerface membrane includes an architecture that creates a fluid-filled space surrounding an implanted device, which allows the passage of the analyte, but protects sensitive portions of the device from substantial fibrous tissue ingrowth and associated forces.

In general, the first domain, also referred to as the cell disruptive domain, comprises an open-celled configuration comprising interconnected cavities and solid portions. The distribution of the solid portion and cavities of the first domain preferably includes a substantially co-continuous solid domain and includes more than one cavity in three dimensions substantially throughout the entirety of the first domain. However, some short-term embodiments cannot require co-continuity of the cavities. Generally, cells can enter into the cavities; however, they cannot travel through or wholly exist within the solid portions. The cavities permit most substances to pass through, including, for example, cells and molecules. One example of a suitable material is expanded polytetrafluoraethylene (ePTFE).

Figure 5B:
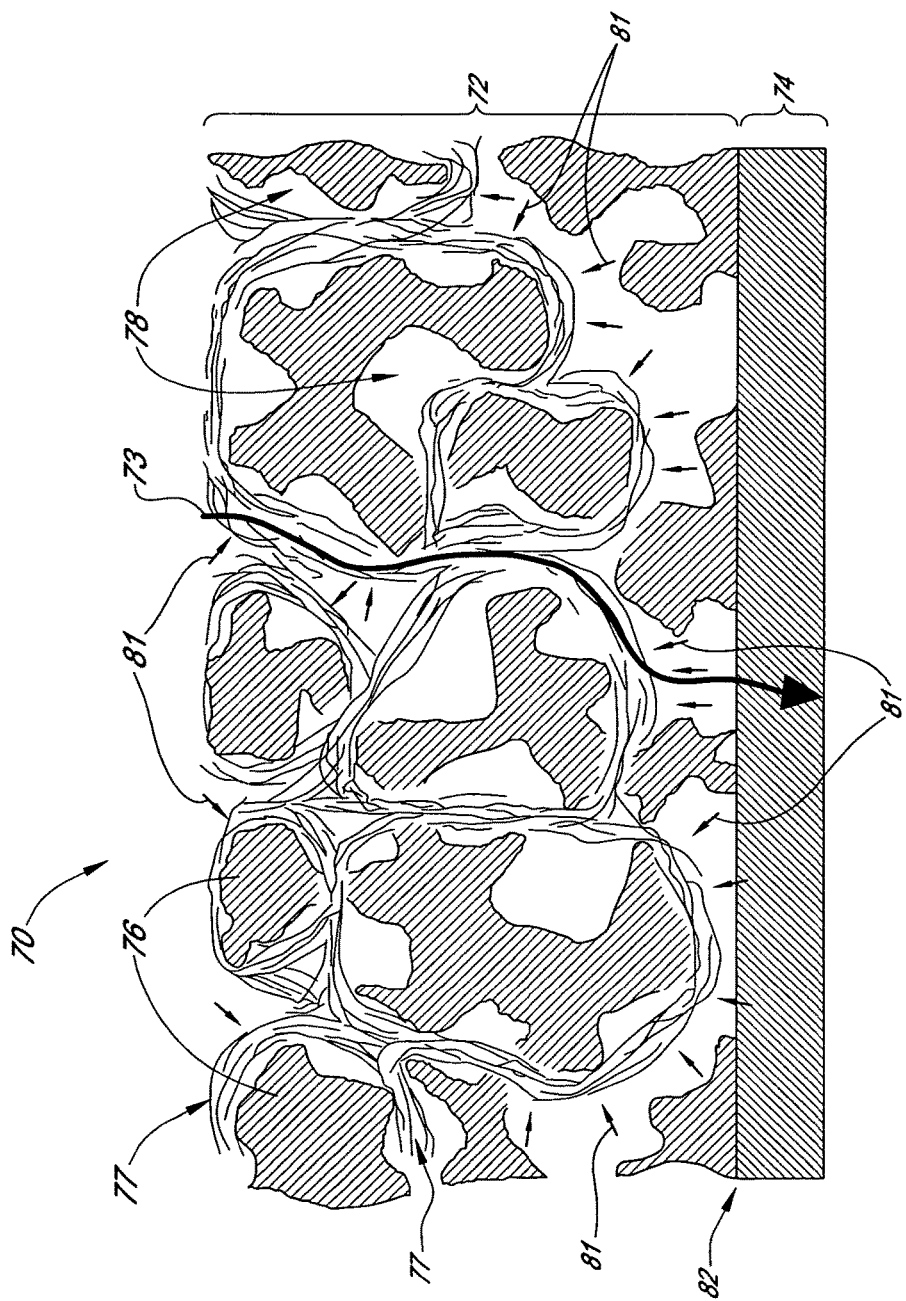
FIG. 5B is a cross-sectional schematic view of the membrane of FIG. 5A showing contractile forces caused by the fibrous tissue of the FBR.

Reference is now made to FIG. 5B, which is an illustration of the membrane of FIG. 5A, showing contractile forces 81 caused by the fibrous tissue in the long-term (e.g., after about 3 weeks), for example, from the fibroblasts and fibrous matrix, of the FBR. Specifically, the architecture of the first domain, including the cavity interconnectivity and multiple-cavity depth, (namely, two or more cavities in three dimensions throughout a substantial portion of the first domain) can affect the tissue contracture that typically occurs around a foreign body.

The architecture of the first domain of the biointerface membrane, including the interconnected cavities and solid portion, is advantageous because the contractile forces caused by the downward tissue contracture that can otherwise cause cells to flatten against the device and occlude the transport of analytes, is instead translated to, disrupted by, and/or counteracted by the forces 81 that contract around the solid portions 76 (for example, throughout the interconnected cavities 78) away from the device. That is, the architecture of the solid portions 76 and cavities 78 of the first domain cause contractile forces 81 to disperse away from the interface between the first domain 72 and second domain 74. Without the organized contracture of fibrous tissue toward the tissue-device interface 82 typically found in a FBC (FIG. 5B), macrophages and foreign body giant cells do not form a substantial monolayer of cohesive cells (namely, a barrier cell layer) and therefore the transport of molecules across the second domain and/or membrane is not blocked, as indicated by free transport of analyte 73 through the first and second domains in FIGS. 5A and 5B.

Various methods are suitable for use in manufacturing the first domain in order to create an architecture with preferred dimensions and overall structure. The first domain can be manufactured by forming particles, for example, sugar granules, salt granules, and other natural or synthetic uniform or non-uniform particles, in a mold, wherein the particles have shapes and sizes substantially corresponding to the desired cavity dimensions, such as described in more detail below. In some methods, the particles are made to coalesce to provide the desired interconnectivity between the cavities. The desired material for the solid portion can be introduced into the mold using methods common in the art of polymer processing, for example, injecting, pressing, vacuuming, vapor depositing, pouring, and the like. After the solid portion material is cured or solidified, the coalesced particles are then dissolved, melted, etched, or otherwise removed, leaving interconnecting cavities within the solid portion. In such embodiments, sieving can be used to determine the dimensions of the particles, which substantially correspond to the dimensions of resulting cavities. In sieving, also referred to as screening, the particles are added to the sieve and then shaken to produce overs and unders. The overs are the particles that remain on the screen and the unders are the particles that pass through the screen. Other methods and apparatus known in the art are also suitable for use in determining particle size, for example, air classifiers, which apply opposing air flows and centrifugal forces to separate particles having sizes down to 2 µm, can be used to determine particle size when particles are smaller than 100 µm.

In one embodiment, the cavity size of the cavities 78 of the first domain is substantially defined by the particle size(s) used in creating the cavities. In some embodiments, the particles used to form the cavities can be substantially spherical, thus the dimensions below describe a diameter of the particle and/or a diameter of the cavity. In some alternative embodiments, the particles used to form the cavities can be non-spherical (for example, rectangular, square, diamond, or other geometric or non-geometric shapes), thus the dimensions below describe one dimension (for example, shortest, average, or longest) of the particle and/or cavity.

In some embodiments, a variety of different particle sizes can be used in the manufacture of the first domain. In some embodiments, the dimensions of the particles can be somewhat smaller or larger than the dimensions of the resulting cavities, due to dissolution or other precipitation that can occur during the manufacturing process.

Although one method of manufacturing porous domains is described above, a variety of methods known to one of ordinary skill in the art can be employed to create the structures of preferred embodiments, see section entitled, "Formation of the Biointerface onto the Sensor," below. For example, molds can be used in the place of the particles described above, such as coral, self-assembly beads, etched or broken silicon pieces, glass frit pieces, and the like. The dimensions of the mold can define the cavity sizes, which can be determined by measuring the cavities of a model final product, and/or by other measuring techniques known in the art, for example, by a bubble point test. In U.S. Pat. No. 3,929,971, Roy discloses a method of making a synthetic membrane having a porous microstructure by converting calcium carbonate coral materials to hydroxyapatite while at the same time retaining the unique microstructure of the coral material.

Other methods of forming a three-dimensional first domain can be used, for example holographic lithography, stereolithography, and the like, wherein cavity sizes are defined and precisely formed by the lithographic or other such process to form a lattice of unit cells, as described in U.S. Publication No. US-2005-0251083-A1, and in U.S. Pat. No. 6,520,997, which discloses a photolithographic process for creating a porous membrane.

The first domain 72 can be defined using alternative methods. In an alternative preferred embodiment, fibrous non-woven or woven materials, or other such materials, such as electrospun, felted, velvet, scattered, or aggregate materials, are manufactured by forming the solid portions without particularly defining the cavities therebetween. Accordingly, in these alternative embodiments, structural elements that provide the three-dimensional conformation can include fibers, strands, globules, cones, and/or rods of amorphous or uniform geometry. These elements are hereinafter referred to as "strands." The solid portion of the first domain can include a plurality of strands, which generally define apertures formed by a frame of the interconnected strands. The apertures of the material form a framework of interconnected cavities. Formed in this manner, the first domain is defined by a cavity size of about 0.6 to about 1 mm in at least one dimension.

Referring to the dimensions and architecture of the first domain 72, the porous biointerface membranes can be loosely categorized into at least two groups: those having a micro-architecture and those having a macro-architecture.

FIGS. 5A and 5B illustrate one preferred embodiment wherein the biointerface membrane includes a macro-architecture as defined herein. In general, the cavity size of a macro-architecture provides a configuration and overall thickness that encourages vascular tissue ingrowth and disrupts tissue contracture that is believed to cause barrier cell formation in the long-term in vivo (as indicated by the blood vessels 79 formed throughout the cavities), while providing a long-term, robust structure. Referring to the macro-architecture, a substantial number of the cavities 78, defined using any of the methods described above, are greater than or equal to about 20 µm in one dimension. In some other embodiments, a substantial number of the cavities are greater than or equal to about 30, 40, 50, 60, 70, 80, 90, 100, 120, 180, 160, 180, 200, 280, 280, 320, 360, 400, 500, 600, 700 µm, and preferably less than about 1 mm in one dimension.

The biointerface membrane can also be formed with a micro-architecture as defined herein. Generally, at least some of the cavities of a micro-architecture have a sufficient size and structure to allow inflammatory cells to partially or completely enter into the cavities. However, in contrast to the macro-architecture, the micro-architecture does not allow extensive ingrowth of vascular and connective tissues within the cavities. Therefore, in some embodiments, the micro-architecture of preferred embodiments is defined by the actual size of the cavity, wherein the cavities are formed from a mold, for example, such as described in more detail above. However, in the context of the micro-architecture it is preferable that the majority of the mold dimensions, whether particles, beads, crystals, coral, self-assembly beads, etched or broken silicon pieces, glass frit pieces, or other mold elements that form cavities, are less than about 20 µm in at least one dimension.

In some alternative embodiments, wherein the biointerface membrane is formed from a substantially fibrous material, the micro-architecture is defined by a strand size of less than about 6 µm in all but the longest dimension, and a sufficient number of cavities are provided of a size and structure to allow inflammatory cells, for example, macrophages, to completely enter through the apertures that define the cavities, without extensive ingrowth of vascular and connective tissues.

In certain embodiments, the micro-architecture is characterized, or defined, by standard pore size tests, such as the bubble point test. The micro-architecture is selected with a nominal pore size of from about 0.6 µm to about 20 µm. In some embodiments, the nominal pore size from about 1, 2, 3, 4, 5, 6, 7, 8, or 9 µm to about 10, 11, 12, 13, 14, 15, 16, 17, 18, or 19 µm. It has been found that a porous polymer membrane having an average nominal pore size of about 0.6 to about 20 µm functions satisfactorily in creating a vascular bed within the micro-architecture at the device-tissue interface. The term "nominal pore size" in the context of the micro-architecture in certain embodiments is derived from methods of analysis common to membrane, such as the ability of the membrane to filter particles of a particular size, or the resistance of the membrane to the flow of fluids. Because of the amorphous, random, and irregular nature of most of these commercially available membranes, the "nominal pore size" designation cannot actually indicate the size or shape of the apertures and cavities, which in reality have a high degree of variability. Accordingly, as used herein with reference to the micro-architecture, the term "nominal pore size" is a manufacturer's convention used to identify a particular membrane of a particular commercial source which has a certain bubble point; as used herein, the term "pore" does not describe the size of the cavities of the material in the preferred embodiments. The bubble point measurement is described in Pharmaceutical Technology, May 1983, pp. 76 to 82.

The optimum dimensions, architecture (for example, micro-architecture or macro-architecture), and overall structural integrity of the membrane can be adjusted according to the parameters of the device that it supports. For example, if the membrane is employed with a glucose-measuring device, the mechanical requirements of the membrane can be greater for devices having greater overall weight and surface area when compared to those that are relatively smaller.

In some embodiments, improved vascular tissue ingrowth in the long-term is observed when the first domain has a thickness that accommodates a depth of at least two cavities throughout a substantial portion of the thickness. Improved vascularization results at least in part from multi-layered interconnectivity of the cavities, such as in the preferred embodiments, as compared to a surface topography such as seen in the prior art, for example, wherein the first domain has a depth of only one cavity throughout a substantial portion thereof. The multi-layered interconnectivity of the cavities enables vascularized tissue to grow into various layers of cavities in a manner that provides mechanical anchoring of the device with the surrounding tissue. Such anchoring resists movement that can occur in vivo, which results in reduced sheer stress and scar tissue formation. The optimum depth or number of cavities can vary depending upon the parameters of the device that it supports. For example, if the membrane is employed with a glucose-measuring device, the anchoring that is required of the membrane is greater for devices having greater overall weight and surface area as compared to those that are relatively smaller.

The thickness of the first domain can be optimized for decreased time-to-vascularize in vivo, that is, vascular tissue ingrowth can occur somewhat faster with a membrane that has a thin first domain as compared to a membrane that has a relatively thicker first domain. Decreased time-to-vascularize results in faster stabilization and functionality of the biointerface in vivo. For example, in a subcutaneous implantable glucose device, consistent and increasing functionality of the device is at least in part a function of consistent and stable glucose transport across the biointerface membrane, which is at least in part a function of the vascularization thereof. Thus, quicker start-up time and/or shortened time lag (as when, for example, the diffusion path of the glucose through the membrane is reduced) can be achieved by decreasing the thickness of the first domain.

The thickness of the first domain is typically from about 20 µm to about 2000 µm, preferably from about 50, 60, 70, 80, 90, or 100 µm to about 800, 900, 1000, 1100, 1200, 1300, 1400, 1500, 1600, 1700, 1800, or 1900 µm, and most preferably from about 150, 200, 250, 300, 350, or 400 µm to about 450, 500, 550, 600, 650, 700, or 750 µm. However, in some alternative embodiments a thinner or thicker cell disruptive domain (first domain) can be desired.

The solid portion preferably includes one or more materials such as silicone, polytetrafluoroethylene, expanded polytetrafluoroethylene, polyethylene-co-tetrafluoroethylene, polyolefin, polyester, polycarbonate, biostable polytetrafluoroethylene, homopolymers, copolymers, terpolymers of polyurethanes, polypropylene (PP), polyvinylchloride (PVC), polyvinylidene fluoride (PVDF), polyvinyl alcohol (PVA), polybutylene terephthalate (PBT), polymethylmethacrylate (PMMA), polyether ether ketone (PEEK), polyamides, polyurethanes, cellulosic polymers, polysulfones and block copolymers thereof including, for example, diblock, tri-block, alternating, random and graft copolymers. In some embodiments, the material selected for the first domain is an elastomeric material, for example, silicone, which is able to absorb stresses that can occur in vivo, such that sheer and other environmental forces are significantly minimized at the second domain. The solid portion can comprises a silicone composition with a hydrophile such as Polyethylene Glycol (PEG) covalently incorporated or grafted therein, such as described in U.S. Publication No. US-2005-0090607-A1 or as disclosed in copending U.S. patent application Ser. No. 11/404,417, filed Apr. 14, 2006 and entitled "SILICONE BASED MEMBRANES FOR USE IN IMPLANTABLE GLUCOSE SENSORS."

One preferred material that can be used to form the solid portion of the biointerface matrix is a material that allows the passage of the analyte (e.g., glucose) there through. For example, the biointerface matrix can be formed from a silicone polymer/hydrophobic-hydrophilic polymer blend. In one embodiment, The hydrophobic-hydrophilic polymer for use in the blend can be any suitable hydrophobic-hydrophilic polymer, including but not limited to components such as polyvinylpyrrolidone (PVP), polyhydroxyethyl methacrylate, polyvinylalcohol, polyacrylic acid, polyethers such as polyethylene glycol or polypropylene oxide, and copolymers thereof, including, for example, di-block, tri-block, alternating, random, comb, star, dendritic, and graft copolymers (block copolymers are discussed in U.S. Pat. Nos. 4,803,243 and 4,686,044, which are incorporated herein by reference). In one embodiment, the hydrophobic-hydrophilic polymer is a copolymer of poly(ethylene oxide) (PEO) and poly(propylene oxide) (PPO). Suitable such polymers include, but are not limited to, PEO-PPO diblock copolymers, PPO-PEO-PPO triblock copolymers, PEO-PPO-PEO triblock copolymers, alternating block copolymers of PEO-PPO, random copolymers of ethylene oxide and propylene oxide, and blends thereof. In some embodiments, the copolymers can be optionally substituted with hydroxy substituents. Commercially available examples of PEO and PPO copolymers include the PLURONIC® brand of polymers available from BASF®. In one embodiment, PLURONIC® R F-127 is used. Other PLURONIC® polymers include PPO-PEO-PPO triblock copolymers (e.g., PLURONIC® R products). Other suitable commercial polymers include, but are not limited to, SYNPERONICS® products available from UNIQEMA®.

The silicone polymer for use in the silicone/hydrophobic-hydrophilic polymer blend can be any suitable silicone polymer. In some embodiments, the silicone polymer is a liquid silicone rubber that can be vulcanized using a metal- (e.g., platinum), peroxide-, heat-, ultraviolet-, or other radiation-catalyzed process. In some embodiments, the silicone polymer is a dimethyl- and methylhydrogensiloxane copolymer. In some embodiments, the copolymer has vinyl substituents. In some embodiments, commercially available silicone polymers can be used. For example, commercially available silicone polymer precursor compositions can be used to prepare the blends, such as described below. In one embodiment, MED-4840 available from NUSIL® Technology LLC is used as a precursor to the silicone polymer used in the blend. MED-4840 consists of a 2-part silicone elastomer precursor including vinyl-functionalized dimethyl- and methylhydroger-siloxane copolymers, amorphous silica, a platinum catalyst, a crosslinker, and an inhibitor. The two components can be mixed together and heated to initiate vulcanization, thereby forming an elastomeric solid material. Other suitable silicone polymer precursor systems include, but are not limited to, MED-2174 peroxide-cured liquid silicone rubber available from NUSIL® Technology LLC, SILASTIC® MDX4-4210 platinum-cured biomedical grade elastomer available from DOW CORNING®, and Implant Grade Liquid Silicone Polymer (durometers 10-50) available from Applied Silicone Corporation.

Silicone polymer/hydrophobic-hydrophilic polymer blends are described in more detail in U.S. patent application Ser. No. 11/404,417, entitled "SILICONE BASED MEMBRANES FOR USE IN IMPLANTABLE GLUCOSE SENSORS," filed on Apr. 14, 2006.

Additionally, elastomeric materials with a memory of the original configuration can withstand greater stresses without affecting the configuration, and thus the function, of the device.

In some embodiments, the first domain can include a macro-architecture and a micro-architecture located within at least a portion of the macro-architecture, such as is described in U.S. Publication No. US-2005-0251083-A1. For example, the macro-architecture includes a porous structure with interconnected cavities such as described with reference to the solid portion of the first domain, wherein at least some portion of the cavities of the first domain are filled with the micro-architecture that includes a fibrous or other fine structured material that aids in preventing formation of a barrier cell layer, for example in pockets in the bottom of the cavities of the macro-architecture adjacent to the implantable device.

In certain embodiments, other non-resorbable implant materials can be used in forming the first domain, including but not limited to, metals, ceramics, cellulose, polyacrylonitrile-polyvinyl chloride (PAN-PVC), high density polyethylene, acrylic copolymers, nylon, polyvinyl difluoride, polyanhydrides, poly(l-lysine), hydroxyethylmethacrylate, alumina, zirconia, carbon fiber, aluminum, titanium, titanium alloy, nintinol, stainless steel, and CoCr alloy.

Architecture of the Second Domain

FIGS. 5A and 5B, illustrate the optional second domain of the membrane. The second domain is impermeable to cells or cell processes, and is composed of a biostable material. In one exemplary embodiment, the second domain is comprised of polyurethane and a hydrophilic polymer, such as is described in U.S. Pat. No. 6,862,465 to Shults et al., which is incorporated herein by reference in its entirety. Alternatively, the outermost layer of the sensing membrane 32 can function as a cell impermeable domain and therefore a second domain cannot be a discrete component of the biointerface membrane.

In general, the materials preferred for the second domain prevent or hinder cell entry or contact with device elements underlying the membrane and prevent or hinder the adherence of cells, thereby further discouraging formation of a barrier cell layer. Additionally, because of the resistance of the materials to barrier cell layer formation, membranes prepared therefrom are robust long-term in vivo.

The thickness of the cell impermeable biomaterial of the second domain (also referred to as a cell impermeable domain) is typically about 1 µm or more, preferably from about 1, 5, 10, 15, 20, 25, 30, 35, 40, 45, or 50, 55, 60, 65, 70, 75, 80, 85, 90, 95, 100, 110, 120, 130, 140, 150, 160, 170, 180, 190, or 200 µm to about 500, 600, 700, 800, 900, or 1000 µm. In some embodiments, thicker or thinner cell impermeable domains can be desired. Alternatively, the function of the cell impermeable domain is accomplished by the implantable device, or a portion of the implantable device, which can or cannot include a distinct domain or layer.

The characteristics of the cell impermeable membrane prevent or hinder cells from entering the membrane, but permit or facilitate transport of the analyte of interest or a substance indicative of the concentration or presence of the analyte. Additionally the second domain, similar to the first domain, is preferably constructed of a biodurable material (for example, a material durable for a period of several years in vivo) that is impermeable to host cells, for example, macrophages, such as described above.

In embodiments wherein the biointerface membrane is employed in an implantable glucose-measuring device, the biointerface membrane is permeable to oxygen and glucose or a substance indicative of the concentration of glucose. In embodiments wherein the membrane is employed in a drug delivery device or other device for delivering a substance to the body, the cell impermeable membrane is permeable to the drug or other substance dispensed from the device. In embodiments wherein the membrane is employed for cell transplantation, the membrane is semi-permeable, for example, impermeable to immune cells and soluble factors responsible for rejecting transplanted tissue, but permeable to the ingress of glucose and oxygen for the purpose of sustaining the transplanted tissue; additionally, the second domain is permeable to the egress of the gene product of interest (for example, insulin).

The cell disruptive (first) domain and the cell impermeable (second) domain can be secured to each other by any suitable method as is known in the art. For example, the cell impermeable domain can simply be layered or cast upon the porous cell disruptive domain so as to form a mechanical attachment. Alternatively, chemical and/or mechanical attachment methods can be suitable for use. Chemical attachment methods can include adhesives, glues, lamination, and/or wherein a thermal bond is formed through the application of heat and pressure, and the like. Suitable adhesives are those capable of forming a bond between the materials that make up both the barrier cell disruptive domain and the cell impermeable domain, and include liquid and/or film applied adhesives. An appropriate material can be designed that can be used for preparing both domains such that the composite is prepared in one step, thereby forming a unitary structure. For example, when the cell disruptive domain and the cell impermeable domain comprise silicone, the materials can be designed so that they can be covalently cured to one another. However in some embodiments wherein the second domain comprises a part of the implantable device, it can be attached to or simply lie adjacent to the first domain.

In some embodiments wherein an adhesive is employed, the adhesive can comprise a biocompatible material. However, in some embodiments adhesives not generally considered to have a high degree of biocompatibility can also be employed. Adhesives with varying degrees of biocompatibility suitable for use include acrylates, for example, cyanoacrylates, epoxies, methacrylates, polyurethanes, and other polymers, resins, RTV silicone, and crosslinking agents as are known in the art. In some embodiments, a layer of woven or non-woven material (such as ePTFE) is cured to the first domain after which the material is bonded to the second domain, which allows a good adhesive interface between the first and second domains using a biomaterial known to respond well at the tissue-device interface, for example.

Bioactive Agents

In some alternative embodiment, the biointerface membranes include a bioactive agent, which is incorporated into at least one of the first and second domains 72, 74 of the biointerface membrane, or which is incorporated into the device (e.g., sensing membrane 32) and adapted to diffuse through the first and/or second domains, in order to modify the tissue response of the host to the membrane. The architectures of the first and second domains have been shown to create a fluid pocket, support vascularized tissue ingrowth, to interfere with and resist barrier cell layer formation, and to facilitate the transport of analytes across the membrane. However, the bioactive agent can further enhance formation of a fluid pocket, alter or enhance vascularized tissue ingrowth, resistance to barrier cell layer formation, and thereby facilitate the passage of analytes 73 across the device-tissue interface 82.

In embodiments wherein the biointerface includes a bioactive agent, the bioactive agent is incorporated into at least one of the first and second domains of the biointerface membrane, or into the device and adapted to diffuse through the first and/or second domains, in order to modify the tissue response of the host to the membrane. In general, the architectures of the first and second domains support vascularized tissue growth in or around the biointerface membrane, interfere with and resist barrier cell layer formation, and/or allow the transport of analytes across the membrane. However, certain outside influences, for example, faulty surgical techniques, acute or chronic movement of the implant, or other surgery-, host-, and/or implantation site-related conditions, can create acute and/or chronic inflammation at the implant site. When this occurs, the biointerface membrane architecture alone cannot be sufficient to overcome the acute and/or chronic inflammation. Alternatively, the membrane architecture can benefit from additional mechanisms that aid in reducing this acute and/or chronic inflammation that can produce a barrier cell layer and/or a fibrotic capsule surrounding the implant, resulting in compromised solute transport through the membrane.

In general, the inflammatory response to biomaterial implants can be divided into two phases. The first phase consists of mobilization of mast cells and then infiltration of predominantly polymorphonuclear (PMN) cells. This phase is termed the acute inflammatory phase. Over the course of days to weeks, chronic cell types that comprise the second phase of inflammation replace the PMNs. Macrophage and lymphocyte cells predominate during this phase. While not wishing to be bound by any particular theory, it is believed that short-term stimulation of vascularization, or short-term inhibition of scar formation or barrier cell layer formation, provides protection from scar tissue formation, thereby providing a stable platform for sustained maintenance of the altered foreign body response, for example.

Accordingly, bioactive intervention can modify the foreign body response in the early weeks of foreign body capsule formation and alter the long-term behavior of the foreign body capsule. Additionally, it is believed that in some circumstances the biointerface membranes of the preferred embodiments can benefit from bioactive intervention to overcome sensitivity of the membrane to implant procedure, motion of the implant, or other factors, which are known to otherwise cause inflammation, scar formation, and hinder device function in vivo.

In general, bioactive agents that are believed to modify tissue response include anti-inflammatory agents, anti-infective agents, anesthetics, inflammatory agents, growth factors, angiogenic (growth) factors, adjuvants, immunosuppressive agents, antiplatelet agents, anticoagulants, ACE inhibitors, cytotoxic agents, anti-barrier cell compounds, vascularization compounds, anti-sense molecules, and the like. In some embodiments, preferred bioactive agents include S1P (Sphingosine-1-phosphate), Monobutyrin, Cyclosporin A, Anti-thrombospondin-2, Rapamycin (and its derivatives), and Dexamethasone. However, other bioactive agents, biological materials (for example, proteins), or even non-bioactive substances can incorporated into the membranes of preferred embodiments.

Bioactive agents suitable for use in the preferred embodiments are loosely organized into two groups: anti-barrier cell agents and vascularization agents. These designations reflect functions that are believed to provide short-term solute transport through the biointerface membrane, and additionally extend the life of a healthy vascular bed and hence solute transport through the biointerface membrane long-term in vivo. However, not all bioactive agents can be clearly categorized into one or other of the above groups; rather, bioactive agents generally comprise one or more varying mechanisms for modifying tissue response and can be generally categorized into one or both of the above-cited categories.

Anti-Barrier Cell Agents

Generally, anti-barrier cell agents include compounds exhibiting affects on macrophages and foreign body giant cells (FBGCs). It is believed that anti-barrier cell agents prevent closure of the barrier to solute transport presented by macrophages and FBGCs at the device-tissue interface during FBC maturation.

Anti-barrier cell agents generally include mechanisms that inhibit foreign body giant cells and/or occlusive cell layers. For example, Super Oxide Dismutase (SOD) Mimetic, which utilizes a manganese catalytic center within a porphyrin like molecule to mimic native SOD and effectively remove superoxide for long periods, thereby inhibiting FBGC formation at the surfaces of biomaterials in vivo, is incorporated into a biointerface membrane of a preferred embodiment.

Anti-barrier cell agents can include anti-inflammatory and/or immunosuppressive mechanisms that affect early FBC formation. Cyclosporine, which stimulates very high levels of neovascularization around biomaterials, can be incorporated into a biointerface membrane of a preferred embodiment (see U.S. Pat. No. 5,569,462 to Martinson et al.). Alternatively, Dexamethasone, which abates the intensity of the FBC response at the tissue-device interface, can be incorporated into a biointerface membrane of a preferred embodiment. Alternatively, Rapamycin, which is a potent specific inhibitor of some macrophage inflammatory functions, can be incorporated into a biointerface membrane of a preferred embodiment.

Other suitable medicaments, pharmaceutical compositions, therapeutic agents, or other desirable substances can be incorporated into the membranes of preferred embodiments, including, but not limited to, anti-inflammatory agents, anti-infective agents, necrosing agents, and anesthetics.

Generally, anti-inflammatory agents reduce acute and/or chronic inflammation adjacent to the implant, in order to decrease the formation of a FBC capsule to reduce or prevent barrier cell layer formation. Suitable anti-inflammatory agents include but are not limited to, for example, nonsteroidal anti-inflammatory drugs (NSAIDs) such as acetometaphen, aminosalicylic acid, aspirin, celecoxib, choline magnesium trisalicylate, diclofenac potassium, diclofenac sodium, diflunisal, etodolac, fenoprofen, flurbiprofen, ibuprofen, indomethacin, interleukin (IL)-10, IL-6 mutein, anti-IL-6 iNOS inhibitors (for example, L-NAME or L-NMDA), Interferon, ketoprofen, ketorolac, leflunomide, melenamic acid, mycophenolic acid, mizoribine, nabumetone, naproxen, naproxen sodium, oxaprozin, piroxicam, rofecoxib, salsalate, sulindac, and tolmetin; and corticosteroids such as cortisone, hydrocortisone, methylprednisolone, prednisone, prednisolone, betamethesone, beclomethasone dipropionate, budesonide, dexamethasone sodium phosphate, flunisolide, fluticasone propionate, paclitaxel, tacrolimus, tranilast, triamcinolone acetonide, betamethasone, fluocinolone, fluocinonide, betamethasone dipropionate, betamethasone valerate, desonide, desoximetasone, fluocinolone, triamcinolone, triamcinolone acetonide, clobetasol propionate, and dexamethasone.

Generally, immunosuppressive and/or immunomodulatory agents interfere directly with several key mechanisms necessary for involvement of different cellular elements in the inflammatory response. Suitable immunosuppressive and/or immunomodulatory agents include anti-proliferative, cell-cycle inhibitors, (for example, paclitaxol (e.g., Sirolimus), cytochalasin D, infiximab), taxol, actinomycin, mitomycin, thospromote VEGF, estradiols, NO donors, leptin, QP-2, tacrolimus, tranilast, actinomycin, everolimus, methothrexate, mycophenolic acid, angiopeptin, vincristing, mitomycine, statins, C MYC antisense, sirolimus (and analogs), RestenASE, 2-chloro-deoxyadenosine, PCNA Ribozyme, batimstat, prolyl hydroxylase inhibitors, PPARγ ligands (for example troglitazone, rosiglitazone, pioglitazone), halofuginone, C-proteinase inhibitors, probucol, BCP671, EPC antibodies, catchins, glycating agents, endothelin inhibitors (for example, Ambrisentan, Tesosentan, Bosentan), Statins (for example, Cerivasttin), *E. coli* heat-labile enterotoxin, and advanced coatings.

Generally, anti-infective agents are substances capable of acting against infection by inhibiting the spread of an infectious agent or by killing the infectious agent outright, which can serve to reduce immuno-response without inflammatory response at the implant site. Anti-infective agents include, but are not limited to, anthelmintics (mebendazole), antibiotics including aminoclycosides (gentamicin, neomycin, tobramycin), antifungal antibiotics (amphotericin b, fluconazole, griseofulvin, itraconazole, ketoconazole, nystatin, micatin, tolnaftate), cephalosporins (cefaclor, cefazolin, cefotaxime, ceftazidime, ceftriaxone, cefuroxime, cephalexin), beta-lactam antibiotics (cefotetan, meropenem), chloramphenicol, macrolides (azithromycin, clarithromycin, erythromycin), penicillins (penicillin G sodium salt, amoxicillin, ampicillin, dicloxacillin, nafcillin, piperacillin, ticarcillin), tetracyclines (doxycycline, minocycline, tetracycline), bacitracin; clindamycin; colistimethate sodium; polymyxin b sulfate; vancomycin; antivirals including acyclovir, amantadine, didanosine, efavirenz, foscarnet, ganciclovir, indinavir, lamivudine, nelfinavir, ritonavir, saquinavir, silver, stavudine, valacyclovir, valganciclovir, zidovudine; quinolones (ciprofloxacin, levofloxacin); sulfonamides (sulfadiazine, sulfisoxazole); sulfones (dapsone); furazolidone; metronidazole; pentamidine; sulfanilamidum crystallinum; gatifloxacin; and sulfamethoxazole/trimethoprim.

Generally, necrosing agents are any drugs that cause tissue necrosis or cell death. Necrosing agents include cisplatin, BCNU, taxol or taxol derivatives, and the like.

Vascularization Agents

Generally, vascularization agents include substances with direct or indirect angiogenic properties. In some cases, vascularization agents can additionally affect formation of barrier cells in vivo. By indirect angiogenesis, it is meant that the angiogenesis can be mediated through inflammatory or immune stimulatory pathways. It is not fully known how agents that induce local vascularization indirectly inhibit barrier-cell formation, however it is believed that some barrier-cell effects can result indirectly from the effects of vascularization agents.

Vascularization agents include mechanisms that promote neovascularization around the membrane and/or minimize periods of ischemia by increasing vascularization close to the tissue-device interface. Sphingosine-1-Phosphate (SIP), which is a phospholipid possessing potent angiogenic activity, is incorporated into a biointerface membrane of a preferred embodiment. Monobutyrin, which is a potent vasodilator and angiogenic lipid product of adipocytes, is incorporated into a biointerface membrane of a preferred embodiment. In another embodiment, an anti-sense molecule (for example, thrombospondin-2 anti-sense), which increases vascularization, is incorporated into a biointerface membrane.

Vascularization agents can include mechanisms that promote inflammation, which is believed to cause accelerated neovascularization in vivo. In one embodiment, a xenogenic carrier, for example, bovine collagen, which by its foreign nature invokes an immune response, stimulates neovascularization, and is incorporated into a biointerface membrane of the preferred embodiments. In another embodiment, Lipopolysaccharide, which is a potent immunostimulant, is incorporated into a biointerface membrane. In another embodiment, a protein, for example, a bone morphogenetic protein (BMP), which is known to modulate bone healing in tissue, is incorporated into a biointerface membrane of a preferred embodiment.

Generally, angiogenic agents are substances capable of stimulating neovascularization, which can accelerate and sustain the development of a vascularized tissue bed at the tissue-device interface. Angiogenic agents include, but are not limited to, copper ions, iron ions, tridodecylmethylammonium chloride, Basic Fibroblast Growth Factor (bFGF), (also known as Heparin Binding Growth Factor-II and Fibroblast Growth Factor II), Acidic Fibroblast Growth Factor (aFGF), (also known as Heparin Binding Growth Factor-I and Fibroblast Growth Factor-I), Vascular Endothelial Growth Factor (VEGF), Platelet Derived Endothelial Cell Growth Factor BB (PDEGF-BB), Angiopoietin-1, Transforming Growth Factor Beta (TGF-Beta), Transforming Growth Factor Alpha (TGF-Alpha), Hepatocyte Growth Factor, Tumor Necrosis Factor-Alpha (TNF-Alpha), Placental Growth Factor (PLGF), Angiogenin, Interleukin-8 (IL-8), Hypoxia Inducible Factor-I (HIF-1), Angiotensin-Converting Enzyme (ACE) Inhibitor Quinaprilat, Angiotropin, Thrombospondin, Peptide KGHK, Low Oxygen Tension, Lactic Acid, Insulin, Leptin, Copper Sulphate, Estradiol, prostaglandins, cox inhibitors, endothelial cell binding agents (for example, decorin or vimentin), glenipin, hydrogen peroxide, nicotine, and Growth Hormone.

Generally, pro-inflammatory agents are substances capable of stimulating an immune response in host tissue, which can accelerate or sustain formation of a mature vascularized tissue bed. For example, pro-inflammatory agents are generally irritants or other substances that induce chronic inflammation and chronic granular response at the implantation-site. While not wishing to be bound by theory, it is believed that formation of high tissue granulation induces blood vessels, which supply an adequate, or rich supply of analytes to the device-tissue interface. Pro-inflammatory agents include, but are not limited to, xenogenic carriers, Lipopolysaccharides, S. aureus peptidoglycan, and proteins.

Other substances that can be incorporated into membranes of preferred embodiments include various pharmacological agents, excipients, and other substances well known in the art of pharmaceutical formulations.

U.S. Publication No. US-2005-0031689-A1 discloses a variety of systems and methods by which the bioactive agent can be incorporated into the biointerface membranes and/or implantable device. Although the bioactive agent is preferably incorporated into the biointerface membrane and/or implantable device, in some embodiments the bioactive agent can be administered concurrently with, prior to, or after implantation of the device systemically, for example, by oral administration, or locally, for example, by subcutaneous injection near the implantation site. A combination of bioactive agent incorporated in the biointerface membrane and bioactive agent administration locally and/or systemically can be preferred in certain embodiments.

Generally, numerous variables can affect the pharmacokinetics of bioactive agent release. The bioactive agents of the preferred embodiments can be optimized for short- and/or long-term release. In some embodiments, the bioactive agents of the preferred embodiments are designed to aid or overcome factors associated with short-term effects (for example, acute inflammation) of the foreign body response, which can begin as early as the time of implantation and extend up to about one month after implantation. In some embodiments, the bioactive agents of the preferred embodiments are designed to aid or overcome factors associated with long-term effects, for example, chronic inflammation, barrier cell layer formation, or build-up of fibrotic tissue of the foreign body response, which can begin as early as about one week after implantation and extend for the life of the implant, for example, months to years. In some embodiments, the bioactive agents of the preferred embodiments combine short- and long-term release to exploit the benefits of both. U.S. Publication No. US-2005-0031689-A1 discloses a variety of systems and methods for release of the bioactive agents.

The amount of loading of the bioactive agent into the biointerface membrane can depend upon several factors. For example, the bioactive agent dosage and duration can vary with the intended use of the biointerface membrane, for example, cell transplantation, analyte measuring-device, and the like; differences among hosts in the effective dose of bioactive agent; location and methods of loading the bioactive agent; and release rates associated with bioactive agents and optionally their carrier matrix. Therefore, one skilled in the art will appreciate the variability in the levels of loading the bioactive agent, for the reasons described above. U.S. Publication No. US-2005-0031689-A1 to Shults et al. discloses a variety of systems and methods for loading of the bioactive agents.

Biointerface Membrane Formation onto the Sensor

Due to the small dimension(s) of the sensor (sensing mechanism) of the preferred embodiments, some conventional methods of porous membrane formation and/or porous membrane adhesion are inappropriate for the formation of the biointerface membrane onto the sensor as described herein. Accordingly, the following embodiments exemplify systems and methods for forming and/or adhering a biointerface membrane onto a small structured sensor as defined herein. For example, the biointerface membrane of the preferred embodiments can be formed onto the sensor using techniques such as electrospinning, molding, weaving, direct-writing, lyophilizing, wrapping, and the like.

Although FIGS. 6 to 10 describe systems and methods for the formation of porous biointerface membranes, including interconnected cavities and solid portion(s). In some embodiments, a cell impermeable (second domain) can additionally be formed using known thin film techniques, such as dip coating, spray coating, spin coating, tampo printing, and the like, prior to formation of the interconnected cavities and solid portion(s). Alternatively, the porous biointerface membrane (e.g., first domain) can be formed directly onto the sensing membrane.

Figure 6:
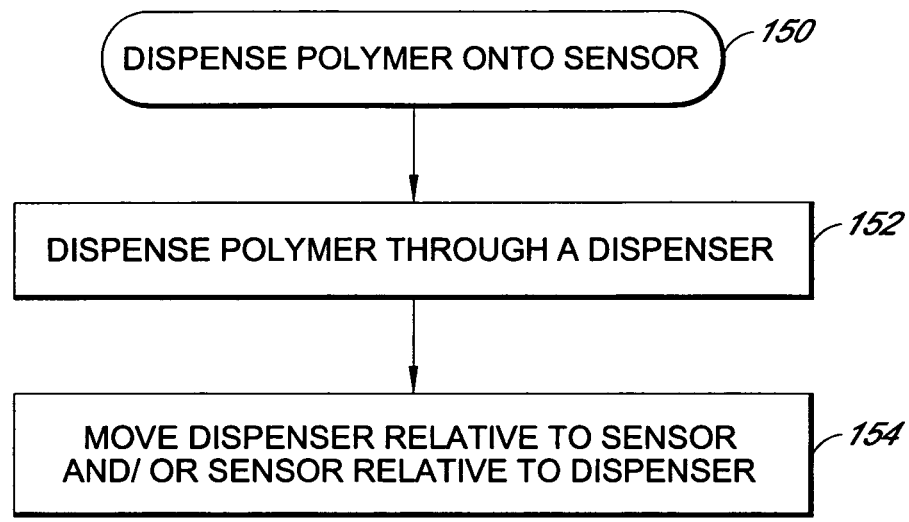
FIG. 6 is a flow chart that illustrates the process of forming a biointerface-coated small structured sensor in one embodiment.

FIG. 6 is a flow chart that illustrates the process 150 of forming a biointerface-coated small structured sensor in one embodiment. In this embodiment, the biointerface membrane includes woven or non-woven fibers formed directly onto the sensor. Generally, fibers can be deposited onto the sensor using methods suitable for formation of woven- or non-woven fibrous materials. In some embodiments, the biointerface membrane is electrospun directly onto the sensor; electrospinning advantageously allows the biointerface membranes to be made with small consistent fiber diameters that are fused at the nodes and are without aggregation.

In some embodiments, the biointerface membrane is directly written onto the sensor; direct writing can advantageously allow uniform deposition of stored patterns (e.g., in a computer system) for providing consistent and reproducible architectures. In these embodiments, a curing step is included either during or after the writing step to solidify the material being written (e.g., heat, UV curing, radiation, etc.). Direct writing is described in more detail, below.

At block 152, one or more dispensers dispense a polymeric material used to form the fibers. A variety of polymeric materials are contemplated for use with the preferred embodiments, including one or more of silicone, polytetrafluoroethylene, expanded polytetrafluoroethylene, polyethylene-co-tetrafluoroethylene, polyolefin, polyester, polycarbonate, biostable polytetrafluoroethylene, homopolymers, copolymers, terpolymers of polyurethanes, polypropylene (PP), polyvinylchloride (PVC), polyvinylidene fluoride (PVDF), polyvinyl alcohol (PVA), polybutylene terephthalate (PBT), polymethylmethacrylate (PMMA), polyether ether ketone (PEEK), polyamides, polyurethanes, cellulosic polymers, poly(ethylene oxide), poly(propylene oxide) and copolymers and blends thereof, polysulfones and block copolymers thereof including, for example, di-block, tri-block, alternating, random and graft copolymers.

The coating process can be performed in a vacuum or in a gaseous medium, which environment can affect the architecture of the biointerface membrane as is appreciated by one skilled in the art.

In embodiments wherein the biointerface is electrospun onto the sensor, the dispenser dispenses a charged liquefied polymer within an electric field, to thereby form a jet of polymer fibers, for example, such as described in PCT International Publication No. WO 2005/032400, which is incorporated herein by reference in its entirety.

In embodiments wherein the biointerface is directly-written onto the sensor, a dispenser dispenses a polymer solution using a nozzle with a valve, or the like, for example as described in U.S. Publication No. US-2004-0253365-A1. In general, a variety of nozzles and/or dispensers can be used to dispense a polymeric material to form the woven or non-woven fibers of the biointerface membrane.

In general, a direct-write patterning system is suitable for either fine-pattern micro dispensing and/or fine-focused laser-beam writing over flat or conformal surfaces to create exact replicas of a preferred biointerface structure. In certain embodiments, the biointerface materials described herein can be deposited using these integrated tool technologies for the direct-write deposition and laser micromachining of a wide variety of biointerface architectures described herein. Additionally, the direct-write patterning system can provide the capability for concurrent detection and imaging methods during additive and subtractive processes.

In another aspect, alternative embodiments of the direct-writing deposition technique utilize a tool in which constituent materials can be dispensed through multiple, discrete dispensing heads. In yet another alternative embodiment, the biointerface structure is directly written onto a removable substrate, after which the substrate is removed and the biointerface applied to the sensor (e.g., wrapped around the sensor or the sensor is inserted into the biointerface).

At block 154, the dispenser(s) is moved relative to the sensor and/or the sensor is moved relative to the dispenser(s) so as to coat the sensor with the fibers. In embodiments wherein the biointerface membrane is electrospun onto the sensor, the dispenser(s) can change the direction and/or magnitude of the electric field during motion in order to effect the orientation of the polymer fibers on the sensor. Additionally, the path of the dispenser is preferably selected so as to coat the portions of or the entire object. In one exemplary embodiment, wherein it is desirable for the biointerface membrane to substantially circumscribe the sensor (e.g., a substantially cylindrical shape), the dispenser can be moved along a helix path, a circular path, a zigzag path, or the like. Additionally, the dispenser can move rotationally and/or translationally relative to the sensor. The number of sweeps is preferably selected according to the desired architecture of the biointerface membrane. Additionally, the density of the fibers and/or the type of liquefied polymer can be changed from one sweep to the other to thereby control the architecture of the membrane.

In embodiments wherein the biointerface membrane is directly written onto the sensor, the dispenser is programmed to write a pattern that creates the desired membrane architecture, including the interconnected cavities and solid portion(s). Namely, the dispenser is programmed to move in the x, y, and optionally z direction in order to create the desired membrane architecture. See, for example, U.S. Publication No. US-2004-0253365-A1 cited above.

Although the preferred embodiments described moving the dispenser(s) relative to the sensor, alternatively, the dispenser can remain stationary and the sensor moved, as is appreciated by one skilled in the art.

In some embodiments, the sensor is moved in a rotational or translational motion, which can be performed in combination with, or instead of, movement of the dispenser. In this step, the sensor is moved so as to ensure coating throughout the entirety of the biointerface region (or a portion thereof). In one exemplary embodiment, wherein a substantially circumscribing biointerface membrane is desired (e.g., for a substantially cylindrically shaped sensing sensor) such as illustrated in FIG. 3A, the sensor can be rotated so to aid in coating the entire circumference of the sensor. In another exemplary embodiment, wherein a substantially planar biointerface membrane is desired (e.g., for a substantially planar sensor), the sensor can be translated so as to aid in coating the desired planar surface area.

Figure 7:
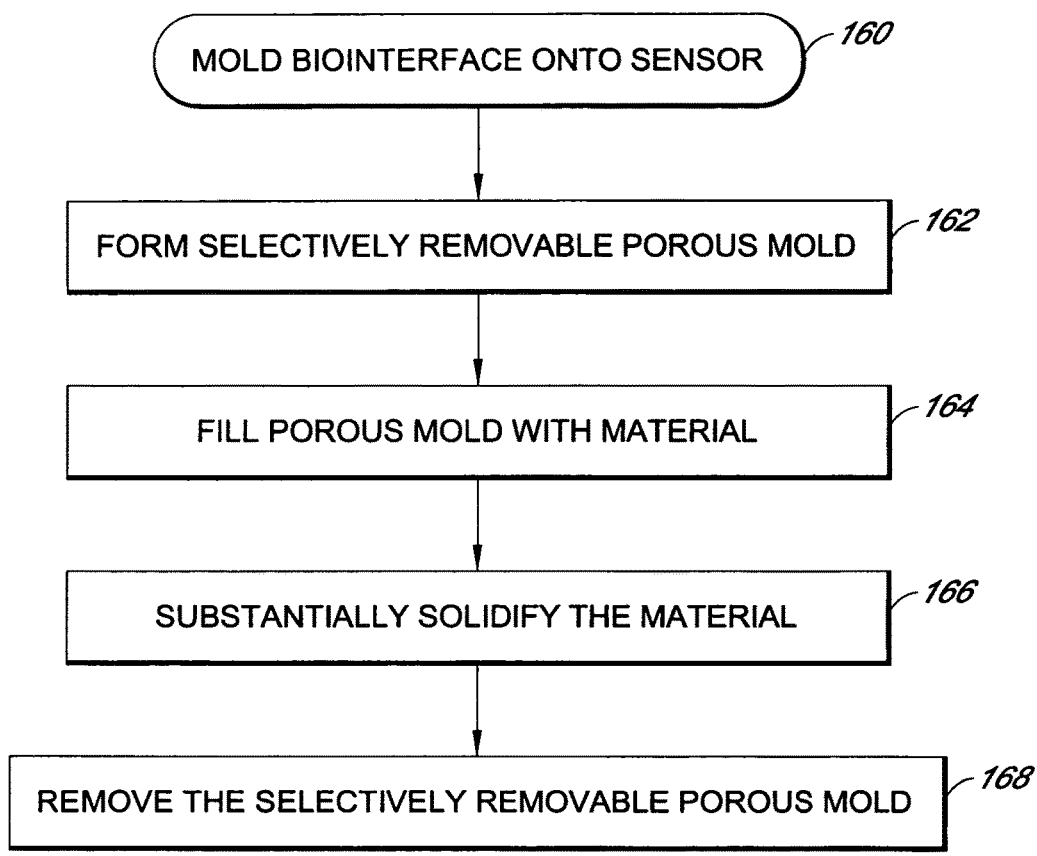
FIG. 7 is a flow chart that illustrates the process of forming a biointerface-coated sensor in an alternative embodiment.

FIG. 7 is a flow chart that illustrates the process 160 of forming a biointerface-coated sensor in an alternative embodiment. In this embodiment, the interconnected cavities and solid portion(s) of the biointerface membrane are amorphous in configuration, such as illustrated in FIGS. 5A and 5B, for example.

At block 162, a selectively removable porogen (e.g., porous mold) is formed by spraying, coating, rolling, or otherwise forming selectively removable particles, for example, sugar crystals, onto the surface of the sensor. Additional examples of materials suitable as selectively removable mold material include thermoplastic polymers such as waxes, paraffin, polyethylene, nylon, polycarbonate, or polystyrene in naturally available particles or processed into specific sizes, shapes, molded forms, spheres or fibers, salt or other particles which cannot be made to inherently stick together coated with sugar, and certain drug crystals such as gentamycin, tetracycline, or cephalosporins. In general, any dissolvable, burnable, meltable, or otherwise removable particle, which can be made to stick together, could be used. Preferably, the particles have shapes and sizes substantially corresponding to the desired cavity dimensions, such as described in more detail above. In some embodiments, the particles are made to adhere to the sensor by environmental conditions, for example, humidity can be used to cause sugar to adhere to the sensor.

In some embodiments, the particles are made to coalesce to provide the desired interconnectivity between the cavities. In an exemplary porous silicone embodiment, sugar crystals are exposed to a humid environment sufficient to cause coalescence of the sugar crystals. In some alternative embodiments, other molds can be used in the place of the particles described above, for example, coral, self-assembly beads, etched and broken silicon pieces, glass frit pieces, and the like, as shown in FIG. 11B.

At block 164, a material (e.g., a moldable or conformable material) is filled or coated into the interconnected cavities of the mold using methods common in the art of polymer processing, for example, injecting, pressing, vacuuming, vapor depositing, extruding, pouring, and the like. Examples of materials suitable for the resulting porous device include polymers, metals, metal alloys, ceramics, biological derivatives, and combinations thereof, in solid or fiber form. In an exemplary porous silicone embodiment, silicone is pressed into the interconnected cavities of the mold.

At block 166, the material is substantially cured or solidified to form the solid portion(s) of the biointerface membrane. Solidification of the material can be accelerated by supplying dry air (which can be heated) to the material, for example. Additionally, freezing, freeze drying or vacuum desiccation, with or without added heat, can also be utilized to cause the material to solidify. In some circumstances, a skin or any excess material can be removed (e.g., shaved, etched, or the like) after curing. In the exemplary porous silicone embodiment, an outer skin of silicone is removed to expose the interconnected cavities at an outer surface.

Figure 11A:
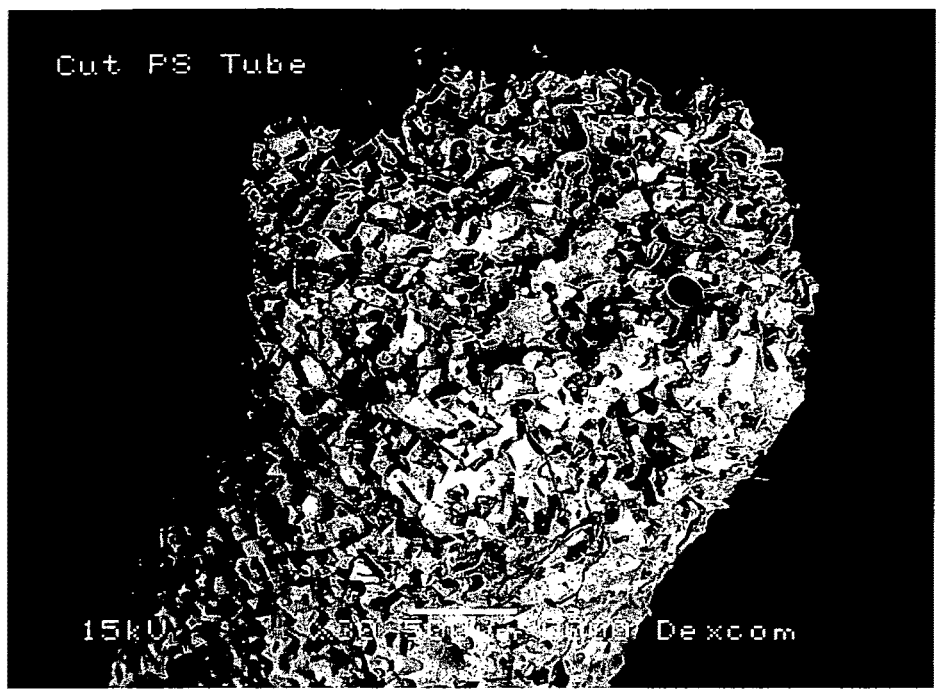
FIG. 11A is a scanning electron micrograph showing a cross-sectional view of a cut porous silicone tube. The scale line equals 500 µm.
Figure 11B:
FIG. 11B is a scanning electron micrograph of a sugar mold formed on a sensor, prior to silicone application. The scale line equals 100 µm.

At block 168, the selectively removable porogen (e.g., porous mold) is dissolved, melted, etched, or otherwise removed, leaving interconnecting cavities within the solid portion (FIG. 11A). Preferably, the selectively removable porogen is readily removable without significantly altering the final product (or product material). This removal can be by dissolution by some solvent that does not significantly dissolve the final product material. Alternatively, the mold material can be melted (or burned) out of the final product material if the melting point (or burning point) of the mold material is below that of the final product material. In the exemplary porous silicone embodiment, water is used to dissolve the sugar crystals.

Figure 8:
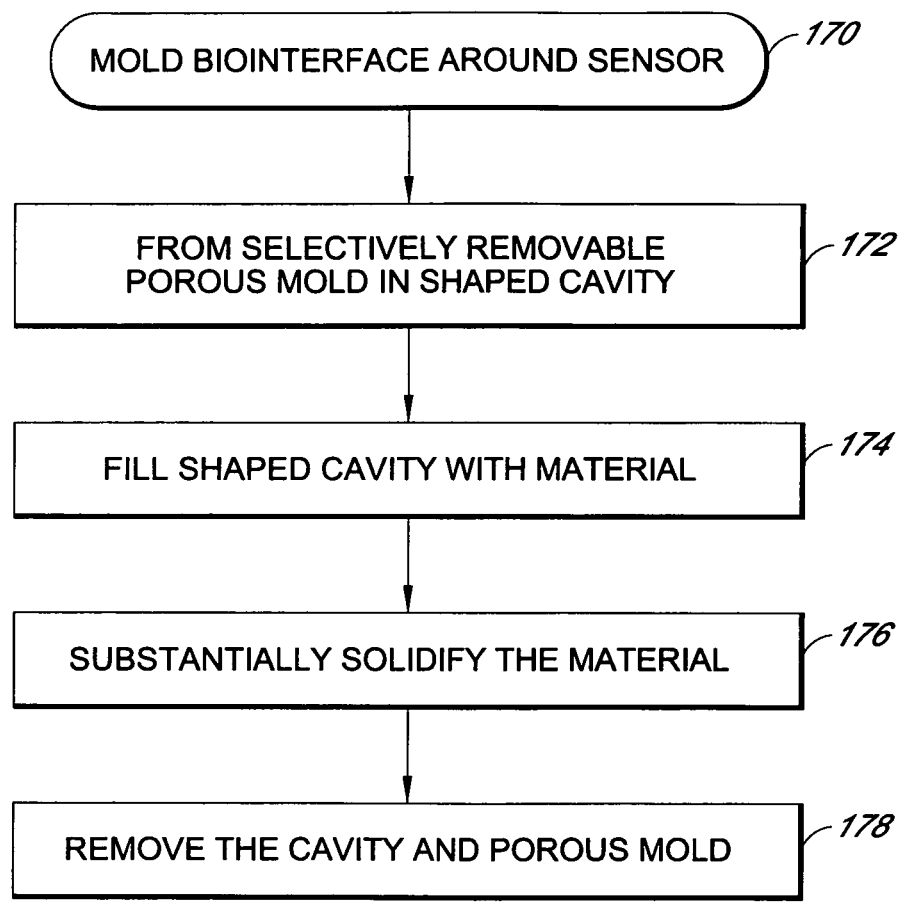
FIG. 8 is a flow chart that illustrates the process of forming a biointerface-coated sensor in another alternative embodiment.

FIG. 8 is a flow chart that illustrates the process 170 of forming a biointerface-coated small structured sensor in another alternative embodiment. In this embodiment, the interconnected cavities and solid portion(s) of the biointerface membrane are amorphous in configuration, such as illustrated in FIGS. 4A and 4B, for example, and the solid portion is molded around the sensor.

At block 172, a selectively removable porogen is formed by filling a shaped cavity with selectively removable particles, for example, sugar crystals, wherein the sensor is located within the shaped cavity, and wherein the selectively removable particles substantially surround the sensor. Additional examples of materials suitable as selectively removable mold material are described with reference to block 162, above. In some embodiments, the shaped cavity mold is formed from a selectively removable material (e.g., sacrificial cavity mold) similar the selectively removable particles described above. One such example includes a tube formed from a dissolvable polymer. Alternatively, the shaped cavity can be a non-selectively removable material, and instead, a sacrificial layer of selectively removable material is formed directly onto the cavity walls, enabling the removal of the biointerface membrane after dissolution of the sacrificial layer.

Preferably the shape of the cavity mold substantially corresponds to the desired final shape of the biointerface membrane. In one exemplary embodiment, the cavity mold is substantially cylindrical, for example using a syringe or cannula as the cavity mold.

In some embodiments, the particles are made to coalesce to provide the desired interconnectivity between the cavities. In an exemplary porous silicone embodiment, sugar crystals are exposed to humidity or spray of water sufficient to cause coalescence of the sugar crystals. In some alternative embodiments, other molds can be used in the place of the particles described above, for example, coral, self-assembly beads, etched and broken silicon pieces, glass frit pieces, and the like.

At block 174, a material (e.g., a moldable or conformable material) is filled into the interconnected cavities of the mold using methods common in the art of polymer processing, for example, injecting, pressing, vacuuming, vapor depositing, pouring, and the like. Examples of materials suitable for the resulting porous device are described in more detail with reference to block 164, above. In an exemplary porous silicone embodiment, silicone is pressed into the interconnected cavities of the mold.

At block 176, the material is substantially cured or solidified to form the solid portion(s) of the biointerface membrane. Solidification of the material can be accelerated as described in more detail with reference to block 166, above.

At block 178, the selectively removable porogen is dissolved, melted, etched, or otherwise removed, leaving interconnecting cavities within the solid portion surrounding the sensor. In some embodiments, wherein a sacrificial layer is formed as described above, the sacrificial layer can be removed before, during, or after the removal of the selectively removable porogen. In some embodiments, the final product is removed from the cavity mold before, during, or after the removal of the selectively removable porogen.

Preferably, the selectively removable porogen is readily removable without significantly altering the final product (or product material). This removal can be by dissolution by some solvent that does not significantly dissolve the final product material. Alternatively, the mold material can be melted (or burned) out of the final product material if the melting point (or burning point) of the mold material is below that of the final product material. In one exemplary embodiment, a sacrificial tube forms the mold cavity; wherein the sacrificial tube is removed prior to, during, or after dissolution of the selectively removable porogen. One skilled in the art can appreciate a variety of modifications or combinations of the above described removal step without departing from the spirit of the invention.

Figure 9:
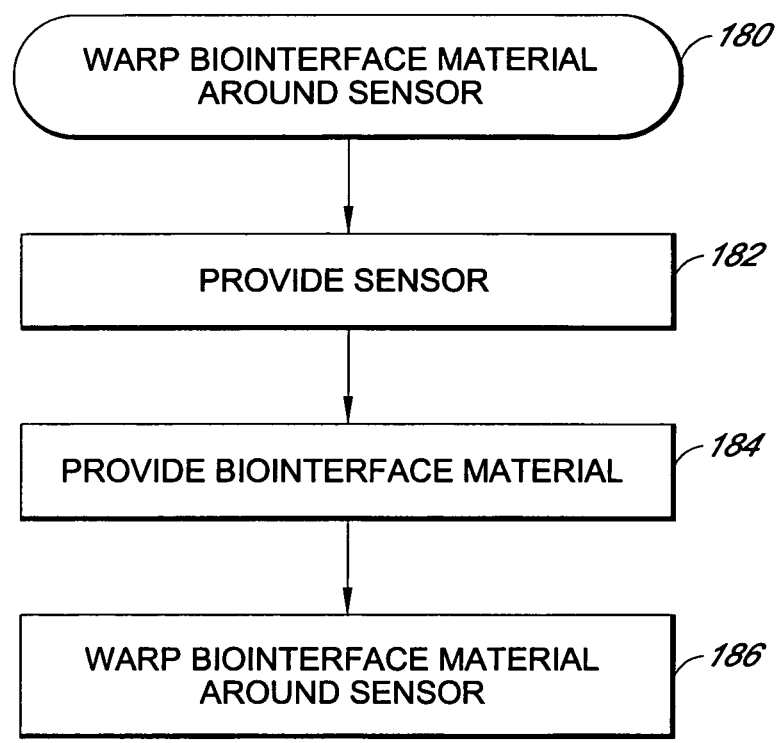
FIG. 9 is a flow chart that illustrates the process of forming a biointerface-wrapped sensor in one embodiment.

FIG. 9 is a flow chart that illustrates the process 180 of forming a biointerface-wrapped sensor in one embodiment. In this embodiment, the interconnected cavities and solid portion(s) of the biointerface membrane can be fibrous or amorphous in configuration. In fact, substantially any biointerface membrane with an architecture as described in more detail above, which is formed in substantially any manner, can be used with this embodiment.

At block 182, a sensor is manufactured and provided, wherein the sensor is formed with a small structure as defined herein.

At block 184, a biointerface membrane with an architecture as described herein is manufactured in substantially any desired manner, wherein the biointerface membrane is formed substantially as a sheet or tube of membrane. Biointerface membranes suitable for wrapping around the sensor and providing the desired host interface are described in more detail above (see section entitled, "Architecture of the First Domain.")

At block 186, the biointerface membrane is wrapped around the sensor manually, or using an automated device, as can be appreciated by one skilled in the art. Namely, the biointerface membrane is wrapped such that it substantially surrounds the sensor, or the sensing mechanism of the sensor (e.g., the electroactive surfaces or sensing membrane). The number of wraps can be from less than 1 to about 100, preferably 1, 1½, 2, 2½, 3, 3½, 4, 5, 6, 7, 8, 9, 10, or more. The number of wraps depends on the architecture of the sheet of biointerface membrane, and the desired architecture of the biointerface surrounding the sensor.

In some embodiments, the circumference (or a portion thereof (e.g., an edge)) of the biointerface membrane with an architecture as described herein can be adhered or otherwise attached or sealed to form a substantially consistent outer surface (of the biointerface membrane). In an aspect of this embodiment, the biointerface membrane is wrapped around the sensor one time, wherein the "wrap" includes a tubular biointerface membrane configured to slide over the sensor (or sensing mechanism), for example, be stretching the tubular biointerface membrane and inserting the sensor therein.

Figure 10:
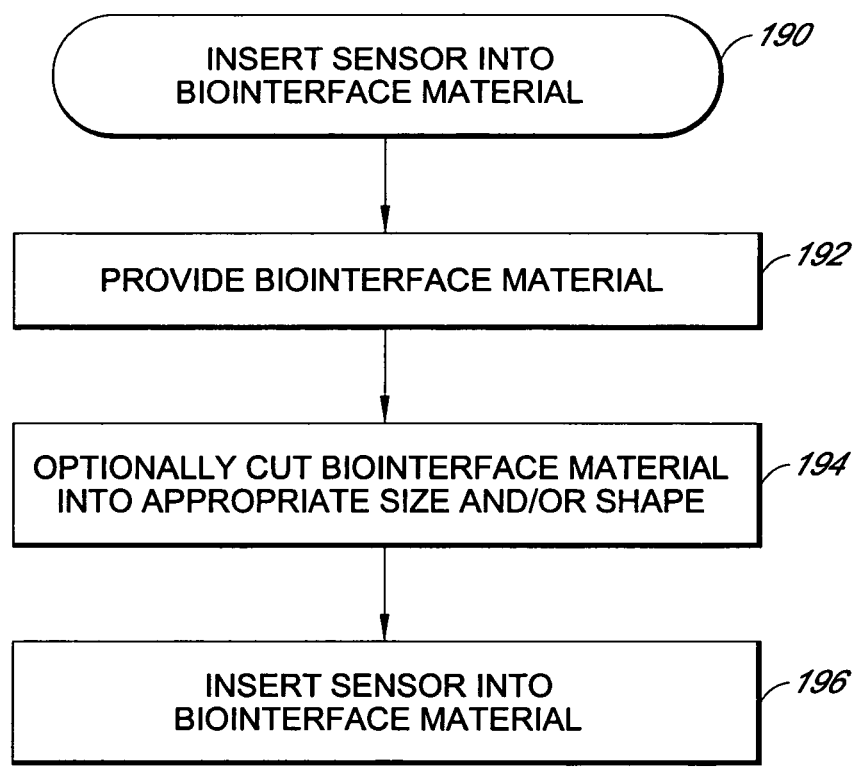
FIG. 10 is a flow chart that illustrates the process of forming a sensing biointerface in one embodiment.

FIG. 10 is a flow chart that illustrates the process 190 of forming a sensing biointerface in one embodiment. In this embodiment, the sensor is inserted into the biointerface membrane so that it is encompassed therein.

At block 192, a biointerface membrane is manufactured in substantially any desired manner. Biointerface membranes suitable for the sensing biointerface are described in more detail above (see for example, section entitled, "Architecture of the First Domain"). In some embodiments, the biointerface membrane is molded into the desired final shape to surround the sensor and implant into a host. Alternatively, the biointerface membrane can be provided as a sheet of bulk material.

At block 194, a particularly shaped or sized biointerface membrane can be (optionally) cut. Namely, in embodiments wherein the biointerface membrane is provided in bulk, e.g., as a sheet of material, the desire shape or size can be cut there from. In these embodiments, bulk biointerface membrane sheet is preferably of the appropriate thickness for the desired final product. In one exemplary embodiment, the biointerface membrane (bulk sheet) is compressed, for example between two substantially rigid structures, and the final size/shape biointerface membrane cut there from, after which the biointerface membrane is released. While not wishing to be bound by theory, it is believed that by compressing the biointerface membrane during cutting, a more precise shape can be achieved. Biointerface membranes can have sufficient elasticity, such that the thickness is returned after release from compression, as is appreciated by one skilled in the art.

At block 196, a sensor is inserted into the biointerface membrane. Preferably, the sensor is inserted into the membrane such that the sensing mechanism contacts at least one or more of the interconnected cavities so that the host analyte can be measured. Alternatively, the biointerface can be formed from a material that allows the flux of the analyte there through. In some embodiments, the sensor is inserted with the aid of a needle. Alternatively, the sensor is formed with appropriate sharpness and rigidity to enable insertion through the biointerface membrane.

In some embodiments, an anchoring mechanism, such as a barb, is provided on the sensor, in order to anchor the sensor within the biointerface membrane (and/or host tissue). A variety of additional or alternative aspects can be provided to implement the biointerface membrane surrounded sensors of the preferred embodiments.

A porous membrane material applied to the sensor can act as a spacer between the sensor and the surrounding tissue at the site of sensor insertion, in either the short-term or long-term sensors. For example, a spacer from 60-300 microns thick can be created of porous silicone having pore sizes of 0.6 microns and greater (e.g., up to about 1,000 microns or more). When inserted into the tissues, the adipose cells come to rest against the outermost aspects of the porous membrane, rather than against the surface of the sensor (FIG. 2C), allowing open space for transport of water-soluble molecules such as oxygen and glucose.

Porous membrane material can be manufactured and applied to a sensor using any advantageous method known to one skilled in the art. As discussed elsewhere, porous membranes can be manufactured from a variety of useful materials known in the art, depending upon the desired membrane parameters.

FIG. 11A is a scanning electron micrograph showing a cross-section of an exemplary porous silicone tube that does not contain a sensor. Note the open porous structure of cavities and channels within the solidified silicone. Porous silicone can be manufactured and applied to the sensor by a variety of means. The material in FIG. 11A, for example, was formed by sieving sugar to give crystals having a size and shape approximate to that of the desired pore size. The sugar was humidified and then compressed into a mold. The mold was then baked, to harden the sugar within the mold. Silicone was forced into the mold and then cured. After the silicone was cured, the mold was removed and the sugar dissolved away. A sensor could subsequently be inserted into the porous silicone tube.

FIG. 11B is a scanning electron micrograph of sugar molded onto a sensor. In this example, a sugar mold was formed directly on the sensor. Note the clumps of sugar crystals attached to the surface of the sensor. In this example, the sensor was placed into the mold, which was then filled with humidified sugar crystals. The mold containing the sensor and sugar was baked to solidify the sugar on the surface of the sensor. The sensor, with sugar crystals attached, was removed from the mold, in order to prepare the electron micrograph. In some embodiments, the sensor can be rolled in the humidified sugar, to attach a layer of sugar to the sensor surface, and then baked to solidify the sugar. In some embodiments, the sugarcoated sensor can be rolled in humidified sugar additional times to form a thicker sugar mold (i.e., 2 or more layers) around the sensor. In some embodiments, silicone is pumped or injected into the solidified sugar and cured. After curing, the sugar is removed, such as by washing, to give a porous silicone covered sensor.

In an alternative embodiment, porous silicone is preformed as a sheet or plug and then applied to the sensor. For example, a sugar mold lacking a sensor therein is formed using the usual means. As previously described, silicone is injected into the mold and then cured. After the mold material is removed from the cured silicone, the sensor is inserted into the plug, thereby creating a sensor having a porous silicone biointerface membrane.

Alternatively, a thin sheet of porous silicone is manufactured and then wrapped around the sensor. For example, a thin porous silicone sheet is manufactured by pressing a thin layer of sieved, humidified sugar into a Petri dish. The sugar is baked. Silicone is applied to the sugar mold by injection, pressing, or the like, and then cured. The sugar is removed from the porous silicone sheet, such as by washing. The manufactured porous silicone is then wrapped around the sensor to form a biointerface membrane of a desired thickness.

In still another embodiment, other materials can be used to manufacture the biointerface membrane. For example, the sensor can be wrapped in a layer of ePTFE having a pore size of about 0.6 microns and above, to create a layer about 12-100 microns thick. See U.S. Pat. No. 6,862,465. In yet another embodiment, the spacer can be either a smooth or porous hydrogel.

Methods of Use

One aspect of the present invention contemplates new methods of use to reduce noise. In one embodiment, noise is reduced by first providing a device of the present invention, such as an implantable analyte sensor, preferably a glucose sensor. The sensor is pre-inserted through the host's skin and into the host. The term "pre-insertion" or "pre-inserted" as used herein is a broad term and is used in its ordinary sense, including, without limitation, to refer to inserting a sensor a period of time (e.g., a "waiting period") before it is to be used, such as about 1-24 hours or longer, e.g., without operatively connecting the sensor to the electronics. The period of time is associated with an amount of time necessary for wound healing to occur. For example, the wound healing process progresses for the first few hours or days. Preferably, interferents that build up around the sensor will be diluted or removed by bulk fluid flow and/or an increase in the fluid bulk around at least a portion of the sensor.

In one embodiment of the present method, the host waits about 1, 2, 3, 4, 5, 6, 7, 8, 9, 10, 11 or 12 hours or longer, before operatively connecting the electronics to the sensor. In another embodiment, the host can wait about 24, 36 or 48 hours or longer, before connecting the electronics. In yet another embodiment, the host can wait about 1-2, 2-4, 4-6, 6-8, 8-10, 10-12, 12-15, 12-24, 12-36, 12-48, 24-36 or 36-48 hours or longer, before operatively connecting the electronics.

In some embodiments, a cap is provided to cover the electrical components (e.g., contacts), until the electronics are coupled to the sensor. The cap can be manufactured of any convenient material, such as plastic, tape, foil, glass or a combination thereof. The cap can attach to the sensor using any convenient method known to those of skill in the art. For example, the cap can attach with a snap fit, adhesive, pins, or the like. After the waiting period has been completed, the host can remove the cap and operably attach the electronics to the sensor.

After the electronics have been operatively connected to the sensor (e.g., the sensor electronics are connected to the sensor), a signal from the sensor is detected, as described in detail above. The sensor will be used for a prescribed period of time, after operably connecting the electronics to the sensor (e.g., in addition to pre-insertion or a waiting period). For example, a 3-day sensor will be used for 3-days and then removed (after three days of data collection). In another example, a 7-day sensor will be removed after seven days of data collection. In the case of sensors configured for shorter or longer periods of use, the sensor will be removed after that period of time. In additional embodiments, noise can be reduced by sensor pre-insertion and/or overlapping sensor insertion as described in co-pending U.S. patent application Ser. No. 11/373,628, filed Mar. 9, 2006 and entitled "SYSTEM AND METHODS FOR PROCESSING ANALYTE SENSOR DATA FOR SENSOR CALIBRATION."

In another embodiment, of the present invention, a second sensor can be pre-inserted into the host before removal of the first sensor. Preferably, the amount of time the second sensor is pre-inserted, before the first sensor, corresponds to the waiting period required for wound healing, as described above. For example, if the waiting period is 6-hours, the host would pre-insert the second sensor at least about 6 hours before he removed the first sensor. In another example, if the waiting period is 24 hours, he would pre-insert the second sensor on the second-to-the-last day (e.g., about 24 hours before removal of the first sensor).

Pre-inserting a sensor, waiting a period of time associated with wound healing and then operatively connecting the electronics, allows time for a fluid pocket to form and/or wound healing to progress, and thereby avoids presenting data to a user during the early time after sensor insertion when early, sedentary noise is most likely to occur, while maintaining the full period of sensor utility (e.g., number of days the sensor is to be used, such as but not limited to 1, 2, 3, 4, 5, 6, 7, 8, 9, 10, 11, 12, 13, 14, or 15 days). By pre-inserting a sensor, in a series of sensor used by a host (e.g., a host changes to a new 5-day sensor after every 5 days of use), the host can have daily use of a sensor without having days of disuse due to a waiting period such as can be necessitated by procedures such as calibration, break-in or wound healing. Advantageously, the host is provided with an extended period of continuous use (instead of the intermittent periods of use required by some implantable analyte sensors, such as implantable glucose sensors) and is provided with substantially increased or improved information/data on his analyte levels (e.g., glucose concentration) so that he can make more informed treatment decisions. Accordingly, due to more informed treatment decisions, the host can benefit from improved disease management, with improved health and quality of life.

Methods and devices that are suitable for use in conjunction with aspects of the preferred embodiments are disclosed in U.S. Pat. No. 4,994,167; U.S. Pat. No. 4,757,022; U.S. Pat. No. 6,001,067; U.S. Pat. No. 6,741,877; U.S. Pat. No. 6,702,857; U.S. Pat. No. 6,558,321; U.S. Pat. No. 6,931,327; and U.S. Pat. No. 6,862,465.

Methods and devices that are suitable for use in conjunction with aspects of the preferred embodiments are disclosed in U.S. Publication No. US-2005-0176136-A1; U.S. Publication No. US-2005-0251083-A1; U.S. Publication No. US-2005-0143635-A1; U.S. Publication No. US-2005-0181012-A1; U.S. Publication No. US-2005-0177036-A1; U.S. Publication No. US-2005-0124873-A1; U.S. Publication No. US-2005-0051440-A1; U.S. Publication No. US-2005-0115832-A1; U.S. Publication No. US-2005-0245799-A1; U.S. Publication No. US-2005-0245795-A1; U.S. Publication No. US-2005-0242479-A1; U.S. Publication No. US-2005-0182451-A1; U.S. Publication No. US-2005-0056552-A1; U.S. Publication No. US-2005-0192557-A1; U.S. Publication No. US-2005-0154271-A1; U.S. Publication No. US-2004-0199059-A1; U.S. Publication No. US-2005-0054909-A1; U.S. Publication No. US-2005-0112169-A1; U.S. Publication No. US-2005-0051427-A1; U.S. Publication No. US-2003-0032874-A1; U.S. Publication No. US-2005-0103625-A1; U.S. Publication No. US-2005-0203360-A1; U.S. Publication No. US-2005-0090607-A1; U.S. Publication No. US-2005-0187720-A1; U.S. Publication No. US-2005-0161346-A1; U.S. Publication No. US-2006-0015020-A1; U.S. Publication No. US-2005-0043598-A1; U.S. Publication No. US-2003-0217966-A1; U.S. Publication No. US-2005-0033132-A1; U.S. Publication No. US-2005-0031689-A1; U.S. Publication No. US-2004-0045879-A1; U.S. Publication No. US-2004-0186362-A1; U.S. Publication No. US-2005-0027463-A1; U.S. Publication No. US-2005-0027181-A1; U.S. Publication No. US-2005-0027180-A1; U.S. Publication No. US-2006-0020187-A1; U.S. Publication No. US-2006-0036142-A1; U.S. Publication No. US-2006-0020192-A1; U.S. Publication No. US-2006-0036143-A1; U.S. Publication No. US-2006-0036140-A1; U.S. Publication No. US-2006-0019327-A1; U.S. Publication No. US-2006-0020186-A1; U.S. Publication No. US-2006-0020189-A1; U.S. Publication No. US-2006-0036139-A1; U.S. Publication No. US-2006-0020191-A1; U.S. Publication No. US-2006-0020188-A1; U.S. Publication No. US-2006-0036141-A1; U.S. Publication No. US-2006-0020190-A1; U.S. Publication No. US-2006-0036145-A1; U.S. Publication No. US-2006-0036144-A1; U.S. Publication No. US-2006-0016700-A1; U.S. Publication No. US-2006-0142651-A1; U.S. Publication No. US-2006-0086624-A1; U.S. Publication No. US-2006-0068208-A1; U.S. Publication No. US-2006-0040402-A1; U.S. Publication No. US-2006-0036142-A1; U.S. Publication No. US-2006-0036141-A1; U.S. Publication No. US-2006-0036143-A1; U.S. Publication No. US-2006-0036140-A1; U.S. Publication No. US-2006-0036139-A1; U.S. Publication No. US-2006-0142651-A1; U.S. Publication No. US-2006-0036145-A1; and U.S. Publication No. US-2006-0036144-A1.

Methods and devices that are suitable for use in conjunction with aspects of the preferred embodiments are disclosed in U.S. application Ser. No. 09/447,227 filed Nov. 22, 1999 and entitled "DEVICE AND METHOD FOR DETERMINING ANALYTE LEVELS"; U.S. application Ser. No. 11/335,879 filed Jan. 18, 2006 and entitled "CELLULOSIC-BASED INTERFERENCE DOMAIN FOR AN ANALYTE SENSOR"; U.S. application Ser. No. 11/334,876 filed Jan. 18, 2006 and entitled "TRANSCUTANEOUS ANALYTE SENSOR"; U.S. application Ser. No. 11/333,837 filed Jan. 17, 2006 and entitled "LOW OXYGEN IN VIVO ANALYTE SENSOR".

All references cited herein, including but not limited to published and unpublished applications, patents, and literature references, are incorporated herein by reference in their entirety and are hereby made a part of this specification. To the extent publications and patents or patent applications incorporated by reference contradict the disclosure contained in the specification, the specification is intended to supersede and/or take precedence over any such contradictory material.

The term "comprising" as used herein is synonymous with "including," "containing," or "characterized by," and is inclusive or open-ended and does not exclude additional, unrecited elements or method steps.

All numbers expressing quantities of ingredients, reaction conditions, and so forth used in the specification are to be understood as being modified in all instances by the term "about." Accordingly, unless indicated to the contrary, the numerical parameters set forth herein are approximations that may vary depending upon the desired properties sought to be obtained. At the very least, and not as an attempt to limit the application of the doctrine of equivalents to the scope of any claims in any application claiming priority to the present application, each numerical parameter should be construed in light of the number of significant digits and ordinary rounding approaches.

The above description discloses several methods and materials of the present invention. This invention is susceptible to modifications in the methods and materials, as well as alterations in the fabrication methods and equipment. Such modifications will become apparent to those skilled in the art from a consideration of this disclosure or practice of the invention disclosed herein. Consequently, it is not intended that this invention be limited to the specific embodiments disclosed herein, but that it cover all modifications and alternatives coming within the true scope and spirit of the invention.

The invention claimed is:

1. An analyte sensing device for detecting an analyte in a host, comprising:
   a transcutaneous continuous sensor configured to measure a clinically useful analyte concentration in a tissue of a host for a time period from one day to fifteen days post implantation, the sensor comprising:
      a sensor configured to measure an analyte in a host;
      a sensing membrane located over the sensor; and
      a biointerface membrane disposed on the sensing membrane, wherein the biointerface membrane is configured to interface with biological fluid, wherein the biointerface membrane has a dry thickness from 0.2 microns to 5 microns, wherein the biointerface membrane comprises a material that has from 20 wt. % to about 80 wt. % water during sensor use, wherein the sensor has a sensitivity of 1 pA/mg/dL to 100 pA/mg/dL during a sensor session.

2. The device of claim 1, wherein the biointerface membrane comprises a bioactive agent, wherein the bioactive agent comprises a substance that releases into the tissue upon implantation into the host, wherein the bioactive agent suppresses wound healing by promoting irritation and/or inflammation around at least a portion of the sensor in vivo.

3. The device of claim 1, wherein the biointerface membrane comprises a shape-memory material configured to be applied to the sensor in a first configuration, wherein after insertion into the tissue of the host the shape-memory material is configured to transform to a second configuration.

4. The device of claim 1, wherein the biointerface membrane comprises an irritating architecture configured to promote fluid bulk surrounding at least a portion of the sensor in vivo by promoting an irritation and/or inflammation surrounding the sensor in vivo, thereby discouraging cells from stabilizing and building up an ordered, fibrous capsule during the time period.

* * * * *

UNITED STATES PATENT AND TRADEMARK OFFICE
CERTIFICATE OF CORRECTION

PATENT NO. : 9,986,942 B2
APPLICATION NO. : 11/503367
DATED : June 5, 2018
INVENTOR(S) : James H. Brauker It is certified that error appears in the above-identified patent and that said Letters Patent is hereby corrected as shown below:

In Column 1 (page 14, item (56)) at Line 22, Under Other Publications, change "Blosensors" to --Biosensors--.

In Column 1 (page 14, item (56)) at Line 50, Under Other Publications, change "Amperomehic" to --Amperometric--.

In Column 2 (page 16, item (56)) at Line 33, Under Other Publications, change "DuPont" to --DuPont1--.

In Column 1 (page 19, item (56)) at Line 8, Under Other Publications, change "Aced" to --Acad--.

In Column 1 (page 20, item (56)) at Line 20, Under Other Publications, change "H2O2on" to --H2O2 on--.

Sheet 14 or 19 (reference Numeral 154) (FIG. 6) at Line 2, Change "AND/ OR" to --AND/OR--.

In Column 2 at Line 26, Change "hydroxyapeptite," to --hydroxyapatite,--.

In Column 2 at Line 27-28, Change "nintinol," to --nitinol,--.

In Column 4 at Line 37, Change "would" to --wound--.

In Column 4 at Line 62, Change "configures" to --configured--.

In Column 8 at Line 17, Change "andrenostenedione;" to --androstenedione;--.

In Column 8 at Line 33, Change "diptheria/" to --diphtheria/--.

In Column 8 at Line 53, Change "duodenalisa," to --duodenalis,--.

Signed and Sealed this
Eleventh Day of September, 2018

Andrei Iancu
*Director of the United States Patent and Trademark Office*

CERTIFICATE OF CORRECTION (continued)
U.S. Pat. No. 9,986,942 B2

In Column 8 at Line 61, Change "Trepenoma pallidium," to --Treponema pallidum,--.

In Column 8 at Line 62, Change "stomatis" to --stomatitis--.

In Column 9 at Line 15-16, Change "(barbituates," to --(barbiturates,--.

In Column 10 at Line 34, Change "material" to --materials--.

In Column 17 at Line 26, Change "sound" to --wound--.

In Column 17 at Line 42, Change "μm" to --gm--.

In Column 20 at Line 49, Change "flammatory" to --inflammatory--.

In Column 23 at Line 15, After "Intermittent" insert --,--.

In Column 24 at Line 61, Change "poly(1-lysine)," to --poly(l-lysine),--.

In Column 27 at Line 62, Change "alterative" to --alternative--.

In Column 30 at Line 19, Change "solublized" to --solubilized--.

In Column 32 at Line 54, Change "absolution" to --a solution--.

In Column 33 at Line 61, Change "glenipin," to --genipin,--.

In Column 34 at Line 26, Change "alterative" to --alternative--.

In Column 35 at Line 11, Change "dexchlorphenamine," to --dexchlorpheniramine,--.

In Column 35 at Line 40, Change "solublized," to --solubilized,--.

In Column 35 at Line 52, Change "acetometaphen," to --acetaminophen,--.

In Column 35 at Line 58, Change "melenamic" to --mefenamic--.

In Column 35 at Line 63, Change "betamethesone," to --betamethasone,--.

In Column 36 at Line 28, Change "infiximab)," to --infliximab),--.

In Column 36 at Line 31, Change "methothrexate," to --methotrexate,--.

In Column 36 at Line 31-32, Change "angiopeptin, vincristing, mitomycine," to --angiopoietin, vincristine, mitomycin,--.

CERTIFICATE OF CORRECTION (continued)
U.S. Pat. No. 9,986,942 B2

In Column 36 at Line 34, Change "batimstat," to --batimastat,--.

In Column 36 at Line 37, Change "catchins," to --catechins,--.

In Column 36 at Line 39, Change "Tesosentan," to --Tezosentan,--.

In Column 36 at Line 39, Change "Cerivasttin)," to --Cerivastatin),--.

In Column 37 at Line 2, Change "aminoclycosides" to --aminoglycosides--.

In Column 39 at Line 53, Change "can by" to --can be--.

In Column 40 at Line 26, Change "Bellafonte," to --Bellefonte,--.

In Column 43 at Line 66, Change "(EDC)))" to --(EDC))--.

In Column 44 at Line 22, Change "emzyme" to --enzyme--.

In Column 44 at Line 24, Change "icons" to --ions--.

In Column 44 at Line 35, Change "6,002,067" to --6,001,067--.

In Column 50 at Line 4, Change "York))" to --York.--.

In Column 54 at Line 6, Change "can not" to --cannot--.

In Column 60 at Line 64, Change "poly(1-lysine)," to --poly(l-lysine),--.

In Column 60 at Line 65, Change "hydroxyapeptite," to --hydroxyapatite,--.

In Column 60 at Line 67, Change "nintinol," to --nitinol,--.

In Column 62 at Line 45, Change "growth" to --ingrowth--.

In Column 63 at Line 23, Change "polytetrafluoraethylene" to --polytetrafluoroethylene--.

In Column 67 at Line 55, After "PLURONIC®" delete "R".

In Column 67 at Line 66, Change "methylhydrogensiloxane" to --methylhydrogen-siloxane--.

In Column 68 at Line 9, Change "methylhydroger-siloxane" to --methylhydrogen-siloxane--.

In Column 68 at Line 49, Change "nintinol," to --nitinol,--.

In Column 72 at Line 16, Change "acetometaphen," to --acetaminophen,--.

CERTIFICATE OF CORRECTION (continued)
U.S. Pat. No. 9,986,942 B2

In Column 72 at Line 22, Change "melenamic" to --mefenamic--.

In Column 72 at Line 29, Change "betamethesone," to --betamethasone,--.

In Column 72 at Line 40, Change "infiximab)," to --infliximab),--.

In Column 72 at Line 43, Change "methothrexate," to --methotrexate,--.

In Column 72 at Line 43-44, Change "angiopeptin, vincristing, mitomycine," to --angiopoietin, vincristine, mitomycin,--.

In Column 72 at Line 46, Change "batimstat," to --batimastat,--.

In Column 72 at Line 49, Change "catchins," to --catechins,--.

In Column 72 at Line 50-51, Change "Tesosentan," to --Tezosentan,--.

In Column 72 at Line 51, Change "Cerivasttin)," to --Cerivastatin),--.

In Column 72 at Line 59, Change "aminoclycosides" to --aminoglycosides--.

In Column 74 at Line 8, Change "glenipin," to --genipin,--.

In Column 81 at Line 23, Change "sugarcoated" to --sugar coated--.